(12) United States Patent
Todd et al.

(10) Patent No.: US 9,862,990 B2
(45) Date of Patent: Jan. 9, 2018

(54) SIGNAL AMPLIFICATION

(75) Inventors: Alison Velyian Todd, Glebe (AU); Evelyn Meiria Linardy, Woodcraft (AU); Elisa Mokany, Caringbah (AU); Dina Lonergan, Coogee (AU)

(73) Assignee: SPEEDX PTY LTD, Eveleigh, NSW (AU)

( * ) Notice: Subject to any disclaimer, the term of this patent is extended or adjusted under 35 U.S.C. 154(b) by 745 days.

(21) Appl. No.: 13/885,554

(22) PCT Filed: Nov. 21, 2011

(86) PCT No.: PCT/AU2011/001504
§ 371 (c)(1),
(2), (4) Date: Sep. 3, 2013

(87) PCT Pub. No.: WO2012/065231
PCT Pub. Date: May 24, 2012

(65) Prior Publication Data
US 2014/0017669 A1    Jan. 16, 2014

(30) Foreign Application Priority Data

Nov. 19, 2010    (AU) .................................. 2010905152

(51) Int. Cl.
*C12Q 1/68* (2006.01)
*C07H 21/02* (2006.01)

(52) U.S. Cl.
CPC ................................... *C12Q 1/682* (2013.01)

(58) Field of Classification Search
CPC .............. C12Q 1/682; C12Q 2537/162; C12Q 2565/101; C12Q 2521/301; C12Q 2521/337
See application file for complete search history.

(56) References Cited

U.S. PATENT DOCUMENTS

| 2008/0220425 A1* | 9/2008 | Ma ........................ C12N 9/1252 435/5 |
| 2010/0041049 A1 | 2/2010 | Smith et al. |
| 2010/0136536 A1 | 6/2010 | Todd et al. |

FOREIGN PATENT DOCUMENTS

| EP | 0552931 A1 | 7/1993 |
| WO | WO 2007/041774 A1 | 4/2007 |
| WO | WO 2009/022125 A1 | 2/2009 |
| WO | WO 2010/017246 A1 | 2/2010 |
| WO | WO 2012/065231 A1 | 5/2012 |

OTHER PUBLICATIONS

EP Application No. 11840792.3 (PublishedasEP2640852), Supplementary European Search Report and European Search Opinion dated Apr. 10, 2014.

(Continued)

*Primary Examiner* — Teresa Strzelecka
(74) *Attorney, Agent, or Firm* — Alston & Bird LLP

(57) ABSTRACT

The present invention relates to compositions and methods for the use of enzymes composed of nucleic acid and/or protein enzymes to generate and amplify a signal indicative of the presence of a target. More particularly, the invention relates to compositions comprising nucleic acid structures that serve as partial or complete enzyme substrates and methods for using these structures to facilitate detection of targets.

15 Claims, 30 Drawing Sheets

(56) References Cited

OTHER PUBLICATIONS

WIPO Application No. PCT/AU2011/001504, PCT International Preliminary Report on Patentability completed Jan. 11, 2013.
WIPO Application No. PCT/AU2011/001504, PCT International Preliminary Report on Patentability dated Jan. 11, 2013. (Corrected Version).
WIPO Application No. PCT/AU2011/001504, PCT International Search Report dated Feb. 17, 2012.
WIPO Application No. PCT/AU2011/001504, PCT Written Opinion of the International Searching Authority dated Feb. 17, 2012.

\* cited by examiner

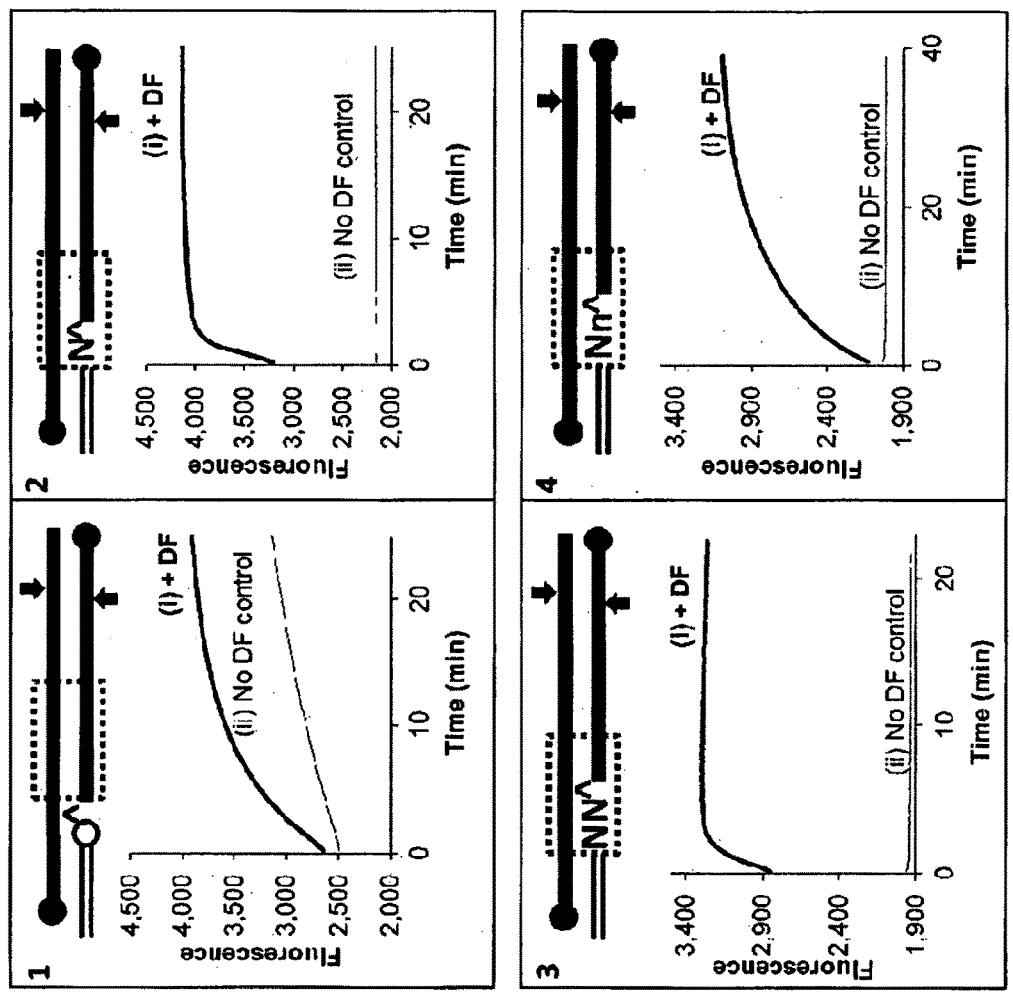
Figure 15 (1-4)

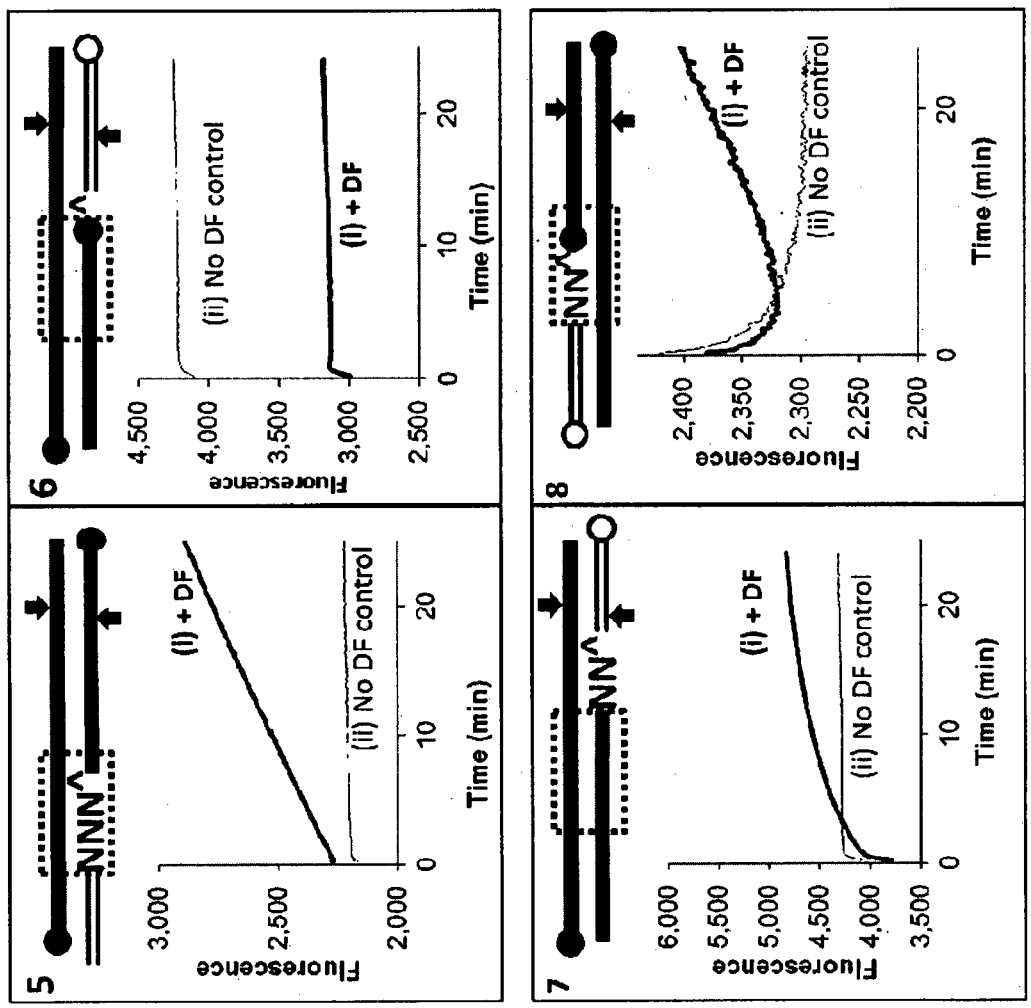
Figure 15 (5-8)

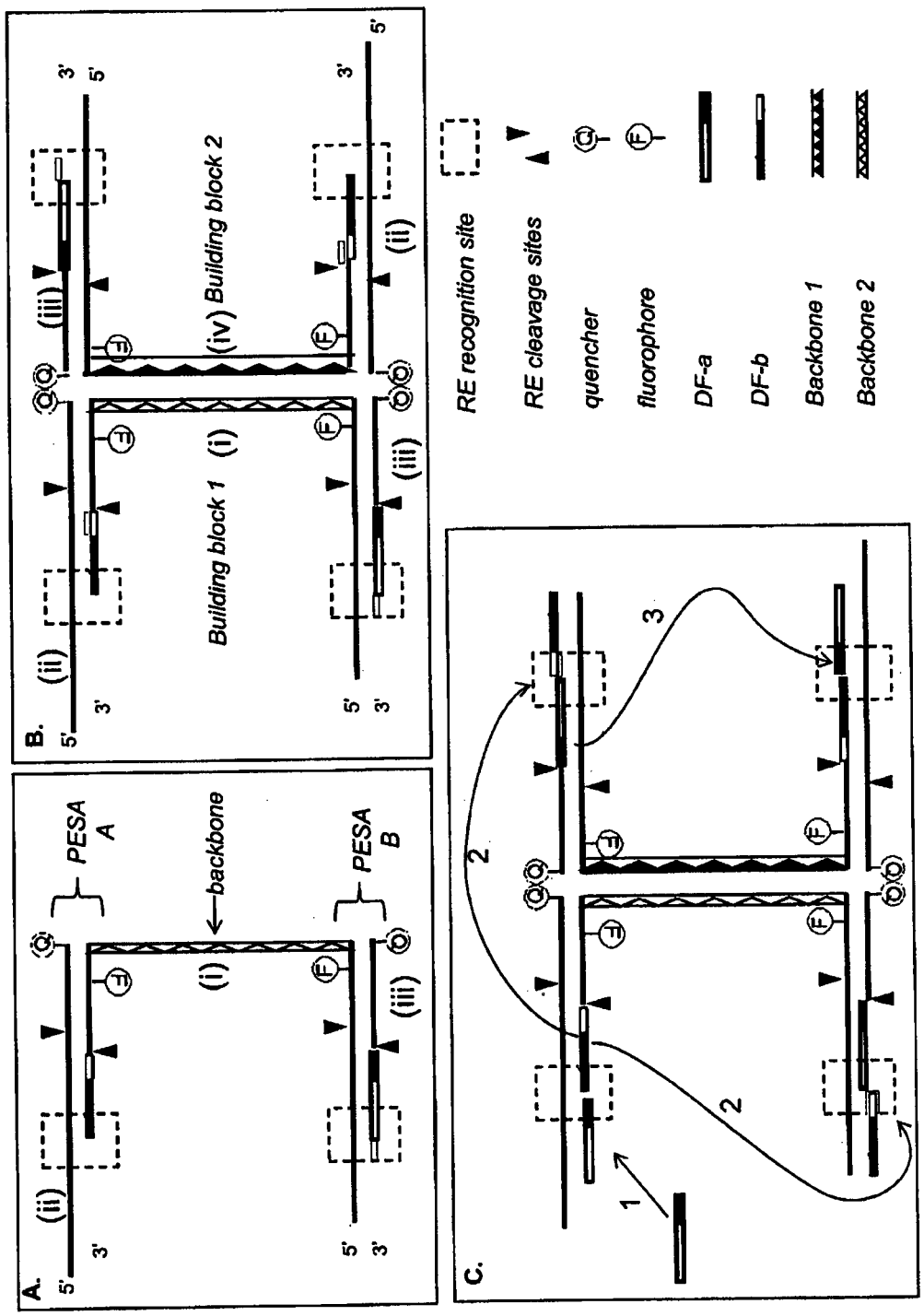
Figure 22A-C

SEQUENCE LISTING

<160> NUMBER OF SEQ ID NOS: 104

<210> SEQ ID NO 1
<211> LENGTH: 15
<212> TYPE: DNA
<213> ORGANISM: Artificial Sequence
<220> FEATURE:
<223> OTHER INFORMATION: Description of Artificial Sequence: Nt.AlwI
      restriction enzyme recognition sequence
<220> FEATURE:
<221> NAME/KEY: misc_feature
<222> LOCATION: (4)..(11)
<223> OTHER INFORMATION: n is a, c, g, or t

<400> SEQUENCE: 1
tgannnnnnn ntgct                                                   15

<210> SEQ ID NO 2
<211> LENGTH: 15
<212> TYPE: DNA
<213> ORGANISM: Artificial Sequence
<220> FEATURE:
<223> OTHER INFORMATION: Description of Artificial Sequence:
      Eco606ORF4215P restriction enzyme recognition sequence
<220> FEATURE:
<221> NAME/KEY: misc_feature
<222> LOCATION: (4)..(11)
<223> OTHER INFORMATION: n is a, c, g, or t

<400> SEQUENCE: 2
tgannnnnnn ntgct                                                   15

<210> SEQ ID NO 3
<211> LENGTH: 11
<212> TYPE: DNA
<213> ORGANISM: Artificial Sequence
<220> FEATURE:
<223> OTHER INFORMATION: Description of Artificial Sequence: Bgl I
      restriction enzyme recognition sequence
<220> FEATURE:
<221> NAME/KEY: misc_feature
<222> LOCATION: (4)..(8)
<223> OTHER INFORMATION: n is a, c, g, or t

<400> SEQUENCE: 3
gccnnnnngg c                                                       11

<210> SEQ ID NO 4
<211> LENGTH: 12
<212> TYPE: DNA
<213> ORGANISM: Artificial Sequence
<220> FEATURE:
<223> OTHER INFORMATION: Description of Artificial Sequence: Bcg I
      restriction enzyme recognition sequence
<220> FEATURE:
<221> NAME/KEY: misc_feature
<222> LOCATION: (4)..(9)
<223> OTHER INFORMATION: n is a, c, g, or t

<400> SEQUENCE: 4
cgannnnnnt gc                                                      12

<210> SEQ ID NO 5
<211> LENGTH: 15
<212> TYPE: DNA
<213> ORGANISM: Artificial Sequence
<220> FEATURE:
<223> OTHER INFORMATION: Description of Artificial Sequence: CfrAI,
      M.CfrAI, S.CfrAI restriction enzyme recognition sequence
<220> FEATURE:

```
<221> NAME/KEY: misc_feature
<222> LOCATION: (4)..(11)
<223> OTHER INFORMATION: n is a, c, g, or t

<400> SEQUENCE: 5
gcannnnnnn ngtgg                                                    15

<210> SEQ ID NO 6
<211> LENGTH: 15
<212> TYPE: DNA
<213> ORGANISM: Artificial Sequence
<220> FEATURE:
<223> OTHER INFORMATION: Description of Artificial Sequence: Eco37I,
      M.Eco37I, S.Eco37I, Eco377I, M.Eco377I, S.Eco377I restriction
      enzyme recognition sequence
<220> FEATURE:
<221> NAME/KEY: misc_feature
<222> LOCATION: (4)..(11)
<223> OTHER INFORMATION: n is a, c, g, or t

<400> SEQUENCE: 6
ggannnnnnn natgc                                                    15

<210> SEQ ID NO 7
<211> LENGTH: 14
<212> TYPE: DNA
<213> ORGANISM: Artificial Sequence
<220> FEATURE:
<223> OTHER INFORMATION: Description of Artificial Sequence: EcoprrI,
      M.EcoprrI, S.EcoprrI restriction enzyme recognition sequence
<220> FEATURE:
<221> NAME/KEY: misc_feature
<222> LOCATION: (4)..(10)
<223> OTHER INFORMATION: n is a, c, g, or t

<400> SEQUENCE: 7
ccannnnnnn rtgc                                                     14

<210> SEQ ID NO 8
<211> LENGTH: 14
<212> TYPE: DNA
<213> ORGANISM: Artificial Sequence
<220> FEATURE:
<223> OTHER INFORMATION: Description of Artificial Sequence: KpnBI,
      M.KpnBI, S.KpnBI restriction enzyme recognition sequence
<220> FEATURE:
<221> NAME/KEY: misc_feature
<222> LOCATION: (5)..(10)
<223> OTHER INFORMATION: n is a, c, g, or t

<400> SEQUENCE: 8
caaannnnnn rtca                                                     14

<210> SEQ ID NO 9
<211> LENGTH: 13
<212> TYPE: DNA
<213> ORGANISM: Artificial Sequence
<220> FEATURE:
<223> OTHER INFORMATION: Description of Artificial Sequence: StySBLI,
      M.StySBLI, S.StySBL restriction enzyme recognition sequence
<220> FEATURE:
<221> NAME/KEY: misc_feature
<222> LOCATION: (4)..(9)
<223> OTHER INFORMATION: n is a, c, g, or t

<400> SEQUENCE: 9
cgannnnnnt acc                                                      13

<210> SEQ ID NO 10
```

```
<211> LENGTH: 14
<212> TYPE: DNA
<213> ORGANISM: Artificial Sequence
<220> FEATURE:
<223> OTHER INFORMATION: Description of Artificial Sequence: StySQI,
      M.StySQI, S.StySQI restriction enzyme recognition sequence
<220> FEATURE:
<221> NAME/KEY: misc_feature
<222> LOCATION: (4)..(9)
<223> OTHER INFORMATION: n is a, c, g, or t

<400> SEQUENCE: 10
aacnnnnnnr tayg                                                          14

<210> SEQ ID NO 11
<211> LENGTH: 11
<212> TYPE: DNA
<213> ORGANISM: Artificial Sequence
<220> FEATURE:
<223> OTHER INFORMATION: Description of Artificial Sequence: Bsm DI
      restriction enzyme recognition sequence
<220> FEATURE:
<221> NAME/KEY: misc_feature
<222> LOCATION: (3)..(7)
<223> OTHER INFORMATION: n is a, c, g, or t

<400> SEQUENCE: 11
acnnnnnctc c                                                             11

<210> SEQ ID NO 12
<211> LENGTH: 10
<212> TYPE: DNA
<213> ORGANISM: Artificial Sequence
<220> FEATURE:
<223> OTHER INFORMATION: Description of Artificial Sequence: Bmu
      SORF1564P restriction enzyme recognition sequence
<220> FEATURE:
<221> NAME/KEY: misc_feature
<222> LOCATION: (4)..(8)
<223> OTHER INFORMATION: n is a, c, g, or t

<400> SEQUENCE: 12 gagnnnnngt                                                               10

<210> SEQ ID NO 13
<211> LENGTH: 14
<212> TYPE: DNA
<213> ORGANISM: Artificial Sequence
<220> FEATURE:
<223> OTHER INFORMATION: Description of Artificial Sequence: Aju I
      restriction enzyme recognition sequence
<220> FEATURE:
<221> NAME/KEY: misc_feature
<222> LOCATION: (4)..(10)
<223> OTHER INFORMATION: n is a, c, g, or t

<400> SEQUENCE: 13
gaannnnnnn ttgg                                                          14

<210> SEQ ID NO 14
<211> LENGTH: 12
<212> TYPE: DNA
<213> ORGANISM: Artificial Sequence
<220> FEATURE:
<223> OTHER INFORMATION: Description of Artificial Sequence: Tst I
      restriction enzyme recognition sequence
<220> FEATURE:
<221> NAME/KEY: misc_feature
<222> LOCATION: (4)..(9)
<223> OTHER INFORMATION: n is a, c, g, or t
```

-continued

```
<400> SEQUENCE: 14
cacnnnnnnt cc                                                         12

<210> SEQ ID NO 15
<211> LENGTH: 11
<212> TYPE: DNA
<213> ORGANISM: Artificial Sequence
<220> FEATURE:
<223> OTHER INFORMATION: Description of Artificial Sequence: Bsl I
      restriction enzyme recognition sequence
<220> FEATURE:
<221> NAME/KEY: misc_feature
<222> LOCATION: (3)..(9)
<223> OTHER INFORMATION: n is a, c, g, or t

<400> SEQUENCE: 15
ccnnnnnnng g                                                          11

<210> SEQ ID NO 16
<211> LENGTH: 11
<212> TYPE: DNA
<213> ORGANISM: Artificial Sequence
<220> FEATURE:
<223> OTHER INFORMATION: Description of Artificial Sequence: Mwo I
      restriction enzyme recognition sequence
<220> FEATURE:
<221> NAME/KEY: misc_feature
<222> LOCATION: (3)..(9)
<223> OTHER INFORMATION: n is a, c, g, or t

<400> SEQUENCE: 16
gcnnnnnnng c                                                          11

<210> SEQ ID NO 17
<211> LENGTH: 11
<212> TYPE: DNA
<213> ORGANISM: Artificial Sequence
<220> FEATURE:
<223> OTHER INFORMATION: Description of Artificial Sequence: Mnl I
      restriction enzyme recognition sequence 5' strand
<220> FEATURE:
<221> NAME/KEY: misc_feature
<222> LOCATION: (5)..(11)
<223> OTHER INFORMATION: n is a, c, g, or t

<400> SEQUENCE: 17
cctcnnnnnn n                                                          11

<210> SEQ ID NO 18
<211> LENGTH: 10
<212> TYPE: DNA
<213> ORGANISM: Artificial Sequence
<220> FEATURE:
<223> OTHER INFORMATION: Description of Artificial Sequence: Mnl I
      restriction enzyme recognition sequence 3' strand
<220> FEATURE:
<221> NAME/KEY: misc_feature
<222> LOCATION: (5)..(10)
<223> OTHER INFORMATION: n is a, c, g, or t

<400> SEQUENCE: 18 ggagnnnnnn                                                            10

<210> SEQ ID NO 19
<211> LENGTH: 16
<212> TYPE: DNA
<213> ORGANISM: Artificial Sequence
<220> FEATURE:
<223> OTHER INFORMATION: Description of Artificial Sequence: synthetic
```

```
      oligonucleotide
<220> FEATURE:
<221> NAME/KEY: misc_feature
<222> LOCATION: (1)..(4)
<223> OTHER INFORMATION: n is a, c, g, or t
<220> FEATURE:
<221> NAME/KEY: misc_feature
<222> LOCATION: (9)..(16)
<223> OTHER INFORMATION: n is a, c, g, or t

<400> SEQUENCE: 19
nnnncctcnn nnnnnn                                                          16

<210> SEQ ID NO 20
<211> LENGTH: 16
<212> TYPE: DNA
<213> ORGANISM: Artificial Sequence
<220> FEATURE:
<223> OTHER INFORMATION: Description of Combined DNA/RNA Sequence:
      synthetic oligonucleotide with ribonucleotide at position six
<220> FEATURE:
<223> OTHER INFORMATION: Description of Artificial Sequence: synthetic
      oligonucleotide
<220> FEATURE:
<221> NAME/KEY: misc_feature
<222> LOCATION: (1)..(4)
<223> OTHER INFORMATION: n is a, c, g, t or u
<220> FEATURE:
<221> NAME/KEY: misc_feature
<222> LOCATION: (9)..(16)
<223> OTHER INFORMATION: n is a, c, g, t or u

<400> SEQUENCE: 20
nnnnggagnn nnnnnn                                                          16

<210> SEQ ID NO 21
<211> LENGTH: 10
<212> TYPE: DNA
<213> ORGANISM: Artificial Sequence
<220> FEATURE:
<223> OTHER INFORMATION: Description of Artificial Sequence: synthetic
      oligonucleotide
<220> FEATURE:
<221> NAME/KEY: misc_feature
<222> LOCATION: (1)..(4)
<223> OTHER INFORMATION: n is a, c, g, or t
<220> FEATURE:
<221> NAME/KEY: misc_feature
<222> LOCATION: (7)..(10)
<223> OTHER INFORMATION: n is a, c, g, or t

<400> SEQUENCE: 21 nnnnggnnnn                                                                 10

<210> SEQ ID NO 22
<211> LENGTH: 10
<212> TYPE: DNA
<213> ORGANISM: Artificial Sequence
<220> FEATURE:
<223> OTHER INFORMATION: Description of Artificial Sequence: synthetic
      oligonucleotide
<220> FEATURE:
<221> NAME/KEY: misc_feature
<222> LOCATION: (3)..(10)
<223> OTHER INFORMATION: n is a, c, g, or t

<400> SEQUENCE: 22 agnnnnnnnn                                                                 10

<210> SEQ ID NO 23
<211> LENGTH: 13
```

-continued

```
<212> TYPE: DNA
<213> ORGANISM: Artificial Sequence
<220> FEATURE:
<223> OTHER INFORMATION: Description of Artificial Sequence: Mnl I
      restriction enzyme recognition sequence 5' strand
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (7)..(13)
<223> OTHER INFORMATION: n is a, c, g, or t

<400> SEQUENCE: 23
nncctcnnnn nnn                                                          13

<210> SEQ ID NO 24
<211> LENGTH: 12
<212> TYPE: DNA
<213> ORGANISM: Artificial Sequence
<220> FEATURE:
<223> OTHER INFORMATION: Description of Artificial Sequence: Mnl I
      restriction enzyme recognition sequence 3' strand
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (7)..(12)
<223> OTHER INFORMATION: n is a, c, g, or t

<400> SEQUENCE: 24
nnggagnnnn nn                                                           12

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
ctcttcctcg tcttcacatc cta                                               23

<210> SEQ ID NO 26
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
taggatgtga agacga                                                       16

<210> SEQ ID NO 27
<211> LENGTH: 18
<212> TYPE: DNA
<213> ORGANISM: Artificial Sequence
<220> FEATURE:
<223> OTHER INFORMATION: Description of Combined DNA/RNA Sequence:
      synthetic oligonucleotide with ribonucleotide at position nine
<220> FEATURE:
<223> OTHER INFORMATION: Description of Artificial Sequence: Synthetic
      oligonucleotide

<400> SEQUENCE: 27
```
ctcactatag gaagagat                                               18

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
ctcttcctca gcagttcatc                                             20

<210> SEQ ID NO 29
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
gatgaactgc tga                                                    13

<210> SEQ ID NO 30
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
gctcctcatc cagcagcggt cgaaatagtg ag                               32

<210> SEQ ID NO 31
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
atctcttctc cgagcgtgta cgacaatggc                                  30

<210> SEQ ID NO 32
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
gccattgtcg tacacctgct ggatgaggag c                                31

<210> SEQ ID NO 33
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (9)..(15)
<223> OTHER INFORMATION: n is a, c, g, or t

```
<400> SEQUENCE: 33
tctcttccnn nnnnn                                                15

<210> SEQ ID NO 34
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (12)..(15)
<223> OTHER INFORMATION: n is a, c, g, or t

<400> SEQUENCE: 34
tctcttccgg annnn                                                15

<210> SEQ ID NO 35
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (11)..(15)
<223> OTHER INFORMATION: n is a, c, g, or t

<400> SEQUENCE: 35
tctcttcctc nnnnn                                                15

<210> SEQ ID NO 36
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (14)..(15)
<223> OTHER INFORMATION: n is a, c, g, or t

<400> SEQUENCE: 36
tctcttcctc ttcnn                                                15

<210> SEQ ID NO 37
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(6)
<223> OTHER INFORMATION: n is a, c, g, or t
<220> FEATURE:
<221> NAME/KEY: misc_feature
<222> LOCATION: (12)..(14)
<223> OTHER INFORMATION: n is a, c, g, or t

<400> SEQUENCE: 37
nnnnnncctt cnnn                                                 14

<210> SEQ ID NO 38
```

```
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (12)..(14)
<223> OTHER INFORMATION: n is a, c, g, or t

<400> SEQUENCE: 38
nnngcgcctt cnnn                                                          14

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
ctcttcctca gcagttcatt                                                    20

<210> SEQ ID NO 40
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
aatgaactgc tga                                                           13

<210> SEQ ID NO 41
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (5)..(11)
<223> OTHER INFORMATION: n is a, c, g, or t

<400> SEQUENCE: 41
cctcnnnnnn n                                                             11

<210> SEQ ID NO 42
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (5)..(10)
<223> OTHER INFORMATION: n is a, c, g, or t

<400> SEQUENCE: 42 gaggnnnnnn                                                               10
```

```
<210> SEQ ID NO 43
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
catctcttcc tcagagcctg actt                                              24

<210> SEQ ID NO 44
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
aagtcaggtg ctgagg                                                       16

<210> SEQ ID NO 45
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
aagtcaggtg ctgag                                                        15

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
ctcttcctca gcacctgatt                                                   20

<210> SEQ ID NO 47
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
aatcaggtgc tga                                                          13

<210> SEQ ID NO 48
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
aagtcaggtg ctg                                                          13
```

```
<210> SEQ ID NO 49
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
aggaagagat g                                                          11

<210> SEQ ID NO 50
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
tccgcagcct cccttctcta c                                               21

<210> SEQ ID NO 51
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
gaggctgcgg a                                                          11

<210> SEQ ID NO 52
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
gtagagaagg                                                            10

<210> SEQ ID NO 53
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
gggaggctgc gga                                                        13

<210> SEQ ID NO 54
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
tggttgagca gagagggatc atc                                             23

<210> SEQ ID NO 55
```

```
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
tctctgctca acca                                                       14

<210> SEQ ID NO 56
<211> LENGTH: 10
<212> TYPE: DNA
<213> ORGANISM: Artificial Sequence
<220> FEATURE:
<223> OTHER INFORMATION: Description of Artificial Sequence: nucleic
      acid comprising partial EarI restriction enzyme recognition
      sequence
<220> FEATURE:
<221> NAME/KEY: misc_feature
<222> LOCATION: (7)..(10)
<223> OTHER INFORMATION: n is a, c, g, or t

<400> SEQUENCE: 56 gagaagnnnn                                                            10

<210> SEQ ID NO 57
<211> LENGTH: 10
<212> TYPE: DNA
<213> ORGANISM: Artificial Sequence
<220> FEATURE:
<223> OTHER INFORMATION: Description of Artificial Sequence: nucleic
      acid comprising partial AlwI restriction enzyme recognition
      sequence
<220> FEATURE:
<221> NAME/KEY: misc_feature
<222> LOCATION: (6)..(10)
<223> OTHER INFORMATION: n is a, c, g, or t

<400> SEQUENCE: 57 cctagnnnnn                                                            10

<210> SEQ ID NO 58
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
gatgaactgc tgaggaagag at                                              22

<210> SEQ ID NO 59
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
caggatgtga agacgaggaa gaagat                                          26

<210> SEQ ID NO 60
<211> LENGTH: 21
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 60
ctcttccact tgatcccgta t                                              21

<210> SEQ ID NO 61
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
atacgggatc aagt                                                      14

<210> SEQ ID NO 62
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
atacgggatc aagtggaaga gat                                            23

<210> SEQ ID NO 63
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
ctctccaggc aagaggt                                                   17

<210> SEQ ID NO 64
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
acctacttgc ct                                                        12

<210> SEQ ID NO 65
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
acctacttgc ctggaagaga t                                              21

<210> SEQ ID NO 66
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 66
ctcttccgga gttgct                                                    16

<210> SEQ ID NO 67
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
agcaactccg gaagagat                                                  18

<210> SEQ ID NO 68
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
tcagcagttt aaacaacc                                                  18

<210> SEQ ID NO 69
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
ggttgtttaa                                                           10

<210> SEQ ID NO 70
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
ggttgtttaa actgctga                                                  18

<210> SEQ ID NO 71
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
tcagcagtac acagaacc                                                  18

<210> SEQ ID NO 72
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
ggttctgtgt                                                                10

<210> SEQ ID NO 73
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
ggttctgtgt actgctga                                                       18

<210> SEQ ID NO 74
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
aatcaggtgc tga                                                            13

<210> SEQ ID NO 75
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
tcagtcccac gtgtga                                                         16

<210> SEQ ID NO 76
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
tcagcacctc acacgtggga agag                                                24

<210> SEQ ID NO 77
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
atctcttcct ctacaccttt ttttttttt ttttaggtg tgga                            44

<210> SEQ ID NO 78
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
tccacacctc tcttcctttt tttttttttt tttttggaag aga        43

<210> SEQ ID NO 79
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
ggaagagatg        10

<210> SEQ ID NO 80
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
ggtgctgata ctgcgctctg gg        22

<210> SEQ ID NO 81
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
caaacgagtc ctggccttgt ctacaacgag gttgtgc        37

<210> SEQ ID NO 82
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
ttggtgaggc tagctgtgga gacggattac accttc        36

<210> SEQ ID NO 83
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
gaaggtgtaa tccgtctcca cagacaaggc caggactcgt ttg        43

<210> SEQ ID NO 84
<211> LENGTH: 37
<212> TYPE: DNA
<213> ORGANISM: Artificial Sequence
<220> FEATURE:
<223> OTHER INFORMATION: Description of Combined DNA/RNA Sequence:
      synthetic oligonucleotide with ribonucleotides at positions
      twenty-two and twenty-three
<220> FEATURE:

```
<223> OTHER INFORMATION: Description of Artificial Sequence: Synthetic
      oligonucleotide

<400> SEQUENCE: 84
cccagagcgc agtccacaac cgucaccaat cagcacc                              37

<210> SEQ ID NO 85
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
ctcttcctct cttcccggat gtcggcctcc tagtacagcg                           40

<210> SEQ ID NO 86
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
taggatgtga agacgaggaa gagat                                           25

<210> SEQ ID NO 87
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
tgctcatctc agcggtcgaa atagtgagt                                       29

<210> SEQ ID NO 88
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
catctcttct ccgagcgtct acgacaat                                        28

<210> SEQ ID NO 89
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
attgtcgtag acctgagatg agca                                            24

<210> SEQ ID NO 90
<211> LENGTH: 20
<212> TYPE: DNA
<213> ORGANISM: Artificial Sequence
<220> FEATURE:
<223> OTHER INFORMATION: Description of Combined DNA/RNA Sequence:
``` synthetic oligonucleotide with ribonucleotide at position ten
<220> FEATURE:
<223> OTHER INFORMATION: Description of Artificial Sequence: Synthetic
      oligonucleotide

<400> SEQUENCE: 90
actcactata ggaagagatg                                                    20

<210> SEQ ID NO 91
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
cgacgtcctc aacaggcaac acc                                                23

<210> SEQ ID NO 92
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
ttcgttgcct gttga                                                         15

<210> SEQ ID NO 93
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
ggacgtcgta ctgcgctctg gg                                                 22

<210> SEQ ID NO 94
<211> LENGTH: 57
<212> TYPE: DNA
<213> ORGANISM: Artificial Sequence
<220> FEATURE:
<223> OTHER INFORMATION: Description of Combined DNA/RNA Sequence:
      synthetic oligonucleotide with ribonucleotides at positions
      forty-one and forty-two
<220> FEATURE:
<223> OTHER INFORMATION: Description of Artificial Sequence: Synthetic
      oligonucleotide

<400> SEQUENCE: 94
ggtgctgata ctgcttttt tttttttgca gtccacaacc gucaccaaat cagcacc            57

<210> SEQ ID NO 95
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
tggttggatg ggcaagcatg tgcggtcgaa atagtgagt                               39

```
<210> SEQ ID NO 96
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
catctcttct ccgagcgtgt ttggcaaagt gaaagaag                                    38

<210> SEQ ID NO 97
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
gcgctccatg gcctccac                                                         18

<210> SEQ ID NO 98
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
agatccttgt cgcagtgtat agtgagtgcc tgg                                        33

<210> SEQ ID NO 99
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
cactgcgaca aggatct                                                          17

<210> SEQ ID NO 100
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
ccaggcactc actata                                                           16

<210> SEQ ID NO 101
<211> LENGTH: 16
<212> TYPE: DNA
<213> ORGANISM: Artificial Sequence
<220> FEATURE:
<223> OTHER INFORMATION: Description of Combined DNA/RNA Sequence:
      synthetic oligonucleotide with ribonucleotide at position sixteen
<220> FEATURE:
<223> OTHER INFORMATION: Description of Artificial Sequence: Synthetic
      oligonucleotide

<400> SEQUENCE: 101
ccaggcactc actata                                                           16
```

```
<210> SEQ ID NO 102
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
ccaaaccagg cactcactat aggaagagat g                                          31

<210> SEQ ID NO 103
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
ccaggcactc actatacact gcgacaagga tct                                        33

<210> SEQ ID NO 104
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
atcacatccg ggaagaga                                                         18
```

SIGNAL AMPLIFICATION

INCORPORATION BY CROSS REFERENCE

This application is the U.S. National Stage of PCT/AU2011/001504 filed Nov. 21, 2011, which claims priority from Australian application 2010905152 filed 19 Nov. 2010, the entire contents of both of which are incorporated herein by cross reference.

INCORPORATION BY REFERENCE OF SEQUENCE LISTING

The sequence listing written in file 433372sequencelist.txt is of 29,453 bytes and was created May 12, 2013. The information contained in this filed is hereby incorporated by reference.

TECHNICAL FIELD

The present invention relates to compositions and methods for the use of enzymes composed of nucleic acid and/or protein enzymes to generate and amplify a signal indicative of the presence of a target. More particularly, the invention relates to compositions comprising nucleic acid structures that serve as partial or complete enzyme substrates and methods for using these structures to facilitate detection of targets.

BACKGROUND

Nucleases

Nucleases are enzymes that cleave phosphodiester bonds between the nucleotide subunits of nucleic acids. Deoxyribonucleases act on DNA while ribonucleases act on RNA, however some nucleases utilise both DNA and RNA as substrates.

Nucleases can be further categorised as endonucleases and exonucleases, although some enzymes may have multiple functions and exhibit both endonuclease and exonuclease activity. Endonucleases cleave phosphodiester bonds within a polynucleotide chain. In contrast, exonucleases cleave phosphodiester bonds at the end of a polynucleotide chain. Exonucleases may remove nucleotides from either the 5' end or the 3' end or from both ends of a DNA or RNA strand. Flap endonucleases are structure-specific 5' endonucleases that recognize bifurcated ends of double stranded oligonucleotides and remove single stranded 5' arms after the first overlapping base leaving a 3' hydroxyl nick between the two oligonucleotides.

Nucleases are used extensively as tools for molecular biology. Examples of protein endonucleases include restriction endonucleases, Mung Bean nuclease, Endonuclease IV (*E. coli*), RNase A, RNase I (*E. coli*), RNase III (*E. coli*) or RNase H (*E. coli*). Examples of protein exonucleases include Exonuclease I (*E. coli*), Exonuclease III (*E. coli*), Exonuclease VII and T7 Exonuclease. Catalytic nucleic acids including DNAzymes, ribozymes and MNAzymes can also function as endonucleases and cleave phosphodiester bonds within a polynucleotide chain.

Restriction Enzymes

A restriction enzyme (RE) or restriction endonuclease is a catalytic protein that recognizes a specific Restriction Enzyme Recognition (RER) site or sequence (RERS) of a nucleic acid and cleaves the nucleic acid either at the RERS or distant from the RERS. Restriction enzymes are one of the most widely used tools in molecular biology and they are typically purified from bacteria or archaea. For example, EcoRI is purified from *Escherichia coli* and Hind III is purified from *Haemophilus influenzae*. Thousands of restriction enzymes have been purified and characterized and greater than 250 different Restriction Enzyme Recognition sequences have been identified.

The type of ends generated by restriction enzyme cleavage include termini where there is a 5' overhang or a 3' overhang or the cut may be blunt (no overhang). Most restriction enzymes cleave both strands of a double stranded duplex. Nicking enzymes require a double stranded DNA substrate but only one strand is cleaved. An example of this type of enzyme is Nt.AlwI which recognizes the sequence GGATCNNNN/N and cleaves this strand at the position indicated by the forwardslash (/). Although the majority require a double-stranded DNA as a substrate, a few restriction enzymes have been reported that recognize and cleave single-stranded DNA.

Catalyic Nucleic Acid Enzymes

Catalytic nucleic acid enzymes are enzymes composed of nucleic acid (non-protein enzymes) that can modify nucleic acid substrates. For example, a catalytic nucleic acid enzyme may be a DNA molecule (also known in the art as a DNAzyme or deoxyribozyme or DNA enzyme) or an RNA molecule (known in the art as a ribozyme) or a multi-component nucleic acid enzyme composed of multiple DNA or RNA molecules (known in the art as an MNAzyme). Catalytic nucleic acid endonucleases specifically recognize and cleave distinct nucleic acid substrate sequences. DNAzymes and ribozymes have been shown to be capable of cleaving RNA substrates, DNA substrates and/or chimeric DNA/RNA substrates. Catalytic nucleic acid enzymes can only cleave a nucleic acid substrate (target), provided that the substrate sequence meets minimum sequence requirements. The target substrate must be complementary to the substrate recognition domain (binding arms) of the catalytic nucleic acid and the substrate must contain a specific sequence at the site of cleavage. Examples of such sequence requirements at the cleavage site include the requirement for a purine:pyrmidine sequence for DNAzyme cleavage (10-23 model) and the requirement for the sequence uridine:X where X can equal A, C or U but not G, for the hammerhead ribozymes. The 10-23 DNAzyme is a DNAzyme that is capable of cleaving nucleic acid substrates at specific RNA phosphodiester bonds. This DNAzyme has a catalytic domain of 15 deoxynucleotides flanked by two substrate-recognition domains (binding arms). In the case of DNAzymes and ribozymes, the target substrate sequence that is recognized is the same molecule that is cleaved.

MNAzymes are multi-component nucleic acid enzymes which are assembled and are only catalytically active in the presence of an assembly facilitator. These enzymes are composed of multiple part-enzymes, or partzymes, which self-assemble in the presence of one or more assembly facilitators and form active MNAzymes which catalytically modify substrates. The substrate and assembly facilitators (target) are separate nucleic acid molecules. The partzymes have multiple domains including (i) sensor arms which bind to the assembly facilitator (such as a target nucleic acid); (ii) substrate arms which bind the substrate, and (iii) partial catalytic core sequences which, upon assembly, combine to provide a complete catalytic core. MNAzymes can be designed to recognize a broad range of assembly facilitators including, for example, different target nucleic acid sequences. In response to the presence of the assembly facilitator, MNAzymes modify their substrates. This substrate modification can be linked to signal generation and thus MNAzymes can generate an enzymatically amplified output signal. The assembly facilitator may be a target nucleic acid present in a biological or environmental sample. In such cases, the detection of the modification of the substrate by the MNAyme activity is indicative of the presence of the target. Several MNAzymes capable of cleaving nucleic acid substrates have been reported and additional MNAzymes which can ligate nucleic acid substrates are also known in the art.

Methods Using Restriction Enzymes for Target Detection or Signal Amplification.

Methods using Restriction Enzymes (REs) for detection of target nucleic acid are known in the art. They can distinguish between gene alleles by specifically recognizing single nucleotide polymorphisms (SNPs) in DNA. However, this can only be achieved if the SNP alters the a naturally occurring RERS present in one allele. In this method, the restriction enzyme can be used to genotype a DNA sample without the need for sequencing. Following digestion of genomic DNA with a RE, the resultant DNA fragments can be separated and analysed by gel electrophoresis. In rare instances acquired mutations can be detected if they happen to lie within a naturally occurring RERS.

A number of other methods have been published which exploit RE for target detection using different strategies. One method, known as the Restriction Amplification Assay, uses a labelled oligonucleotide probe which is complementary to the target to be detected and which spans a region of the target that contains a specific RER site (U.S. Pat. No. 5,102,784). Following hybridization of the labelled probe with the target, the resultant duplex is cleaved with a RE and detection of the cleaved probe indicates the presence of the target. Subsequently, another intact probe can bind to a second complementary oligonucleotide and to a cleaved target fragment. This second oligonucleotide binds immediately adjacent to a cleaved target fragment and results in reconstitution of the RE site allowing cleavage of another probe. The disadvantages of this approach include (i) the requirement to have a target containing a specific RERS in the region of interest and (ii) a limited sensitivity, since the maximum number of cleavable duplexes at any time is equal to the original number of target molecules present. The requirement for the target to contain specific RERS in the region of interest significantly limits the flexibility of this assay. The second disadvantage noted above is also of particular importance as the amount of signal-generating complexes present in the assay at any one time is limited to the number of target molecules present which impacts adversely on signal strength and the running time required to achieve satisfactory signal strength. Another example of a target detection assay which employs REs is called the Nicking Endonuclease Signal Amplification (NESA). Similar to the Restriction Amplification Assay, this method employs a labelled oligonucleotide probe which is complementary to the target to be detected and which spans a region of the target that contains a specific RER site, in this case for a nicking RE (Kiesling et al, NAR; 35; 18; e117, 2007). Following hybridization of the labelled probe with the target, one strand of the resultant duplex is cleaved with the nicking RE, and this cleavage results in dissociation of the probe while the target is left intact. Cleavage of the probe generates signal indicative of the presence of the specific target. The target can then hybridize to additional probes causing an increase in the signal. Again, the disadvantages of this approach are (i) the requirement to have a target containing a specific naturally occurring RERS in the region of interest (in this case, specifically the RERS of one of the few nicking RERS adjacent to the target) and (ii) the sensitivity of the approach is limited since the maximum number of cleavable duplexes at any time is equal to the original number of target molecules.

Another protocol, called cascade enzymatic, signal amplification (Zou et al, Angew. Chem. Int Ed; 49 p 1-5; 2010) requires multiple steps, namely; (i) two probes bind to a target creating an overlap that is cleaved by flap endonuclease; (ii) the cleaved flap fragment binds to the loop of a molecular beacon in a position adjacent to a another oligonucleotide also bound to the loop, then T4 ligase joins (ligates) these two oligonucleotides, and this opens the beacon and creates a RERS for a nicking RE; then finally (iii) the nicking RE cleaves the beacon and releases the ligated fragment to bind to another beacon. While this method overcomes the specific need for the nicking RERS to occur naturally in the target, the method teaches that the two fragments must be ligated to create a new RER site. Further, the method is cumbersome, requiring three sequential buffers, one specific for each of the endonclease, ligation and cleavage activity.

None of these methods provide a simple protocol for the amplification of signal generated by the detection of a target in a manner that amplifies the signal independently of the target following an initial target recognition event, regardless of whether or not the specific target has a convenient, naturally occurring RERS.

Other Target and Signal Amplification Technologies

In order to increase the sensitivity of target detection, strategies for target amplification or signal amplification have been employed. Examples of methods which employ target amplification include the polymerase chain reaction (PCR), strand displacement amplification (SDA), loop-mediated isothermal amplification (LAMP), rolling circle amplification (RCA), transcript-mediated amplification (TMA); self-sustained sequence replication (3SR), or nucleic acid sequence based amplification (NASBA).

Several examples of signal amplification cascades, which use catalytic nucleic acids, are known in the art. Ligation cascades use a first ribozyme (A) which ligates two RNA containing oligonucleotides to form a second ribozyme (B). Ribozyme (B) then ligates two other RNA containing oligonucleotides to form a new first ribozyme (A), thus triggering a cascade reaction. Other signal amplification cascades use circularized DNAzyme/substrate molecules. A DNAzyme (A) is inactive when circular, but becomes activated by linearization by a second DNAzyme (B), which cleaves the circular DNAzyme (A). Active linear DNAzyme (A) then cleaves circular DNAzyme (B) molecules thus linearizing and activating them. The two DNAzymes capable of cleaving/linearizing each other result in a cascade of catalytic nucleic acid activity.

Other approaches are available including, for example, combining the use of DNAzymes with the versatility of aptamers and/or with the catalytic power of traditional protein enzymes. This method results in the release of a protein enzyme that can, in turn, catalyze the formation of detectable molecules thereby generating and amplifying signal. This approach allows sensitive detection, but it is expensive as it requires highly customized molecules for each assay. Alternate methods include, for example, the branched DNA assay (bDNA) which amplifies a signal by employing a secondary reporter molecule (e.g. alkaline phosphatase) attached to labeled probes mediating the reaction. The Tyramide Signal Amplification (TSA) method uses horseradish peroxidase to convert tyramide to its active form, which binds to tyrosine residues in proteins. The Invader assay allows for nuclease cleavage leading to greater than 1000 cleavage events per target molecule over time. However, there are limitations and deficiencies in known signal amplification methods. For example, the bDNA assay is not as sensitive as the target amplification methods. Apart from sensitivity, known signal amplification assays have been associated with other disadvantages including protracted running time, overly complex protocols and/or increased cost.

Thus, there is an ongoing need for new and improved methods for detecting and quantifying nucleic acid sequences and other targets which incorporate signal amplification.

SUMMARY OF THE INVENTION

In a first aspect, the invention provides a composition comprising a first Enzyme Amplifier Substrate oligonucleotide (EAS1) and a second Enzyme Amplifier Substrate oligonucleotide (EAS2), wherein a portion of the EAS1 is complementary to a portion of the EAS2, and wherein the EAS1 and EAS2 form a first Complete Enzyme Signal Amplifier (CESA) complex comprising a recognition and a cleavage sequence for a first nuclease only on assembly with a first Driver Fragment oligonucleotide (DF), and wherein a portion of the first DF is complementary to a portion of the EAS1.

In a second aspect, the invention provides a composition comprising an EAS1, an EAS2, and a first nuclease, wherein a portion of the EAS1 is complementary to a portion of the EAS2 and wherein the EAS1 and EAS2 form a first CESA complex comprising a recognition sequence and a cleavage sequence for said first nuclease only on assembly with a first DF wherein a portion of the first DF is complementary to a portion of the EAS1.

In a third aspect, the invention provides a composition comprising a multi-component nucleic acid enzyme (MNAzyme), an MNAzyme substrate, an EAS1, an EAS2, and a first nuclease wherein:

the MNAzyme comprises at least a first partzyme and a second partzyme that self-assemble in the presence of an MNAzyme assembly facilitator to form the MNAzyme, wherein each of said at least first and said second partzymes comprise a substrate arm portion, a catalytic core portion, and a sensor arm portion, and wherein the sensor arms interact with said MNAzyme assembly facilitator so as to maintain the first and second partzymes in proximity for association of their respective catalytic core portions to form the catalytic core of the MNAzyme and said catalytic core is capable of modifying said MNAzyme substrate to form a first DF;

and wherein a portion of the EAS1 is complementary to a portion of the EAS2 and a portion of the EAS1 is complementary to a portion of the first DF, and wherein the first DF is capable of assembly with the EAS1 and the EAS2 to form a first CESA complex containing a recognition site and a cleavage site for said at least first nuclease.

In one embodiment of the third aspect, the MNAzyme substrate is a first strand of an oligonucleotide complex comprising first and second strands, wherein said first strand comprises an internal loop portion and bases within the internal loop portion are not hybridised to bases of the second strand, and wherein the MNAzyme is capable of cleaving the internal loop portion.

In one embodiment of the third aspect, the second strand comprises the first DF.

In one embodiment of the third aspect, the first and second strands are linked at one end by a hairpin loop portion.

In one embodiment of the third aspect, the MNAzyme substrate is a hairpin loop portion of a hairpin oligonucleotide, said MNAzyme is capable of cleaving the hairpin loop portion, and said first driver fragment is located in one strand of a double stranded stem portion in said hairpin oligonucleotide.

In one embodiment of the third aspect, the assembly facilitator is a target to be identified.

In a fourth aspect, the invention provides a composition comprising a first Synthetic Initiator Oligonucleotide (SIO), an EAS1, an EAS2, a first nuclease, and a second nuclease wherein:

the SIO is capable of hybridizing with a target to form a duplex substrate wherein said first nuclease is capable of cleaving the duplex substrate to generate a first DF; and wherein;

a portion of the EAS1 is complementary to a portion of the EAS2 and a portion of the EAS1 is complementary to a portion of the first DF and wherein the EAS1 and the EAS2 form a first CESA complex containing a recognition sequence and a cleavage sequence for said second nuclease only on assembly with the first DF.

In a fifth aspect, the invention provides a composition comprising a first Synthetic Initiator Oligonucleotide (SIO), an EAS1, an EAS2, and a first nuclease, and a second nuclease wherein:

the SIO is capable of hybridizing with a target to form a duplex structure wherein said first nuclease is capable of cleaving said SIO to generate a first DF only when said SIO is hybridized with the target; and wherein;

a portion of the EAS1 is complementary to a portion of the EAS2 and a portion of the EAS1 is complementary to a portion of the first DF and wherein the EAS1 and the EAS2 form a first CESA complex containing a recognition and a cleavage sequence for said second nuclease only on assembly with the first DF.

In a sixth aspect, the invention provides a composition comprising a first Synthetic Initiator Oligonucleotide (SIO), an EAS1, an EAS2, a first nuclease, and a second nuclease wherein:

the SIO is capable of hybridizing with a target to form a duplex structure wherein said first nuclease is capable of cleaving said target to generate a first DF only when said target is hybridized with the SIO;

wherein a portion of the EAS1 is complementary to a portion of the EAS2 and a portion of the EAS1 is complementary to a portion of the first DF and wherein the EAS1 and the EAS2 form a first CESA complex containing a recognition and a cleavage sequence for said second nuclease only on assembly with the first DF;

and wherein the first nuclease is not a restriction endonuclease.

In one embodiment of the fourth to sixth aspects, the first nuclease is capable of cleaving the SIO to generate said first DF only when the SIO is hybridised with the target.

In one embodiment of the fourth to sixth aspects, the first nuclease is capable of cleaving the target to generate said first DF only when the target is hybridised with the SIO.

In one embodiment of the fourth to sixth aspects, the first nuclease is not a restriction enzyme.

In one embodiment of the fourth to sixth aspects, the first nuclease is an exonuclease.

In one embodiment of the fourth to sixth aspects, the first and second nuclease are the same nuclease.

In one embodiment of the fourth to sixth aspects, the first and second nucleases are different nucleases.

In one embodiment of the fourth to sixth aspects, the first nuclease is capable of cleaving a double stranded oligonucleotide comprising a nick in at least one of two strands forming said first CESA complex.

In one embodiment of the fourth to sixth aspects, the second nuclease is capable of cleaving a double stranded oligonucleotide comprising a nick in at least one of two strands forming said first CESA complex.

In one embodiment of the fourth to sixth aspects, the nick is located within the nuclease recognition site, at the nuclease cleavage site, or between the nuclease recognition and cleavage sites.

In one embodiment of the fourth to sixth aspects, the nuclease is selected from the group consisting of Mnl I, Rsa I, Pme I, Hpy 8I, Msp I, Ear I, and TspR I.

In one embodiment of the fourth to sixth aspects, the binding of the first DF to said EAS1 completes a partial nuclease recognition sequence.

In one embodiment of the first to sixth aspects, the binding of the first DF to said EAS1 completes a partial nuclease cleavage sequence.

In one embodiment of the first to sixth aspects, the first DF contributes at least one base to said sequence.

In one embodiment of the first to sixth aspects, the first DF contributes at least two bases to said sequence.

In one embodiment of the first to sixth aspects, the first DF contributes at least three bases to said sequence.

In one embodiment of the first to sixth aspects, the bases are immediately 3' of a partial nuclease recognition site formed by the binding of said EAS1 and EAS2.

In one embodiment of the first to sixth aspects, the bases are immediately 5' of a partial nuclease recognition site formed by the binding of said EAS1 and EAS2.

In one embodiment of the first to sixth aspects, the first DF does not contribute any bases to said nuclease recognition sequence or said nuclease cleavage sequence.

In one embodiment of the first to sixth aspects, the EAS1 and EAS2 are components of a hairpin oligonucleotide comprising a double-stranded stem portion formed by hybridisation of complementary portions of said EAS1 and the EAS2, and a hairpin loop portion linking one end of said EAS1 with one end of said EAS2.

In one embodiment of the first to sixth aspects, the hairpin loop portion is an oligonucleotide linker or a non-oligonucleotide linker.

In one embodiment of the first to sixth aspects, the hairpin oligonucleotide comprises a single stranded 5' or 3' overhang portion extending from either of said EAS1 or EAS2.

In one embodiment of the first to sixth aspects, a portion of said EAS1 or EAS2 comprises a second DF, and wherein said second DF can be released upon modification of said first CESA complex by the nuclease.

In one embodiment of the first to sixth aspects, a portion of said hairpin loop portion comprises a second DF, and wherein said second DF can be released upon modification of said first CESA complex by the nuclease.

In one embodiment of the first to sixth aspects, the first DF and said second DF are not identical.

In one embodiment of the first to sixth aspects, the first DF and said second DF are identical.

In one embodiment of the first to sixth aspects, the second DF is a fragment of said first DF, or said first DF is a fragment of said second DF.

In one embodiment of the first to sixth aspects, the second DF, EAS1, and EAS2 are capable of assembly to form said first CESA complex.

In one embodiment of the first to sixth aspects, the composition further comprises a third Enzyme Amplifier Substrate oligonucleotide (EAS3) and a fourth Enzyme Amplifier Substrate oligonucleotide (EAS4), wherein a portion of the EAS3 is complementary to a portion of the EAS4 and a portion of the EAS3 is complementary to a portion of the second DF, and wherein the EAS3 and the EAS4 form a second CESA complex containing a recognition sequence and a cleavage sequence for an additional nuclease only on assembly with the second DF.

In one embodiment of the first to sixth aspects, the EAS3 or EAS4 comprises a third DF.

In one embodiment of the first to sixth aspects, the third DF is identical to said first DF.

In one embodiment of the first to sixth aspects, the third DF is not identical said first DF.

In one embodiment of the first to sixth aspects, the additional nuclease is identical to another nuclease in said composition.

In one embodiment of the first to sixth aspects, the additional nuclease is not identical to another nuclease in said composition, and wherein said composition comprises said additional nuclease.

In one embodiment of the first to sixth aspects, the additional nuclease is capable of cleaving a double stranded oligonucleotide comprising a nick in at least one of two strands forming said, second CESA complex In one embodiment of the first to sixth aspects, the nuclease is selected from the group consisting of Mnl I, Rsa I, Pme I, Hpy 8I, Msp I, Ear I, and TspR I.

In one embodiment of the first to sixth aspects, binding of the second DF to said EAS3 completes a partial nuclease recognition sequence and/or a nuclease cleavage sequence.

In one embodiment of the first to sixth aspects, the second DF does not contribute any bases to said nuclease recognition sequence or said nuclease cleavage sequence.

In one embodiment of the first to sixth aspects, the EAS3 and EAS4 are components of a hairpin oligonucleotide comprising a double-stranded stem portion formed by hybridisation of complementary portions of EAS3 and EAS4, and a hairpin loop portion linking one end of said EAS3 with one end of said EAS4.

In one embodiment of the first to sixth aspects, the hairpin loop portion is an oligonucleotide linker or a non-oligonucleotide linker.

In one embodiment of the first to sixth aspects, the hairpin oligonucleotide comprises a single stranded 5' or 3' overhang portion extending from either of said EAS3 or EAS4.

In a seventh aspect, the invention provides a composition comprising a first complex, said first complex comprising a backbone oligonucleotide, an EAS1, an EAS2, an EAS3, and an EAS4, wherein said backbone oligonucleotide comprises:

(i) a first portion comprising said EAS1, wherein a portion of said EAS1 is complementary to a portion of EAS2, a portion of the EAS2 is complementary to a portion of a first DF, and a portion of the EAS1 or EAS2 comprises a second DF, and wherein the EAS1 and the EAS2 form a first CESA complex containing a recognition sequence and a cleavage sequence for a first nuclease only on assembly with said first DF;

(ii) a second portion comprising said EAS3, wherein a portion of said EAS3 is complementary to a portion of said EAS4, a portion of said EAS3 is complementary to a portion of the second DF, and a portion of said EAS3 or EAS4 comprises said first DF, and wherein the EAS3 and the EAS4 form a second CESA complex containing a recognition sequence and a cleavage sequence for a second nuclease only on assembly with said second DF; and (iii) a third portion connecting the first and second portions.

In one embodiment of the seventh aspect, the composition further comprises a second complex, said second complex comprising a backbone oligonucleotide, a fifth Enzyme Amplifier Substrate Oligonucleotide (EAS5), a sixth Enzyme Amplifier Substrate Oligonucleotide (EAS6), a seventh Enzyme Amplifier Substrate Oligonucleotide (EAS7), and an eighth Enzyme Amplifier Substrate Oligonucleotide (EAS8), wherein said backbone oligonucleotide comprises:

(i) a first portion comprising said EAS5, wherein a portion of said EAS5 is complementary to a portion of said EAS6, a portion of said EAS5 is complementary to a portion of said second DF, and a portion of said EAS5 or EAS6 comprises said first DF, and wherein the EAS5 and the EAS6 form a third CESA complex containing a recognition sequence and a cleavage sequence for a third nuclease only on assembly with said second DF; and (ii) a second portion comprising said EAS7, wherein a portion of said EAS7 is complementary to a portion of EAS8, a portion of said EAS8 is complementary to a portion of said first DF, and a portion of said EAS7 or EAS8 comprises said second DF, and wherein the EAS7 and the EAS8 form a fourth CESA complex containing a recognition sequence and a cleavage sequence for a fourth nuclease only on assembly with said first DF; and (iii) a third portion connecting the first and second portions, wherein said third portion is complementary to the third portion of the backbone of said first complex.

In one embodiment of the seventh aspect, the EAS1 is identical to EAST, EAS2 is identical to EAS8, EAS3 is identical to EAS5, and/or EAS4 is identical to EAS6.

In one embodiment of the seventh aspect, the first nuclease is identical to the third nuclease, and/or the second nuclease is identical to the fourth nuclease, and/or the first, second, third and fourth nucleases are identical.

In one embodiment of the seventh aspect, the first and second complexes are hybridised via their respective complementary third portions forming a first double complex.

In one embodiment of the seventh aspect, the first double complex is linked to a second double complex.

In one embodiment of the seventh aspect, the first double complex is linked to said second double complex by linking any one or more of EAS1-EAS8 of said first double complex with any one or more of EAS1-EAS8 of said second double complex.

In one embodiment of the seventh aspect, the first double complex is linked to said second double complex by linking EAS2 and/or EAS8 of said first double complex with EAS2 and/or EAS8 of said second double complex.

In one embodiment of the seventh aspect, the linking is achieved using any one or more of chemical hybridisation, antibodies, oligonucleotide linkers, non-oligonucleotide linkers, covalent bonding and peptide linkers.

In one embodiment of the seventh aspect, the linking is achieved via biotinylation of any one or more of said Enzyme Amplifier Substrate Oligonucleotides and the complexing of multiple biotinylated Enzyme Amplifier Substrate Oligonucleotides using avidin.

In one embodiment of the seventh aspect, the first and/or said second nuclease is capable of cleaving a double stranded oligonucleotide comprising a nick in at least one of two strands forming said second CESA complex In one embodiment of the seventh aspect, the first and/or said second nuclease is selected from the group consisting of Mnl I, Rsa I, Pme I, Hpy 8I, Msp I, Ear I, and TspR I.

In one embodiment of the seventh aspect, binding of said first DF to said EAS2 or EAS8 and/or the binding of said second DF to said EAS3 or EAS5 completes a partial nuclease recognition sequence and/or a partial nuclease cleavage sequence.

In one embodiment of the seventh aspect, binding of said first DF to said EAS2 or EAS8 and/or the binding of said second DF to said EAS3 or EAS5 does not contribute any bases to said nuclease recognition sequence or said nuclease cleavage sequence.

In one embodiment of the seventh aspect, a pair of Enzyme Amplifier Substrates selected from EAS1 and EAS2; EAS3 and EAS4; EAS5 and EAS6; and EAST and EAS8, is a component of a hairpin oligonucleotide comprising a double-stranded stem portion formed by hybridisation of complementary portions of each member of said pair, and a hairpin loop portion linked to one end of the stem portion.

In one embodiment of the seventh aspect, the hairpin loop portion is an oligonucleotide linker or a non-oligonucleotide linker.

In one embodiment of the seventh aspect, the hairpin oligonucleotide comprises a single stranded 5' or 3' overhang portion.

In an eighth aspect, the invention provides a composition comprising a SIO, said SIO comprising:

(i) a first portion complementary to a target strand and a second portion that is not complementary to said target strand, wherein said first and second portions are separated by a phosphorothioate, and said second portion comprises a first DF; and, (ii) an EAS1 and an EAS2, wherein
 a portion of the EAS1 is complementary to a portion of the EAS2 and hybridization of the EAS1 and the EAS2 provides a duplex structure with a 3' overhang at either end,
 a portion of the EAS1 is complementary to a portion of the first DF, and
 the EAS1 and the EAS2 are capable of forming a first CESA complex comprising a recessed 3' end capable of, digestion by a first nuclease, only on assembly with said first DF.

In one embodiment of the eighth aspect, the SIO is a hairpin oligonucleotide comprising a double-stranded stem formed by hybridisation of two complementary portions, a single stranded hairpin loop, and a 3' overhang.

In one embodiment of the eighth aspect, the nuclease is an exonuclease.

In one embodiment of the eighth aspect, the exonuclease cannot digest single stranded oligonucleotides, double stranded oligonucleotides comprising a 3' overhang of 5 or more bases, or phosphorothioate internucleotide linkages.

In one embodiment of the first to eighth aspects, any said first DF is generated using an endonuclease or an exonuclease.

In one embodiment of the first to eighth aspects, the exonuclease is selected from the group consisting of Nuclease BAL-31, Exonuclease I, Exonuclease III, T7 Exonuclease, T7 Exonuclease I and Exonuclease T.

In one embodiment of the first to eighth aspects, the exonuclease is Exonuclease III.

In one embodiment of the first to eighth aspects, the endonuclease is T7 Endonuclease I, RNase H, Flap Nuclease, or Mung Bean Nuclease.

In one embodiment of the first to eighth aspects, any said EAS comprises one or more detectable labels.

In one embodiment of the first to eighth aspects, any said EAS comprises a fluorophore portion and/or a quencher portion.

In one embodiment of the first to eighth aspects, any said partzyme, assembly facilitator, MNAzyme substrate, DF, EAS1, EAS2, EAS3, EAS4, EAS5, EAS6, EAST, EAS8, or SIO comprises at least one nucleotide substitution or addition selected from the group consisting of phosphorothioate, 4-acetylcytidine, 5-(carboxyhydroxylmethyl)uridine, 2'-O-methylcytidine, 5-carboxymethylaminomethyl thiouridine, dihydrouridine, 2'-O-methylpseudouridine, beta D-galactosylqueosine, 2'-O-methylguanosine, inosine, N6-isopentenyl adenosine, 1-methyl adenosine, 1-methylpseudouridine, 1-methyl guanosine, 1-methylinosine, 2,2-dimethylguanosine, 2-methyladenosine, 2-methylguanosine, 3-methylcytidine, 5-methylcytidine, N6-methyladenosine, 7-methylguanosine, 5-methylaminomethyluridine, 5-methoxyaminomethyl-2-thiouridine, beta D-mannosylmethyluridine, 5-methoxycarbonylmethyluridine, 5-methoxyuridine, 2-methylthio-N-6-isopentenyl adenosine, N49-beta-ribofuranosyl-2-methylthiopurine-6-yl)carbamoyl)threonine, N-((9-beta-ribofuranosylpurine-6-yl)N-methyl-carbamoyl)threonine, uridine-5-oxyacetic acid methylester, uridine-5-oxyacetic acid (v), wybutoxosine, pseudouridine, queosine, 2-thiocytidine, 5-methyl-2-thiouridine, 2-thiouridine, 4-thiouridine, 5-methyluridine, N-((9-beta-D-ribofuranosylpurine-6-yl)carbamoyl)threonine, 2'-O-methyl-5-methyluridine, 2'-O-methyluridine, wybutosine, 3-(3-amino-3-carboxypropyl)uridine, beta D-arabinosyl uridine and beta D-arabinosyl thymidine.

In one embodiment of the third aspect, at least one of the MNAzyme partzymes, MNAzyme substrate or a combination thereof further comprises an aptamer or portion thereof.

In one embodiment of the third aspect, the aptamer or portion thereof comprises at least one of: a nucleic acid, peptide, polypeptide, protein, a derivative thereof, or a combination thereof.

In one embodiment of the first to eighth aspects, any said MNAzyme partzyme, MNAzyme substrate, EAS1, EAS2, EAS3, EAS4, EAS5, EAS6, EAS7, EAS8, SIO, DF or nuclease is attached to a solid support.

In one embodiment of the first, second and seventh aspects, said first DF is produced only in the presence of a target.

In one embodiment of the third aspect, and fourth to seventh aspects, said first DF is distinct from said target.

In one embodiment of the first and second aspects, the composition is for detecting a target, and first DF is distinct from said target.

In one embodiment of the third aspect, any said EAS can hybridise with another EAS to from a Partial Enzyme Signal Amplifier (PESA) complex capable of hybridizing with more than one DF.

In one embodiment of the third aspect, the composition comprises first and second MNAzymes specific for different portions of a target molecule.

In one embodiment of the third aspect, the MNAzymes specific for different portions of said target molecule recognize and cleave the same substrate upon assembly in the presence of said target.

In one embodiment of the third aspect, the composition comprises at least two different MNAzymes having specificity for distinct targets.

In one embodiment of the fourth to sixth and eighth aspects, the composition comprises at least two different SIO with complementarity for distinct targets.

In one embodiment of the fourth to sixth and eighth aspects, the composition comprises at least two distinct first CESA complexes assembled with a different first DF.

In a ninth aspect, the invention provides a method for detecting a target comprising:

(a) providing two or more partzymes and at least one multi-component nucleic acid (MNAzyme) substrate, wherein the partzymes self-assemble in the presence of the target to form at least one MNAzyme;

(b) contacting the partzymes with a sample putatively containing the target under conditions permitting self-assembly and catalytic activity of the MNAzyme, and wherein catalytic activity of said MNAzyme produces a first Driver Fragment oligonucleotide (DF) from said at least one MNAzyme substrate;

(c) providing a first Enzyme Amplifier Substrate Oligonucleotide (EAS1) and a second Enzyme Amplifier Substrate Oligonucleotide (EAS2) wherein a portion of the EAS1 is complementary to a portion of the EAS2, and wherein a portion of the EAS1 is complementary to a portion of the first DF and;

(d) contacting the EAS1 and the EAS2 with the first DF under conditions permitting;
  (1) assembly of the first DF with the EAS1 and the EAS2 to form a first Complete Enzyme Signal Amplifier (CESA) complex, and
  (2) formation of a recognition site and a cleavage site for a first nuclease;

(e) providing the first nuclease; and (f) contacting the first nuclease with the first CESA complex under conditions permitting interaction of the nuclease with the recognition site and cleavage at the cleavage site wherein the cleavage by said first nuclease produces a detectable effect indicative of the presence of the target.

In one embodiment of the ninth aspect, the first nuclease is capable of cleaving a double stranded oligonucleotide comprising a nick in at least one of two strands forming said recognition site and/or said cleavage site for said first nuclease.

In one embodiment of the ninth aspect, the first DF is produced by cleavage of the MNAzyme substrate.

In one embodiment of the ninth aspect, the first DF is produced by ligation of two or more MNAzyme substrates.

In one embodiment of the ninth aspect, the MNAzyme substrate is a first strand of an oligonucleotide complex comprising first and second strands, wherein said first strand comprises an internal loop portion and bases within the internal loop portion are not hybridised to bases of the second strand, and wherein the MNAzyme is capable of cleaving the internal loop portion.

In one embodiment of the ninth aspect, the second strand comprises the first DF.

In one embodiment of the ninth aspect, the first and second strands are linked at one end by a hairpin loop portion.

In one embodiment of the ninth aspect, the MNAzyme substrate is a hairpin loop portion of a hairpin oligonucleotide, said MNAzyme is capable of cleaving the hairpin loop portion, and said first driver fragment is located in one strand of a double stranded stem portion in said hairpin oligonucleotide.

In a tenth aspect, the invention provides a method of detecting a target comprising:
(a) providing at least a first Synthetic Initiator Oligonucleotide (SIO);
(b) contacting the SIO with a sample putatively containing the target under conditions permitting hybridizing of the SIO with the target thus creating a duplex substrate for a first nuclease;
(c) providing a first nuclease capable of cleaving the duplex substrate formed by hybridization of the SIO and the target wherein cleavage of the duplex substrate by the first nuclease generates a first DF;
(d) providing an EAS1 and an EAS2 wherein a portion of the EAS1 is complementary to a portion of the EAS2, and wherein a portion of the EAS1 is complementary to a portion of the first DF and;
(e) contacting the EAS1 and the EAS2 with the first DF under conditions permitting:
  (1) assembly of the first DF with the EAS1 and the EAS2 to form a first CESA, and
  (2) formation of a recognition site and a cleavage site for a second nuclease;
(f) providing a second nuclease; and
(g) contacting the second nuclease with the first CESA under conditions permitting interaction of the second nuclease with the recognition site and cleavage at the cleavage site wherein cleavage by the second nuclease produces a detectable effect indicative of the presence of the target.

In an eleventh aspect, the invention provides a method of detecting a target comprising:
(a) providing at least a first Synthetic Initiator Oligonucleotide (SIO);
(b) contacting the SIO with a sample putatively containing the target under conditions permitting hybridizing of the SIO with the target thus creating a duplex structure for a first nuclease;
(c) contacting the duplex structure with a first nuclease capable of cleaving the SIO only when the SIO is hybridized with the target, wherein said first nuclease cleaves the SIO to produce a first DF;
(d) providing an EAS1 and an EAS2 wherein a portion of the EAS1 is complementary to a portion of the EAS2, and wherein a portion of the EAS1 is complementary to a portion of the first DF and;
(e) contacting the EAS1 and the EAS2 with the first DF under conditions permitting:
  (1) assembly of the first DF with the EAS1 and the EAS2 to form a first CESA, and
  (2) formation of a recognition site and a cleavage site for a second nuclease;
(f) providing a second nuclease; and
(g) contacting the second nuclease with the first CESA under conditions permitting interaction of the second nuclease with the recognition site and cleavage at the cleavage site wherein cleavage by the second nuclease produces a detectable effect indicative of the presence of the target.

In a twelfth aspect, the invention provides a method of detecting a target comprising:
(a) providing at least a first Synthetic Initiator Oligonucleotide (SIO);
(b) contacting the SIO with a sample putatively containing the target under conditions permitting hybridizing of the SIO with the target thus creating a duplex structure for a first nuclease;
(c) contacting the duplex structure with a first nuclease capable of cleaving the target only when the target is hybridized with the SIO, wherein said first nuclease cleaves the target to produce a first DF;
(d) providing an EAS1 and an EAS2 wherein a portion of the EAS1 is complementary to a portion of the EAS2, and wherein a portion of the EAS1 is complementary to a portion of the first DF and;
(e) contacting the EAS1 and the EAS2 with the first DF under conditions permitting:
  (1) assembly of the first DF with the EAS1 and the EAS2 to form a first CESA, and
  (2) formation of a recognition site and a cleavage site for a second nuclease;
(f) providing a second nuclease; and
(g) contacting the second nuclease with the first CESA under conditions permitting interaction of the second nuclease with the recognition site and cleavage at the cleavage site wherein cleavage by the second nuclease produces a detectable effect indicative of the presence of the target.

In one embodiment of the tenth to twelfth aspects, the first nuclease cleaves said SIO to generate said first DF only when said SIO is hybridised with the target.

In one embodiment of the tenth to twelfth aspects, the first nuclease cleaves said target to generate said first DF only when said target is hybridised with the SIO.

In one embodiment of the tenth to twelfth aspects, the first nuclease is not a restriction enzyme.

In one embodiment of the tenth to twelfth aspects, the first nuclease is an exonuclease.

In one embodiment of the tenth to twelfth aspects, the cleavage of the first CESA complex allows release of a further DF, and the further DF assembles with further Enzyme Amplifier Substrate Oligonucleotides to form a further CESA complex, and at least one nuclease is used to cleave the further CESA complex to produce further detectable effect and release further DF, thereby facilitating a further increase in the detectable effect.

In a thirteenth aspect, the invention provides a method of detecting a target using a cascade comprising:
(a) producing a first DF, wherein said first DF is produced only in the presence of said target,
(b) providing:
(i) an EAS1 and an EAS2 wherein:
  a portion of the EAS1 is complementary to a portion of the EAS2:
  a portion of the EAS1 is complementary to a portion of the first DF; and
  a portion of the EAS1 or the EAS2 comprises a second DF; and,
(ii) a third Enzyme Amplifier Substrate Oligonucleotide (EAS3) and a fourth Enzyme Amplifier Substrate Oligonucleotide (EAS4) wherein:
  a portion of the EAS3 is complementary to a portion of the EAS4;
  a portion of the EAS3 is complementary to a portion of the second DF;
(c) contacting:
(i) the EAS1 and the EAS2 with the first DF of (a) under conditions permitting assembly of the first DF with the EAS1 and the EAS2 to form a first CESA complex comprising a recognition site and a cleavage site for a first nuclease;
(ii) the first CESA complex with the first nuclease under conditions permitting interaction of the first nuclease with the recognition site and cleavage site of the first CESA complex, wherein cleavage at the cleavage site by the first nuclease releases the second DF;

(d) contacting:
(i) the EAS3 and the EAS4 with the second DF under conditions permitting assembly of the second DF with the EAS3 and the EAS4 to form a second CESA complex comprising a recognition site and a cleavage site for a second nuclease;
(ii) the second CESA complex with the second nuclease under conditions permitting interaction of the second nuclease with the recognition site and cleavage site of the second CESA complex, wherein the second nuclease cleaves said second CESA complex at said cleavage site;

and wherein cleavage of said first CESA complex and/or said second CESA complex produces a detectable effect.

In one embodiment of the thirteenth aspect, cleavage of said first CESA complex and said second CESA complex each produces a detectable effect.

In one embodiment of the thirteenth aspect, the first nuclease and the second nuclease are the same nuclease.

In one embodiment of the thirteenth aspect, the first nuclease and the second nuclease are different nucleases.

In one embodiment of the thirteenth aspect, a portion of said EAS3 or said EAS4 comprises an additional DF and cleavage at said cleavage site of the second CESA complex by the second nuclease releases said additional DF.

In one embodiment of the thirteenth aspect, a portion of said additional DF is complementary to a first portion of a fifth Enzyme Amplifier Substrate Oligonucleotide (EAS5), wherein a second portion of said EAS5 is complementary to a portion of a sixth Enzyme Amplifier Substrate Oligonucleotide (EAS6), and wherein said EAS5 and EAS6 assemble with said additional DF to form third CESA complex.

In one embodiment of the thirteenth aspect:
(i) a portion of the additional DF is identical to said first DF;
(ii) the additional DF is identical to said first DF; or
(iii) the additional DF is a fragment of said first DF;
and said additional DF can assemble with said EAS1 and EAS2 to form said first CESA complex.

In a fourteenth aspect, the invention provides a method of detecting a plurality of distinct targets using a cascade comprising:

(a) producing at least a first DF and a second DF, wherein said first DF is produced only in the presence of a first target, and said second DF is produced only in the presence of a second target;

(b) providing:
(i) an EAS1 and an EAS2 wherein:
a portion of the EAS1 is complementary to a portion of the EAS2:
a portion of the EAS1 is complementary to a portion of the first DF; and
(ii) an EAS3 and an EAS4 wherein:
a portion of the EAS3 is complementary to a portion of the EAS4:
a portion of the EAS3 is complementary to a portion of the second DF;

(c) contacting:
(i) the EAS1 and the EAS2 with the first DF of (a) under conditions permitting assembly of the first. DF with the EAS1 and the EAS2 to form a first CESA complex comprising a recognition site and a cleavage site for a first nuclease;
(ii) the first CESA complex with the first nuclease under conditions permitting interaction of the first nuclease with said recognition site and cleavage site of the first CESA complex, wherein said first nuclease cleaves said first CESA complex at said cleavage site producing a first detectable effect;

(d) contacting:
(i) the EAS3 and the EAS4 with the second DF under conditions permitting assembly of the second DF with the EAS3 and the EAS4 to form a second CESA complex comprising a recognition site and a cleavage site for a second nuclease;
(ii) the second CESA complex with the second nuclease under conditions permitting interaction of the second nuclease with the recognition site and cleavage site of the second CESA complex, wherein said second nuclease cleaves said second CESA complex at said cleavage site producing a second detectable effect;

and wherein said first detectable effect is distinct from said second detectable effect.

In one embodiment of the fourteenth aspect, the first nuclease and said second nuclease are the same nuclease.

In one embodiment of the fourteenth aspect, the first nuclease and said second nuclease are different nucleases.

In one embodiment of the fourteenth aspect:
(i) a portion of said EAS1 or said EAS2 comprises an additional DF and cleavage at said cleavage site of the first CESA complex by the first nuclease releases said additional DF; and
(ii) said additional DF assembles with at least two additional EAS oligonucleotides to form an additional CESA complex and cleavage of said additional CESA complex by a nuclease increases said first detectable effect.

In one embodiment of the fourteenth aspect:
(i) a portion of said EAS3 or said EAS4 comprises an additional DF and cleavage at said cleavage site of the second CESA complex by the second nuclease releases said additional DF; and
(ii) said additional DF assembles with at least two additional EAS oligonucleotides to form an additional CESA complex and cleavage of said additional CESA complex by a nuclease increases said second detectable effect.

In a fifteenth aspect, the invention provides a method of detecting a target using a cascade comprising:

(a) producing a first driver fragment, wherein said first driver fragment is provided only in the presence of said target;

(b) providing:
(i) an EAS1 and an EAS2 wherein:
a portion of the EAS1 is complementary to a portion of the EAS2;
a portion of the EAS1 is complementary to a portion of the first DF;
a portion of the EAS1 or EAS2 comprises a second DF; and
the EAS1 or the EAS2 is tethered to a support;
(ii) an EAS3 and an EAS4 wherein:
a portion of the EAS3 is complementary to a portion of the EAS4:
a portion of the EAS3 is complementary to a portion of the second DF;
a portion of the EAS3 or EAS4 comprises a third DF; and
the EAS3 or the EAS4 is tethered to a support;

(c) contacting:
(i) the EAS1 and the EAS2 with said first DF of (a) under conditions permitting assembly of the first DF with the EAS1 and the EAS2 to form a first CESA comprising a recognition site and a cleavage site for a first nuclease;

(ii) the first CESA with the first nuclease under conditions permitting interaction of the first nuclease with the recognition site and cleavage site of the first CESA, wherein cleavage at said cleavage site by the first releases the second DF;

(d) contacting:
(i) the EAS3 and the EAS4 with the second DF under conditions permitting assembly of the second DF with the EAS3 and the EAS4 to form a second CESA comprising a recognition site and a cleavage site for a second nuclease;
(ii) the second CESA with the second nuclease under conditions permitting interaction of the second nuclease with the recognition site and cleavage site of the second CESA, wherein cleavage at said cleavage site by the second nuclease releases the third DF which can assemble with said EAS1 and EAS2 to form said first CESA;

and wherein cleavage of said first CESA complex and/or said second CESA complex produces a detectable effect.

In one embodiment of the thirteenth to fifteenth aspects, the first DF of (a) is produced by
contacting a SIO with a sample putatively containing the target under conditions permitting hybridizing of the SIO with the target to form a duplex structure amenable to modification by an initiator nuclease, and
contacting the duplex structure with said initiator nuclease,
wherein modification of paired or unpaired regions in the duplex structure by the initiator nuclease releases said first DF.

In one embodiment of the fourteenth aspect, the second DF of (a) is produced by
contacting a SIO with a sample putatively containing the target under conditions permitting hybridizing of the SIO with the target to form a duplex structure amenable to modification by an initiator nuclease, and
contacting the duplex structure with said initiator nuclease,
wherein modification of paired or unpaired regions in the duplex structure by the initiator nuclease releases said second DF.

In one embodiment of the thirteenth to fifteenth aspects, the initiator nuclease cleaves the SIO to generate said DF only when the SIO is hybridised with the target.

In one embodiment of the thirteenth to fifteenth aspects, the initiator nuclease cleaves the target to generate said DF only when the target is hybridised with the SIO.

In one embodiment of the thirteenth to fifteenth aspects, the initiator nuclease is not a restriction enzyme.

In one embodiment of the thirteenth to fifteenth aspects, the initiator nuclease is an exonuclease.

In one embodiment of the thirteenth to fifteenth aspects, the SIO is attached to a support.

In one embodiment of the thirteenth to fifteenth aspects, the first DF of (a) is produced by providing two or more partzymes and at least one MNAzyme substrate, and, contacting the partzymes with a sample putatively containing the target under conditions permitting self-assembly and catalytic activity of the MNAzyme in the presence of said target, wherein said catalytic activity modifies said substrate thereby providing said first DF.

In one embodiment of the fourteenth aspect, the second DF of (a) is produced by providing two or more partzymes and at least one MNAzyme substrate, and, contacting the partzymes with a sample putatively containing the target under conditions permitting self-assembly and catalytic activity of the MNAzyme in the presence of said target, wherein said catalytic activity modifies said substrate thereby providing said second DF.

In one embodiment of the thirteenth to fifteenth aspects, the MNAzyme substrate is a first strand of an oligonucleotide complex comprising first and second strands, wherein said first strand comprises an internal loop portion and bases within the internal loop portion are not hybridised to bases of the second strand, and wherein the MNAzyme is capable of cleaving the internal loop portion.

In one embodiment of the thirteenth to fifteenth aspects, the second strand comprises said DF.

In one embodiment of the thirteenth to fifteenth aspects, the first and second strands are linked at one end by a hairpin loop portion.

In one embodiment of the thirteenth to fifteenth aspects, the hairpin loop portion is an oligonucleotide linker or a non-oligonucleotide linker.

In one embodiment of the thirteenth to fifteenth aspects, the MNAzyme substrate is a hairpin loop portion of a hairpin oligonucleotide, said MNAzyme is capable of cleaving the hairpin loop portion, and said driver fragment is located in one strand of a double stranded stem portion in said hairpin oligonucleotide.

In one embodiment of the thirteenth to fifteenth aspects, the EAS3 and EAS4 are components of a hairpin oligonucleotide complex comprising a double-stranded portion formed between complementary portions of said EAS3 and EAS4, and a hairpin loop portion linking one end of said EAS3 with one end of said EAS4.

In one embodiment of the ninth to fifteenth aspects, the EAS1 and EAS2 are components of a hairpin oligonucleotide complex comprising a double-stranded portion formed between complementary portions of said EAS1 and EAS2, and a hairpin loop portion linking one end of said EAS1 with one end of said EAS2.

In one embodiment of the ninth to fifteenth aspects, the hairpin loop portion is an oligonucleotide linker or a non-oligonucleotide linker.

In one embodiment of the ninth to fifteenth aspects, the hairpin oligonucleotide complex further comprises a 5' or a 3' overhanging single stranded portion extending from one EAS oligonucleotide.

In one embodiment of the ninth to fifteenth aspects, the hairpin loop portion comprises a detectable portion and/or a quencher portion.

In one embodiment of the ninth to fifteenth aspects, the EAS3 and/or EAS4 comprises a detectable portion and/or a quencher portion, and said detectable portion and quencher portion separate upon cleavage of the second CESA by the second nuclease providing a detectable effect.

In one embodiment of the ninth to fifteenth aspects, the EAS3 comprises a detectable portion and a quencher portion, the EAS4 comprises a further quencher portion, and said detectable portion and further quencher portion separate upon cleavage of the second CESA by the second nuclease providing a detectable effect.

In one embodiment of the ninth to fifteenth aspects, the EAS1 and/or EAS2 comprises a detectable portion and/or a quencher portion, and said detectable portion and quencher portion separate upon cleavage of the first CESA by the first nuclease providing a detectable effect.

In one embodiment of the ninth to fifteenth aspects, the EAS1 comprises a detectable portion and a quencher portion, the EAS2 comprises a further quencher portion, and said detectable portion and further quencher portion separate upon cleavage of the first CESA by the first nuclease providing a detectable effect.

In one embodiment of the ninth to fifteenth aspects, the detectable portion is a fluorophore.

In one embodiment of the ninth aspect, the first nuclease is capable of cleaving a double stranded oligonucleotide comprising a nick in at least one of two strands forming said first CESA complex.

In one embodiment of the tenth to twelfth aspects, the second nuclease is capable of cleaving a double stranded oligonucleotide comprising a nick in at least one of two strands forming said first CESA complex.

In one embodiment of the thirteenth to fifteenth aspects, the first nuclease is capable of cleaving a double stranded oligonucleotide comprising a nick in at least one of two strands forming said first CESA complex, and/or said second nuclease is capable of cleaving a double stranded oligonucleotide comprising a nick in at least one of two strands forming said second CESA complex.

In one embodiment of the ninth to fifteenth aspects, the nick is located within the nuclease recognition site, at the nuclease cleavage site, or between the nuclease recognition and cleavage sites.

In one embodiment of the ninth to fifteenth aspects, the nuclease is selected from the group consisting of Mnl I, Rsa I, Pme I, Hpy 8I, Msp I, Ear I, and TspR I.

In one embodiment of the ninth to fifteenth aspects, binding of the first DF to said EAS1 completes a partial nuclease recognition site and/or a partial nuclease cleavage site.

In one embodiment of the ninth to fifteenth aspects, binding of the second DF to said EAS2 completes a partial nuclease recognition site and/or a partial nuclease cleavage site.

In one embodiment of the ninth to fifteenth aspects, the DF contributes at least one base to said partial nuclease recognition sequence and/or a partial nuclease cleavage site.

In one embodiment of the ninth to fifteenth aspects, the DF contributes at least two bases to said partial nuclease recognition site and/or a partial nuclease cleavage site.

In one embodiment of the ninth to fifteenth aspects, the bases are immediately 3' of a partial nuclease recognition site formed by the binding of said Enzyme Amplifier Substrate oligonucleotides.

In one embodiment of the ninth to fifteenth aspects, the bases are immediately 5' of a partial nuclease recognition site formed by the binding of said Enzyme Amplifier Substrate oligonucleotides.

In one embodiment of the ninth to fifteenth aspects, the first DF does not contribute any bases to said nuclease recognition site or said nuclease cleavage site.

In one embodiment of the thirteenth to fifteenth aspects, the second DF does not contribute any bases to said nuclease recognition site or said nuclease cleavage site.

In a sixteenth aspect, the invention provides a method of detecting a target using a cascade comprising:
(a) producing a first driver fragment, wherein said first driver fragment is produced only in the presence of said target;
(b) providing a first complex comprising a first backbone oligonucleotide, said first backbone oligonucleotide comprising:
(i) a first portion comprising an EAS1, wherein
a portion of said EAS1 is complementary to a portion of an EAS2;
a portion of the EAS2 is complementary to a portion of the first driver fragment; and
a portion of the EAS1 or EAS2 comprises a second driver fragment;
(ii) a second portion comprising an EAS3, wherein
a portion of said EAS3 is complementary to an EAS4;
a portion of said EAS3 is complementary to a portion of the second driver fragment; and
a portion of the EAS3 or EAS4 comprises said first driver fragment; and,
(iii) a third portion connecting the first and second portions; and,
(c) contacting:
(i) the EAS1 and the EAS2 with said first DF of (a) under conditions permitting assembly of the first DF with the EAS1 and the EAS2 to form a first CESA comprising a recognition site and a cleavage site for a first nuclease;
(ii) the first CESA with the first nuclease under conditions permitting interaction of the first nuclease with the recognition site and cleavage site of the first CESA, wherein cleavage at said cleavage site by the first nuclease releases the second DF;
(d) contacting:
(i) the EAS3 and the EAS4 with the second DF under conditions permitting assembly of the second DF with the EAS3 and the EAS4 to form a second CESA comprising a recognition site and a cleavage site for a second nuclease;
(ii) the second CESA with the second nuclease under conditions permitting interaction of the second nuclease with the recognition site and cleavage site of the second CESA, wherein cleavage at said cleavage site by the second nuclease releases the first DF which can assemble with said EAS1 and EAS2 to form said first CESA;

and wherein cleavage of said first CESA complex and/or said second CESA complex produces a detectable effect.

In one embodiment of the sixteenth aspect, the cleavage of said first CESA complex and cleavage of said second CESA complex each produces a detectable effect.

In one embodiment of the sixteenth aspect, the method further comprises:
(a) providing a second complex, said second complex comprising a backbone oligonucleotide comprising:
(i) a first portion comprising a fifth Enzyme Amplifier Substrate Oligonucleotide (EAS5), wherein
a portion of said EAS5 is complementary to a portion of a sixth Enzyme Amplifier Substrate Oligonucleotide (EAS6); and
a portion of the EAS5 is complementary to a portion of the second driver fragment; and
a portion of the EAS5 or EAS6 comprises the first driver fragment; and
(ii) a second portion comprising a seventh Enzyme Amplifier Substrate Oligonucleotide (EAS7), wherein
a portion of said EAS7 is complementary to a portion of an eighth Enzyme Amplifier Substrate Oligonucleotide (EAS8);
a portion of said EAS8 is complementary to a portion of the first driver fragment;
a portion of the EAS7 or EAS8 comprises said second driver fragment; and,
(iii) a third portion connecting the first and second portions, wherein said third portion is complementary to the third portion of the backbone of said first complex; and, (b) contacting said first and second complexes under conditions permitting hybridisation of the third portion of said first complex with the third portion of said second complex, thereby forming a first double complex;

(c) contacting:
  (i) the EAS5 and the EAS6 with said second DF of (a) under conditions permitting assembly of the second DF with the EAS5 and the EAS6 to form a third CESA comprising a recognition site and a cleavage site for a third nuclease;
  (ii) the third CESA with the third nuclease under conditions permitting interaction of the third nuclease with the recognition site and cleavage site of the third CESA, wherein cleavage at said cleavage site by the third nuclease releases the first DF which can assemble with said EAS1 and EAS2 to form said first CESA, and assemble with said EAS7 and EAS8 to form said fourth CESA; and, (d) contacting:
  (i) the EAS7 and the EAS8 with the first DF under conditions permitting assembly of the first DF with the EAS7 and the EAS8 to form a fourth CESA comprising a recognition site and a cleavage site for a fourth nuclease;
  (ii) the fourth CESA with the fourth nuclease under conditions permitting interaction of the fourth nuclease with the recognition site and cleavage site of the fourth CESA, wherein cleavage at said cleavage site by the fourth nuclease releases the second DF which can assemble with said EAS3 and EAS4 to form said second CESA, and assemble with said EAS5 and EAS6 to form said third CESA;

and wherein cleavage of said third CESA complex and/or said fourth CESA complex produces a detectable effect.

In one embodiment of the sixteenth aspect, cleavage of said third CESA complex and cleavage of said fourth CESA complex each produces a detectable effect.

In one embodiment of the sixteenth aspect, EAS1 is identical to EAS7, EAS2 is identical to EAS8, EAS3 is identical to EAS5, and/or EAS4 is identical to EAS6.

In one embodiment of the sixteenth aspect, the first double complex is linked to a second double complex.

In one embodiment of the sixteenth aspect, the first double complex is linked to said second double complex by linking any one or more of EAS1-EAS8 of said first double complex with any one or more of EAS1-EAS8 of said second double complex.

In one embodiment of the sixteenth aspect, the first double complex is linked to said second double complex by linking EAS2 and/or EAS8 of said first double complex with EAS2 and/or EAS8 of said second double complex.

In one embodiment of the sixteenth aspect, the linking is achieved using any one or more of chemical hybridisation, antibodies, oligonucleotide linkers, non-oligonucleotide linkers, and peptide linkers.

In one embodiment of the sixteenth aspect, the linking is achieved via biotinylation of any one or more of said Enzyme Amplifier Substrate Oligonucleotides and the complexing of multiple biotinylated Enzyme Amplifier Substrate Oligonucleotides using avidin.

In one embodiment of the sixteenth aspect, the first DF of (a) is produced by
contacting a SIO with a sample putatively containing the target under conditions permitting hybridizing of the SIO with the target to form a duplex structure amenable to modification by an initiator nuclease, and
contacting the duplex structure with said initiator nuclease,
wherein modification of paired or unpaired regions in the duplex structure by the initiator nuclease releases said second DF.

In one embodiment of the sixteenth aspect, the initiator nuclease cleaves the SIO to generate said DF only when the SIO is hybridised with the target.

In one embodiment of the sixteenth aspect, the initiator nuclease cleaves the target to generate said DF only when the target is hybridised with the SIO.

In one embodiment of the sixteenth aspect, the initiator nuclease is not a restriction enzyme.

In one embodiment of the sixteenth aspect, the first DF of (a) is produced by providing two or more partzymes and at least one MNAzyme substrate, and, contacting the partzymes with a sample putatively containing the target under conditions permitting self-assembly and catalytic activity of the MNAzyme in the presence of said target, wherein said catalytic activity modifies said substrate thereby providing said first DF.

In one embodiment of the sixteenth aspect, any one or more of said EAS1, EAS2, EAS3, EAS4, EAS5, EAS6, EAS7 and EAS8 comprises a detectable portion and a quencher portion, wherein said detectable portion and quencher portion separate upon cleavage of the first, second, third, and/or fourth CESA providing a detectable effect.

In one embodiment of the sixteenth aspect:
  (i) the EAS1 comprises a detectable portion and said EAS2 comprises a quencher portion or visa versa; and/or
  (ii) the EAS3 comprises a detectable portion and said EAS4 comprises a quencher portion or visa versa; and/or
  (iii) the EAS5 comprises a detectable portion and said EAS6 comprises a quencher portion or visa versa;
  (iv) the EAS7 comprises a detectable portion and said EAS8 comprises a quencher portion or visa versa; and, wherein said detectable portion and quencher portion separate upon cleavage of the first, second, third, and/or fourth CESA providing a detectable effect.

In one embodiment of the sixteenth aspect, the nuclease is capable of cleaving a double stranded oligonucleotide comprising a nick in at least one of two strands forming said recognition sequence for said first, second or third nuclease.

In one embodiment of the sixteenth aspect, the nuclease is selected from the group consisting of Mnl I, Rsa I, Pme I, Hpy 8I, Msp I, Ear I, and TspRI.

In one embodiment of the sixteenth aspect, binding of any said DF to an Enzyme Amplifier Substrate oligonucleotide completes a partial nuclease recognition site and/or a partial nuclease cleavage site.

In one embodiment of the ninth to sixteenth aspects, a pair of Enzyme Amplifier Substrates is selected from EAS1 and EAS2; EAS3 and EAS4; EAS5 and EAS6; and EAS7 and EAS8, is a component of a hairpin oligonucleotide comprising a double-stranded stem portion formed by hybridisation of complementary portions of each member of said pair, and a hairpin loop portion linked to one end of the stem portion.

In one embodiment of the ninth to sixteenth aspects, any said first DF is generated using a nuclease selected from an endonuclease and an exonuclease.

In one embodiment of the ninth to sixteenth aspects, the exonuclease is selected from the group consisting of Nuclease BAL-31, Exonuclease I, Exonuclease III, T7 Exonuclease, T7 Exonuclease I and Exonuclease T.

In one embodiment of the ninth to sixteenth aspects, the endonuclease is T7 Endonuclease I, RNase H, Flap Nuclease, or Mung Bean Nuclease.

In a seventeenth aspect, the invention provides a method of detecting a target using a cascade comprising:
(a) providing:
  (i) a first portion complementary to a target strand and a second portion that is not complementary to said target strand, wherein said first and second portions are separated by a phosphorothioate, and said second portion comprises a first DF; and,
  (ii) an EAS1 and an EAS2, wherein a portion of the EAS1 is complementary to a portion of the EAS2 and hybridization of the EAS1 and the EAS2 provides a duplex structure with a 3' overhang at either end, and a portion of the EAS1 is complementary to a portion of the first DF;
  (iii) a first exonuclease; and
(b) contacting:
  (i) said SIO with a sample putatively containing the target under conditions permitting hybridizing of the SIO with the target thus creating a duplex structure for a first exonuclease, wherein modification of the duplex structure by the first exonuclease releases said first DF from said duplex substrate;
  (ii) the EAS1 and EAS2 with the first DF of (b) under conditions permitting assembly of the first DF and said EAS1 and EAS2 to form a first CESA complex comprising a substrate for a second exonuclease;
  (iii) the first CESA with the second exonuclease under conditions permitting interaction of the second exonuclease with the first CESA complex, wherein modification of the first CESA complex by the second exonuclease releases said first DF from said first CESA complex which can assemble with additional EAS1 and EAS2 to form an additional first CESA complex;
and wherein said modification of the duplex structure and/or said modification of the first CESA complex provides a detectable effect.

In one embodiment of the seventeenth aspect, modification of the duplex structure and said modification of the first CESA complex provides a detectable effect.

In one embodiment of the seventeenth aspect, the SIO is a hairpin oligonucleotide comprising a double-stranded stem formed by hybridisation of two complementary portions, a single stranded hairpin loop, and a 3' overhang.

In one embodiment of the seventeenth aspect, the first and/or second exonuclease is Exonuclease III.

In one embodiment of the seventeenth aspect, the SIO and/or said EAS1 comprises a detectable portion and a quencher portion, and wherein said detectable portion and quencher portion can separate upon modification by said exonuclease to provide a detectable effect.

In one embodiment of seventeenth aspect, the detectable portion is a fluorophore.

In one embodiment of the ninth to seventeenth aspects, the detectable effect is detected by fluorescence spectroscopy, surface plasmon resonance, mass spectroscopy, NMR, electron spin resonance, polarization fluorescence spectroscopy, circular dichroism, immunoassay, chromatography, radiometry, photometry, scintigraphy, electronic methods, UV, visible light or infra red spectroscopy, enzymatic methods or any combination thereof.

In one embodiment of the ninth to seventeenth aspects, the detectable effect is measured and wherein the magnitude of said measurement and/or rate of accumulation of the detectable effect is indicative of the quantity of a target.

In one embodiment of the ninth to seventeenth aspects, the target is selected from the group consisting of nucleic acids, proteins, glycoproteins, lipids, lipoproteins, cells, viruses, bacteria, archaea, fungi, antibodies, metabolites, pathogens, toxins, contaminants, poisons, small molecules, polymers, metal ions, metal salts, prions, nucleic acids or any derivatives, portions or combinations thereof.

In one embodiment of the ninth to seventeenth aspects, the nucleic acid is selected from the group consisting of DNA, methylated DNA, alkylated DNA, RNA, methylated RNA, microRNA, siRNA, shRNA, mRNA, tRNA, snoRNA, stRNA, smRNA, pre- and pri-microRNA, other non-coding RNAs, ribosomal RNA, derivatives thereof, amplicons thereof and any combination thereof.

In one embodiment of the ninth to seventeenth aspects, the source of the nucleic acid is selected from the group consisting of synthetic, mammalian, human, animal, plant, fungal, bacterial, viral, archael and any combination thereof.

In one embodiment of the ninth to seventeenth aspects, the nucleic acid is amplified.

In one embodiment of the tenth to sixteenth aspects, the first DF is distinct from said target.

In one embodiment of the ninth to seventeenth aspects, the any said EAS can hybridise with another EAS to froma Partial Enzyme Signal Amplifier (PESA) complex capable of hybridizing with more than one DF.

In one embodiment of the ninth and thirteenth to sixteenth aspects, the method comprises using first and second MNAzymes specific for different portions of a target molecule.

In one embodiment of the ninth and thirteenth to sixteenth aspects, the MNAzymes specific for different portions of said target molecule recognize and cleave the same substrate upon assembly in the presence of said target.

In one embodiment of the ninth and thirteenth to sixteenth aspects, the method comprises using at least two different MNAzymes having specificity for distinct targets.

In one embodiment of the tenth to sixteenth aspects, the method comprises using at least two different SIO with complementarity for distinct targets.

In one embodiment of the ninth to sixteenth aspects, the method comprises using at least two distinct first CESA complexes assembled with a different first DF.

In an eighteenth aspect, the invention provides a kit for amplifying a signal comprising;
  a nuclease; and
  an EAS1 and an EAS2 wherein a portion of the EAS1 and EAS2 are complementary and wherein the EAS1 and EAS2 form a complex comprising a recognition sequence and a cleavage sequence for said nuclease only on assembly with a Driver Fragment oligonucleotide.

In a nineteenth aspect, the invention provides a kit for detecting a target comprising;
  a nuclease;
  an EAS1 and an EAS2 wherein a portion of the EAS1 and EAS2 are complementary
  a plurality of partzymes designed to assemble an MNAzyme corresponding to the target and
  an MNAzyme substrate wherein a portion of said substrate is complementary to a portion of the EAS1; and
  wherein the EAS1 and EAS2 form a complex comprising a recognition sequence and a cleavage sequence for said nuclease only on assembly with a Driver Fragment oligonucleotide.

In a twentieth aspect, the invention provides a kit for detecting a target comprising a nuclease;

an EAS1 and an EAS2 wherein a portion of the EAS1 and EAS2 are complementary;

a plurality of SIOs designed to hybridize to the target to form a nuclease substrate;

wherein a portion of said nuclease substrate is complementary to a portion of the EAS1 wherein the EAS1 and EAS2 form a complex comprising a recognition sequence and a cleavage sequence for said nuclease only on assembly with a Driver Fragment Oligonucleotide (DF).

In a twenty-first aspect, the invention provides a kit comprising a first Enzyme Amplifier Substrate oligonucleotide (EAS1) and a second Enzyme Amplifier Substrate oligonucleotide (EAS2), wherein a portion of the EAS1 is complementary to a portion of the EAS2, and wherein the EAS1 and EAS2 form a first Complete Enzyme Signal Amplifier (CESA) complex comprising a recognition and a cleavage sequence for a first nuclease only on assembly with a first Driver Fragment oligonucleotide (DF), and wherein a portion of the first DF is complementary to a portion of the EAS1.

In a twenty-second aspect, the invention provides a kit comprising an EAS1, an EAS2, and a first nuclease, wherein a portion of the EAS1 is complementary to a portion of the EAS2 and wherein the EAS1 and EAS2 form a first CESA complex comprising a recognition sequence and a cleavage sequence for said first nuclease only on assembly with a first DF wherein a portion of the first DF is complementary to a portion of the EAS1.

In a twenty-third aspect, the invention provides a kit comprising a multi-component nucleic acid enzyme (MNAzyme), an MNAzyme substrate, an EAS1, an EAS2, and a first nuclease wherein:

the MNAzyme comprises at least a first partzyme and a second partzyme that self-in the presence of an MNAzyme assembly facilitator to form the MNAzyme, wherein each of said at least first and said second partzymes comprise a substrate arm portion, a catalytic core portion, and a sensor arm portion, and wherein the sensor arms interact with said MNAzyme assembly facilitator so as to maintain the first and second partzymes in proximity for association of their respective catalytic core portions to form the catalytic core of the MNAzyme and said catalytic core is capable of modifying said MNAzyme substrate to form a first DF;

and wherein a portion of the EAS1 is complementary to a portion of the EAS2 and a portion of the EAS1 is complementary to a portion of the first DF, and wherein the first DF is capable of assembly with the EAS1 and the EAS2 to form a first CESA complex containing a recognition site and a cleavage site for said at least first nuclease.

In one embodiment of the twenty-third aspect, the MNAzyme substrate is a first strand of an oligonucleotide complex comprising first and second strands, wherein said first strand comprises an internal loop portion and bases within the internal loop portion are not hybridised to bases of the second strand, and wherein the MNAzyme is capable of cleaving the internal loop portion.

In one embodiment of the twenty-third aspect, the second strand comprises the first DF.

In one embodiment of the twenty-third aspect, the first and second strands are linked at one end by a hairpin loop portion.

In one embodiment of the twenty-third aspect, the MNAzyme substrate is a hairpin loop portion of a hairpin oligonucleotide, said MNAzyme is capable of cleaving the hairpin loop portion, and said first driver fragment is located in one strand of a double stranded stem portion in said hairpin oligonucleotide.

In one embodiment of the twenty-third aspect, the assembly facilitator is a target to be identified.

In a twenty-fourth aspect, the invention provides a kit comprising a first Synthetic Initiator Oligonucleotide (SIO), an EAS1, an EAS2, a first nuclease, and a second nuclease wherein:

the SIO is capable of hybridizing with a target to form a duplex substrate wherein said first nuclease is capable of cleaving the duplex substrate to generate a first DF; and wherein;

a portion of the EAS1 is complementary to a portion of the EAS2 and a portion of the EAS1 is complementary to a portion of the first DF and wherein the EAS1 and the EAS2 form a first CESA complex containing a recognition sequence and a cleavage sequence for said second nuclease only on assembly with the first DF.

In a twenty-fifth aspect, the invention provides a kit comprising a first Synthetic Initiator Oligonucleotide (SIO), an EAS1, an EAS2, and a first nuclease, and a second nuclease wherein:

the SIO is capable of hybridizing with a target to form a duplex structure wherein said first nuclease is capable of cleaving said SIO to generate a first DF only when said SIO is hybridized with the target; and wherein;

a portion of the EAS1 is complementary to a portion of the EAS2 and a portion of the EAS1 is complementary to a portion of the first DF and wherein the EAS1 and the EAS2 form a first CESA complex containing a recognition and a cleavage sequence for said second nuclease only on assembly with the first DF.

In a twenty-sixth aspect, the invention provides a kit comprising a first Synthetic Initiator Oligonucleotide (SIO), an EAS1, an EAS2, a first nuclease, and a second nuclease wherein:

the SIO is capable of hybridizing with a target to form a duplex structure wherein said first nuclease is capable of cleaving said target to generate a first DF only when said target is hybridized with the SIO;

wherein a portion of the EAS1 is complementary to a portion of the EAS2 and a portion of the EAS1 is complementary to a portion of the first DF and wherein the EAS I and the EAS2 form a first CESA complex containing a recognition and a cleavage sequence for said second nuclease only on assembly with the first DF;

and wherein the first nuclease is not a restriction endonuclease.

In one embodiment of the twenty-fourth to twenty-sixth aspects, the nuclease is capable of cleaving the SIO to generate said first DF only when the SIO is hybridised with the target.

In one embodiment of the twenty-fourth to twenty-sixth aspects, the first nuclease is capable of cleaving the target to generate said first DF only when the target is hybridised with the SIO.

In one embodiment of the twenty-fourth to twenty-sixth aspects, the first nuclease is not a restriction enzyme.

In one embodiment of the twenty-fourth to twenty-sixth aspects, the first nuclease is an exonuclease.

In one embodiment of the twenty-fourth to twenty-sixth aspects, the first and second nuclease are the same nuclease.

In one embodiment of the twenty-fourth to twenty-sixth aspects, the first and second nucleases are different nucleases.

In one embodiment of the twenty-first to twenty-sixth aspects, the first nuclease is capable of cleaving a double stranded oligonucleotide comprising a nick in at least one of two strands forming said first CESA complex.

In one embodiment of the twenty-fourth to twenty-sixth aspects, the second nuclease is capable of cleaving a double stranded oligonucleotide comprising a nick in at least one of two strands forming said first CESA complex.

In one embodiment of the twenty-first to twenty-sixth aspects, the nick is located within the nuclease recognition site, at the nuclease cleavage site, or between the nuclease recognition and cleavage sites.

In one embodiment of the twenty-first to twenty-sixth aspects, the nuclease is selected from the group consisting of Mnl I, Rsa I, Pme I, Hpy 8I, Msp I, Ear I, and TspR I.

In one embodiment of the eighteenth to twenty-sixth aspects, the EAS1 and EAS2 are components of a hairpin oligonucleotide comprising a double-stranded stem portion formed by hybridisation of complementary portions of said EAS1 and the EAS2, and a hairpin loop portion linking one end of said EAS1 with one end of said EAS2.

In one embodiment of the eighteenth to twenty-sixth aspects, the hairpin oligonucleotide comprises a single stranded 5' or 3' overhang portion extending from either of said EAS1 or EAS2.

In one embodiment of the eighteenth to twenty-sixth aspects, a portion of said EAS1 or EAS2 comprises a second DF, and wherein said second DF can be released upon modification of said first CESA complex by the nuclease.

In one embodiment of the eighteenth to twenty-sixth aspects, a portion of said hairpin loop portion comprises a second DF, and wherein said second DF can be released upon modification of said first CESA complex by the nuclease.

In one embodiment of the eighteenth to twenty-sixth aspects, the first DF and the second DF are not identical.

In one embodiment of the eighteenth to twenty-sixth aspects, the first DF and the second DF are identical.

In one embodiment of the eighteenth to twenty-sixth aspects, the second DF is a fragment of said first DF, or said first DF is a fragment of said second DF.

In one embodiment of the eighteenth to twenty-sixth aspects, the second DF, EAS1, and EAS2 are capable of assembly to form said first CESA complex.

In one embodiment of the eighteenth to twenty-sixth aspects, the kit further comprises a third Enzyme Amplifier Substrate oligonucleotide (EAS3) and a fourth Enzyme Amplifier Substrate oligonucleotide (EAS4), wherein a portion of the EAS3 is complementary to a portion of the EAS4 and a portion of the EAS3 is complementary to a portion of the second DF, and wherein the EAS3 and the EAS4 form a second CESA complex containing a recognition sequence and a cleavage sequence for an additional nuclease only on assembly with the second DF.

In one embodiment of the eighteenth to twenty-sixth aspects, the EAS3 or EAS4 comprises a third DF.

In one embodiment of the eighteenth to twenty-sixth aspects, the third DF is identical to said first DF.

In one embodiment of the eighteenth to twenty-sixth aspects, the third DF is not identical said first DF.

In one embodiment of the eighteenth to twenty-sixth aspects, the additional nuclease is identical to another nuclease in said kit.

In one embodiment of the eighteenth to twenty-sixth aspects, the additional nuclease is not identical to another nuclease in said kit, and wherein said kit comprises said additional nuclease.

In one embodiment of the eighteenth to twenty-sixth aspects, the additional nuclease is capable of cleaving a double stranded oligonucleotide comprising a nick in at least one of two strands forming said second CESA complex In one embodiment of the eighteenth to twenty-sixth aspects, the nuclease is selected from the group consisting of Mnl I, Rsa I, Pme I, Hpy 8I, Msp I, Ear I, and TspR I.

In one embodiment of the eighteenth to twenty-sixth aspects, the EAS3 and EAS4 are components of a hairpin oligonucleotide comprising a double-stranded stem portion formed by hybridisation of complementary portions of EAS3 and EAS4, and a hairpin loop portion linking one end of said EAS3 with one end of said EAS4.

In one embodiment of the eighteenth to twenty-sixth aspects, the hairpin oligonucleotide comprises a single stranded 5' or 3' overhang portion extending from either of said EAS3 or EAS4.

In a twenty-seventh aspect, the invention provides a kit comprising a first complex, said first complex comprising a backbone oligonucleotide, an EAS1, an EAS2, an EAS3, and an EAS4, wherein said backbone oligonucleotide comprises:

(i) a first portion comprising said EAS1, wherein a portion of said EAS1 is complementary to a portion of EAS2, a portion of the EAS2 is complementary to a portion of a first DF, and a portion of the EAS1 or EAS2 comprises a second DF, and wherein the EAS1 and the EAS2 form a first CESA complex containing a recognition sequence and a cleavage sequence for a first nuclease only on assembly with said first DF;

(ii) a second portion comprising said EAS3, wherein a portion of said EAS3 is complementary to a portion of said EAS4, a portion of said EAS3 is complementary to a portion of the second DF, and a portion of said EAS3 or EAS4 comprises said first DF, and wherein the EAS3 and the EAS4 form a second CESA complex containing a recognition sequence and a cleavage sequence for a second nuclease only on assembly with said second DF; and (iii) a third portion connecting the first and second portions.

In one embodiment of the twenty-seventh aspect, the kit further comprises a second complex, said second complex comprising a backbone oligonucleotide, a fifth Enzyme Amplifier Substrate Oligonucleotide (EAS5), a sixth Enzyme Amplifier Substrate Oligonucleotide (EAS6), a seventh Enzyme Amplifier Substrate Oligonucleotide (EAST), and an eighth Enzyme Amplifier Substrate Oligonucleotide (EAS8), wherein said backbone oligonucleotide comprises:

(i) a first portion comprising said EAS5, wherein a portion of said EAS5 is complementary to a portion of said EAS6, a portion of said EAS5 is complementary to a portion of said second DF, and a portion of said EAS5 or EAS6 comprises said first DF, and wherein the EAS5 and the EAS6 form a third CESA complex containing a recognition sequence and a cleavage sequence for a third nuclease only on assembly with said second DF; and (ii) a second portion comprising said EAS7, wherein a portion of said EAS7 is complementary to a portion of EAS8, a portion of said EAS8 is complementary to a portion of said first DF, and a portion of said EAS7 or EAS8 comprises said second DF, and wherein the EAS7 and the EAS8 form a fourth CESA complex containing a recognition sequence and a cleavage sequence for a fourth nuclease only on assembly with said first DF; and (iii) a third portion connecting the first and second portions, wherein said third portion is complementary to the third portion of the backbone of said first complex.

In one embodiment of the twenty-seventh aspect, the EAS1 is identical to EAS7, EAS2 is identical to EAS8, EAS3 is identical to EAS5, and/or EAS4 is identical to EAS6.

In one embodiment of the twenty-seventh aspect, the first nuclease is identical to the third nuclease, and/or the second nuclease is identical to the fourth nuclease, and/or the first, second, third and fourth nucleases are identical.

In one embodiment of the twenty-seventh aspect, the first and second complexes are hybridised via their respective complementary third portions forming a first double complex.

In one embodiment of the twenty-seventh aspect, the first double complex is linked to a second double complex.

In one embodiment of the twenty-seventh aspect, the first double complex is linked to said second double complex by linking any one or more of EAS1-EAS8 of said first double complex with any one or more of EAS1-EAS8 of said second double complex.

In one embodiment of the twenty-seventh aspect, the first double complex is linked to said second double complex by linking EAS2 and/or EAS8 of said first double complex with EAS2 and/or EAS8 of said second double complex.

In one embodiment of the twenty-seventh aspect, the linking is achieved using any one or more of chemical hybridisation, antibodies, oligonucleotide linkers, non-oligonucleotide linkers, and peptide linkers.

In one embodiment of the twenty-seventh aspect, the linking is achieved via biotinylation of any one or more of said Enzyme Amplifier Substrate Oligonucleotides and the complexing of multiple biotinylated Enzyme Amplifier Substrate Oligonucleotides using avidin.

In one embodiment of the twenty-seventh aspect, the first and/or said second nuclease is capable of cleaving a double stranded oligonucleotide comprising a nick in at least one of two strands forming said second CESA complex.

In one embodiment of the twenty-seventh aspect, the first and/or said second nuclease is selected from the group consisting of Mnl I, Rsa I, Pme I, Hpy 8I, Msp I, Ear I, and TspR I.

In one embodiment of the twenty-seventh aspect, a pair of Enzyme Amplifier Substrates selected from EAS1 and EAS2; EAS3 and EAS4; EAS5 and EAS6; and EAS7 and EAS8, is a component of a hairpin oligonucleotide comprising a double-stranded stem portion formed by hybridisation of complementary portions of each member of said pair, and a hairpin loop portion linked to one end of the stem portion.

In a twenty-eighth aspect, the invention provides a kit comprising a SIO, said SIO comprising:
 (i) a first portion complementary to a target strand and a second portion that is not complementary to said target strand, wherein said first and second portions are separated by a phosphorothioate, and said second portion comprises a first DF; and,
 (ii) an EAS1 and an EAS2, wherein
  a portion of the EAS1 is complementary to a portion of the EAS2 and hybridization of the EAS1 and the EAS2 provides a duplex structure with a 3' overhang at either end,
  a portion of the EAS1 is complementary to a portion of the first DF, and the EAS1 and the EAS2 are capable of forming a first CESA complex comprising a recessed 3' end capable of digestion by a first nuclease, only on assembly with said first DF.

In one embodiment of the twenty-eighth aspect, the SIO is a hairpin oligonucleotide comprising a double-stranded stem formed by hybridisation of two complementary portions, a single stranded hairpin loop, and a 3' overhang.

In one embodiment of the twenty-eighth aspect, the nuclease is an exonuclease.

In one embodiment of the eighteenth to twenty-eighth aspects, any said EAS comprises one or more detectable labels.

In one embodiment of the eighteenth to twenty-eighth aspects, any said EAS comprises a fluorophore portion and a quencher portion.

In one embodiment of the eighteenth to twenty-eighth aspects, any said MNAzyme partzyme, MNAzyme substrate, EAS1, EAS2, EAS3, EAS4, EAS5, EAS6, EAS7, EAS8, SIO, DF or nuclease is attached to a solid support.

In one embodiment of the nineteenth, twentieth, and twenty-third to twenty-sixth aspects, any first DF is distinct from said target.

In one embodiment of the nineteenth and twenty-third aspects, the kit comprises first and second MNAzymes specific for different portions of a target molecule.

In one embodiment of the nineteenth and twenty-third aspects, the MNAzymes specific for different portions of said target molecule recognize and cleave the same substrate upon assembly in the presence of said target.

In one embodiment of the nineteenth and twenty-third aspects, the kit comprises at least two different MNAzymes having specificity for distinct targets.

In one embodiment of the twentieth, twenty-fourth to twenty-sixth, and twenty-eighth aspects, the kit comprises at least two different SIO with complementarity for distinct targets.

In a twenty-ninth aspect, the invention provides a kit comprising a composition of any one of the first to eighth aspects.

In one embodiment of the nineteenth to twenty-ninth aspects, the kit further comprises instructions for use of said kit.

In another aspect there is provided a composition comprising at least a first Enzyme Amplifier Substrate oligonucleotide (EAS1) and at least a second Enzyme Amplifier Substrate oligonucleotide (EAS2) wherein a portion of the EAS1 is complementary to a portion of the EAS2 and wherein the EAS1 and EAS2 form a Complete Enzyme Signal Amplifier complex (CESA) comprising a recognition and cleavage sequence for a nuclease only on assembly with a Driver Fragment oligonucleotide (DF) wherein a portion of the DF is complementary to a portion of the EAS1.

In another aspect there is provided a composition comprising at least a first Enzyme Amplifier Substrate oligonucleotide (EAS1) and at least a second Enzyme Amplifier Substrate oligonucleotide (EAS2) and at least a first nuclease wherein a portion of the EAS1 is complementary to a portion of the EAS2 and wherein the EAS1 and EAS2 form a Complete Enzyme Signal Amplifier complex (CESA) comprising a recognition and cleavage sequence for said first nuclease only on assembly with a Driver Fragment oligonucleotide (DF) wherein a portion of the DF is complementary to a portion of the EAS1. The nuclease may be a restriction enzyme.

In another aspect there is provided a composition comprising at least a first Synthetic Initiator Oligonucleotide (SIO), at least a first Enzyme Amplifier Substrate oligonucleotide (EAS1), at least a second Enzyme Amplifier Substrate oligonucleotide (EAS2), at least a first nuclease and at least a second nuclease wherein;

the SIO is capable of hybridizing with a target to form a duplex substrate wherein the said first nuclease is capable of cleaving the duplex substrate to generate a Driver Fragment (DF); and wherein;

a portion of the EAS1 is complementary to a portion of the EAS2 and a portion of the EAS1 is complementary to a portion of the DF and wherein the EAS1 and the EAS2 form a Complete Enzyme Signal Amplifier complex (CESA) containing a recognition and a cleavage sequence for a second nuclease only on assembly with the DF.

The first and second nuclease may be the same nuclease, alternatively the first and second nuclease may be different nucleases.

In another aspect there is provided a composition comprising at least one MNAzyme, at least one MNAzyme substrate and at least a first Enzyme Amplifier Substrate oligonucleotide (EAS1) and at least a second Enzyme Amplifier Substrate oligonucleotide (EAS2) and at least a first nuclease wherein:

the MNAzyme comprises at least a first partzyme and a second partzyme that self-assemble in the presence of an MNAzyme assembly facilitator to form the MNAzyme and wherein each of said at least first and said second partzymes comprise a substrate arm portion, a catalytic core portion, and a sensor arm portion and wherein the sensor arms interact with said MNAzyme assembly facilitator so as to maintain the first and second partzymes in proximity for association of their respective catalytic core portions to form the catalytic core of the MNAzyme, said catalytic core capable of modifying the said MNAzyme substrate to form a Driver Fragment (DF);

and wherein a portion of the EAS1 is complementary to a portion of the EAS2 and a portion of the EAS1 is complementary to a portion of the DF and wherein the DF is capable of assembly with the EAS1 and the EAS2 to form a Complete Enzyme Signal Amplifier complex (CESA) containing a recognition site and cleavage site for said at least first nuclease.

The assembly facilitator may be a target to be identified. The first and/or second nuclease may be selected from the group comprising restriction enzymes, endonucleases or exonucleases. The endonuclease may be T7 Endonuclease I or Mung Bean Nuclease. The exonuclease may be Nuclease BAL-31, Exonuclease 1, Exonuclease III, T7 Exonuclease, T7 Exonuclease I or Exonuclease T. In one embodiment the exonuclease is Exonuclease III.

In another aspect there is provided a method of detecting a target comprising (a) providing at least a first Synthetic Initiator Oligonucleotide (SIO);

(b) contacting the SIO with a sample putatively containing the target under conditions permitting hybridizing of the SIO with the target thus creating a duplex substrate for a first nuclease, (c) providing a first nuclease capable of cleaving the duplex substrate formed by hybridization of the SIO and the target wherein cleavage of the duplex substrate by the first nuclease generates a Driver Fragment (DF);

(d) providing a first Enzyme Amplifier Substrate Oligonucleotide (EAS1) and a second Enzyme Amplifier Substrate Oligonucleotide (EAS2) wherein a portion of the EAS1 is complementary to a portion of the EAS2 and wherein a portion of EAS1 is complementary to a portion of the DF and;

(e) contacting the EAS1 and the EAS2 with the Driver Fragment under conditions permitting:
(1) assembly of the DF with the EAS1 and the EAS2 to form a CESA, and
(2) formation of a recognition and a cleavage site for a second nuclease;

(f) providing a second nuclease; and (g) contacting the second nuclease with the CESA under conditions permitting interaction of the second nuclease with the recognition site and cleavage at the cleavage site wherein cleavage by the second nuclease produces a detectable effect indicative of the presence of the target.

In another aspect there is provided a method for detecting a target comprising (a) providing two or more partzymes and at least one MNAzyme substrate, wherein the partzymes self-assemble in the presence of the target to form at least one MNAzyme;

(b) contacting the partzymes with a sample putatively containing the target under conditions permitting self-assembly and catalytic activity of the MNAzyme, and wherein catalytic activity of said MNAzyme produces a Driver Fragment (DF) from the said at least one MNAzyme substrate;

(c) providing a first Enzyme Amplifier Substrate Oligonucleotide (EAS1) and a second Enzyme Amplifier Substrate Oligonucleotide (EAS2) wherein a portion of the EAS1 is complementary to a portion of the EAS2 and wherein a portion of EAS1 is complementary to a portion of the DF and;

(d) contacting the EAS1 and the EAS2 with the Driver Fragment under conditions permitting
(1) assembly of the DF with the EAS1 and the EAS2 to form a CESA, and
(2) formation of a nuclease recognition and a cleavage site (e) providing a nuclease;

(f) contacting the nuclease with the CESA under conditions permitting interaction of the nuclease with the recognition site and cleavage at the cleavage site wherein the cleavage by said nuclease produces a detectable effect indicative of the presence of the target.

The nuclease in the method of the fifth and sixth aspects may be selected from the group restriction enzymes, endonucleases or exonucleases. The endonuclease may be T7 Endonuclease I or Mung Bean Nuclease. The exonuclease may be Nuclease BAL-31, Exonuclease 1, Exonuclease III, T7 Exonuclease, T7 Exonuclease I or Exonuclease T. In one embodiment the exonuclease is Exonuclease III.

The Driver Fragment may be produced by cleavage of the MNAzyme substrate or ligation of two or more MNAzyme substrates.

The EAS1 may comprise a detectable portion and a quencher portion wherein upon cleavage of the EAS1 by the nuclease a detectable effect provided by the detectable portion is increased or decreased. In another embodiment the EAS1 may comprise a detectable portion and the EAS2 may comprise a quencher portion. Alternatively, the EAS2 may comprise a detectable portion and the EAS1 may comprise a quencher portion. Upon cleavage by the nuclease a detectable effect provided by the detectable portion may be increased or decreased.

Cleavage of the CESA allows release of further Driver Fragment and the Driver Fragment may assemble with further EAS1 and EAS2 to form a further CESA wherein at least one further nuclease cleaves the further CESA to produce further detectable effect/s and release of further Driver Fragment thereby facilitating a further increase in the detectable effect.

The detectable effect may be detected by fluorescence spectroscopy, surface plasmon resonance, mass spectroscopy, NMR, electron spin resonance, polarization fluorescence spectroscopy, circular dichroism, immunoassay, chromatography, radiometry, photometry, scintigraphy, electronic methods, UV, visible light or infra red spectroscopy, enzymatic methods or any combination thereof.

The detectable effect may be measured and the magnitude of the measurement may be indicative of the quantity of a target.

The target may be selected from the group nucleic acids, proteins, glycoproteins, lipids, lipoproteins, cells, viruses, bacteria, archaea, fungi, antibodies, metabolites, pathogens, toxins, contaminants, poisons, small molecules, polymers, metal ions, metal salts, prions, nucleic acids or any derivatives, portions or combinations thereof.

The nucleic acid may be selected from the group DNA, methylated DNA, alkylated DNA, RNA, methylated RNA, microRNA, siRNA, shRNA, mRNA, tRNA, snoRNA, stRNA, smRNA, pre- and pri-microRNA, other non-coding RNAs, ribosomal RNA, derivatives thereof, amplicons thereof or any combination thereof.

The source of the nucleic acid may be selected from the group synthetic, mammalian, human, animal, plant, fungal, bacterial, viral, archael and any combination thereof.

The nucleic acid may be amplified. The amplification may comprise one or more of: polymerase chain reaction (PCR), strand displacement amplification (SDA), loop-mediated isothermal amplification (LAMP), rolling circle amplification (RCA), transcription-mediated amplification (TMA), self-sustained sequence replication (3SR), nucleic acid sequence based amplification (NASBA), or reverse transcription polymerase chain reaction (RT-PCR).

At least one of the partzymes, assembly facilitator, MNAzyme substrate, Driver Fragment, EAS1, EAS2 or SIO comprise at least one nucleotide substitution or additionselected from the group consisting of phosphothioate, 4-acetylcytidine, 5-(carboxyhydroxylmethyl)uridine, 2'-O-methylcytidine, 5-carboxymethylaminomethyl thiouridine, dihydrouridine, 2'-O-methylpseudouridine, beta D-galactosylqueosine, 2'-O-methylguanosine, inosine, N6-isopentenyladenosine, 1-methyladenosine, 1-methylpseudouridine, 1-methylguanosine, 1-methylinosine, 2,2-dimethylguanosine, 2-methyladenosine, 2-methylguanosine, 3-methylcytidine, 5-methylcytidine, N6-methyladenosine, 7-methylguanosine, 5-methylaminomethyluridine, 5-methoxyaminomethyl-2-thiouridine, beta D-mannosylmethyluridine, 5-methoxycarbonylmethyluridine, 5-methoxyuridine, 2-methylthio-N-6-isopentenyladenosine, N-((9-beta-ribofuranosyl-2-methylthiopurine-6-yl)carbamoyl)threonine, N-((9-beta-ribofuranosylpurine-6-yl)N-methyl-carbamoyl)threonine, uridine-5-oxyacetic acid methylester, uridine-5-oxyacetic acid (v), wybutoxosine, pseudouridine, queosine, 2-thiocytidine, 5-methyl-2-thiouridine, 2-thiouridine, 4-thiouridine, 5-methyluridine, N-((9-beta-D-ribofuranosylpurine-6-yl)carbamoyl)threonine, 2'-O-methyl-5-methyluridine, 2'-O-methyluridine, wybutosine, 3-(3-amino-3-carboxypropyl)uridine, beta D-arabinosyl uridine and beta D-arabinosyl thymidine.

In some embodiments nucleotide analogues may be included to prevent specific endonuclease or exonuclease digestion of oligonucleotide fragments at site(s) which would interfere with the generation of a signal by targeted cleavage of a CESA. In preferred embodiments phosphorothioate linkages can be used to inhibit cleavage of nucleases such as T7 Exonuclease, Exonuclease III and/or Exonuclease I.

At least one of the MNAzyme partzymes, MNAzyme substrate or a combination thereof may further comprise at least one aptamer or portion thereof. The aptamer or portion thereof may comprise at least one of nucleic acid, peptide, polypeptide or protein or a derivative or combination thereof.

The aptamer, or portion thereof, may bind a target selected from the group nucleic acids, proteins, glycoproteins, lipids, lipoproteins, cells, viruses, bacteria, archaea, fungi, antibodies, metabolites, pathogens, toxins, contaminants, poisons, small molecules, polymers, metal ions, metal salts, prions or any derivatives, portions or combinations thereof.

At least one of the MNAzyme partzymes, MNAzyme substrate, EAS1, EAS2, SIO or at least one nuclease may be attached to a solid support.

In another aspect there is provided a kit for amplifying a signal comprising;
a nuclease; and
an EAS1 and an EAS2 wherein a portion of the EAS1 and EAS2 are complementary; and wherein the EAS I and EAS2 form a Complete Enzyme Signal Amplifier omplex (CESA) comprising a recognition sequence and a cleavage sequence for said nuclease only on assembly with a Driver Fragment oligonucleotide.

In another aspect there is provided a kit for detecting a target comprising;
a nuclease;
an EAS1 and an EAS2 wherein a portion of the EAS1 and EAS2 are complementary,
a plurality of partzymes designed to assemble an MNAzyme corresponding to the target, and
an MNAzyme substrate wherein a portion of said substrate is complementary to a portion of the EAS1; and
wherein the EAS1 and EAS2 form a Complete Enzyme Signal Amplifier omplex (CESA) comprising a recognition sequence and a cleavage sequence for said nuclease only on assembly with a Driver Fragment oligonucleotide.

In another aspect there is provided a kit for detecting a target comprising;
a nuclease;
an EAS1 and an EAS2 wherein a portion of the EAS1 and EAS2 are complementary;
a plurality of SIOs designed to hybridize to the target to form a nuclease substrate;
wherein a portion of said nuclease substrate is complementary to a portion of the EAS1; and
wherein the EAS1 and EAS2 form a Complete Enzyme Signal Amplifier complex (CESA) comprising a recognition sequence and a cleavage sequence for said nuclease only on assembly with a Driver Fragment oligonucleotide.

These and other aspects of the invention will be described in more detail below and with reference to the figures and examples, which are illustrative of several aspects of the invention, yet do not encompass the entirety of the invention, which the skilled artisan will plainly understand is capable of variation and alteration within the meaning and scope of the appended claims.

BRIEF DESCRIPTION OF THE DRAWINGS

Preferred embodiments of the present invention will now be described by way of example only, with reference to the accompanying drawings wherein.

Structure B (i) illustrates an example of a Enzyme Inhibitory Complex (EIC) which is a multi-oligonucleotide complex resistant to cleavage by a nuclease, such as a RE, due to the presence of an additional sequence which disrupts formation of a duplex structure amenable to cleavage. This EIC is composed of three oligonucleotides, namely EAS1, EAS2 and an Inhibitory Fragment (InF). The InF contains the sequence of the DF plus additional sequence which disrupts the junction with EAS2 and renders the EIC complex resistant to nuclease digestion. In EIC B (i) the 5' end of InF disrupts the 3' end of the EAS2. A second EIC is illustrated in B (ii) where the 3' end of InF disrupts the 5' end of the EAS2.

Structure C (i) illustrates an example of a Partial Enzyme Signal Amplifier (PESA) complex which is a multi-oligonucleotide complex which is resistant to cleavage by a nuclease, such as a RE, due to the lack of a sequence required to form a duplex structure amenable to cleavage. In this illustration the PESA is composed of two oligonucleotides, namely EAS1 and EAS2. This PESA does not contain sufficient duplex sequence for recognition and/or cleavage by a nuclease. In PESA C (i) there is insufficient duplex sequence at the 5' end of the EAS1. A second PESA is illustrated in C (ii) where there is insufficient duplex sequence at the 3' end of the EAS1.

Figure 2:
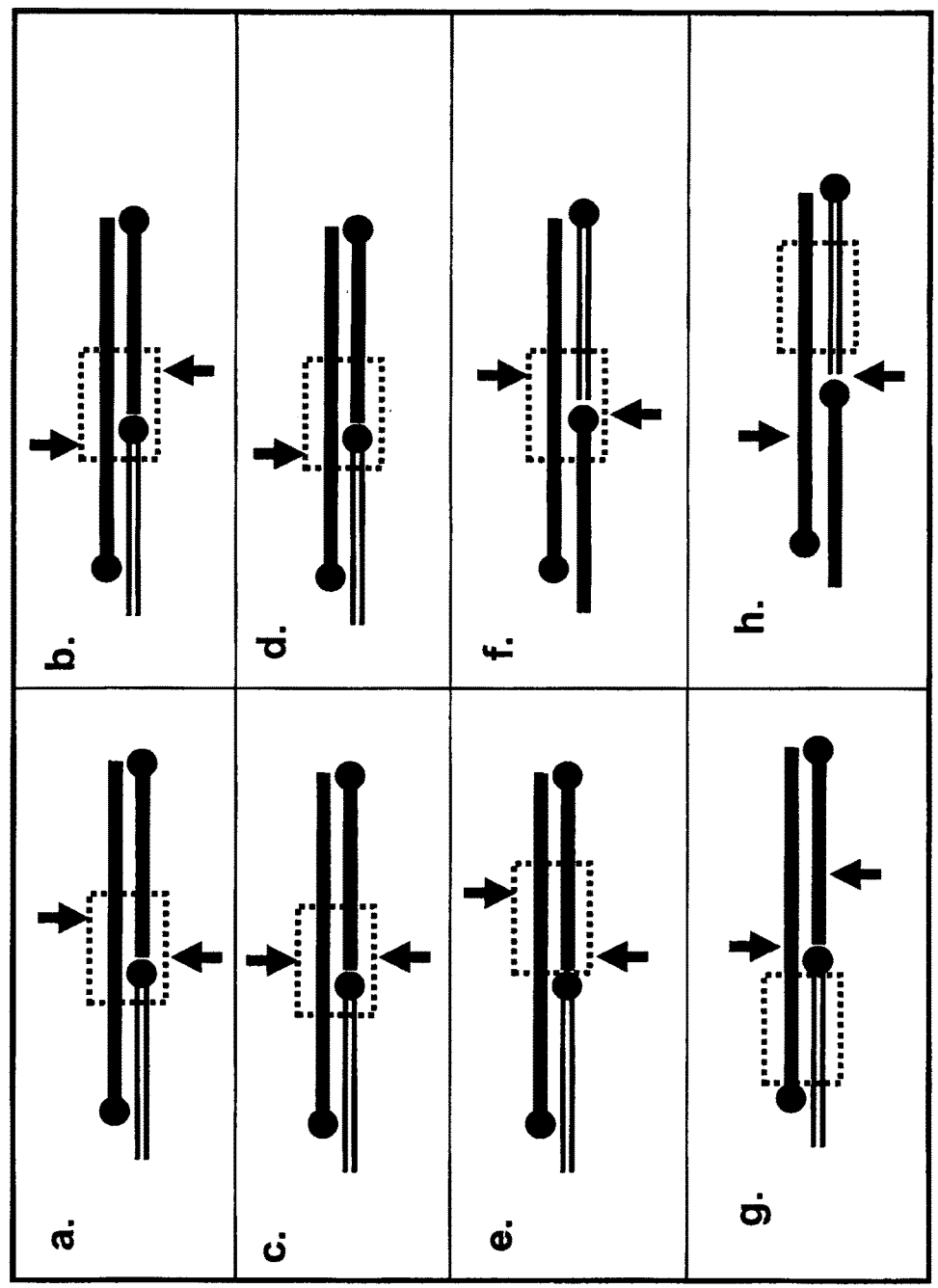

FIG. 2 shows exemplary schemata for various fully assembled Complete Enzyme Signal Amplifier (CESA) complexes designed to be cleaved by restriction endonucleases (REs). In these diagrams the top black solid line represents the Enzyme Amplifier Substrate oligo Fragment 1 (EAS1) and the bottom solid black line represents the Enzyme Amplifier Substrate oligo 2 (EAS2) of the CESA. The Driver Fragment (DF represented by black lines with white centers) may be required to complete the recognition sequence of the RE (represented as a hatched box) and/or may provide additional sequence adjacent to the RE recognition site which is required for cleavage by the RE. The cleavage site(s) are represented by solid black vertical arrows.

Cleavage by the RE may result in either a 5' overhang, a 3' overhang or it may generate blunt ends. The RE may cleave one or both strands of the double stranded assembled CESA comprising EAS1, EAS2 and DF. The position where EAS2 and the DF abut may be at a position where the RE would normally cleave a continuous (unbroken) double stranded duplex or it may be elsewhere with the sequences required for recognition and cleavage by the RE. The end of the DF which abuts the EAS2 may have been generated by cleavage of a longer oligo, for example an Inhibitory Fragment (InF) in a previous step. The InF may comprise, for example, a Synthetic Initiator Oligo (SIO) cleavable by a nuclease, or an MNAzyme substrate cleavable by an MNAzyme. Cleavage of such longer oligos by a protein enzyme or an MNAzyme, can result in a 5' and a 3' fragment, one or both of which could serve as a DF for completion of a CESA. In such cases the end of the DF which abuts the EAS2 must be the 5' end of the 3' fragment of the cleaved oligo, or the 3' end of the 5' fragment of the cleaved oligo.

Panel (a): An assembled CESA with a DF where the DF is required to complete the recognition sequence of the RE and RE cleavage results in a 3' overhang. The terminus of the DF which abuts with the EAS2 is the 5' end of a 3' cleavage fragment in this example.

Panel (b): An assembled CESA with DF where the DF is required to complete the recognition sequence of the RE and RE cleavage results in a 5' overhang. The terminus of the DF which abuts with the EAS2 is the 5' end of a 3' cleavage fragment in this example.

Panel (c): An assembled CESA with DF where the DF is required to complete the recognition sequence of the RE and RE cleavage results in blunt ends. The terminus of the DF which abuts with the EAS2 is the 5' end of a 3' cleavage fragment in this example.

Panel (d): An assembled CESA with DF where the DF is required to complete the recognition sequence of the RE and the RE cleaves only one strand, in this illustration, the EAS1. The terminus of the DF which abuts with the EAS2 is the 5' end of a 3' cleavage fragment in this example.

Panel (e): An assembled CESA with DF where the DF is not required to complete the recognition sequence of the RE but rather provides sequence adjacent to the RE recognition site which is required by the RE for cleavage. The terminus of the DF which abuts with the EAS2 is the 5' end of a 3' cleavage fragment in this example.

Panel (f): An assembled CESA with DF where the DF is required to complete the recognition sequence of the RE and RE cleavage results in a 5' overhang. The terminus of the DF which abuts with the EAS2 is the 3' end of a 5' cleavage fragment in this example.

Panel (g): An assembled CESA with DF where the DF completes the recognition sequence of the RE by providing one strand of the complete RE recognition sequence which is required by the RE for cleavage. The terminus of the DF which abuts with the EAS2 is the 5' end of a 3' cleavage fragment in this example.

Panel (h): An assembled CESA with DF where the DF completes the recognition sequence of the RE by providing the one strand of the complete RE recognition sequence which is required by the RE for cleavage. The terminus of the DF which abuts with the EAS2 is the 3' end of a 5' cleavage fragment in this example.

Figure 3:
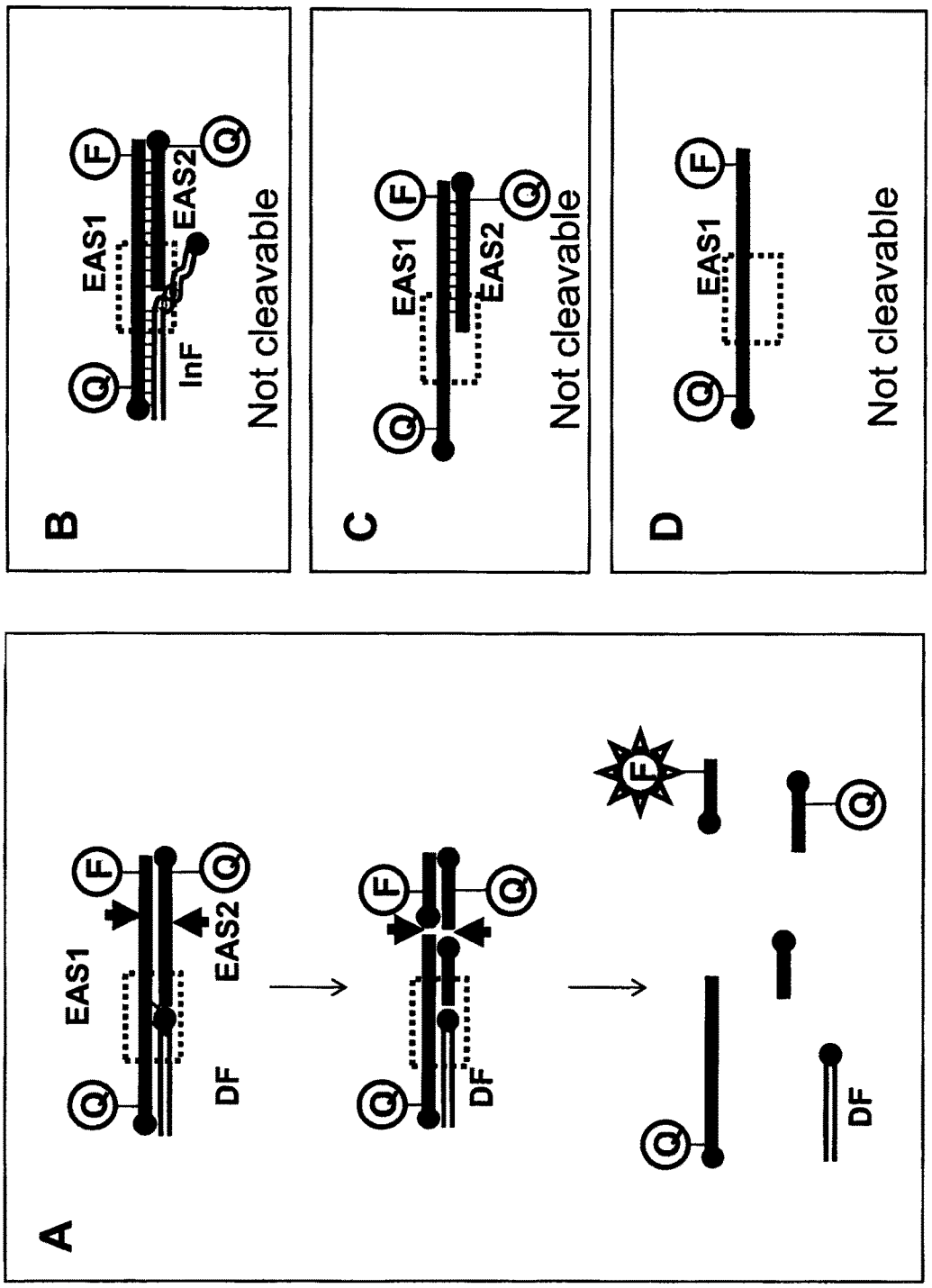

FIG. 3 is an exemplary illustration for various cleavable and uncleavable duplex oligonucleotide structures of Example 1. The 5' end of each oligonucleotide fragment is indicated by a circle. The complete or partial restriction enzyme recognition site is indicated as a dashed box and the restriction enzyme cleavage sites are indicated as vertical solid arrows. Panel A illustrates an example of a Complete Enzyme Signal Amplifier (CESA) complex which is a multi-oligonucleotide complex which is amenable to cleavage by an enzyme. In this figure and in Example 1 the enzyme is the restriction enzyme (RE) Mnl I which cleaves at a distance from its recognition site. This CESA is composed of three oligonucleotides, namely Enzyme Amplifier Substrate oligo 1 (EAS1 represented by the upper solid black line) which is labeled with a fluorophore and a quencher, Enzyme Amplifier Substrate oligo 2 (EAS2 represented by the lower solid black line) labeled with a quencher and a Driver Fragment (DF represented by black lines with a white centre). In this CESA, the 5' end DF abuts with the 3' end of the EAS2. Cleavage of this CESA results in an increase in fluorescence, due to the cleavage of the EAS1 and EAS2 oligonucleotides by the RE, however, the DF is not cleaved and as such would be available to bind to another Partial Enzyme Signal Amplifier (PESA) complex. A reaction, such as this one, which amplifies a signal by means of cleavage of an CESA is termed an "EzyAmp" reaction.

Panel B illustrates an example of an Enzyme Inhibitory Complex (EIC) which is a multi-oligonucleotide complex which is resistant to cleavage by a RE. This EIC is composed of three oligonucleotides, namely EAS1, EAS2 and an Inhibitory Fragment (InF). The InF comprises the entire sequence of the DF (including those bases required to complete the RER), but also comprises additional sequence which disrupts formation of the structure required for cleavage by the RE. In this EIC the 5' end of the InF abuts and disrupts binding at the 3' end of the EAS2. The InF may comprise a oligo sequence which can only be cleaved to produce a DF in the presence of a target. For example, the InF may comprise a SIO cleavable in a target-specific manner by a nuclease or an MNAzyme substrate cleavable by an MNAzyme.

Panel C illustrates an example of a Partial Enzyme Signal Amplifier complex (PESA) which is a multi-oligonucleotide complex which is resistant to cleavage by a nuclease, for example the RE, Mnl I. This PESA is composed of two oligonucleotides, namely EAS1 and EAS2. This PESA does not contain the double stranded recognition sequence required by the RE.

Panel D illustrates an example of a control which contains only EAS1 and hence is not amenable to cleavage by a RE. Cleavage cannot occur because sequence, complementary to EAS1 is required to form RE recognition and cleavage sites.

Figure 4:
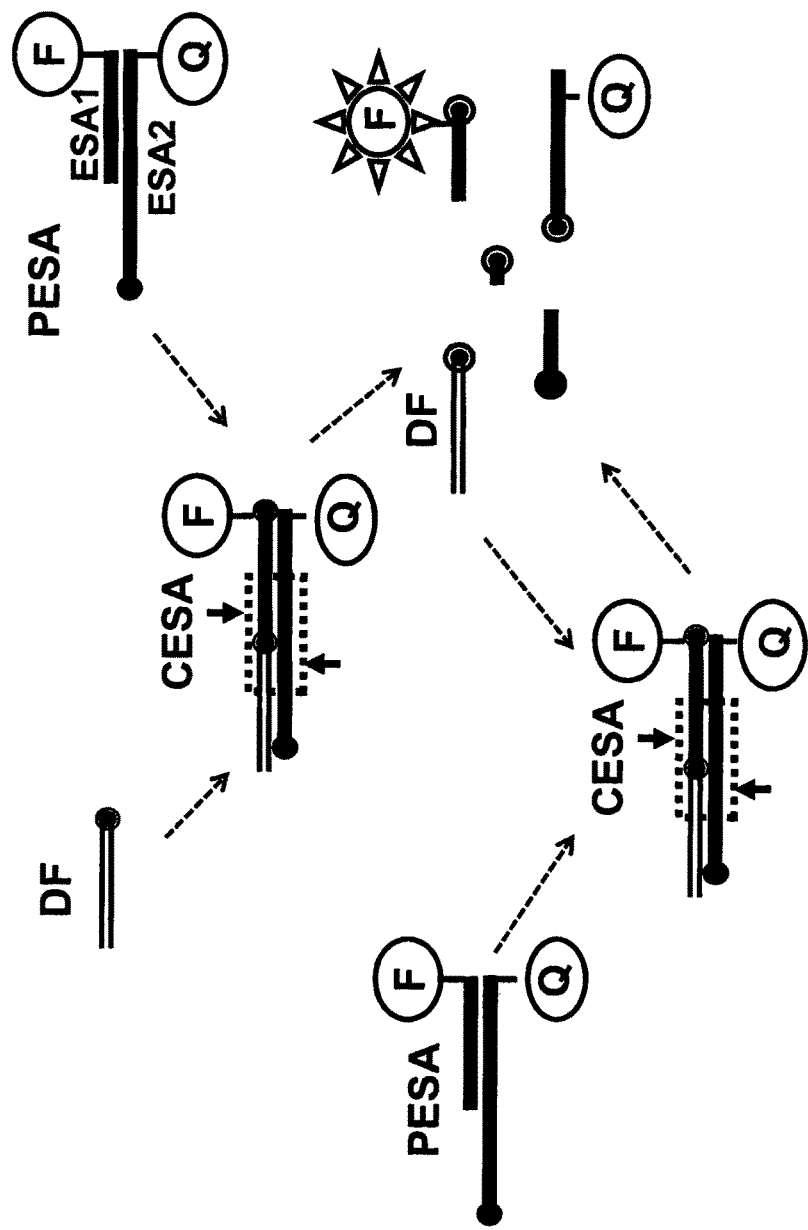

FIG. 4 illustrates one example of an EzyAmp reaction. A Driver Fragment (DF) (generated by target-dependent enzyme modification or added directly to a reaction mix) is present in a reaction which contains PESA complexes comprising a first Enzyme Amplifier Substrate oligo (EAS1) and a second Enzyme Amplifier Substrate (EAS2) oligo. The DF assembles with a PESA complex to create a CESA which contains a nuclease recognition and cleavage site, in this illustration the nuclease is a restriction enzyme. The circle on each of EAS1, EAS2 and the DF indicate the 5' end of each oligo. The restriction enzyme recognition site is indicated as a dashed box and the restriction enzyme cleavage sites are indicated by vertical solid arrows. In this illustration the first EAS1 is labeled with a fluorophore (F) and the second EAS2 is labeled with a quencher (Q). Cleavage of the assembled CESA followed by subsequent dissociation of the components results in generation of a fluorescent signal and release of the intact DF. The DF is then free to associate with another PESA to form another CESA which leads to further enzymatic cleavage of the oligos and subsequent fluorescence. The process thus continues and results in signal amplification whereby a fluorescent signal is produced by the nuclease (e.g. restriction enzyme) mediated cleavage of further CESA.

Figure 5:
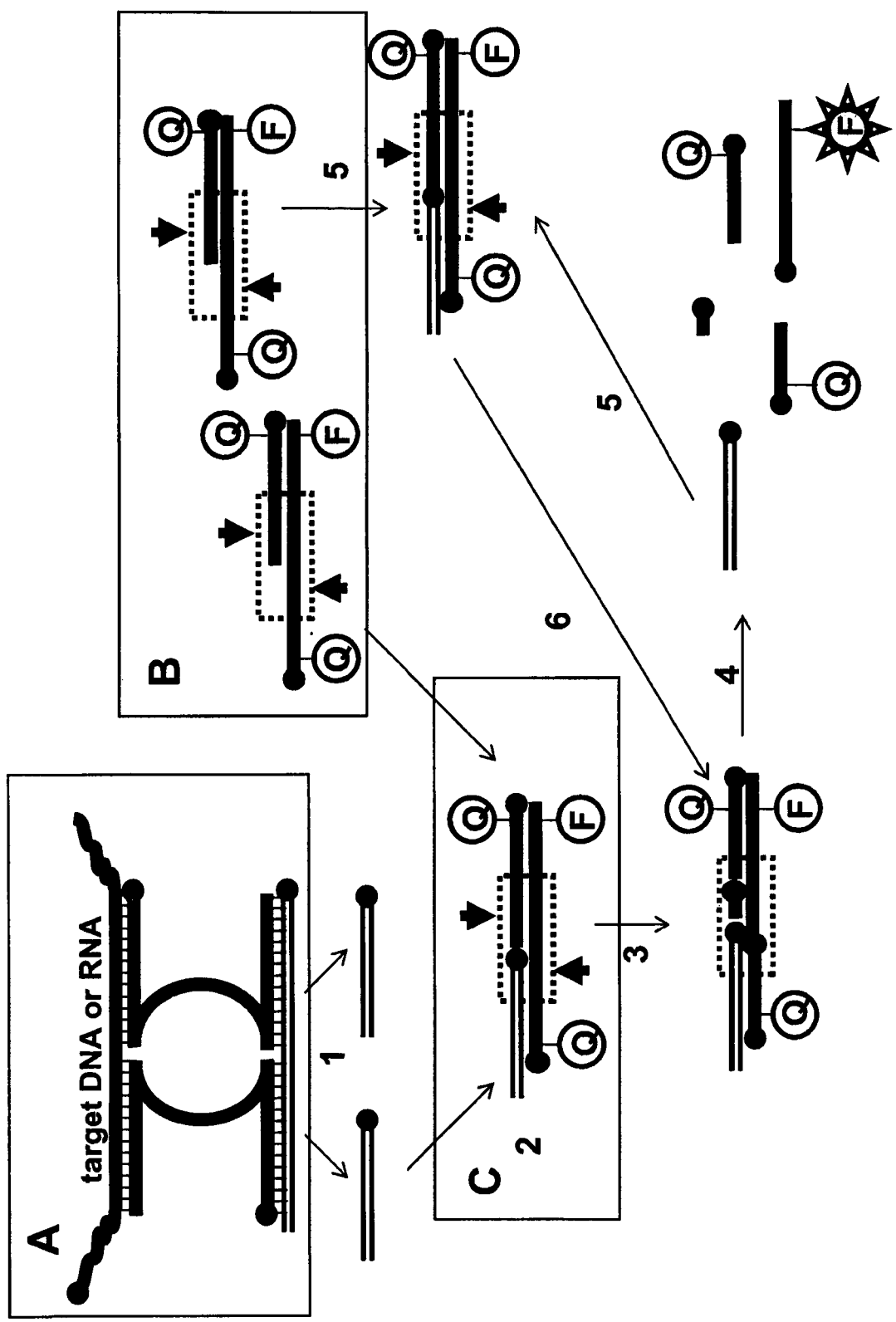

FIG. 5 is an exemplary schema for an MNAzyme-initiated EzyAmp reaction where the signal amplification is mediated by cleavage of the CESA by a RE. Box A illustrates an assembled MNAzyme (solid grey lines) bound to its substrate (black line with white center) and Box B which illustrates two Partial Enzyme Signal Amplifier (PESA) complexes (solid black lines) each of which constitutes an Enzyme Amplifier Substrate oligo 1 (EAS1) labeled in this illustration with a fluorophore (F) and quencher (Q), and an Enzyme Amplifier Substrate oligo 2 (EAS2) labeled in this illustration with a quencher (Q). Box C illustrates the Complete Enzyme Signal Amplifier (CESA) complex which is formed by EAS1, EAS2 and one fragment of the cleaved MNAzyme substrate which now functions as a Driver Fragment (DF). The circle on each of EAS1, EAS2, the MNAzyme partzymes, the MNAzyme substrate, and the DF indicate the 5' end of each oligonucleotide. The restriction enzyme recognition site is indicated as a dashed box and the restriction enzyme cleavage sites are indicated as vertical solid arrows. The various steps in the reaction are numbered 1 to 6. This reaction allows detection of target DNA or RNA using the following steps. In Step 1 the target assembles with partzymes to form an MNAzyme which cleaves the MNAzyme substrate. In Step 2 one fragment of the cleaved MNAzyme substrate binds with a PESA where it functions as a DF and results in formation of a CESA. In Step 3 the fully assembled CESA is cleaved by a RE. In Step 4 the cleaved CESA fragments dissociate leading to separation of the fluorophore and the quencher thus producing an increase in fluorescence indicative of the presence of the target nucleic acid. Since the DF is not actually cleaved itself by the RE in this scheme it is free to associate with another PESA (Step 5) to form a new CESA which can be cleaved by the RE (Step 6) thus leading to further amplification of the fluorescent signal.

Figure 6:
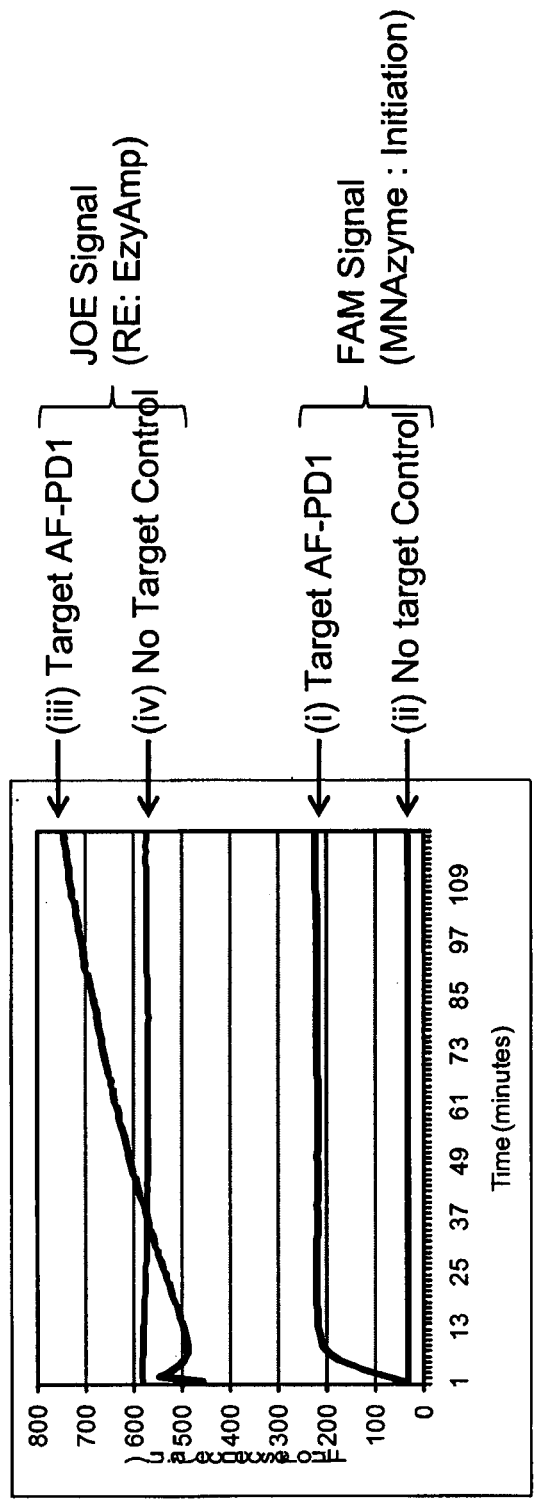

FIG. 6 is an illustration of the fluorescent signal generated by an MNAzyme-initiated EzyAmp reaction where the signal amplification is mediated by cleavage of the CESA by a RE, in this example Mnl I. In this example the two steps of initiation (by the MNAzyme) and signal amplification (by the RE) were simultaneously monitored by observing changes in fluorescence associated with each step. The target dependent initiation step of MNAzyme cleavage of an MNAzyme reporter substrate (Sub1(8:9)*FB) in the presence of the target assembly facilitator (AF-PD1) was monitored by an increase in FAM following separation of FAM from a quencher (both present on the MNAzyme reporter substrate). The signal amplifying EzyAmp step was monitored by an increase in JOE fluorescence following cleavage of the EAS1 oligo between JOE and a quencher when this EAS1 was incorporated into a CESA complex formed from EAS1, EAS2 and the DF. All components of the reactions, either containing target (AF-PD1) or lacking target (control) were present in one reaction chamber and the fluorescence of both FAM and JOE were monitored simultaneously. In the FAM channel, MNAzyme mediated cleavage of Sub1 (8:9)-FB in the presence of target assembly facilitator AF-PD1 ((i) Target AF-PD1) resulted in an increase in FAM fluorescence over time and production of a DF. In the reaction which lacked AF-PD1 ((ii) No Target Control) there was no increase in FAM fluorescence over time. In the JOE channel, RE activity in the presence of the DF generated by MNAzyme cleavage of Sub1-FB in the presence of target AF-PD1 ((iii) Target AF-PD1) caused cleavage of the CESA and an increase in JOE fluorescence over time. In contrast, the reaction which lacked AF-PD1 ((iv) No Target Control) did not show an increase in JOE fluorescence over time.

Figure 7:
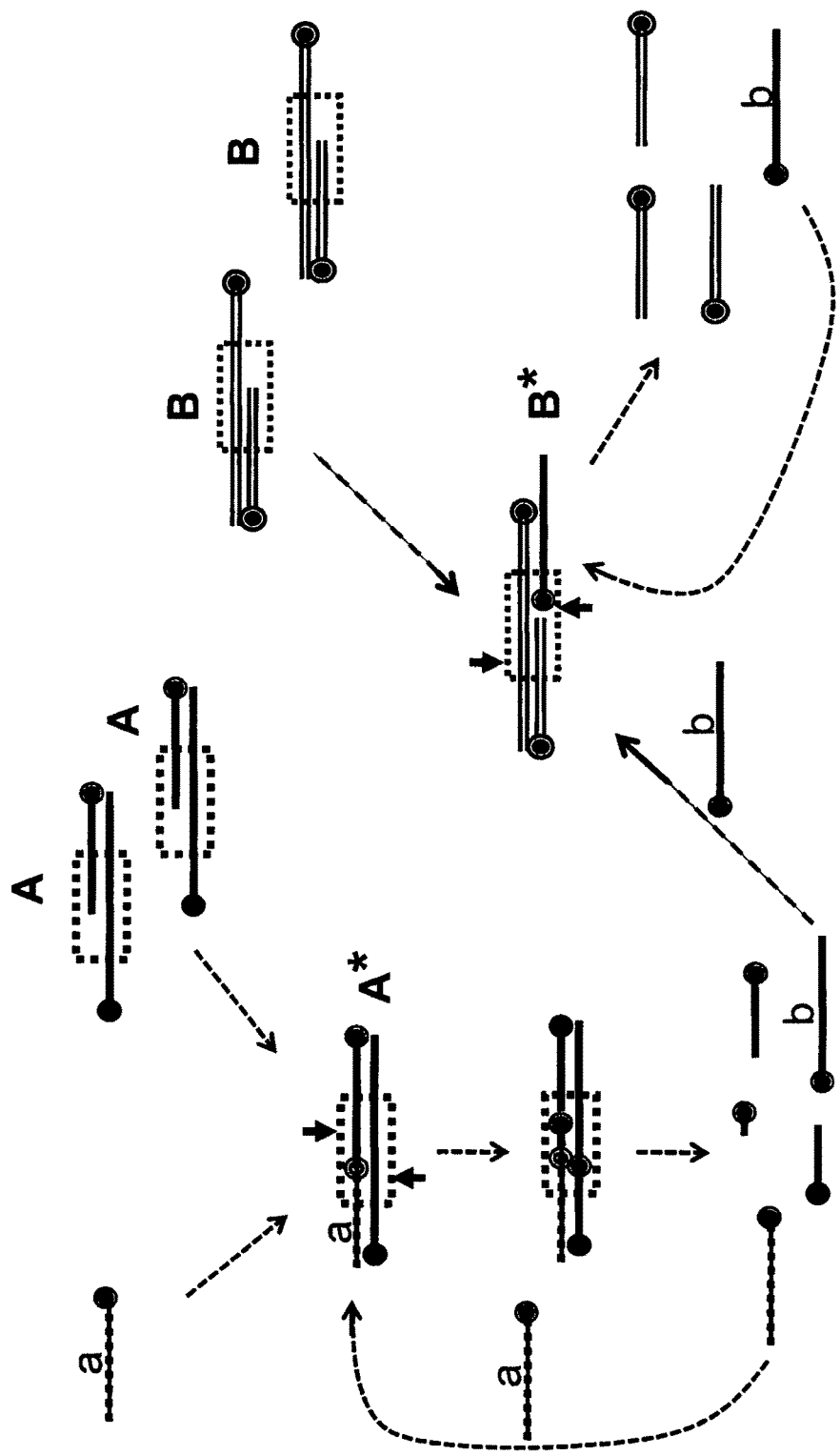

FIG. 7 is an exemplary schema for an EzyAmp system which contains multiple CESA complexes. The circle on each of EAS1, EAS2 and the DF indicate the 5' end of each oligo. The restriction enzyme recognition site is indicated as a dashed box and the restriction enzyme cleavage sites are indicated as vertical solid arrows. In this illustration a CESA A* is formed from PESA A combined with DF-a. CESA B* is formed from PESA B combined with DF-b. DF-a is formed in the presence of a target analyte under conditions whereby the presence of the analyte results in cleavage of a larger oligonucleotide fragment, for example target dependent nuclease cleavage of a SIO or target dependent MNAzyme cleavage of an MNAzyme substrate. DF-a combines with PESA A to form CESA A* which is cleaved by a RE to produce DF-b without modification to DF-a and signal can be generated. DF-a can then form new CESA A* and amplify both the signal and the number of DF-b molecules. In addition, DF-b can combine with PESA B to form CESA B* which can be cleaved by a RE to produce additional signal without modifying DF-b. DF-b is therefore available to form addition CESA B* and further amplify the signal.

Figure 8:
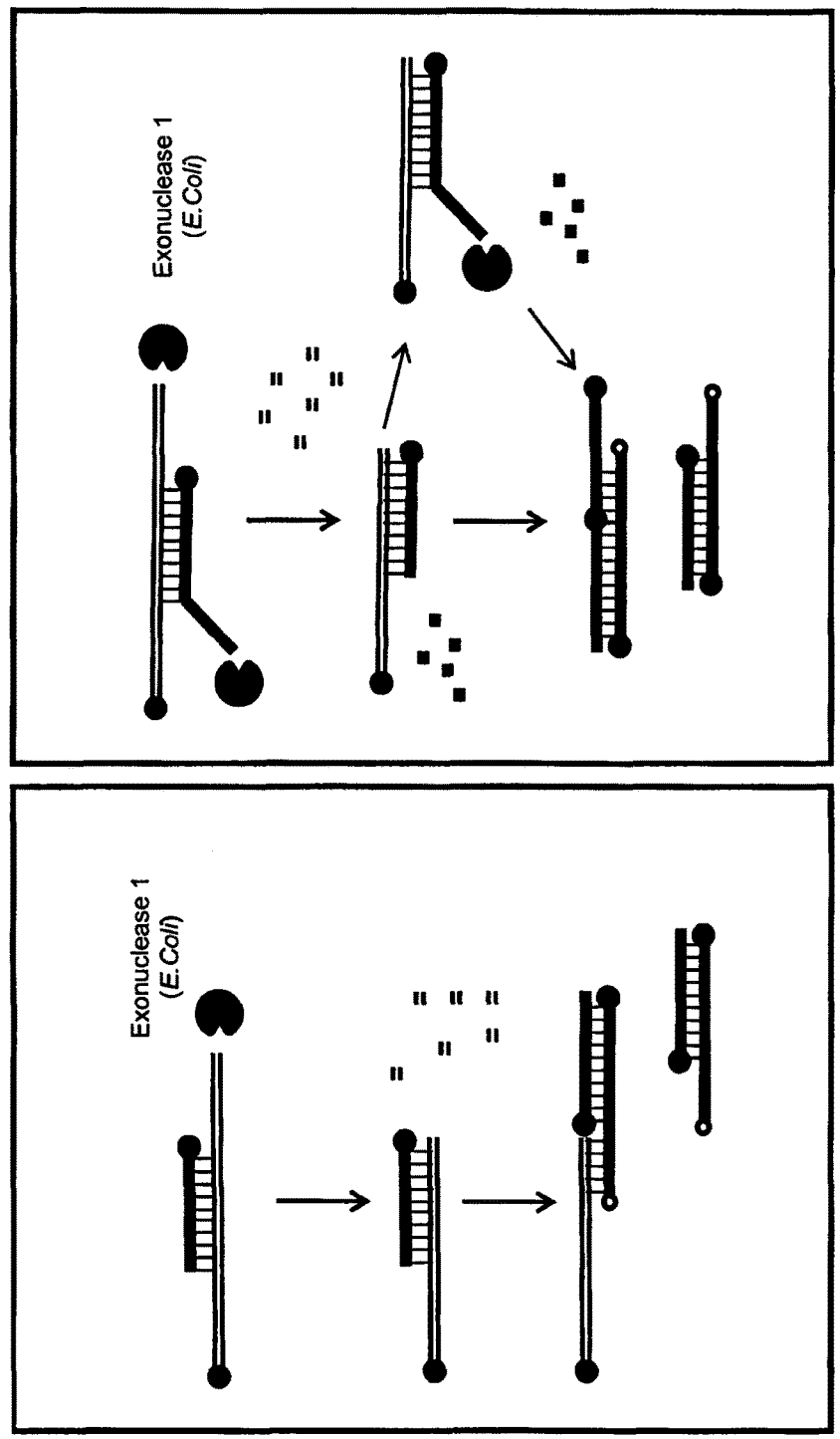

FIG. 8 illustrates mechanisms for generating Driver Fragments (DFs) using the 3' to 5' exonuclease activity of Exonuclease I from E. coli. This enzyme removes 3' single stranded overhangs from DNA duplexes. The striped grey lines represent the target DNA and the solid black lines represent a Synthetic Initiator Oligo (SIO) added to the mix to facilitate generation of a Driver Fragment. The closed circles represent the 5' end of the oligos. The solid grey lines represent PESA which are converted to CESA by hybridization of the DF. The open circles represent phosphorothioate on the 3' overhang which are incorporated to prevent cleavage of complexes at this location by Exonuclease I. In the left panel the Driver Fragment is derived from the target. In the right panel the DF is derived from the Synthetic Initiator Oligo. In the scheme on the right panel the target can be recycled to generate more DF.

Figure 9:
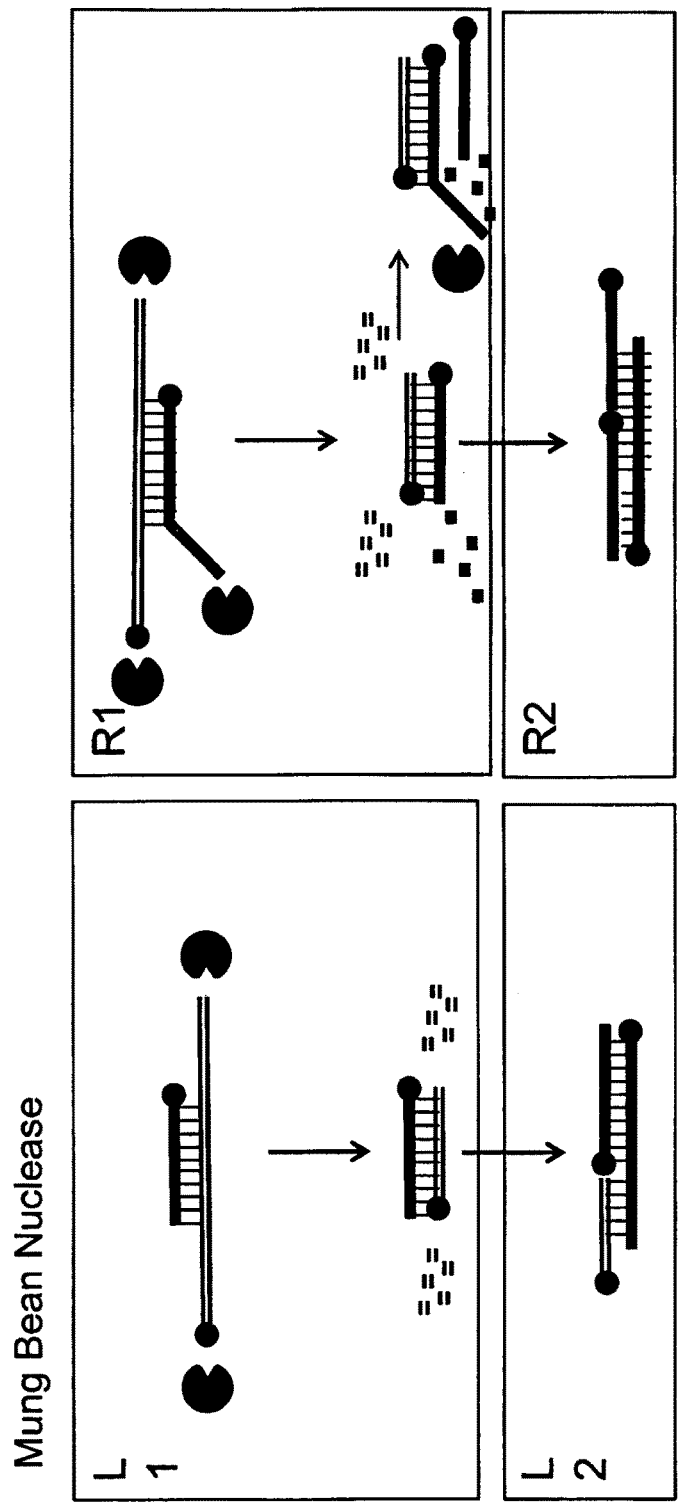

FIG. 9 illustrates mechanisms for generating Driver Fragments using the exonuclease activity of Mung Bean Nuclease. This endonuclease degrades single stranded overhangs from DNA duplexes from either the 3' or the 5' direction leaving blunt ends. The striped grey lines represent the target DNA and the solid black lines represent a Synthetic Initiator Oligo (SIO) added to the mix to facilitate generation of a DF. The closed circles represent the 5' end of the oligos. The solid grey lines represent PESA which are converted to CESA by hybridization of the DF. In the left panel the Driver Fragment is derived from the target. In the right panel the DF is derived from the Synthetic Initiator Oligo. The methods depicted in both the left (L) or right (R) panels could be performed in 2 steps (1 and 2) to prevent digestion of the PESA or CESA by Mung Bean Nuclease. This could be achieved by physical separation or other means.

Figure 10:
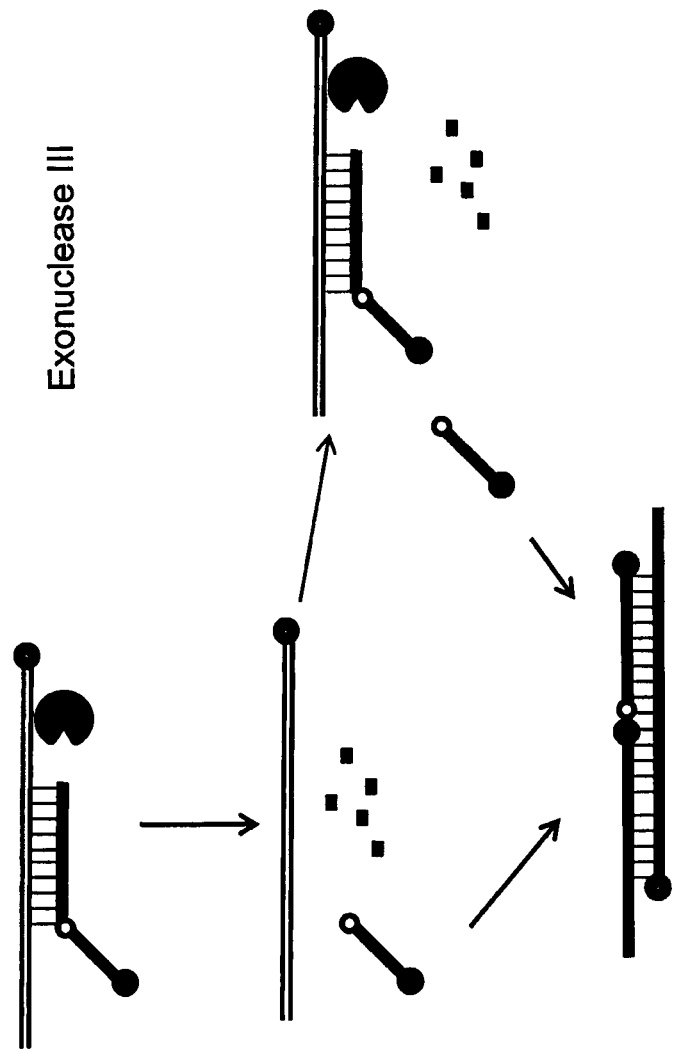

FIG. 10 illustrates a mechanism for generating Driver Fragments using the exonuclease activity of Exonuclease III. This enzyme removes nucleotides' from 3' termini of DNA duplexes. The enzyme is active on blunt or recessed 3' termini, but is not active on single stranded DNA and hence will not cleave 3' protruding termini. The enzyme can also start hydrolysis from nicks in a duplex DNA to produce single stranded gaps. The presence of a phosphorothioate nucleotide (indicated by a hollow circle) on oligos blocks this exonuclease activity. The striped grey lines represent the target DNA and the solid black lines represent a Synthetic Initiator Oligo added to the mix to facilitate generation of a DF. The closed circles represent the 5' ends of the oligos. The solid grey lines represent PESA which are converted to CESA by hybridization of the DF. The phosphorothioate in the 3' flap of the DF prevents cleavage at the nick created when this fragment completes the CESA. The DF is derived from the SIO, and the intact target can be recycled to generate more DFs.

Figure 11:
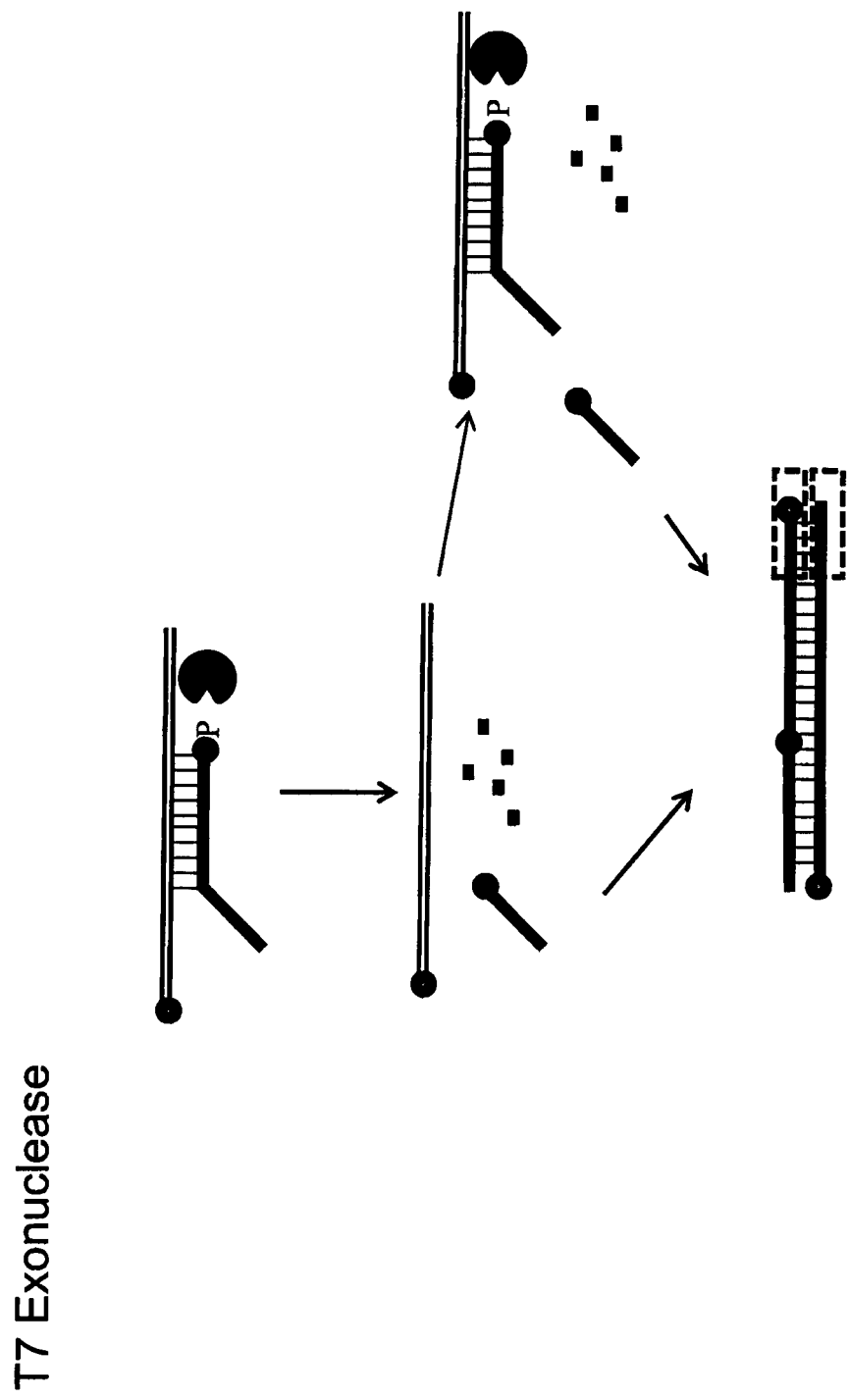

FIG. 11 illustrates a mechanism for generating Driver Fragments using the exonuclease activity of T7 Exonuclease. This enzyme removes nucleotides from the 5' end of DNA duplexes or DNA/RNA duplexes, with a higher activity on phosphorylated 5' nucleotides. The activity on 5' ends without a 5' phosphate is greatly reduced in the presence of phosphorylated substrate. The striped grey lines represent the target RNA and the solid black lines represent a Synthetic Initiator Oligo added to the mix to facilitate generation of a DF. P represents a phosphorylated nucleotide at the 5' termini. The solid grey lines represent PESA which are converted to CESA by hybridization of the DF. The DF is derived from the Synthetic Initiator Oligo (SIO), and the RNA target can be recycled to generate more DF. The PESA is composed of DNA but may have some RNA at the 5' termini of the duplex (dotted box) to prevent degradation by the T7 exonuclease.

Figure 12:
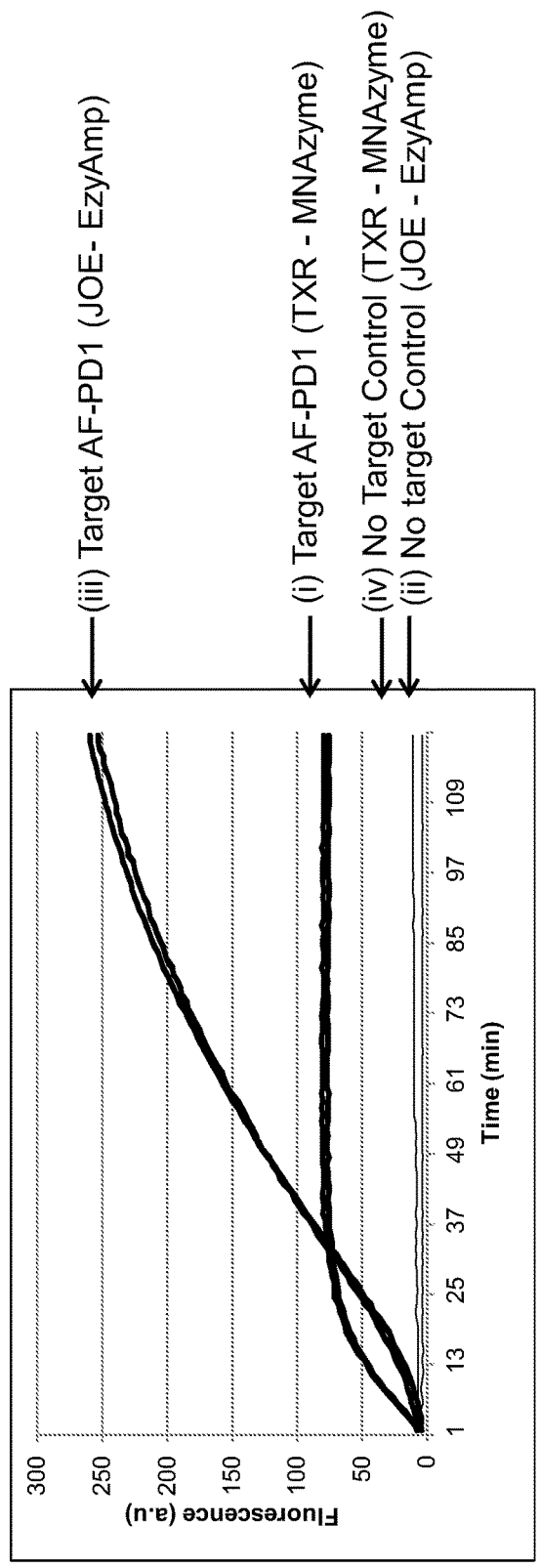

FIG. 12 is an illustration of the fluorescent signal generated by an MNAzyme-initiated EzyAmp reaction where the signal amplification is mediated by cleavage of the CESA by a RE, such as Mnl I. In this example the two steps of initiation and signal amplification were simultaneously monitored by observing changes in fluorescence associated with each step. The target dependent initiation step of MNAzyme cleavage of an MNAzyme reporter substrate (Sub1-TRB2-labelled with TXR and a quencher) in the presence of the target assembly facilitator (AF-PD1) was monitored by an increase in TXR following separation of TXR from the quencher. The signal amplifying EzyAmp step was monitored by an increase in JOE fluorescence following cleavage of the EAS1 oligo between JOE and a quencher when this EAS1 was incorporated into a CESA complex formed from EAS1, EAS2 and the DF. All components of the reactions, either containing target (AF-PD1) or lacking target (control) were present in one reaction chamber and the fluorescence of both TXR and JOE were monitored simultaneously. In the TXR channel, MNAzyme cleavage of Sub1-TRB2 in the presence of target assembly facilitator AF-PD1 ((i) Target AF-PD1) resulted in an increase in TXR fluorescence over time and production of a DF. In the reaction which lacked AF-PD1 ((ii) No Target Control) there was no increase in TXR fluorescence over time. In the JOE channel, RE activity in the presence of the DF generated by MNAzyme cleavage in the presence of target AF-PD1 ((iii) Target AF-PD1) caused cleavage of the CESA and an increase in JOE fluorescence over time. In contrast, the reaction which lacked AF-PD1 ((iv) No Target Control) did not show an increase in JOE fluorescence over time.

Figure 13:
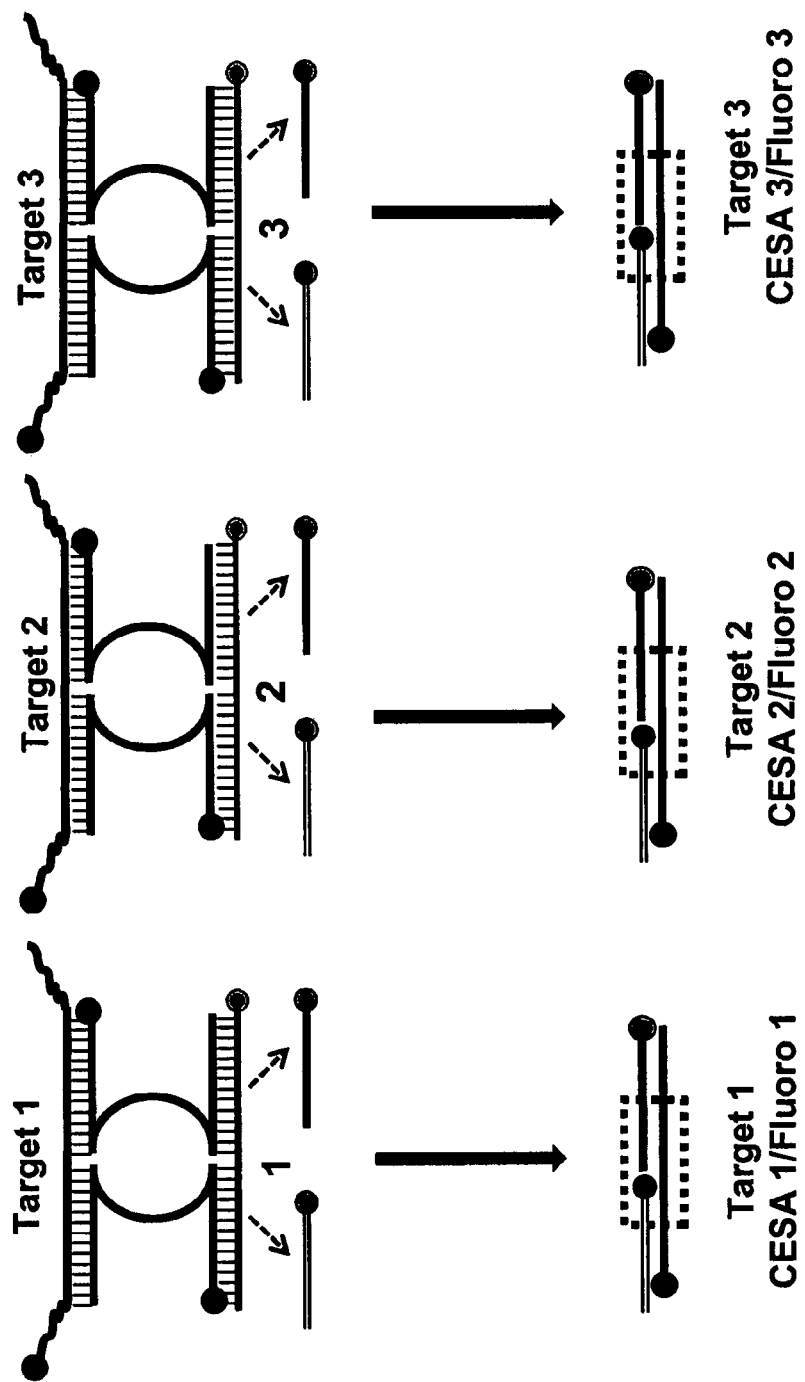

FIG. 13 illustrates a strategy for multiplex isothermal universal signal amplification for any set of targets. The circle on each of oligonucleotides represents the 5' end of each oligo. The restriction enzyme recognition site is indicated as a dashed box. The strategy for multiplex analysis of multiple targets uses multiple MNAzymes which cleave multiple universal substrates to generate multiple universal Driver Fragments which can assemble with multiple universal PESAs to form multiple universal CESAs. The strategy is illustrated for detection of three targets, Target 1, Target 2 and Target 3. Target 1 could cause assembly of an MNAzyme capable of cleaving a universal MNAzyme substrate 1. Cleavage of universal MNAzyme substrate 1 could result in generation of universal Driver Fragment 1 which could assemble with PESA 1 to form CESA 1. CESA 1 could be labelled with a unique Fluorophore 1, which upon cleavage with a nuclease, would result in fluorescence at a unique wavelength indicating the presence of Target 1. Similarly Target 2 could cause assembly of an MNAzyme capable of cleaving a universal MNAzyme substrate 2. Cleavage of universal MNAzyme substrate 2 could result in generation of universal Driver Fragment 2 which could assemble with PESA 2 to form CESA 2. CESA 2 could be labelled with a unique Fluorophore 2, which upon cleavage with a nuclease, could result in fluorescence at a unique wavelength indicating the presence of Target 2. Target 3 could cause assembly of an MNAzyme capable of cleaving a universal MNAzyme substrate 3. Cleavage of universal MNAzyme substrate 3 could result in generation of universal Driver Fragment 3 which could assemble with PESA 3 to form CESA 3. CESA 3 could be labelled with a unique Fluorophore 3, which upon cleavage with a nuclease, could result in fluorescence at a unique wavelength inducting the presence of Target 3. The fluorescence associated with Fluorophores 1 and 2 and 3 upon cleavage of CESA 1 and 2 and 3 could be monitored simultaneously in a single reaction.

In such universal multiplex systems, a new target can be easily substituted into the multiplex reaction. For example, the universal MNAzyme substrate 1/PESA 1/CESA 1/Fluorophore 1 system would only require synthesis of a new MNAzyme which has sensor arms specific for the new target, but retains substrate arms suitable for binding to MNAzyme substrate 1. Since cleavage of MNAzyme substrate 1 always produces the same driver fragment 1, the new target will result in assembly and subsequent cleavage of CESA 1 as before.

Figure 14:
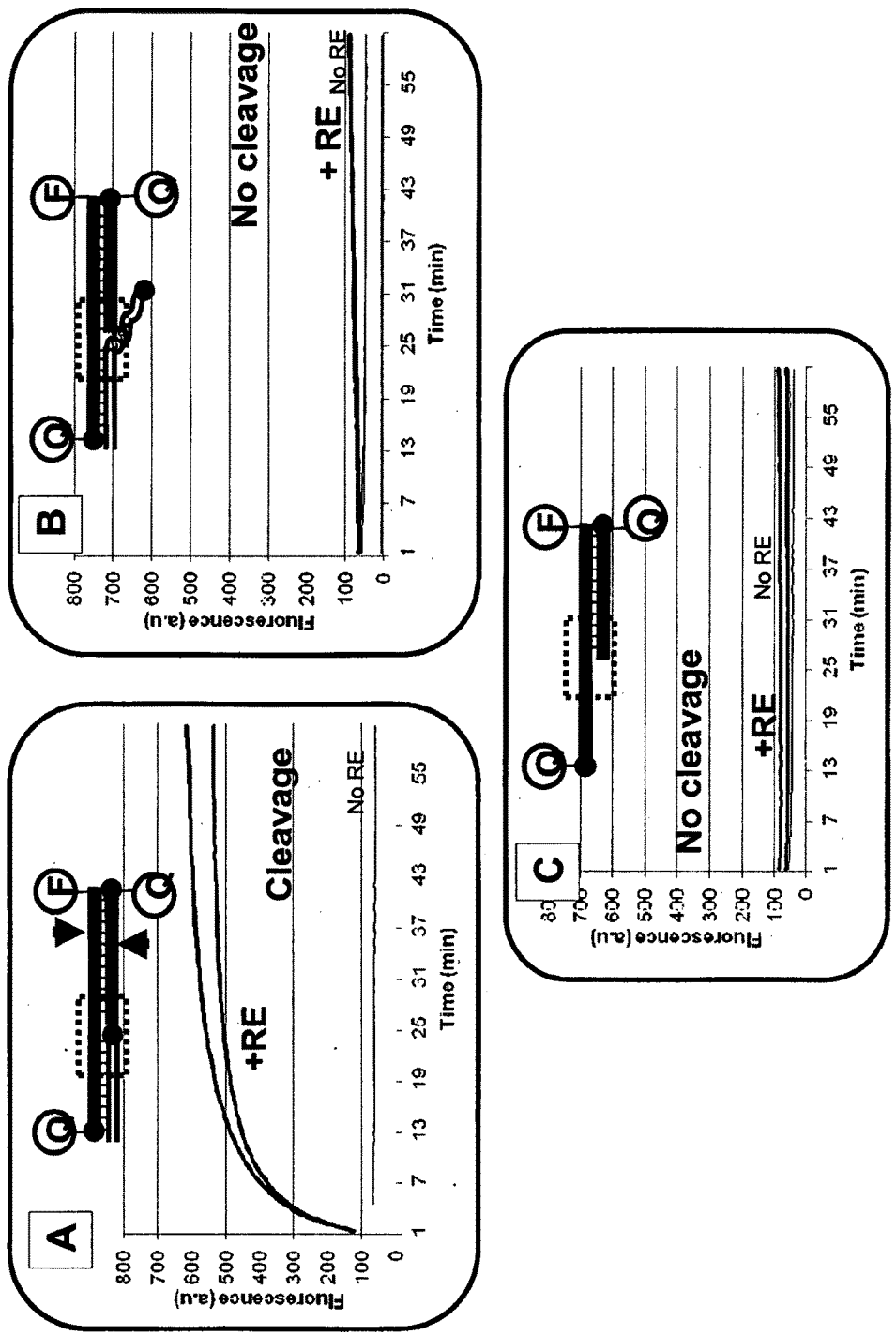

FIG. 14 shows the results of analysing various duplex structures. The duplex structures illustrated in panels A, B and C all comprise a top solid black oligo (EAS1) labelled with a fluorophore (F) and a quencher (Q) and a bottom solid black line (EAS2) labelled with a quencher. Together EAS1 and EAS2 comprise a PESA. In addition panel A has a striped bottom oligo which represents a Driver Fragment (DF) and panel B has a striped bottom oligo which represents an Inhibitory Fragment (InF).

In panel A, the presence of EAS1, EAS2 and a DF1 in the reaction resulted in the formation of a cleavable CESA duplex substrate for the RE Mnl I as indicated by the observed increase in FAM fluorescence over time (FIG. 14A). This observation is consistent with the ability of restriction enzymes to recognise and cleave double stranded complexes which contain breaks or nicks in at least one of the two strands within the region which is required for recognition and cleavage by the RE. In contrast, in panel B, where reactions lacked the DF1 fragment but included an InF, the duplexes that formed were not cleaved and hence no increase in fluorescence was observed over time (FIG. 14B). This occurred despite the fact that the InF included the entire sequence of DF1. The sequence present in the InF, which is additional to that specific sequence which is also present in the DF, inhibited the formation of cleavable duplex substrates. Indeed the additional sequence resulted in formation of non-cleavable complexes, termed Enzyme Inhibitory Complexes (EICs).

In panel C, where reactions contained only EAS1 and EAS2 and lacked both DF1 and the InF, no increase in fluorescence was observed indicating that these two oligos alone (EAS1 and EAS2) are insufficient for recognition and cleavage of the duplex by the RE (FIG. 14C). The oligos EAS1 and EAS2 hybridize to form a Partial Enzyme Signal Amplifier (PESA) complex, however, an additional oligo namely the DF, is required to convert the non-cleavable PESA to a cleavable CESA.

FIG. 15 illustrates various structures in which a DF could bind to a candidate PESA, whereby some variations result in a cleavable CESA duplex substrates for the RE Mnl I. These structures were tested in Reactions 1 to 8 of Example 5. In this example, Mnl I cleavage was monitored by observing changes in fluorescence associated with the separation of fluorophore and quencher moieties in the presence (traces labeled (i)) or absence (traces labeled (ii)) of DF. Each panel, numbered 1 to 8, indicates the structure of the candidate PESA (solid black lines) and the position of a candidate DF (striped line). Circles indicate the 5' end of the oligonucleotides. The RERS is indicated as a dashed box. "N" equals the deoxyribonucleotide(s) present in the DF which are required to complete the RERS (ie. the nucleotides from the RERS missing from the PESA), except in reaction 7 where N refers to the deoxyribonucleotide(s) present between the DF and RERS. In reaction 4 "n" indicates a ribonucleotide. Solid vertical arrows indicate the cleavage sites for Mnl I, '^' indicates absence of phosphodiester bond between adjacent nucleotides. Below the schematic of the candidate PESA and DF structures are the plots of fluorescence levels over time during incubation of these oligonucleotides with Mnl I as described in Example 5. The averages of duplicate reactions are shown.

In panel 1 (Reaction 1 of Example 5), the DF was designed as the 3' sequence immediately before the 5'GAGG3' partial Mnl I recognition site (GAGG^). A faster rate of increase in fluorescence was observed in the presence of the DF (i) compared to the increase in fluorescence in the absence of DF (ii). The PESA in this reaction contained the entire RER sequence, but the addition of the extra sequence flanking the RERS (provided by the DF) resulted in faster cleavage.

In panel 2 (Reaction 2 of Example 5), the DF was designed to complete the partial Mnl I recognition sequence of 5'GAGG3' by one nucleotide from the 3' end (GAGAG). An increase in fluorescence was observed over time in the presence of the DF (i). In contrast, no increase in fluorescence was observed over time when no DF was present (ii). This result indicates that a cleavable CESA can be formed when the DF completes the partial Mnl I recognition sequence of 5'GAGG3' by one nucleotide from the 3' end (G).

In panel 3 (Reaction 3 of Example 5), the DF was designed to complete the partial Mnl I recognition sequence of 5'GAGG3' by two nucleotides from the 3' end (GAAGG). An increase in fluorescence was observed over time in the presence of the DF (i). In contrast, no increase in fluorescence was observed over time when no DF was present (ii). This result indicates that a cleavable CESA can be formed when the DF completes the partial Mnl I recognition sequence of 5'GAGG3' by two nucleotides from the 3' end (GG).

In panel 4 (Reaction 4 of Example 5), the DF was designed to complete the partial Mnl I recognition sequence of 5' GAGG3' by two nucleotides from the 3' end, with the second base being a ribonucleotide (GA^gG). An increase in fluorescence was observed over time in the presence of the DF (i). In contrast, no increase in fluorescence was observed over time when no DF was present (ii). This result indicates that a cleavable CESA can be formed when the DF completes the partial Mnl I recognition sequence of 5'GAGG3' by two nucleotides from the 3' end (GG) even when the second nucleotide is a ribonucleotide (Gg).

In panel 5 (Reaction 5 of Example 5), the DF was designed to complete the partial Mnl I recognition sequence of 5' GAGG3' by three nucleotides from the 3' end (G^AGG). An increase in fluorescence was observed over time in the presence of the DF (i). In contrast, no increase in fluorescence was observed over time when no DF was present (ii). This result indicates that a cleavable CESA can be formed when the DF completes the partial Mnl I recognition sequence of 5'GAGG3' by three nucleotides from the 3' end (GGA).

In panel 6 (Reaction 6 of Example 5), the DF was designed to bind as the 5' sequence directly upstream from the Mnl I recognition sequence of 5'GAGG3' (AGAGG). No increase in fluorescence was observed over time in the presence (i) or absence of the DF (ii). This result indicates that no cleavable CESA was formed when the DF binds at the 5' end directly upstream from the Mnl I recognition sequence of 5'GAGG3'.

In panel 7 (Reaction 7 of Example 5), the DF was designed to bind as the 5' sequence, two nucleotides upstream from the Mnl I recognition sequence of 5'GAGG3' (^NNGAGG). An increase in fluorescence was observed over time in the presence of the DF (i). In contrast, no increase in fluorescence was observed over time when no DF was present (ii). This result indicates that a cleavable CESA can be formed when the DF binds two nucleotides upstream from the Mnl I RERS completing the RE cleavage site.

In panel 8 (Reaction 8 of Example 5), the DF was designed to complete the partial Mnl I recognition sequence of 5'CCTC3' by two nucleotides from the 5' end (CC^TC). An increase in fluorescence was observed over time in the presence of the DF (i). In contrast, no increase in fluorescence was observed over time when no DF was present (ii). This result indicates that a cleavable CESA can be formed when the DF completes the partial Mnl I recognition sequence of 5'CCTC3' by two nucleotides from the 5' end (CC).

Figure 16:
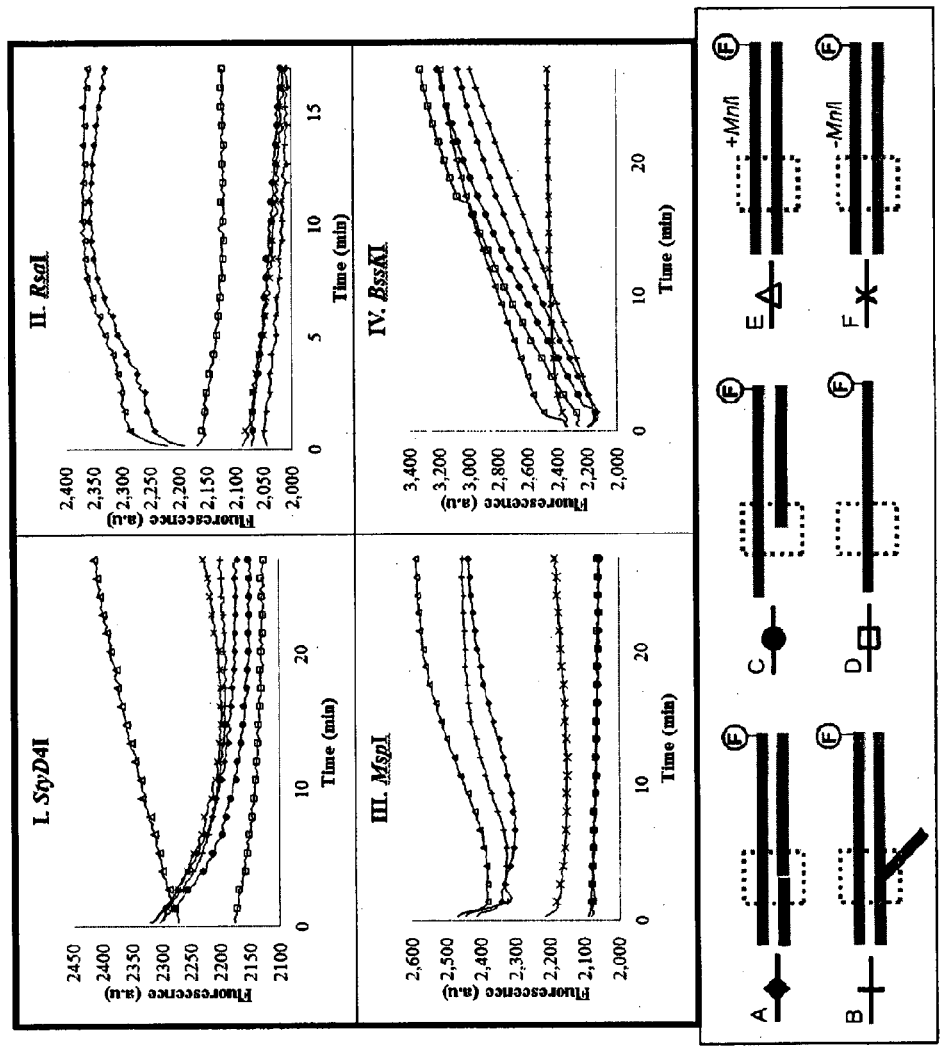

FIG. 16 illustrates the pattern of cleavage for various structures exemplified by the RE StyD 4I (Panel I), Rsa I (Panel II), Msp I (Panel III) and BssK I (Panel IV) as described in Example 6. The reactions contained the structures listed as follows: Reaction A: CESA; Reaction B: PESA plus InF; Reaction C: PESA; Reaction D: labeled EAS1 oligo; Reaction E (positive control) and F (negative control): double stranded contiguous RE substrate. Reaction A to E contained a RE, whereas negative control Reaction F did not contain a RE. The averages of duplicate reactions are shown.

These enzymes, and all other enzymes analyzed in this experiment (data not shown), exhibited an increase in fluorescence over time for the positive control (Reaction E). These observations are consistent with the ability of REs to recognize and cleave contiguous double stranded complexes, which contain a full RERS. All negative control reactions (Reaction F) did not exhibit an increase in fluorescence over time.

Panel I shows the data obtained for the RE StyD4 I as described in Row I Table 13. No increase in fluorescence was observed over time in Reactions A to D for this RE. This is indicative of the inability of this RE to cleave double stranded complexes that contain a nick in at least one of the two strands within the region which is required for recognition and cleavage by the RE, under the conditions tested. Further, this RE was unable to cleave when the reaction only contained a partially formed RERS.

Panel II shows the data obtained for the RE Rsa I as described in Row II Table 13. Two other REs, Pme I and Hpy 8I, also showed a similar pattern as reported for Rsa I. In Reaction A, the presence of EAS1, EAS2 and a DF resulted in the formation of cleavable CESA as indicated by the observed increase in fluorescence over time. These observations are indicative of the ability of these REs to recognise and cleave double stranded complexes that contain nicks in the RERS under the reaction conditions tested. In contrast, in Reaction B, which lacked the DF but included an InF, no increase in fluorescence was observed over time, indicating that the double stranded complexes that formed were not cleaved. Under this reaction condition, an EIC was formed. An increase in fluorescence was not observed over time for Reactions C and D for these REs indicating that this RE cannot cleave a structure that contains an incomplete RERS.

Panel III shows the data obtained for the RE Msp I as described in Row III Table 13. The RE Ear I also showed a similar pattern of results as those reported for Msp I. An increase in fluorescence was observed over time for Reaction A and Reaction B. In Reaction A, the presence of EAS1, EAS2 and a DF resulted in the formation of a cleavable CESA, as indicated by the increase in fluorescence over time. These observations are indicative of the ability of the REs to recognise and cleave double stranded complexes that contain nicks in the RERS. However, the RE also exhibited an increase in fluorescence in Reaction B, which lacked the DF but included an InF. These observations indicate that the InF does not form an EIC under the reaction conditions. An increase in fluorescence was not observed for Reactions C and D for these REs indicating that this RE cannot cleave a structure that contains an incomplete RERS.

Panel IV of FIG. 16 shows the data obtained for the RE, BssK I as described in Row IV of Table 13. The RE Alw I also showed a similar pattern of results as those reported for BssK I. In Reactions A to D, an increase in fluorescence was observed over time. In these reactions, the complexes contained either a full or partial RERS. This is indicative of these REs being able to recognise and cleave both full and partial RERS under the conditions tested.

FIG. 17 Panel A illustrates the strategy for an EzyAmp feedback cascade reaction. In this example, two PESAs (PESA A and PESA B) are present. PESA A (black) is comprised of ESA1A (top strand) and EAS2A (bottom strand); and PESA B (grey) is comprised of EAS1B (top strand) and EA2B (bottom strand). Both PESAs contain a partial recognition site for an RE, in this example, Mnl I. When PESA A (top structure; left hand side) hybridizes with DF-a (white line, grey border), a cleavable CESA A complex (middle structure, left hand side) is formed which contains a complete recognition site for Mnl I (dotted black box). Cleavage of CESA A (bottom fragments, left hand side) results in an increase in fluorescence due to separation of a fluorophore, for example JOE (J), and a quencher (Q). In addition, cleavage of CESA A results in release of multiple cleavage fragments, one of which can function as a new DF-b (striped line). When PESA B (top structure; right hand side) hybridizes with DF-b, a CESA B (middle structure, right hand side) is formed which contains a complete recognition site for Mnl I (dotted grey box). Cleavage of CESA B results in an increase in fluorescence due to separation of a fluorophore, for example FAM (F), and a quencher (Q) (bottom fragments, right hand side). In addition, cleavage of CESA B results in release of multiple cleavage fragments, one of which can function as a new DF-a. Cleavage of each CESA A generates a new DF that can result in formation of a new CESA B, and cleavage of each CESA B generates a new DF that can result in formation of a new CESA A thus creating a feedback cascade. In addition to the creation of new DF at each step, the DFs already present in the mix can be recycled to form additional CESA. This strategy can be used to amplify the signal in response to target-dependent generation of either DF-a or DF-b.

Panels B and C show fluorescent results from an example of the cascade described in Panel A. Data shown represents the average of duplicates. Panel B (Reaction A) shows increases in fluorescence in both the JOE and FAM channels upon addition of DF-a to PESA A and B. The increasing signal in the JOE channel (trace labelled "(ii) JOE: CESA A+DF-a") is indicative of DF-a hybridizing to PESA A to form CESA A. CESA A was cleaved by Mnl I resulting in dissociation of the oligonucleotide fragments of EAS1A and EAS2A, which lead to separation of the JOE fluorophore from two quencher moieties. The increasing signal in the FAM channel (trace labelled "(i) FAM: CESA B+DF-a") shows that DF-b, one of the cleavage fragments of EASA2, dissociated from the cleaved CESA A and hybridized to PESA B, to produce CESA B. Cleavage of CESA B by Mnl I resulted in dissociation of the oligonucleotide fragments of EAS1B and EAS2B leading to separation of the FAM fluorophore from a quencher moiety. One of the cleavage fragments of EAS2B is a new DF-a molecule which hybridized to PESA A to produce more CESA A. This completed a feedback cascade between PESA A, PESA B, CESA A and CESA B. The delay in the increase in fluorescence in the FAM channel indicates that this reaction relies on production of DF-b from cleavage of CESA A. There was no increase in JOE or FAM fluorescence in the reaction which lacked DF-a (traces labelled "(II) No DF-a control").

Panel B (Reaction B) shows increase in fluorescence in both the FAM and JOE channels upon addition of DF-b to a reaction containing both PESA A and PESA B. The increasing signal in the FAM channel (trace labelled "(v) FAM: CESA B+DF-b") is indicative of the DF-b hybridizing to PESA B to form CESA B. CESA B was cleaved by Mnl I resulting in dissociation of the oligonucleotide fragments of EAS1B and EAS2B, which lead to separation of the FAM fluorophore and a quencher moiety. The increasing signal in the JOE channel (trace labelled "(vi) JOE: CESA A+DF-b") shows that DF-a, one of the cleavage fragments of EAS2B, dissociated from the cleaved CESA B and hybridized to PESA A to form CESA A. Cleavage of CESA A by Mnl I resulted in dissociation of the oligonucleotide fragments of EAS1A and EAS2A leading to separation of the JOE fluorophore and two quencher moieties. One of the cleavage fragments of EAS2A is a new DF-b molecule which hybridized to PESA B to form more CESA B. This completed a feedback cascade between PESA A, PESA B, CESA A and CESA B. The delay in the increase in fluorescence in the JOE channel indicates that this reaction relied on production of DF-a from cleavage of CESA B. There was no increase in JOE or FAM fluorescence in the reaction which lacked DF-b (traces labelled "(IV) No DF-b control").

In this experiment PESA A and PESA B were labelled with different fluorophores, FAM and JOE, in order to demonstrate the cascade reaction between the two CESA complexes. In other formats both PESA A and PESA B can be labelled with the same fluorophore so that the signals from cleavage of CESA A and CESA B are additive.

Figure 18:
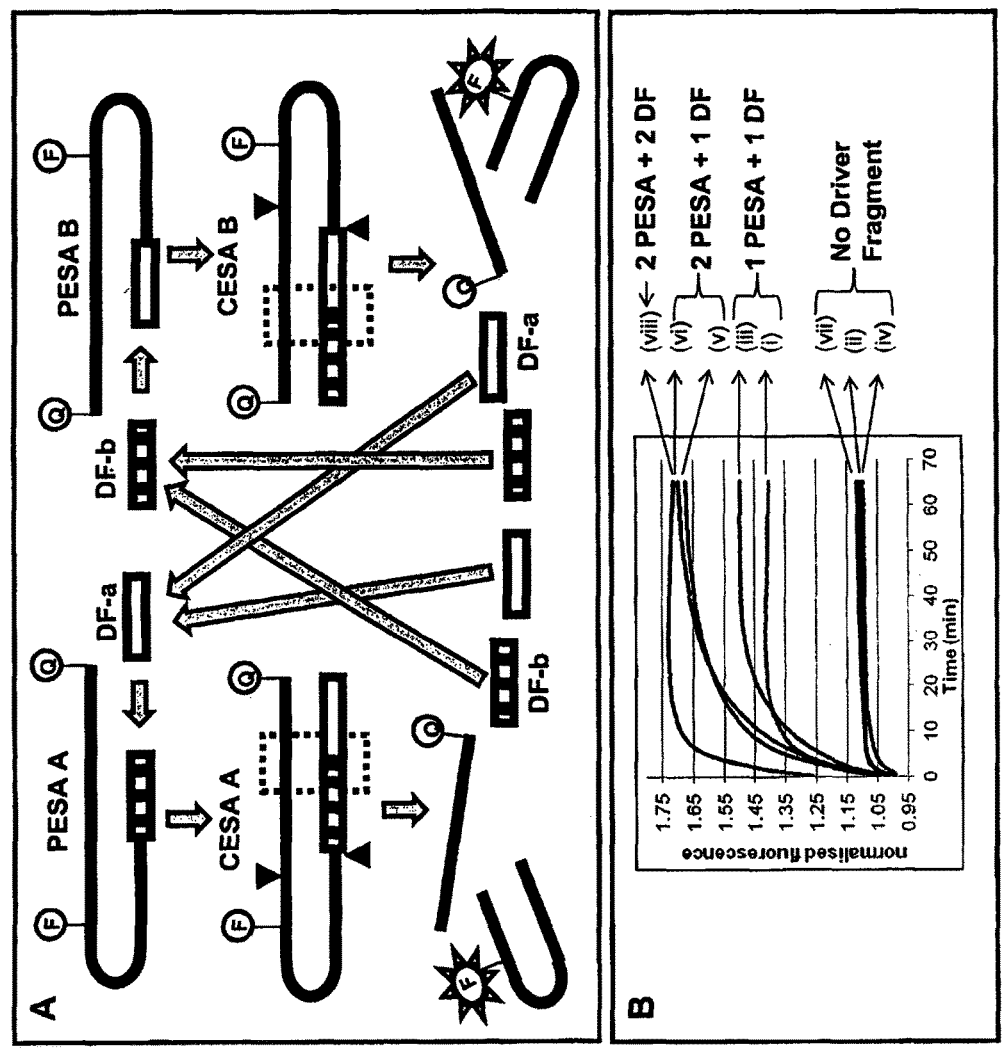

FIG. 18 Panel A illustrates a strategy for an EzyAmp feedback cascade reaction which employs ESA oligonucleotides that form hairpin PESAs. In this cascade reaction two dual labeled (fluorophore-quencher) PESA hairpin oligonucleotides are present. Both contain a partial site for a RE, in this example Mnl I. When PESA A (top structure; left hand side) hybridizes with DF-a (white line), CESA A (middle structure, left hand side) is formed which now contains a complete recognition site for Mnl I (dotted box). Cleavage of CESA A (bottom fragments, left hand side) results in an increase in fluorescence due to separation of fluorophore (F) and quencher (Q) moieties on PESA A. In addition, cleavage of CESA A results in release of multiple cleavage fragments, one of which can function as a new DF-b (striped line). When PESA B (top structure; right hand side) hybridizes with DF-b, a CESA B (middle structure, right hand side) is formed which now contains a complete recognition site for Mnl I (dotted box). Cleavage of CESA B results in an increase in fluorescence due to separation of fluorophore and quencher moieties on PESA B (bottom fragments, right hand side). In addition, cleavage of CESA B results in release of multiple, cleavage fragments, one of which can function as a new DF-a. Cleavage of each CESA A complex generates a new DF-b that can result in formation of a new CESA B, and cleavage of each CESA B complex generates a new DF-a that can result in formation of a new CESA A thus creating a feedback cascade. In addition to the creation of new DF at each step, the DFs already present in the mix can be recycled to form additional CESA. This strategy can be used to amplify the signal in response to target-dependent generation of either DF-a or DF-b.

Panel B shows the results obtained in Example 7 which uses the strategy in Panel A. In this experiment CESA A was composed of PESA A and DF-a, and CESA B was composed of PESA B and DF-b. PESA A contained a region within it which can function as DF-b, and PESA B contained a region within it which can function as DF-a. In each reaction all components were present in the one reaction chamber. RE activity was monitored by the change in fluorescence associated with cleavage of a dual labeled PESA. Fluorescence is shown as the normalized average of duplicate reactions.

The results in Panel B demonstrate that the presence of DF-a and hairpin PESA A resulted in the formation of a cleavable CESA A (Reaction (i)) as indicated by the increase in fluorescence over time. In contrast the reaction which contained PESA A in the absence of any DF (Reaction (ii)) showed no change in fluorescence over time, indicating PESA A alone is not a cleavable oligonucleotide. In Reaction (iii), the presence of DF-b with hairpin PESA B resulted in the formation of a cleavable CESA B, as indicated by the increase in fluorescence over time. In contrast, in Reaction (iv) which contained PESA B in the absence of any DF, no change in fluorescence was observed over time indicating PESA B alone is not a cleavable oligonucleotide. In Reaction (v), the presence of DF-a together with both PESA A and PESA B resulted in an almost doubling of the increase in fluorescence over time compared to Reaction (i). This is indicative of the release of DF-b from CESA A cleavage, which then formed a cleavable CESA B, which in turn cleaved and released more DF-a. This reaction represents a signal amplification feedback cascade initiated by the presence of DF-a. In Reaction (vi), the presence of DF-b with both PESA A and PESA B resulted in an almost doubling of the increase in fluorescence over time compared to Reaction (iii). This is indicative of the release of DF-a from CESA B cleavage, which then formed a cleavable CESA A which in turn released more DF-b. This reaction represents a signal amplification feedback cascade initiated by the presence of DF-b. Reaction (vii) is a negative control reaction containing PESA A and PESA B with no DF present. This reaction showed no increase in fluorescence over time indicating that no cleavable CESA structures were formed between PESA A and PESA B in the absence of DF. Reaction (viii) is a positive control reaction containing DF-a, DF-b, PESA A and PESA B at equal concentrations, such that all PESA present could form CESA and be cleaved thus giving an indication of the maximum fluorescence obtainable in the system. The final fluorescence levels at 70 minutes in Reactions (viii), (vi) & (v) were similar indicating the feedback cascades in Reactions (v) and (vi) reached completion.

Figure 19:
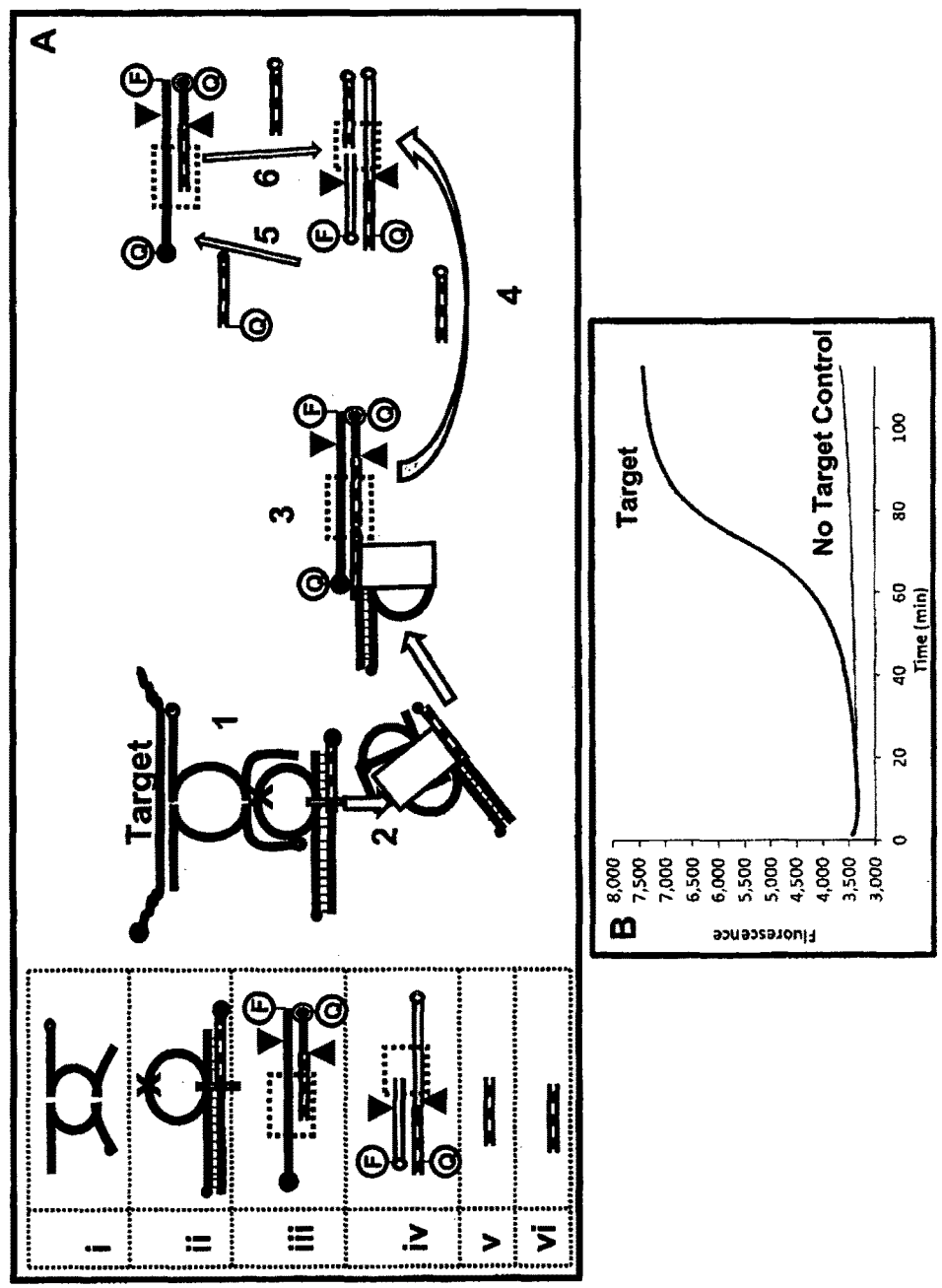

FIG. 19 Panel A illustrates an exemplary schema for an EzyAmp cascade system whereby the initiating DF sequence is not part of an MNAzyme substrate sequence. The components of this system are illustrated in the table on the left hand side of panel A. On these structures a filled in circle indicates the 5' end of each oligonucleotide; the RE recognition site is indicated as a dashed box; the restriction enzyme cleavage sites are indicated as solid arrow heads; the presence of fluorophore and quencher moieties is indicated by F and Q respectively. Structure (i) illustrates the target specific partzymes which associate in the presence of target to form an MNAzyme. Complex (ii) illustrates a substrate blocker-DF-a complex consisting of an oligonucleotide comprised partially of DF-a (as in (v)) and a second oligo referred to as a substrate blocker oligonucleotide which contains substrate sequence which is flanked by sequence that is complementary to the DF oligonucleotide. These oligos are locked by hybridization to form a double stranded oligo complex that contains a looped out region which is a substrate for the MNAzyme (substrate loop is indicated by the circular region where the grey cross (X) indicates the site of cleavage by the MNAzyme). Complex (ii) is designed such that the cleavage of the substrate loop by an MNAzyme results in dissociation of the cleaved fragment bound to DF-a, thus releasing DF-a as a single stranded extension of the longer double stranded oligo complex. Structure (iii) illustrates the first PESA (PESA A) which requires DF-a sequence to form CESA A. This PESA A contains within its sequence a region which constitutes DF-b (oligo vi) which is designed to be released following cleavage of CESA A by the RE. Structure (iv) illustrates the second PESA (PESA B) which requires DF-b to form CESA B. This PESA B contains within its sequence a region that can function as DF-a which is designed to be released following cleavage of CESA B by the RE. Structure (v) shows DF-a required to form CESA A from PESA A. Structure (vi) shows DF-b required to form CESA B from PESA B.

The scheme on the right hand side of panel A illustrates the steps in an assay of this design. In step 1, partzymes assemble on a target and form an MNAzyme designed to cleave the substrate loop of structure (ii). In Step 2, cleavage by the MNAzyme results in dissociation of the sequence complementary to DF-a thus allowing DF-a to hybridize to PESA A and form CESA A (as depicted in Step 3). In step 4, cleavage of CESA A releases DF-b. This step can also generate a concomitant increase in fluorescence if cleavage of CESA A separates fluorophore and quencher moieties. In Step 4, the released DF-b can associate with PESA B to form CESA B which is then cleavable by the RE. Cleavage of CESA B results in release of DF-a, and can also result in a concomitant increase in fluorescence if cleavage separates fluorophore and quencher moieties. In steps 5 and 6, the system forms a feedback cascade whereby CESA A and CESA B are continually formed and cleaved to release more DF-a and DF-b resulting in the formation of more CESA A and CESA B. In more complex reactions there may be multiple substrate-blocker-DF complexes each containing unique DFs designed to be released by unique MNAzymes (indicating unique targets).

Panel B shows data described in example 9, which demonstrates an MNAzyme-initiated EzyAmp reaction using the schema similar to that described in Panel A. Components in the EzyAmp reaction included; substrate-blocker oligonucleotide; DF-a oligonucleotide (which together form the substrate-blocker-DF-a complex); partzymes that can hybridize to the target and form an MNAzyme that can cleave the looped substrate; PESA A and PESA B. PESA A was composed of EAS1A and EAS2A, where ESA2A includes sequence that can function as DF-b. PESA B was composed of EAS1B and EAS2B, where ESA2B includes sequence that can function as DF-a. All components of the reactions were present in a single reaction chamber and either contained target (Target) or lacked target (No Target Control). Signal amplification was monitored by an increase in FAM fluorescence following cleavage of EAS1A and EAS1B leading to separation of FAM and quencher moieties. MNAzyme cleavage of the looped substrate in the presence of target resulted in partial dissociation of the double stranded substrate blocker-DF-b oligonucleotide complex. The DF-a portion of the dissociated complex hybridised with PESA A resulting in the formation of CESA A, which was then cleaved by Mnl I. This in turn released DF-b allowing the formation of CESA B, resulting in cleavage of CESA B by Mnl I, thus releasing more DF-a to complete a feedback cascade between CESA A and CESA B.

In contrast, the reaction which lacked target (No Target Control) did not show an exponential increase in fluorescence over time (only low level of fluorescence drift was observed after 80 minutes). This indicates that target was required to initiate MNAzyme cleavage of looped substrate in order to release DF-a which, in turn, initiated the subsequent EzyAmp cascade reaction.

Figure 20:
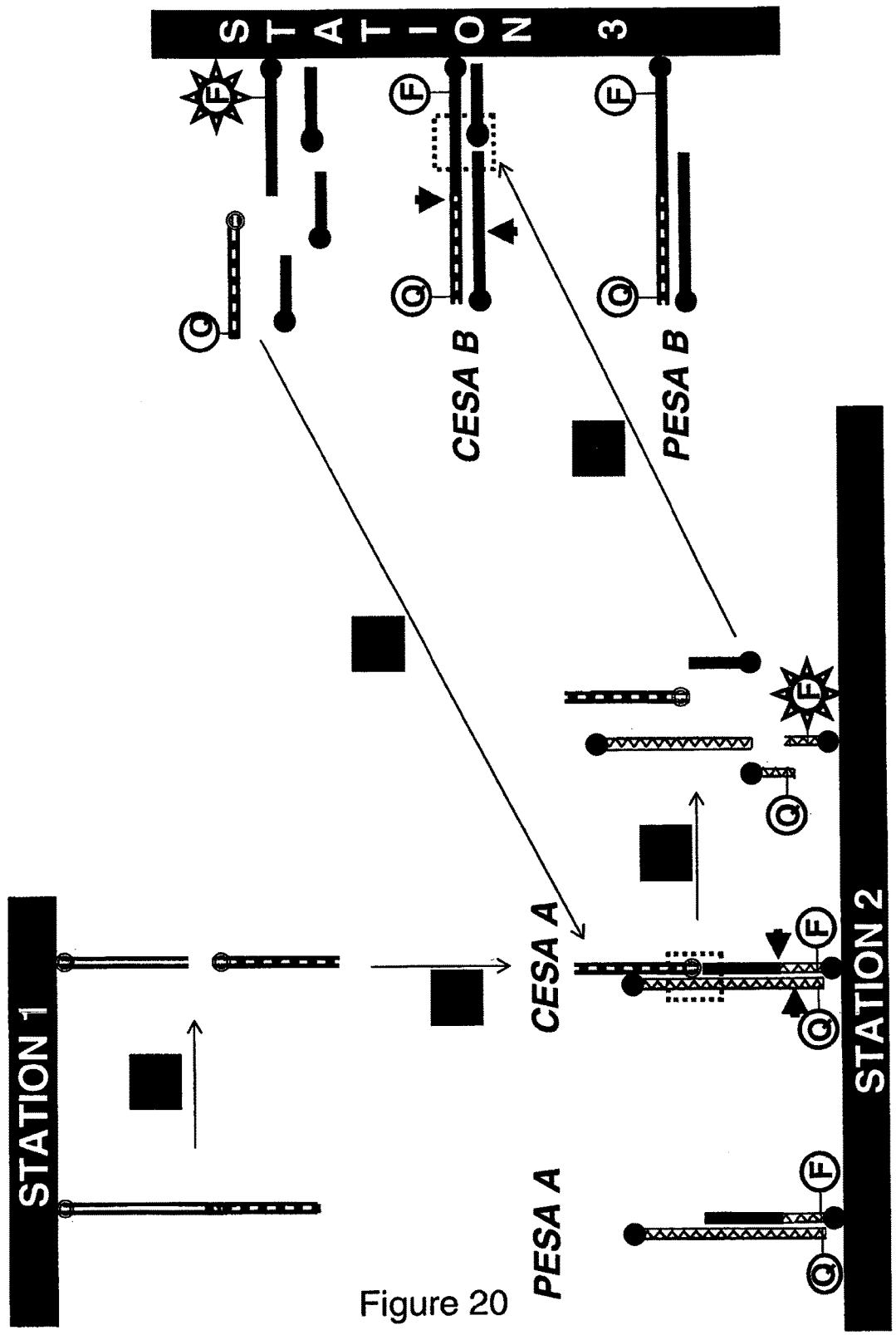

FIG. 20 illustrates an exemplary schema for an EzyAmp system containing multiple CESA complexes which are tethered to solid supports. The components of this system are illustrated as follows: the filled in circles indicate the 5' end of each oligonucleotide; the RERS is indicated as a dashed box; the cleavage sites are indicated as solid arrows. Station 1 illustrates a tethered oligonucleotide (MNAzyme substrate or SIO) which, when cleaved in a target-dependent manner (step 1—for example using an MNAzyme to cleave an MNAzyme sustrate), would result in release of a first DF (striped line). This DF could then migrate to the tethered PESA A at Station 2 and hybridize to form CESA A (step 2). Cleavage of CESA A by a RE (step 3) would release a second DF (solid black line) which could migrate to PESA B at Station 3. If the second DF hybridizes with PESA B, the CESA B would be formed (step 4). Cleavage of CESA B by a RE would result in release of a sequence capable of functioning as the first DF (striped line). This first DF could then migrate to Station 2 (step 5) and form more CESA A which could be cleaved to release more of the second DF. In this way a cascade reaction could be initiated allowing for continual formation and cleavage of CESA A and CESA B (steps 3, 4 and 5). If the PESA were labeled with fluorophore (F) and quencher (Q) moieties, cleavage of the EAS between theses moieties could generate florescent signal. This signal could be retained on the solid surface at Station 2 or 3 (as illustrated in this figure) or could be released in solution, for example if the locations of the fluorophore and quencher moieties were reversed.

Figure 21:
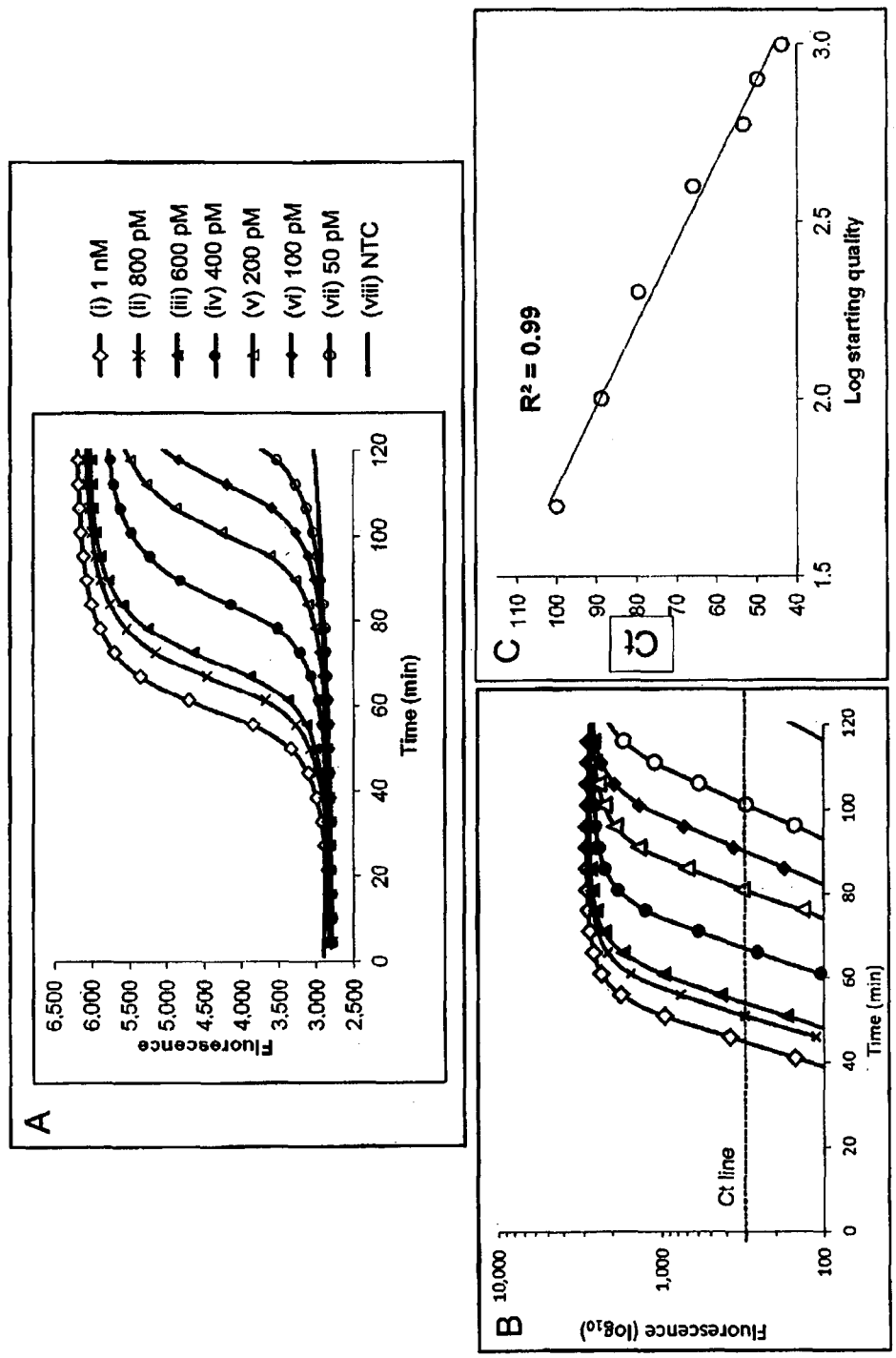

FIG. 21 shows the results of EzyAmp target titration described in Example 11. These reactions were initiated by target-dependent cleavage of a substrate by an MNAzyme to produce a DF followed by signal amplification using an EzyAmp feedback cascade which contained two PESA complexes, each of which produced a DF for the other. All steps were performed in a single tube. Panels A and B show the change in fluorescence over time (linear and log plots respectively) in MNAzyme-initiated EzyAmp reactions containing decreasing concentrations of target (i to vii). The change in fluorescence over time increased exponentially in reactions containing target. Reaction (viii) is a no target control (NTC). Panel C shows a standard curve generated by plotting the concentration of target against Ct, where Ct is the time point at which that concentration reached the detection threshold. The relationship between the Ct and the log of the target concentration displays a line with a regression value of 0.99.

FIG. 22 illustrates an exemplary method for localising EzyAmp components by incorporating PESA complexes into branched structures. Panel A illustrates the first basic Building Blocks required to form a branched structure which could consist of (i) a first oligonucleotide (Building Block 1) containing (from 5' to 3') EAS1B, backbone 1 and EAS2A; (ii) a second oligo EAS1A which would be complementary to EAS2A and where (i) and (ii) could hybridize to form PESA A; and (iii) a third oligo EAS2B which would be complementary to ESA1B and where (i) and (iii) could hybridize to form PESA B. Panel B illustrates a fourth oligo which could constitute Building Block 2 (iv) consisting of (from 5' to 3') EAS1B, backbone 2 and EAS2A; (ii) a second oligo EAS1A which would be complementary to EAS2A and where (i) and (ii) could hybridize to form PESA A; and (iii) a third oligo EAS2B which would be complementary to ESA1B and where (i) and (iii) could hybridize to form PESA B. Backbone 1 could be complementary to backbone 2. This would result in formation of a branched complex containing the Building Blocks 1 and 2. Each building block would have EAS1A and EAS2B bound such that the complex would contain two PESA A and two PESA B. Building Blocks 1 and 2 could be labelled with fluorophores (F) and the second and third oligos of each Building Block could be labelled with quenchers (Q) positioned such that, upon binding with the Building Blocks 1 & 2, the fluorescence from the labels on these oligos could be quenched.

Panel C illustrates the steps in an EzyAmp cascade which could use the branched complex, as illustrated in Panel B, following the generation of DF-a in a target-specific manner. In step 1, hybridization of DF-a to PESA A (e.g. on building block 1) would result in the formation of CESA A at this location. In step 2, cleavage of CESA A by a restriction enzyme (e.g. Mnl I) would result in dissociation of the EAS1A cleavage fragments causing an increase in fluorescence due to separation of the fluorophore and quencher and the generation of DF-b. In step 2 hybridization of DF-b to the EAS1B region of Building Block 1 or 2 would lead to the formation of CESA B. In step 3, cleavage of CESA B by a restriction enzyme (e.g. Mnl I) would result in dissociation of the EAS2B cleavage fragments causing an increase in fluorescence and the generation of DF-a. These steps could then be repeated on the same complex or another similar complex. The process could continue until all building blocks had been cleaved. Alternatively, a similar cascade could be initiated via the generation of DF-b in a target-specific manner.

The complexity of the branched structure can be increased by several strategies. By way of example, if the 5' ends of EAS1A were biotinylated then structures as shown in Panel D could be formed by incubation of the building blocks with Avidin. This would result in the tethering together of building block complexes through Avidin molecules. This branched structure and variants thereof (through addition of biotin or other tethering molecules on any oligo component) would allow for the localisation of released DF with PESA complexes.

Figure 23:
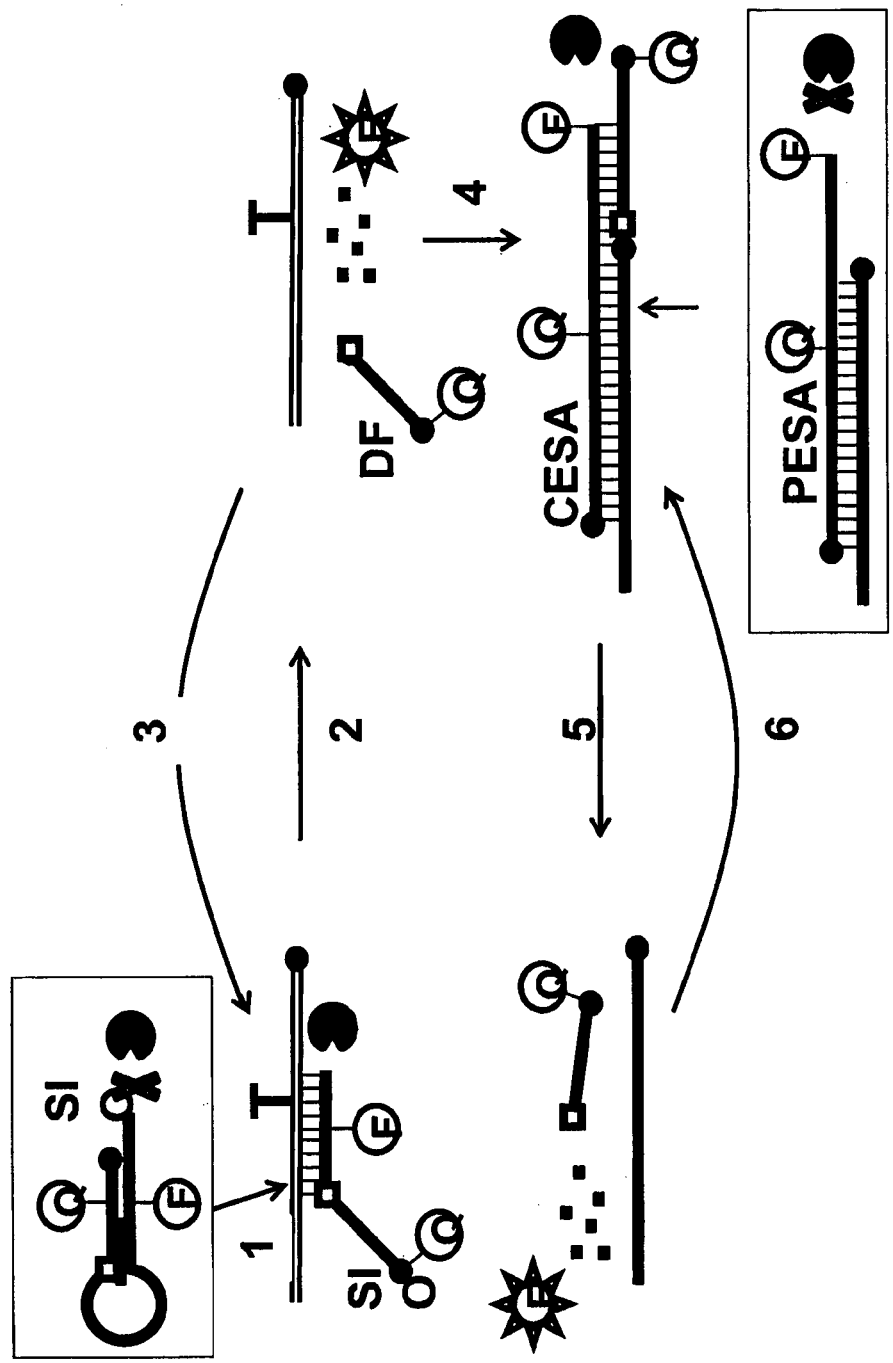

FIG. 23 is an exemplary schema of an EzyAmp reaction where the signal amplification could be initiated and mediated by Exonuclease III (Exo III). This enzyme is known to remove nucleotides from 3' hydroxyl termini of DNA duplexes when the termini are either blunt or recessed. The enzyme does not digest single stranded oligos, including duplexes with a 3' overhang with at least 5 bases. The presence of a phosphorothioate nucleotide (indicated by a hollow square on oligos) is known to block exonuclease activity. The striped grey lines represent the DNA target (T) and the solid black lines represent a Synthetic Initiator Oligo (SIO) which would be added to the mix to facilitate generation of a DF. An SIO, which could be labeled with a fluorophore (F) and a quencher (Q), is represented in a hairpin conformation with an overhanging 3' terminus. Exo III cannot digest the SOI prior to a target binding as it contains a 3' overhang of more than five bases. The phosphorothioate nucleotide in the SIO would prevent hydrolysis from this position onwards, thus leaving the DF intact. The closed circles represent the 5' ends of the SIO, PESA and CESA oligos. The solid grey lines represent a PESA with two 3' overhanging ends comprising at least 5 bases. The PESA is represented as two oligos (EAS1 and EAS2) where EAS1 is labeled with a fluorophore and a quencher. Exo III cannot digest the PESA prior to binding of a DF as the 3' ends of the PESA contain a 3' overhang of more than five bases.

The EzyAmp reaction would have the following steps: In step 1 the SIO could bind to a complementary region of the target and in step 2 the now recessed 3' end of the SIO would be hydrolyzed by Exo III up to the phosphorothioate base, thus releasing an intact DF and causing an increase in fluorescence. The DF would correspond to the 5' portion of the SIO which was not complementary to the target. The target, which would no longer be bound to the SIO, would then be free to be recycled to bind with another SIO and thus generate another DF (step 3). The DF could then bind to EAS1 of the PESA (step 4) and form a CESA in which the 3' end of EAS1 would now be recessed. Exo III could then hydrolyze the EAS1 strand of the CESA (step 5) causing an increase in fluorescence and release of the DF. The DF would now be free to be recycled (step 6) to convert more PESA to CESA.

Figure 24:
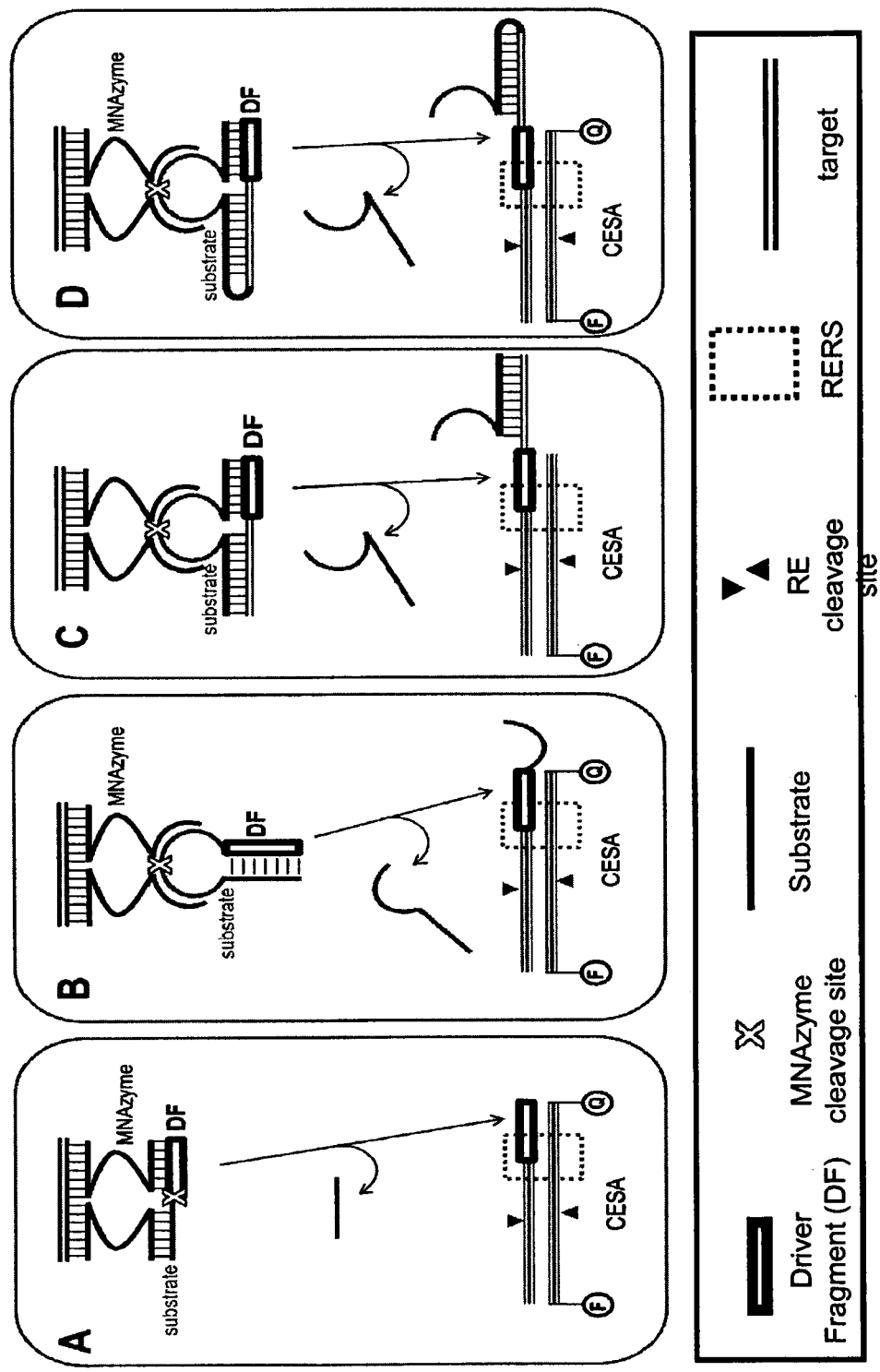

FIG. 24 is an exemplary schema illustrating various methods for generating Driver Fragments (DFs) using target-dependent MNAzymes. DFs are represented as white lines with a black outline; the MNAzyme substrate cleavage sites are represented as a cross; the oligos containing substrate sequences are represented as grey lines; the RE cleavage sites are represented as arrowheads; the RERS are presented as dotted boxes; the targets are represented as a black and white striped line; PESA oligonucleotides that can combine with the DF to form a CESA are represented as striped grey lines; and the MNAzymes are represented as solid black lines.

Panel A illustrates the generation of DF via the direct cleavage of an MNAzyme substrate, where the DF sequence is part of the substrate sequence. In the presence of target a catalytically active MNAzyme assembles and cleaves its substrate. One fragment of the cleaved substrate binds with a PESA where it functions as a DF and results in formation of a CESA. The fully assembled CESA can then be cleaved by a RE. Examples 2, 4 and 11 demonstrate the use of this strategy to generate a DF.

Panel B illustrates a method which would allow generation of DF via the cleavage of an MNAzyme substrate, where the DF sequence was not within the part of the substrate sequence that is recognized by the MNAzyme, but was still contained within the same oligonucleotide as the substrate. The substrate-containing oligonucleotide could form a hairpin structure such that the region of the substrate which would be recognized by the MNAzyme would form the loop of the hairpin and the DF would be locked by hybridization within the stem of the hairpin. In the presence of target, a catalytically active MNAzyme would assemble and cleave its substrate. The cleavage of the substrate would disrupt the hairpin, leading to the dissociation of the stem and thus separation of the cleaved fragments. One of the cleaved fragments could bind with a PESA where it could function as a DF and result in the formation of a CESA. The fully assembled CESA could then be cleaved by a RE.

Panel C illustrates the generation of DF via the MNAzyme cleavage of a double stranded substrate-blocker-DF complex. In this complex, the DF sequence is not part of the substrate sequence recognized by the MNAzyme and is not contained within the same oligonucleotide as the substrate. The DF is contained within a second oligo that hybridizes with the substrate oligo. In the substrate oligo a sequence which can be recognized as an MNAzyme substrate is flanked by additional sequence that is complementary to the DF oligo. This oligo, which serves both as a substrate and to bind (hence block) the DF, is termed a substrate-blocker oligo. The sequence within the substrate-blocker oligo, which is recognized by the MNAzyme, is not complementary to the DF oligonucleotide and therefore this substrate sequence is looped out. In the absence of target, the formation of the double stranded substrate-blocker-DF complex is favoured, preventing the DF from interacting with the PESA. In the presence of target, a catalytically active MNAzyme assembles and cleaves the substrate loop. Cleavage of the substrate loop results in the dissociation of the portion of the substrate-blocker oligo that was bound to the DF, hence releasing the DF so that it can bind with a PESA to form a CESA. The fully assembled CESA can then be cleaved by a RE. Example 9 demonstrates the use of this strategy to generate a DF.

Panel D illustrates the generation of a DF via the MNAzyme cleavage of a hair-pinned substrate-blocker-DF complex. In this complex, the DF sequence is not part of the substrate sequence recognized by the MNAzyme although it is still contained within the same oligonucleotide as the substrate. The hair-pinned substrate-blocker-DF complex is similar to the double stranded substrate-blocker-DF complex described in Panel C except there is now a linking sequence between the substrate-blocker oligo and the DF oligo resulting in the formation of a hairpin. In the absence of target, the formation of the substrate-blocker-DF hairpin structure is favoured, preventing the DF from interacting with the PESA. In the presence of target a catalytically active MNAzyme assembles and cleaves the looped substrate portion. The cleavage of the substrate loop results in the dissociation of the stem portion bound to the DF. The single stranded DF sequence can now bind to a PESA to form a CESA. The fully assembled CESA can then be cleaved by a RE. Example 14 demonstrates the use of this strategy to generate a DF.

Figure 25:
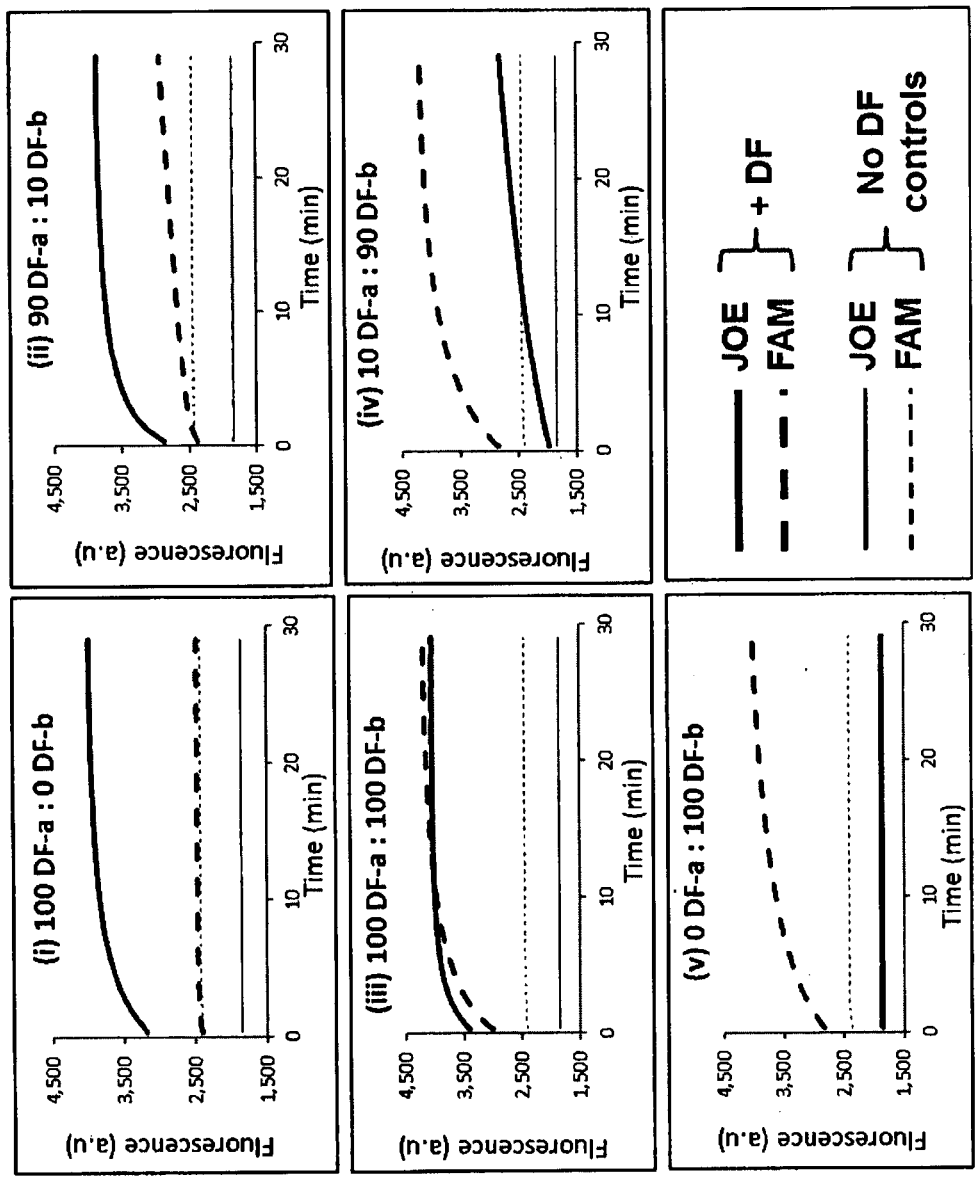

FIG. 25 demonstrates the multiplex analysis where two EzyAmp reactions occur simultaneously in a single tube and are monitored independently. Reactions were initiated with either DF-a and/or DF-b in the presence of both PESA A and PESA B. Binding of DF-a to PESA A results in formation of CESA A, which when cleaved, generates an increase in JOE fluorescence (thick solid black line). Binding of DF-b to PESA B results in formation of CESA B which when cleaved generates an increase in FAM fluorescence (thick dashed black line). Test reactions contained 100 nM of each PESA and either (i) 100 nM DF-a, (ii) 90 nM DF-a and 10 nM DF-b, (iii) 100 nM DF-a and 100 nM DF-b, (iv) 10 nM DF-a and 90 nM DF-b or (v) 100 nM DF-b. Control reactions contained no DF and are indicated by solid thin lines (JOE) or dashed thin lines (FAM). The increase in fluorescence for FAM and/or JOE is plotted against time. In reaction (i) there was an increase in JOE fluorescence but no increase in FAM fluorescence indicating that DFa only allowed the formation of PESA A. In reaction (v), there was an increase in FAM fluorescence but no increase in JOE fluorescence indicating that DF-b only allowed the formation of PESA B. In reactions (ii), (iii) (iv) & (v) there was an increase in both FAM and JOE fluorescence indicating the cleavage of both CESA A and CESA B when both DF-a and DF-b were present and the strength of the fluorescence signal was related to the concentration of the DF used.

Figure 26:
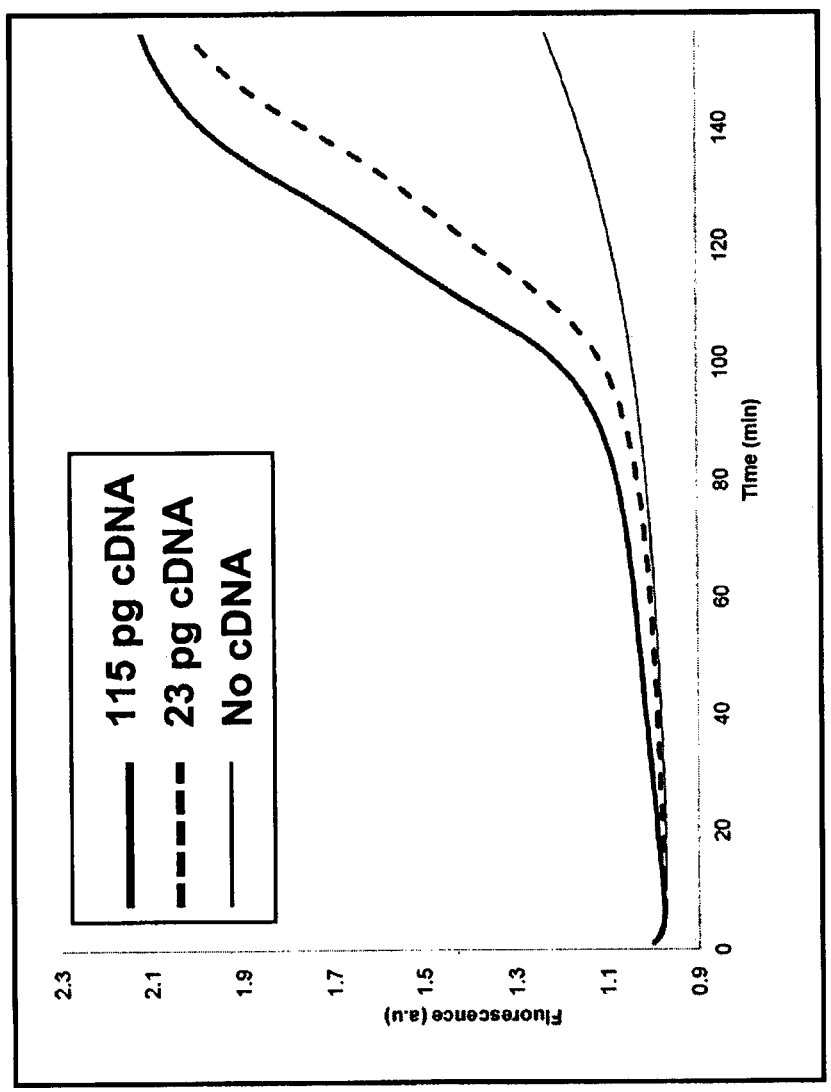

FIG. 26 illustrates an MNAzyme-initiated EzyAmp reaction, which allowed detection of a human cDNA target (PPIA cDNA). The EzyAmp signal amplification resulted from Mnl I cleavage of multiple CESA which formed a feedback loop. In this, example both the initiation and signal amplification were monitored by observing cumulative changes in fluorescence generated by (i) the target dependent MNAzyme cleavage of a reporter MNAzyme substrate and (ii) cleavage of CESA A and CESA B following the production of a DF-a from cleavage of the MNAzyme substrate. The figure shows normalised fluorescence plotted over time. At 150 minutes a strong fluorescent signal was observed in the reactions containing 115 pg (thick solid black line) and 23 pg (dashed line) of cDNA, compared to only low level in fluorescence in the absence of cDNA (thin line).

Figure 27:
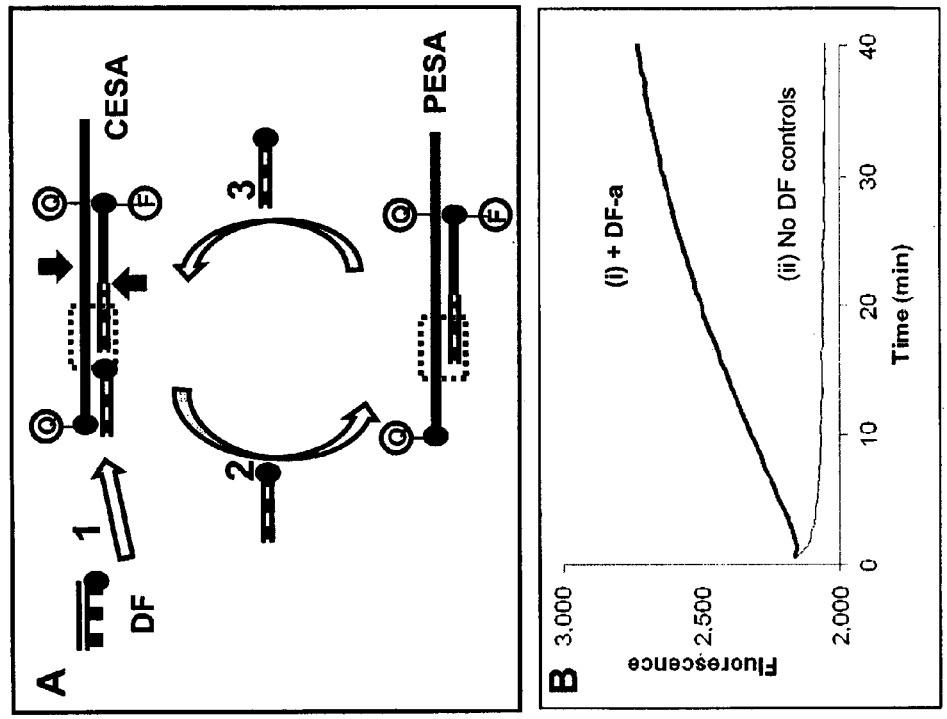

FIG. 27 illustrates an exemplary strategy for cleavage of a CESA by a RE, Mnl I. The CESA is designed to generate a DF capable of binding to a PESA to form the same CESA (Panel A). The CESA (top complex, Panel A) is composed of a PESA (bottom complex, Panel A) and a DF (indicated by striped black line). The circle on each of the lines indicates the 5' end of each oligo. The RERS is indicated as a dashed box and the RE cleavage sites are indicated as vertical solid arrows. The presence of fluorophore and quencher moieties are indicated by F and Q respectively.

Panel A illustrates the strategy where cleavage of a CESA could generate DF for its corresponding PESA. The PESA is composed of EAS1 and EAS2 whereby the EAS2 contains a sequence within it which can function as the DF once cleaved from EAS2. Target-dependent generation of an initial DF and subsequent binding to the PESA would result in the formation of a CESA (Step 1). The CESA could then be cleaved by a RE leading to the dissociation of the cleaved fragments including the fragment that can function as a DF (Step 2). This fragment could then bind to another PESA to act as a DF allowing the formation of more CESA (Step 3).

Panel B shows the increase in fluorescence corresponding to the MnlI cleavage of the CESA illustrated in Panel A. An increase in fluorescence was observed over time in the presence of the DF (i). In contrast, no increase in fluorescence was observed in the control reaction where no DF was added (ii). This indicates that the DF is required to form a CESA which is cleaved by the RE. The cleavage of CESA results in the dissociation of fragments, one of which contains a shortened version of the original DF.

DEFINITIONS

Certain terms and phrases are used herein which shall have the meanings set forth as follows.

As used in this application, the singular form "a", "an" and "the" include plural references unless the context clearly dictates otherwise. For example, the term "an MNAzyme" or a "Complete Enzyme Signal Amplifier complex" or a "Partial Enzyme Signal Amplifier complex" also include a plurality of MNAzymes or Complete Partial Enzyme Signal Amplifier complexes or Partial Enzyme Signal Amplifier complexes, respectively. Unless the context requires otherwise or specifically stated to the contrary, integers, steps, or elements of the invention recited herein as singular integers, steps or elements clearly encompass both singular and plural forms of the recited integers, steps or elements.

The term "comprising" means "including principally, but not necessarily solely". Furthermore, variations of the word "comprising", such as "comprise" and "comprises", have correspondingly varied meanings. Thus, for example, a method "comprising" a given step may consist exclusively of that step, or, may include one or more additional steps.

"Complete Enzyme Signal Amplifier complex", "CESA complex", and "CESA" are used interchangeably herein and have the same meaning. A CESA complex as referred to herein is a multi-oligonucleotide complex which can be recognised and cleaved by an enzyme (e.g. a nuclease), and contains an enzyme recognition sequence/site and an enzyme cleavage sequence/site. The enzyme may be, for example, a nuclease (e.g. a restriction enzyme, an exonuclease or an endonuclease). The enzyme cleavage sequence/site may be internal to, external to, or overlap with, the enzyme recognition sequence/site. A CESA complex referred to herein comprises at least two Enzyme Amplifier Substrate (EAS) oligonucleotides and at least one Driver Fragment (DF), each as defined below. At least a portion of one EAS oligonucleotide of the CESA complex is complementary to at least a portion of another EAS oligonucleotide in the complex. In addition, at least a portion of one of said EAS oligonucleotides is also complementary to at least a portion of at least one DF. The DF may contribute one or more bases to the enzyme recognition sequence/site and/or the enzyme cleavage sequence/site, although it need not necessarily do so. It will be noted that a CESA complex herein may be referred to numerically, such as for example, a "first" CESA complex, a "second" CESA complex, a "third" CESA complex and so on, without departing from the meaning set out above.

"Enzyme Amplifier Substrate oligonucleotide", "Enzyme Amplifier Substrate (EAS) oligonucleotide", "EAS oligonucleotide", "EAS oligo", and "EAS" are used interchangeably herein and have the same meaning. An EAS oligonucleotide referred to herein is an oligonucleotide wherein at least a portion of the oligonucleotide is complementary to at least a portion of another EAS oligonucleotide, such that hybridisation occurs between the two under appropriate conditions. An EAS oligonucleotide may optionally comprise at least one portion that is complementary to at least a portion of a Driver Fragment (DF) as defined below. EAS oligonucleotides may be components of a complex such as, for example, CESA complexes and Partial Enzyme Signal Amplifier (PESA) complexes (as defined below). It will be noted that an EAS oligonucleotide herein may be referred to numerically, such as for example, a "first" Enzyme Amplifier Substrate oligonucleotide (EAS1), a "second" Enzyme Amplifier Substrate oligonucleotide (EAS2), a "third" Enzyme Amplifier Substrate oligonucleotide (EAS3) and so on without departing from the meaning set out above. In some embodiments, an EAS oligonucleotide may be joined to another EAS oligonucleotide by a linker. For example, an EAS1 and an EAS2 may exist within the same oligonucleotide, where they are joined by a linking nucleic acid sequence which may allow the formation of a hairpin structure.

"Partial Enzyme Signal Amplifier complex", "Partial Enzyme Signal Amplifier (PESA) complex", "PESA complex" and "PESA" are used interchangeably herein and have the same meaning. A PESA complex as referred to herein is a multi-oligonucleotide complex that comprises at least two Enzyme Amplifier Substrate (EAS) oligonucleotides, wherein at least a portion of one EAS oligonucleotide is complementary to at least a portion of another EAS oligonucleotide in the complex. In addition, at least a portion of one of said EAS oligonucleotides is also complementary to at least a portion of at least one DF (as defined below). Despite having the capacity to hybridise to a DF, the DF is not hybridised to and thus not a component of the PESA complex. A PESA complex comprises at least a partial recognition sequence/site and/or at least a partial cleavage sequence/site for an enzyme, and may contain a full recognition sequence/site and/or a full cleavage sequence/site for an enzyme. The enzyme may be, for example, a nuclease (e.g. a restriction enzyme, an exonuclease or an endonuclease). In some embodiments, two EAS oligonucleotides of a PESA complex may be joined by a linker. For example, the two EAS oligonucleotides may exist within the same oligonucleotide, where they are joined by a linking nucleic acid sequence in the form of a hairpin structure. It will be noted that a PESA complex herein may be referred to numerically, such as for example, a "first" PESA complex, a "second" PESA complex, a "third" PESA complex and so on, without departing from the meaning set out above.

"Driver fragment oligonucleotide", "Driver Fragment (DF) oligonucleotide", "driver fragment oligo", "DF oligonucleotide", "DF oligo", and "DF" are used interchangeably herein and have the same meaning. A DF oligonucleotide referred to herein is an oligonucleotide wherein at least a portion of the oligonucleotide is complementary to at least a portion of at least one EAS oligonucleotide such that hybridisation occurs between the two under appropriate conditions. A DF oligonucleotide may or may not be a target molecule (e.g. nucleic acid) to be detected by a method of the present invention. A DF oligonucleotide may be a component in a complex such as, for example, a CESA complex. In such cases, a DF oligonucleotide may contribute one or more nucleotides to an enzyme recognition sequence/site and/or an enzyme cleavage sequence/site that may be present in the complex, although it need not necessarily do so. The enzyme may be, for example, a nuclease (e.g. a restriction enzyme, an exonuclease or an endonuclease). It will be noted that a DF oligonucleotide herein may be referred to numerically, such as for example, a "first" DF, a "second" DF, a "third" DF and so on, without departing from the meaning set out above.

A "Synthetic Initiator Oligo" or "SIO" is an oligonucleotide that can hybridise to a target nucleic acid in a sample and thereby form a substrate amenable to cleavage by a nuclease, such that this cleavage produces a shorter oligo that can function as a Driver Fragment (DF). The SIO may function as an Inhibitory Fragment (Inf) prior to its cleavage by the nuclease. The SIO may be comprised of one or multiple oligonucleotides in a partial or fully double stranded conformation. An SIO with multiple oligonucleotides is referred to herein as a "SIO complex". It will be noted that an SIO herein may be referred to numerically, such as for example, a "first" SIO, a "second" SIO, a "third" SIO and so on, without departing from the meaning set out above.

An "Enzyme Inhibitory Complex" or "EIC" is a complex formed by two or more complementary nucleic acid fragments or oligonucleotides which form a duplex not amenable to cleavage by an enzyme due to the presence of additional sequence which disrupts the formation of a duplex structure amenable to cleavage by an enzyme. In one embodiment the EIC comprises an EAS1, an EAS2 and an Inhibitory Fragment (InF). In another embodiment the EIC comprises a PESA and an InF. In a further embodiment the InF comprises sequences useful as a DF but has additional nucleotides which prevents formation of a duplex CESA amenable to cleavage. In further embodiments the InF is an oligonucleotide which can be cleaved only in the presence of a target analyte, into smaller oligonucleotide fragments which can function as DFs to complete the assembly of a CESA. In some embodiments the InF may be a "Synthetic Initiator Oligo" or "SIO" which can be cleaved to produce a DF by a nuclease only in the presence of a target. In other embodiments the InF may be an "MNAzyme substrate" which can be cleaved to become a DF by an MNAzyme only in the presence of a target. In some embodiments cleavage of an InF is dependent on a nucleic acid enzyme or aptazyme. In some embodiments the nucleic acid enzyme or aptazyme comprises an MNAzyme. In other embodiments the cleavage is mediated by a protein enzyme. In some embodiments the enzyme is an endonuclease. In some embodiments the enzyme is an exonuclease. In yet other embodiments cleavage is achieved by chemical means.

An "Ezy-amp" or EzyAmp" reaction is a process whereby target-dependent cleavage of a CESA by a nuclease facilitates generation and/or amplification of a signal wherein the signal is indicative of the presence of the target. An EzyAmp reaction may contain one or more PESA and CESA complexes. In some embodiments, the formation of multiple CESA from multiple PESA complexes can form a feedback loop whereby binding of a first DF (produced from a target-dependent event) to a first PESA forms a first CESA, cleavage of the first CESA releases a second DF which binds to a second PESA forming a second CESA, and cleavage of the second CESA releases a first DF capable of binding the first PESA to form another first CESA. The first CESA may then be cleaved producing another second DF which can bind to another second PESA forming another second CESA, and so on. A detectable signal may be generated upon each cleavage of the first and/or second CESA, thus providing a means of amplifying a signal derived from a single target-dependent event. It will be understood that an EzyAmp reaction as referred to herein encompasses both linear and feedback signal amplication cascades.

An "enzyme" refers to any molecule which can catalyze a chemical reaction. "Catalytic protein", "catalytic amino acid", and "protein enzyme", have the same meaning and are used interchangeably herein to describe a molecule composed of chains of amino acids that recognizes a substrate and catalyzes a chemical modification. An enzyme may recognize another enzyme, aptamer, molecule, or nucleic acid to cleave, to add, or to modify a bond.

"Catalytic nucleic acid molecule", "catalytic nucleic acid", "nucleic acid enzyme" and "catalytic nucleic acid sequence" have the same meaning and are used interchangeably herein to describe a DNA molecule or DNA-containing molecule (also known in the art as a "DNA enzyme", "deoxyribozyme" or "DNAzyme") or an RNA or RNA-containing molecule (also known in the art as a "RNA enzyme" or "ribozyme") or an "MNAzyme", all of which recognizes a substrate and catalyzes the chemical modification of the substrate. The nucleotide residues in MNAzymes, Apta-MNAzymes, DNAzymes, ribozymes, aptazymes, EASs, CESA complexes, PESA complexes, SIOs, Driver Fragments or Inhibitory Fragments may include the bases A, C, G, T, and U, as well as derivatives or analogues thereof examples of which are listed in Table 1. One or more components of MNAzymes, Apta-MNAzymes, DNAzymes, ribozymes, aptazymes, EASs, CESA complexes, PESA complexes, SIOs, Driver Fragments or Inhibitory Fragments may be attached to solid supports which may include, but are not limited to beads, chips, arrays, microcarriers, nanocarriers, encoded microcarriers, encoded nanocarriers.

The term "derivative" when used in relation to a nucleic acid or nucleotide of the present invention includes any functionally equivalent nucleic acids or nucleotides, including any fusion molecules produced integrally (e.g., by recombinant means) or added post-synthesis (e.g., by chemical means). Such fusions may comprise oligonucleotides of the invention with RNA or DNA added thereto or conjugated to a polypeptide (e.g., puromycin or other polypeptide), a small molecule (e.g., psoralen) or an antibody.

The term "analogue" when used in relation to a nucleic acid or nucleotide of the present invention includes a compound having a physical structure that is related to a DNA or RNA molecule or residue, and may be capable of forming a hydrogen bond with a DNA or RNA residue or an analogue thereof (i.e., it is able to anneal with a DNA or RNA residue or an analogue thereof to form a base-pair), but such bonding is not so required for said compound to be encompassed within the term "analogue". Such analogues may possess different chemical and biological properties to the ribonucleotide or deoxyribonucleotide residue to which they are structurally related. Methylated, iodinated, brominated or biotinylated residues are examples of analogues. Active DNAzymes have been described which contain nucleotide analogues, including deoxyinosine, C-5-immidazole deoxyuridine, 3-(aminopropynyl)-7-deaza-dATP, 2'-O-methyl RNA, 2'O-methyl cap. Other analogues could also be compatible with catalytic activity of DNAzymes and MNAzymes. Alteration of a nucleic acid with catalytic activity, for example by substitution of one base for another, by substitution of an analogue for a base, or alteration of the sugar component or phosphodiester backbone, can be straight forward for the skilled artisan. For example, alterations can be made during synthesis or by modification of specific bases after synthesis. Empirical testing of catalytic nucleic acids incorporating alterations such as base changes or base analogues allows for assessment of the impact of the altered sequences, or specific analogues, on catalytic activity. Analogues of the bases A, C, G, T and U are known in the art, and a subset is listed in Table 1. Examples of analogues which can inhibit nuclease digestion are also well known in the art. Such analogues can be strategically placed within oligonucleotides to prevent cleavage by an exonuclease and/or an endonuclease. By way of example, S, stereoisomer of the phosphorothioate linkage is known to greatly inhibit cleavage of many nucleases including Lambda Exonuclease, T7 Exonuclease, Exonuclease III (*E. coli*), Exonuclease. I (*E. coli*), Exonuclease T and RecJ. Inclusion of multiple phosphorothioate linkages can be highly effective in blocking nuclease activity.

TABLE 1

Examples of Nucleotide Analogues

| Abbreviation | Name |
| --- | --- |
| ac4c | 4-acetylcytidine |
| chm5u | 5-(carboxyhydroxylmethyl)uridine |
| Cm | 2'-O-methylcytidine |

TABLE 1-continued

Examples of Nucleotide Analogues

| Abbreviation | Name |
|---|---|
| Cmnm5s2u | 5-carboxymethylaminomethyl thiouridine |
| D | Dihydrouridine |
| Fm | 2'-O-methylpseudouridine |
| Galq | beta, D-galactosylqueosine |
| Gm | 2'-O-methylguanosine |
| I | Inosine |
| i6a | N6-isopentyladenosine |
| m1a | 1-methyladenosine |
| m1f | 1-methylpseudouridine |
| m1g | 1-methylguanosine |
| ml1 | 1-methylinosine |
| m22g | 2,2-dimethylguanosine |
| m2a | 2-methyladenosine |
| m2g | 2-methylguanosine |
| m3c | 3-methylcytidine |
| m5c | 5-methylcytidine |
| m6a | N6-methyladenosine |
| m7g | 7-methylguanosine |
| mam5u | 5-methylaminomethyluridine |
| mam5s2u | 5-methoxyaminomethyl-2-thiouridine |
| Manq | beta, D-mannosylmethyluridine |
| mcm5s2u | 5-methoxycarbonylmethyluridine |
| mo5u | 5-methoxyuridine |
| ms2i6a | 2-methylthio-N6-isopentenyladenosine |
| ms2t6a | N-((9-beta-ribofuranosyl-2-methylthiopurine-6-yl)carbamoyl)threonine |
| mt6a | N-((9-beta-ribofuranosylpurine-6-yl)N-methylcarbamoyl)threonine |
| Mv | Uridine-5-oxyacetic acid methylester |
| o5u | Uridine-5-oxyacetic acid (v) |
| Osyw | Wybutoxosine |
| P | Pseudouridine |
| PS | phosphothioate |
| Q | Queosine |
| s2c | 2-thiocytidine |
| s2t | 5-methyl-2-thiouridine |
| s2u | 2-thiouridine |
| s4u | 4-thiouridine |
| T | 5-methyluridine |
| t6a | N-((9-beta-D-ribofuranosylpurine-6-yl)carbamoyl)threonine tm 2'-O-methyl-5-methyuridine |
| Um | 2'-O-methyluridine |
| Yw | Wybutosine |
| X | 3-(3-amino-3-carboxypropyl)uridine, (acp3)u |
| AraU | beta D-arabinosyl |
| AraT | beta D-arabinosyl |

"Assembly facilitator molecule", "assembly facilitator", "MNAzyme assembly facilitator molecule", "MNAzyme assembly facilitator" have the same meaning and are used interchangeably herein refer to molecules that can facilitate the self-assembly of component partzymes to form a catalytically active MNAzyme. In preferred embodiments an assembly facilitator is required for the self assembly of an MNAzyme. An assembly facilitator molecule, in some embodiments comprises a "target", "target analyte" or "analyte", which, as used herein each refer to a molecule whose presence is to be detected or measured by a particular MNAzyme. Assembly facilitator molecules comprise one or more regions that pair with, or bind to, one or more oligonucleotide "partzymes," which constitute components or portions of an "MNAzyme". It is not required that the assembly facilitator interact with, pair with, or bind to each component partzyme or oligonucleotide provided that it interacts with, pairs with, or binds to, at least one of the component partzymes of an MNAzyme. As used herein, MNAzyme assembly facilitator molecules are intended to encompass the broadest range of constituents which can facilitate self-assembly of an MNAzyme. Targets and analytes are also intended to encompass the broadest range of detectable constituents for which methods of sensitive detection are desirable. Some exemplary targets include nucleic acid sequences, viruses, bacterium, prions, proteins, antibodies, and small molecules. Other target analytes are also contemplated for use herein.

"Substrate", "substrate molecule", and "chemical substrate" have the same meaning and are used interchangeably herein to refer to any molecule which is recognized and chemically modified by a catalytic molecule. In particular embodiments, a substrate is recognized and modified by an enzyme, in other embodiments a substrate is recognized and modified by a catalytic nucleic acid molecule. In particular embodiments, a substrate is recognized and modified by a protein enzyme, in other embodiments a substrate is recognized and modified by a nucleic acid enzyme. In particular embodiments, a substrate may comprise a single stranded nucleic acid molecule or molecules, in other embodiments a substrate may comprise a double stranded nucleic acids molecule or molecules. In further embodiments the substrate may form a hairpin molecule. The chemical modification of a substrate can be measured by the appearance of, or increase in, a product of the reaction, or by the disappearance of, or decrease in, a substrate of the reaction(s). A particular catalytic molecule can recognize one or more different substrate molecules provided each substrate molecule has at least a minimum structure which is recognizable for catalytic activity by the catalytic molecule.

As used herein, the terms "partzyme" and "component partzyme", have the same meaning and are used interchangeably herein to refer to DNA-containing or RNA-containing oligonucleotide, two or more of which, only in the presence of an MNAzyme assembly facilitator molecule, can together form an "MNAzyme." In certain preferred embodiments, one or more component partzymes, preferably at least two, comprise three regions or domains: a "catalytic" domain, which forms part of the MNAzyme's catalytic core that catalyzes the chemical modification; a "sensor arm" domain, which associates with and/or binds to target analytes; and a "substrate arm" domain, which associates with and/or binds to a substrate. The skilled artisan will appreciate that while a partzyme necessarily forms part of an MNAzyme structure, it need not specifically recognize, nor directly bind with, or pair with an MNAzyme assembly facilitator molecule. Thus, it should be clear that one or more partzymes for a given MNAzyme may lack one, or more, or all of the aforementioned domains, in whole or part. In certain embodiments one or more partzymes interact with other partzymes, but necessarily with the assembly facilitator molecule. In other embodiments, one or more particular partzymes may only interact indirectly with an assembly facilitator molecule, without binding directly to it, or pairing with it.

The terms "MNAzyme" and "multi-component nucleic acid enzyme" as used herein, refers to two or more oligonucleotide sequences (e.g. partzymes) which, only in the presence of MNAzyme assembly facilitator molecule (for example, a target analyte), form an active nucleic acid enzyme that is capable of catalytically modifying a substrate molecule or molecules. In one embodiment, Partzymes A and B each bind to a target analyte (e.g., through Watson-Crick base pairing with a nucleic acid target). The MNAzyme only forms when the sensor arms of partzymes A and B hybridize adjacent to each other on the target. The substrate arms of the MNAzyme engage the substrate, the cleavage of which is catalyzed by the catalytic core of the MNAzyme, formed by the interaction of the partial catalytic domains on partzymes A and B. In some embodiments the MNAzyme cleaves the substrate between a fluorophore and a quencher dye pair, thus generating signal. Cleavage of a DNA/RNA chimera (substrate) is exemplified in the drawing (FIG. 5A). In other embodiments an MNAzyme may ligate substrate molecules following binding to partzymes.

It will be understood that the terms "MNAzyme" and "multi-component nucleic acid enzyme" as used herein encompass all known MNAzymes and modified MNAzymes including those disclosed in any one or more of PCT patent publication numbers WO/2007/041774, WO/2008/040095, WO2008/122084, and related US patent publication numbers 2007-0231810, 2010-0136536, and 2011-0143338 (the entire content of each of these documents is incorporated herein by cross reference). Non-limiting examples of MNAzymes and modified MNAzymes encompassed by the terms "MNAzyme" and "multi-component nucleic acid enzyme" include MNAzymes with cleavage catalytic activity (as exemplified herein), disassembled or partially assembled MNAzymes comprising one or more assembly inhibitors, MNAzymes comprising one or more aptamers ("apta-MNAzymes"), MNAzymes comprising one or more truncated sensor arms and optionally one or more stabilizing oligonucleotides, MNAzymes comprising one or more activity inhibitors, multi-component nucleic acid inactive proenzymes (MNAi), and MNAzymes with ligase catalytic activity ("MNAzyme ligases"), each of which is described in detail in one or more of WO/2007/041774, WO/2008/040095, WO2008/122084, US 2007-0231810, US 2010-0136536, and/or US 2011-0143338.

As used herein an "aptamer" comprises a nucleic acid or peptide sequence that has the ability to recognize one or more ligands with great affinity and specificity due to their higher level structure, for example, a 3-D binding domain or pocket. Aptamers can bind nucleic acid, proteins, prions, small organic compounds, or entire organisms. Preferred aptamers herein are short single-strand DNA or RNA oligomers which can be isolated from complex libraries of synthetic nucleic acid by an iterative process of adsorption, recovery, and reamplification. Aptamers can be generated against almost any target, ranging from small molecules such as amino acids, or antibiotics to protein and nucleic acid structures.

An "Oligonucleotide" or "oligo" as used herein denotes a segment or fragment of DNA or a DNA-containing nucleic acid molecule, or RNA or RNA-containing molecule. Examples of oligonucleotides include nucleic acid targets; substrates, for example, those which can be modified by an MNAzyme; primers such as those used for in vitro target amplification by methods such as PCR; and components of MNAzymes. MNAzyme assembly facilitators, in certain embodiments, comprise oligonucleotides as defined herein. Partzymes as used herein also comprise oligonucleotides. Other examples of oligonucleotides include EASs, InFs, SIOs and DFs. An oligonucleotide referred herein may be "complementary" to another oligonucleotide. Any nucleic acid molecule referred to herein as being "complementary" to a second nucleic acid molecule is capable of hybridising to that second nucleic acid molecule (either wholly or in part) via Watson-Crick base pairing under appropriate conditions.

As used herein, the term "base" will be understood to encompass the entire ribonucleotide or deoxyribonucleotide to which the base is attached.

A "hairpin oligonucleotide", or "hairpin", as used herein denotes an oligonucleotide which contains a sequence complementarity within itself which results in intramolecular hybridization bonds forming. The complementary portion is termed the "stem" whereas the region between those that form the stem is termed the "loop". A hairpin may have extra sequence extending from the stem at either the 5' or the 3' termini. The hairpin may contain sequence which is complementary to another oligonucleotide such as, for example, a DF.

"Fluorescent label" and "fluorophore" refer to a substance or moiety capable of exhibiting fluorescence. A "quencher" is a moiety capable of absorbing the emitted energy of a fluorophore when the two moieties are in close proximity. The fluorophore may absorb and emit energy at various wavelengths, and therefore be quenched at different wavelengths. The fluorophore and quencher can be easily manipulated to be in close proximity. For example, both may be placed on the same strand of DNA within zero to twenty base units apart, or placed at opposite ends of the DNA strand. This spatial positioning may result in substantially no signal at the emission wavelength of the fluorophore. Upon physical separation, for example, as a result of enzymatic cleavage of the DNA strand, the quencher and fluorophore may be too far apart for the quencher to effectively absorb the energy from the fluorophore, resulting in a detectable signal at the emission wavelength of the fluorophore.

As used herein, the term "cascade" refers to any succession of processes or operations that occur in successive stages, wherein the occurrence of each stage is typically dependent on the occurrence of a preceding stage. A cascade may therefore include, but is not limited to, an enzymatic cascade or any other signal transduction cascade. In some embodiments, a cascade may comprise amplification of a signal resulting from catalytic activity of a nuclease. In preferred embodiments, such an amplification cascade may involve repeated and therefore cyclic amplification of a signal, wherein catalytic modification of, or by, a first molecule or molecules makes available a required molecule for catalytic modification of, or by, a second molecule or molecules, which in turn makes available a required molecule for catalytic modification of, or by, a first molecule or molecules. In some embodiments, the required molecule may comprise a driver fragment, a partzyme, an enzyme, an assembly facilitator, a substrate, a target, a portion or fragment thereof or a combination thereof. In some embodiments, a cascade may therefore involve production of a cumulative effect, and thus detect a target of low abundance by generating a signal to a level at which it may be detected. In other embodiments, more than two catalytic stages may be employed. The cascade may be linear. In a preferred embodiment, the cascade may be exponential.

As used herein, the term "feedback cascade" refers to any succession of processes or operations that occur in successive stages, where the occurrence of a later stage is dependent on the occurrence of an earlier stage, and the occurrence of that same earlier stage depends at least in part on the occurrence of the later stage.

ABBREVIATIONS

The following abbreviations are used herein and throughout the specification:
RE: restriction endonuclease, restriction enzyme
CESA: complete enzyme signal amplifier complex
PESA: partial enzyme signal amplifier complex
SIO: Synthetic Initiator Oligo
EIC: enzyme inhibitory complex
RERS: restriction enzyme recognition site/sequence
RER: restriction enzyme recognition EAS: enzyme amplifier substrate oligo
EAS1: first enzyme amplifier substrate oligo
EAS2: second enzyme amplifier substrate oligo
EAS3: third enzyme amplifier substrate oligo
EAS4: fourth enzyme amplifier substrate oligo
EAS5: fifth enzyme amplifier substrate oligo
EAS6: sixth enzyme amplifier substrate oligo
EAS7: seventh enzyme amplifier substrate oligo
EAS8: eighth enzyme amplifier substrate oligo
InF: inhibitory fragment
DF: Driver Fragment
MNAzyme: multi-component nucleic acid enzyme
DNAzyme: deoxyribonucleic acid enzyme;
PCR: polymerase chain reaction;
dH$_2$O: deionized distilled water;
LNA: locked nucleic acid;
PNA: peptide nucleic acid;
bDNA: branched DNA assay;
FCS: fluorescence correlation spectroscopy;
TSA: tyramide signal amplification;
An: analyte or target;
F: fluorophore dye molecule;
Q: quencher molecule;
N=A, C, T, G, or any analogue thereof;
N'=any nucleotide complementary to N, or able to base pair with N;
(N)$_x$: any number of N;
(N')$_x$: any number of N';
n=interchangeable with rN
W: A or T;
K: A, G, or AA;
rN: any ribonucleotide base;
(rN)$_x$: any number of rN;
rR: a or g;
rY: c or u;
M: A or C;
H: A, C, or T;
D: G, A, or T;
JOE or 6-JOE: 6-carboxy-4',5'-dichloro-2',7'-dimethoxy-fluorescein;
FAM or 6-FAM: 6-Carboxyfluorescein.
Oligo: oligonucleotide
BHQ=black hole quencher
BHQ1=Black Hole Quencher 1
BHQ2=Black Hole Quencher 2
TXR=Texas Red or sulforhodamine
IAbFQ or IAbkFQ=Iowa black fluorescence quencher

DETAILED DESCRIPTION

It is to be understood at the outset, that the figures and examples provided herein are to exemplify and not to limit the invention and its various embodiments.

Compositions, methods and kits are provided for the detection, identification and/or quantification of a target. The methods generally comprise the use of compositions comprising components for target-dependent generation of a Driver Fragment (DF), which, when incorporated into a Complete Enzyme Signal Amplifier complex, facilitates nuclease-mediated amplification of a detectable signal. In certain embodiments, feedback cascades are provided wherein an initial signal arising from the target-dependent generation of a Driver Fragment (DF) may be amplified irrespective of whether new target molecules are provided (i.e. signal amplification after an initial target-recognition event can occur independently of the target molecule). Although no particular limitation exists in relation to the means by which a DF may be generated from a target recognition event, in some embodiments the DF is generated by cleavage of a substrate by a multi-component nucleic acid enzyme (MNAzyme). The MNAzyme is preferably formed by multiple nucleic acid partzymes that self assemble to form an active nucleic acid enzyme in the presence of an assembly facilitator. In preferred embodiments, the assembly facilitator is the target and therefore the MNAzymes form only in the presence of the target. In other embodiments the DF is generated by target-dependent nuclease cleavage of a duplex formed by hybridization between a Synthetic Initiator Oligonucleotide (SIO) and the target sequence.

1. Compositions and Kits

Provided herein are compositions and kits for carrying out the methods of the invention. By way of non-limiting example only, the compositions and kits may comprise any one or more of an Enzyme Amplifier Substrate (EAS) oligonucleotide, Driver Fragment (DF), Partial Enzyme Signal Amplifier (PESA) complex, Complete Enzyme Signal Amplifier (CESA) complex, Enzyme Inhibitory Complex (EIC), Inhibitory Fragment (InF), Synthetic Initiator Oligo (SIO), catalytic nucleic acid, MNAzyme, MNAzyme component, partzyme, assembly facilitator, MNAzyme substrate, enzyme, restriction enzyme, exonuclease, endonuclease, substrate, aptamer, and/or a hairpin oligonucleotide.

1.1 MNAzymes

Compositions and kits of the present invention may comprise one or more MNAzymes. MNAzymes are catalytically active nucleic acid enzymes, which are capable of self-assembling from two or more oligonucleotide components, also referred to herein as partzymes. The partzyme oligonucleotides self-assemble in the presence of an MNAzyme self assembly facilitator to form an MNAzyme. In some embodiments, the presence of an MNAzyme can be detected, and is indicative of the presence of a target, because the MNAzyme forms only in the presence of the target, wherein the target comprises the assembly facilitator. MNAzymes are well known in the art and described in more detail in any one, or more of PCT patent publication numbers WO/2007/041774, WO/2008/040095, WO2008/122084, and related US patent publication numbers 2007-0231810, 2010-0136536, and 2011-0143338 (the entire content of each of these documents is incorporated herein by cross reference).

In preferred embodiments, the MNAzyme structures are based on one or more DNAzymes and/or ribozymes. More preferred are those MNAzyme structures which are based on a particular DNAzyme structure. Presently preferred structures are based on DNAzymes including the 10:23 and 8:17 DNAzymes. In various embodiments the MNAzymes comprise either or both ribonucleotide bases and deoxyribonucleotide bases. In more preferred embodiments, an MNAzyme structure is based at least in part on the structure of a DNAzyme. In other preferred embodiments, MNAzymes comprise at least some deoxyribonucleotide bases or analogues thereof. In more preferred embodiments, the catalytic core of an MNAzyme comprises one or more deoxyribonucleotide bases or analogues thereof. In still more preferred embodiments, one or more deoxyribonucleotide bases or analogues thereof are involved in the catalysis of a substrate. In other embodiments, at least one deoxyribonucleotide base, or its analogue, in the catalytic core improves catalytic activity. In yet other embodiments, there is a strict requirement for at least one deoxyribonucleotide base, or its analogue, in the catalytic core of the MNAzyme for catalysis to occur at a measurable rate, relative to that of a comparable MNAzyme without the deoxyribonucleotide base present.

MNAzymes may contain one or more substitutions such as analogues, derivatives, modified or altered bases, ribonucleotides, alterations of the sugar or phosphate backbone, various deletions, insertions, substitutions, duplications or other modifications, or any combination of these, well known to those skilled in the art. Such modifications, substitutions, deletions, insertions, etc may be made in the sensor and/or substrate arms and/or in the catalytic core portions such that the molecule retains catalytic activity. Substitutions and modifications to arms that bind the substrate or assembly facilitator may be well tolerated and allow tailoring of the molecules to different substrates/assembly facilitators. For example, modification of the sensor arms allows tailoring to different assembly facilitators, while modification of the substrate arms allows tailoring to different substrates.

By altering only the sensor arms of the partzymes, but by leaving the substrate arms unchanged, a large variety of MNAzymes specific for each of a plurality of targets can be designed all of which utilize a universal MNAzyme substrate for detection. The skilled artisan will appreciate the advantages that this offers in terms of eliminating the need for customized or unique substrates for each target. Each new target requires only one or more changes in one or more of the sensor arm portions of the partzymes; the substrate arm portion and the catalytic core portion can remain constant. Thus, a single MNAzyme substrate can be used for a single target using an MNAzyme, and multiple targets in a series of assays using altered MNAzymes. A plurality of MNAzyme substrates allows multiplexing to detect multiple targets in a single assay using multiple MNAzymes, one for each target. Such multiplexed methods of using MNAzymes are readily accomplished in solution or with attachment to a support system. It is contemplated herein that multiplexed assays can thus be accomplished in systems involving attaching one or more of the substrate, or the MNAzyme partzymes or assembly facilitator, or additional enzyme activities, to a support as described herein.

The skilled artisan will appreciate that MNAzymes comprise either deoxyribonucleotides or ribonucleotides, or both. Those MNAzymes comprising at least one and more preferably all deoxyribonucleotide component oligonucleotides are presently preferred. Also preferred are those MNAzymes comprising at least one deoxyribonucleotide base, or its analogue, within the catalytic core of the MNAzyme. Even more preferred are those embodiments where such a base is required for catalytic activity.

In some embodiments at least one of the partzymes, assembly facilitator or substrate may also include/comprise an aptamer which is capable of binding to a target.

Preferred aptamers may comprise short single-stranded DNA or RNA oligomers or peptides that can be isolated from complex libraries of synthetic nucleic acids or peptides by an iterative process of adsorption, recovery, and reamplification. Aptamers may therefore be generated against almost any target, ranging from small molecules such as amino acids or antibiotics, to protein and nucleic acid structures. In preferred embodiments, aptamers include, for example, nucleic acid binding molecules which are preferably generated by evolution and selection techniques. Preferably, aptamers may comprise DNA or RNA molecules, or a combination of both, including but not limited to the nucleotide analogues as per, for example, Table 1 above.

Strategies for combining the use of aptamers with MNAzymes are known in the art. For example at least one partzyme of an MNAzyme may incorporate an aptamer (an apta-partzyme) as well as a complementary sequence capable of forming a hairpin and therefore inhibiting MNAzyme assembly. An analyte or target to be detected may bind to the apta-partzyme, thus enabling assembly of an active MNAzyme. In the absence of a target analyte the apta-partzyme adopts a hairpin structure which inhibits assembly of an active MNAzyme. In the presence of target analyte, the target analyte binds to the aptamer domain of the apta-partzyme, thus disrupting the hairpin structure and allowing the apta-partzyme to participate in assembly of an active MNAzyme. The active MNAzyme can then modify an MNAzyme substrate to produce a Driver Fragment.

In other embodiments the aptamer may be present as part of an assembly facilitator that incorporates an aptamer as well as complementary inhibitor sequence capable of forming a hairpin structure. In the absence of a target analyte, the assembly facilitator adopts a hairpin structure which inhibits the ability of this component to direct the assembly of active MNAzymes. In the presence of target analyte, the target analyte binds to the aptamer domain of the assembly facilitator, thus disrupting the hairpin structure and allowing the component to direct the assembly of an active MNAzyme. The active MNAzyme can then modify an MNAzyme substrate to produce a Driver Fragment.

One skilled in the art will appreciate that the aptamer may be incorporated into either end of the assembly facilitator molecule or molecules. Further it will be appreciated that multiple aptamers could be incorporated into one or more of the partzyme oligonucleotide components.

In a further embodiment an aptamer sequence may be incorporated at the end of a partzyme (apta-partzyme) in a configuration whereby an active MNAzyme is only formed in the presence of the target analyte. In this case the oligonucleotide components required for the MNAzyme detection strategy include; a standard partzyme; an apta-partzyme which is a partzyme with an aptamer incorporated into one of its ends; an assembly facilitator which binds to both the apta-partzyme and the partzyme enabling assembly of an active MNAzyme (in the presence of target); a substrate; and an assembly inhibitor which hybridises to the apta-partzyme in a region which spans at least part of the aptamer sequence and part of the substrate binding arm of the partzyme sequence. In the absence of a target the assembly inhibitor binds to the apta-partzyme thus blocking binding (and cleavage) of the MNAzyme substrate. In the presence of a target, the target binds to the aptamer sequence of the apta-partzyme, preventing the binding of the assembly inhibitor and allowing the binding and cleavage of the MNAzyme substrate. As such, an active MNAzyme can only form and modify an MNAzyme substrate to produce cleavage fragments for example Driver Fragments, in the presence of target.

Further, it will be appreciated by one skilled in the art that the assembly inhibitor can be a separate molecule or can be incorporated into one of the components that participate in the MNAzyme complex.

It will also be appreciated by one skilled in the art that one or more aptamers could be incorporated into any of the oligonucleotide components, including the partzymes, the assembly facilitator or the MNAzyme substrate. Further, the aptamer could be incorporated into either end of any one of these oligonucleotides.

1.2 MNAzyme Substrates

Compositions and kits of the present invention may comprise one or more MNAzyme substrates. The substrate may be specific to a given MNAzyme or may be a universal/ generic substrate capable of modification by MNAzymes having different target specificities. MNAzymes have an advantageous property in certain embodiments of being able to utilize a universal or generic substrate. Universal MNAzyme substrates allow rapid assay development by allowing facile design changes to create new MNAzymes which recognize different targets. The substrate arm portion and the catalytic core portion of the partzymes may remain unchanged, with changes only to the sensor arm portion of one or more partzymes required for new targets. Universal substrate sequences are provided and thus the same substrate can be incorporated in assays for many different targets. Further, the same substrate can be incorporated into the methods in various embodiments herein, including assays where the substrate is free in solution or is tethered or attached to a support. A series of universal substrates can be used in a multiplex reaction allowing simultaneous detection of multiple targets.

MNAzyme strategies using universal substrates offer a major advantage over detection technologies such as TaqMan® or Molecular Beacons or Hybridization probes which require the design and use of probes specific for each new target.

In certain embodiments, MNAzyme substrates can act as Inhibitory Fragments which bind to Partial Enzyme Substrate Amplifier complexes (PESAs) and form Enzyme Inhibitory Complexes (EICs) which are not susceptible to cleavage by a nuclease, for example a restriction endonuclease.

The modification of an MNAzyme substrate by an MNAzyme may provide one or more components for use in methods of the invention (e.g. an EzyAmp reaction). The modification may, for example, be cleavage of an MNAzyme substrate or ligation of multiple MNAzyme substrates.

In some embodiments, cleavage of the MNAzyme substrate can produce smaller fragments which can function as a Driver Fragments and assemble with PESAs to form CESAs which are amenable to cleavage by restriction enzymes or other nucleases. Since an MNAzyme substrate can be universal and useful for any target, cleavage of a universal MNAzyme substrate may result in the generation of a universal Driver Fragment. As a result, the universal DF can bind to a universal PESA and result in a universal CESA can be cleaved allowing amplification of a signal in the presence of any target.

In other embodiments, ligation of multiple MNAzyme substrates can produce larger fragments which can function as a Driver Fragments and assemble with PESAs to form CESAs which are amenable to cleavage by restriction enzymes or other nucleases. Since an MNAzyme substrate can be universal and useful for any target, ligation of universal MNAzyme substrates may result in the generation of a universal Driver Fragment. As a result, the universal DF can bind to a universal PESA and result in a universal CESA that can be cleaved allowing amplification of a signal in the presence of any target.

1.3 Driver Fragments

Compositions and kits of the present invention may comprise one or more Driver Fragments (DF). Additionally or alternatively, DFs may be generated during use of the compositions and kits in accordance with the methods of the invention.

In certain embodiments, a Driver Fragment may be provided as a component of an oligonucleotide. The oligonucleotide may be a single stranded oligonucleotide or a double stranded oligonucleotide. For example, the oligonucleotide may be an Enzyme Amplifier Substrate (EAS) oligonucleotide, a synthetic initiator oligonucleotide, an MNAzyme substrate oligonucleotide, a hairpin oligonucleotide (e.g. a hairpin oligonucleotide comprising multiple EAS, and preferably two EAS), a tethered oligonucleotide, or a double stranded oligonucleotide with an internal loop portion in one strand. The double stranded and/or hairpin oligonucleotide may comprise an overhanging portion wherein one strand extends further than its complementary strand (e.g. a 5' or 3' overhang). The oligonucleotide may be complexed with other components in a complex (e.g. a PESA or a CESA).

In certain embodiments, Driver Fragments are provided as a component of an EAS oligonucleotide, wherein at least a portion of the EAS oligonucleotide is complementary to another different EAS oligonucleotide, and wherein at least a portion of that different EAS oligonucleotide is complementary to at least a portion of the Driver Fragment.

Driver Fragments may be used to initiate the signal amplification methods disclosed herein (e.g. an EzyAmp reaction). For example, a Driver Fragment made available only upon target detection may be used to initiate a signal amplification cascade upon binding to an EAS in a PESA complex. In such embodiments, the cascade cannot commence in the absence of the Driver Fragment which may thus be referred to as an "initiator" Driver Fragment, although it will be understood that this terminology is only indicative and not a requirement in describing such Driver Fragments.

For example, Driver Fragments may be generated by cleavage of an MNAzyme substrate by an MNAzyme which is assembled only in the presence of a target sequence. It is also contemplated that Driver Fragments may be generated by ligation of multiple substrates by an MNAzyme with ligase activity that assembles only in the presence of a target. The Driver Fragments may be generated by the catalytic activity of apta-MNAzyme or aptazymes (DNA, RNA, or chimeras) which cleave MNAzyme substrates only in the presence of target ligands including proteins, lipids, small molecules, viruses or other ligands detectable by these types of catalytic nucleic acids which incorporate aptamers.

In certain embodiments, a Driver Fragment may be generated using a target-dependent MNAzyme as described, for example, in FIGS. 19 and 24 and Examples 9 and 14. These embodiments describe the generation of Driver Fragments from double stranded oligonucleotide complexes which serve both as a substrate and to bind and hence block the DF, and are thus referred to herein as substrate-blocker oligonucleotides.

By way of non-limiting example only, the MNAzyme substrate may be a component of a double stranded oligonucleotide complex comprising first and second strands, wherein the first strand comprises an internal loop portion that can be modified (e.g. cleaved) by catalytic activity of the MNAzyme. In some embodiments, the first and second strands may be linked by a hairpin loop portion, wherein the 5' end of one strand is linked to the 3' end of the other strand. Bases within the internal loop portion are not hybridised to bases of the second strand. The oligonucleotide complex comprises at least one Driver Fragment which is external to the loop portion and hybridised to a portion of the opposing strand. For example, the Driver Fragment may be a component of the second strand of the complex. In the presence of a target, the MNAzyme may assemble and cleave the loop portion thereby modifying the complex in a manner that releases a single stranded Driver Fragment capable of hybridising with another entity (e.g. an EAS). For example, cleavage of the loop may remove a portion of the loop from the complex thereby removing a portion of the double stranded complex previously hybridised to the Driver Fragment. The Driver Fragment, which has been generated in a target-dependent manner, can trigger an amplification cascade.

Alternatively, the MNAzyme substrate may be a component of a double stranded oligonucleotide complex comprising first and second strands, wherein the first and second stands are linked by a hairpin loop portion joining the 5' end of one strand to the 3' end of the other strand. The hairpin loop portion may be modified (e.g. cleaved) by catalytic activity of the MNAzyme upon assembly in the presence of a target. The oligonucleotide complex comprises at least one Driver Fragment external to the hairpin portion that is hybridised to a portion of the opposing strand. In the presence of a target, the MNAzyme may assemble and cleave the hairpin loop portion thereby modifying the complex in a manner that provides a single stranded Driver Fragment capable of hybridising with another entity (e.g. an EAS). For example, cleavage of the hairpin loop may release a portion of the loop from the complex thereby removing a portion of the double stranded complex previously hybridised to the Driver Fragment. The Driver Fragment, which has been generated in a target-dependent manner, can trigger an amplification cascade.

It is also contemplated that the Driver Fragments could be generated by restriction enzyme cleavage. For example cleavage of a either one or both strands of double stranded genomic DNA template could generate specific fragments which could dissociate and then function as initiating Driver Fragments that could bind PESA to form CESA and thus trigger an EzyAmp cascade reaction which, once initiated, would not be soley reliant on the presence of the initiating Driver Fragments derived from the genomic DNA, but rather would dependent upon new Driver Fragments generated by cleavage of CESA. Methylation sensitive RE could be used to methylate cytosine residues in target DNA.

In other embodiments it is contemplated that the Driver Fragment could be generated using an enzyme or chemical which recognizes and cleaves either a mismatch hetroduplex sequence or a DNA/RNA duplex sequences. The mismatch could be a natural mismatch relating to the sequence which is being interrogated and could be, for example, an acquired mutation or an inherited SNP.

Initiating Driver Fragments may also be generated by cleavage of Synthetic Initiator Oligonucleotides (SIO) complexed with a target including, for example, SIOs tethered to insoluble supports.

Driver Fragments included in compositions and kits of the invention may be generated by nuclease digestion of CESA complexes. The nuclease may be a restriction enzyme, an exonuclease, or an endonuclease. Any suitable restriction enzyme, exonuclease, or endonuclease may be used.

In certain embodiments, the nuclease is a restriction enzyme. The restriction enzyme may be capable of recognising and cleaving a duplex oligonucleotide comprising at least one nick. The nick or nicks may be internal or external to the recognition site of the restriction enzyme. The nick or nicks may be internal or external to the cleavage site of the restriction enzyme. Although any restriction enzyme could potentially be used, non-limiting examples of suitable restriction enzymes include Mnl I, Rsa I, Pme I, Hpy 8I, Msp I, Ear I and TspR I, and any one or more of the restriction enzymes indicated in Table 2 and Table 3.

In certain embodiments, the nuclease is an endonuclease. Without limitation to any particular type of endonuclease, suitable examples include T7 Endonuclease I, Mung Bean Nuclease, RNase H, Flap Nuclease, and MNAzymes.

In certain embodiments, the nuclease is an exonuclease, non-limiting examples of which include Nuclease BAL-31, Exonuclease I, Exonuclease III, T7 Exonuclease, T7 Exonuclease I and Exonuclease T.

1.4 Synthetic Initiator Oligos (SIO)

Compositions and kits of the present invention may comprise one or more Synthetic Initiator Oligos (SIO). SIO are oligonucleotides which are added to samples to induce formation of duplexes between the SIO and a target nucleic acid present in the sample. Cleavage of either paired or unpaired regions of the SIO/target duplex by a nuclease may be used to generate a nucleic acid fragment which can function as a Driver Fragment.

In some embodiments it is contemplated that the Driver Fragment could be generated using an enzyme or chemical which recognizes and cleaves either a mismatch hetroduplex sequence or DNA/RNA duplex sequences. In this embodiment an SIO would not be required. The mismatch could be a natural mismatch relating to the sequence which is being interrogated and could be, for example, an acquired mutation or an inherited SNP. If it is desired to cleave a sequence at a point other than where a mutation or a SNP occurs then a Synthetic Initiator Oligo (SIO) could be added to the sample to induce cleavage of the nucleic acid present in the biological sample at a specific site. The SIO could contain one or more mismatches compared to the target biological template. Alternatively the SIO could be an RNA/DNA chimeric oligos which binds, for example, to a DNA sequence such that a short RNA/DNA duplex is formed that could provide a site for cleavage using an enzyme that recognizes such hybrid sequences.

In such additional embodiments a Driver Fragment could be generated by incubating a biological specimen with a SIO and an enzyme with exonuclease or endonuclease activity such that the enzyme digests a larger fragment to create a Driver Fragment. Non-limiting examples of enzymes which could be utilized in this way are listed in Table 2 (below). While some enzymes may require a two step protocol others may be amenable to a single step reaction. One skilled in the art would recognize that many other enzymes could be used to generate a Driver Fragment using a matched or mismatched SIO, composed of DNA and/or RNA and an enzyme with either exonuclease or endonuclease activity.

The mechanism of the use of exemplary exonuclease and endonucleases may be better understood by reference to FIGS. 8-11.

FIG. 8 illustrates two mechanisms for generating Driver Fragments using the 3' to Do 5' exonuclease activity of Exonuclease I from *E. Coli*. This enzyme hydrolyses 3' single stranded overhangs from DNA duplexes. A Synthetic Initiator Oligo (SIO) is added to a sample containing target DNA to facilitate generation of a Driver Fragment. In the right panel the DF is derived from cleavage of the SIO leaving a partial target fragment intact and available to be recycled to generate more DF. In the left panel the DF is derived from cleavage of the target. Phosphorothioate bases can be incorporated into the 3' overhang extension of the PESA complex to prevent cleavage of this complex by exonuclease I. Once the DF is generated it hybridizes to the PESA thus converting it to a CESA complex.

FIG. 9 illustrates two mechanisms for generating DFs using the exonuclease activity of Mung Bean Nuclease. This endonuclease degrades single stranded overhangs from DNA duplexes from either the 3' or the 5' direction leaving blunt ends. A Synthetic Initiator Oligo (SIO) is added to a sample containing target DNA to facilitate generation of a Driver Fragment. In the right panels the DF is derived from the SIO whereas in the left panels the Driver Fragment is derived from the target. The reaction shown on the left (L) or right (R) could be performed in 2 steps (1 and 2) to prevent nuclease digestion of the PESA or CESA. This could be achieved by physical separation. Once the DF is generated it hybridizes to the PESA thus converting it to a CESA complex.

FIG. 10 illustrates a mechanism for generating DFs using the exonuclease activity of Exonuclease III. This enzyme removes nucleotides from 3' termini of DNA duplexes. The enzyme is active on blunt or recessed 3' termini but is not active on single stranded DNA and hence will not cleave 3' protruding termini. The enzyme can also start hydrolysis from nicks in a duplex DNA to produce single stranded gaps. The presence of a phosphorothioate nucleotide on component oligonucleotides blocks this exonuclease activity. An SIO is added to a sample containing target DNA to facilitate generation of a DF. Phosphorothioates incorporated into the SIO prevents cleavage at the nick created when the DF fragment hybridizes with the PESA or CESA. The DF is derived from the SIO and the target can be recycled to generate more DFs. In this embodiment the SIO could contain a target specific region which forms a duplex with the target and a universal non-target binding region. Cleavage of the target specific region by Exonuclease III could result in generation of a universal Driver Fragment (corresponding to the non-target binding region of the SIO) which could bind to a universal PESA thus forming a universal CESA.

FIG. 11 illustrates a mechanism for generating DFs using the exonuclease activity of T7 Exonuclease. This enzyme removes nucleotides in the 5' direction from DNA duplexes or DNA/RNA duplexes, in particularly phosphorylated 5' termini. The activity on other 5' ends without a 5' phosphate is greatly reduced in the presence of phosphorylated substrate. A SIO is added to a sample containing target DNA or RNA to facilitate generation of a DF. The DF is derived from the Synthetic Initiator Oligo (SIO) and the RNA or DNA target can be recycled to generate more DF. The PESA is composed of DNA but may have some duplex RNA at the 5' termini of the duplex (dotted box) to prevent degradation by the T7 exonuclease. In this embodiment the SIO could contain a target specific region which forms a duplex with the target and a universal non-target binding region. Cleavage of the target specific region by T7 Exonuclease could result in generation of a universal Driver Fragment (corresponding to the non-target binding region of the SIO) which could bind to a universal PESA thus forming a universal CESA.

Further, the SIO may alternatively or additionally incorporate entities such as labeled nucleic acids, nanoparticles, microparticles, proteins, antibodies, RNA, DNA, nucleic acid analogues, proteins, glycoproteins, lipoproteins, peptide nucleic acids, locked nucleic acids, peptide-nucleic acid chimeras, aptamers, or any combination thereof. For example, the nanoparticles may be gold nanoparticles.

In certain embodiments, compositions and kits of the present invention comprise SIO tethered to insoluble support/s.

In certain embodiments, SIO may be provided in a hairpin conformation. By way of non-limiting example, the SIO may comprise a double stranded stem portion arising from sequence complementarity between portions of the oligo which result in intramolecular bonds forming, and a hairpin loop portion at one end of the stem within which bases are not complementary. The hairpin SIO may have extra sequence extending from the stem at either the 5' or the 3' termini thereby forming a 5' or 3' overhang of single stranded sequence. The hairpin SOI may contain sequence which is complementary to another oligonucleotide such as, for example, a DF. FIG. 23 provides a non-limiting example of a hairpin SIO.

1.5 Complete Enzyme Signal Amplifier (CESA) Complexes and Partial Enzyme Signal Amplifier (PESA) Complexes Compositions and kits of the present invention may comprise one or more Complete Enzyme Signal Amplifier (CESA) complexes and/or one or more Partial Enzyme Signal Amplifier (PESA) complexes.

Complete Enzyme Signal Amplifier (CESA) complexes typically comprise two Enzyme Amplifier Substrate (EAS) oligonucleotides (e.g. a first Enzyme Amplifier Substrate (EAS1) oligo and a second Enzyme Amplifier Substrate (EAS2) oligo) and a Driver Fragment. The EAS1 typically comprises one strand of a duplex, which when double stranded, incorporates a recognition sequence and a cleavage sequence for a nuclease. The nuclease may be, for example, a restriction enzyme, an exonuclease, or an endonuclease. In preferred embodiments the EAS1 comprises one strand of a duplex, which when double stranded, incorporates one strand of a restriction enzyme recognition sequence and a cleavage site.

Exemplary CESA complexes are provided in FIGS. 14 and 15. At least a portion of one EAS oligonucleotide of the CESA complex is complementary to at least a portion of another EAS oligonucleotide in the complex, and at least a portion of one of said EAS oligonucleotides is also complementary to at least a portion of at least one DF. As noted above, the CESA complex comprises a recognition sequence and a cleavage sequence for a nuclease. The DF may contribute one or more nucleotides to the recognition sequence and/or the nuclease cleavage sequence, although it need not necessarily do so.

The contribution by a DF of one or more nucleotides to a partial recognition sequence and/or a partial enzyme cleavage sequence formed by the two EAS oligos provides a trigger for nuclease-mediated cleavage upon the binding of a DF to a PESA complex to form a CESA complex. In embodiments where the DF does contribute one or more nucleotides to the recognition sequence and/or cleavage sequence, the DF may contribute any number of nucleotides such as, for example, 1, 2, 3, 4, 5, or more than 5 nucleotides. Alternatively, the DF may contribute less than 5, less than 4, or less than three nucleotides. The nucleotides contributed by the DF may, for example, be immediately 5' or immediately 3' of a partial nuclease recognition sequence or a partial nuclease cleavage sequence formed by the two EAS oligos. Alternatively, the nucleotides contributed by the DF may be positioned 1, 2, 3, 4, 5, or more than 5 nucleotides 5' or 3' from a complete nuclease recognition sequence or complete nuclease cleavage sequence formed by the two EAS oligos.

In alternative embodiments, the DF does not contribute any nucleotides to the nuclease recognition sequence and/or the nuclease cleavage sequence of the CESA complex. Nonetheless, as confirmed by experimental data provided in Example 5 of the present specification, the binding of a DF to a PESA already containing complete nuclease recognition and cleavage sequences can enhance a signal generated upon cleavage of the CESA complex.

Cleavage of CESA complexes is typically used to generate a detectable signal indicative of a specific event. With reference to FIGS. 3 and 5, the first Enzyme Amplifier Substrate oligo (EAS1) comprises both a detectable portion (F) and a quencher portion (Q). The second Enzyme Amplifier Substrate oligo (EAS2) also comprises a quencher portion (Q). The quencher portion is adapted to diminish or eliminate a detectable signal from the detectable portion of the first EAS1 until the CESA is cleaved by the restriction enzyme or other nuclease. For example, the quencher portion may comprise "Black Hole Quencher 1" (BHQ1) or "Black Hole Quencher 2" (BHQ2). One skilled in the art would appreciate that any suitable fluorophore-quencher dye pair could be used in such protocols. Further, one or more EAS oligos of the CESA complex (e.g. EAS1) may alternatively or additionally incorporate entities such as labelled nucleic acids, nanoparticles, microparticles, proteins, antibodies, RNA, DNA, nucleic acid analogues, proteins, glycoproteins, lipoproteins, peptide nucleic acids, locked nucleic acids, peptide-nucleic acid chimeras, aptamers or any combination thereof. For instance, the nanoparticles may be gold nanoparticles.

As a consequence of cleavage of the CESA by the nuclease a detectable effect is generated and the magnitude and/or speed of the effect may therefore be indicative of the quantity of the target in a sample. The detectable effect may be detected by a variety of methods, including fluorescence spectroscopy, surface plasmon resonance, mass spectroscopy, NMR, electron spin resonance, polarization fluorescence spectroscopy, circular dichroism, immunoassay, chromatography, radiometry, photometry, scintigraphy, electronic methods, UV, visible light or infra red spectroscopy, enzymatic methods or any combination thereof.

Figure 1:
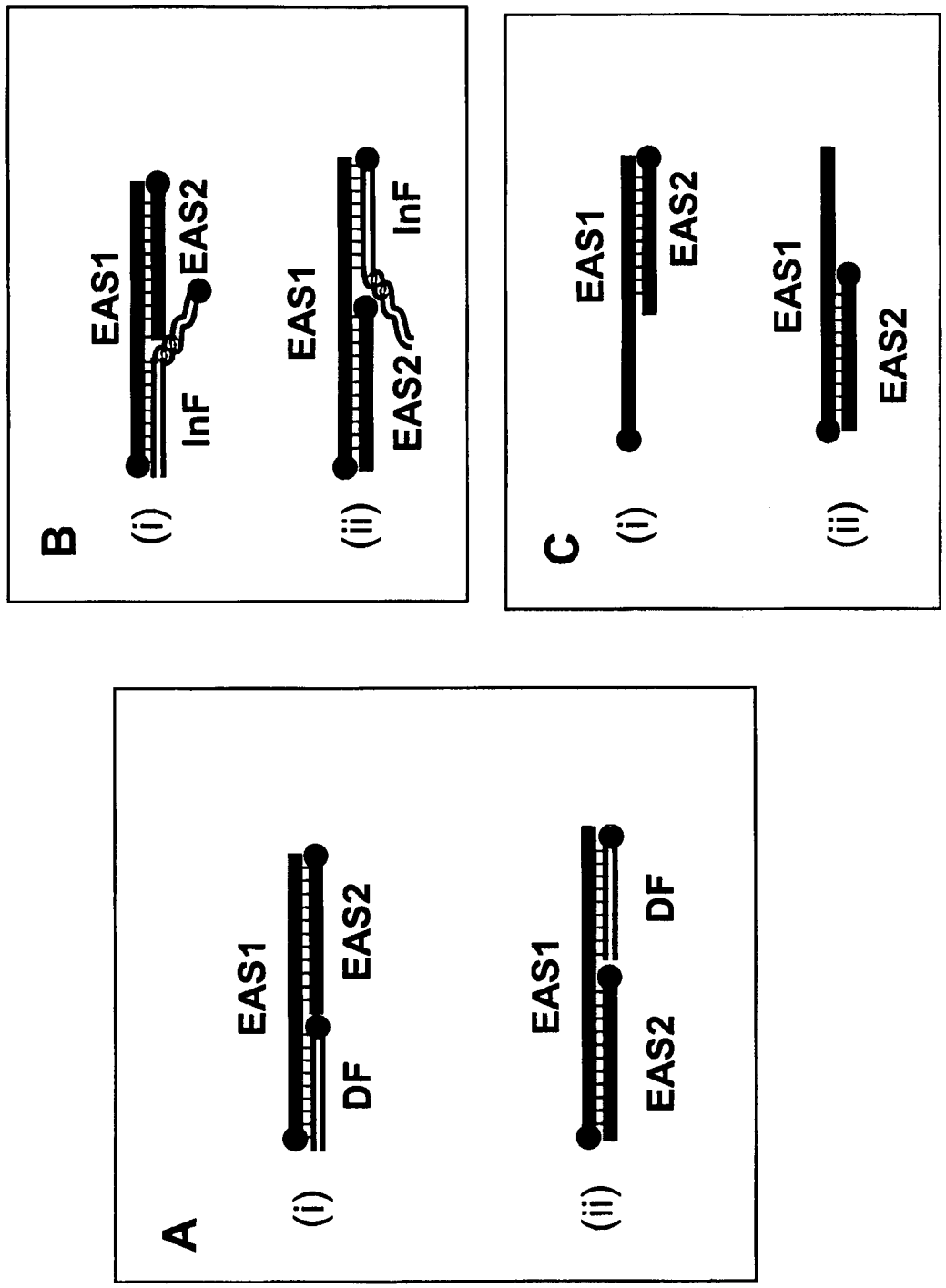
FIG. 1 provides exemplary illustrations of various cleavable and uncleavable duplex oligonucleotide structures. The 5' end of each oligonucleotide fragment is indicated by a circle. Structure A (i) illustrates an example of a Complete Enzyme Signal Amplifier (CESA) complex which is a multi-oligonucleotide complex which is amenable to cleavage by a nuclease. This CESA is composed of three oligonucleotides, namely Enzyme Amplifer Substrate oligo 1 (EAS1), Enzyme Amplifer Substrate oligo 2 (EAS2) and a Driver Fragment (DF). In the CESA illustrated in A (i) the 5' end of the DF abuts with the 3' end of the EAS2. A second CESA is illustrated in A (ii) where the 3' end of the DF abuts with the 5' end of the EAS2.

In some embodiments, one EAS oligo of the CESA complex comprises one strand of a duplex which comprises a portion of a restriction enzyme recognition sequence and/or a portion of a restriction enzyme cleavage sequence. With reference to FIGS. 1, 2 and 3, the first and second Enzyme Amplifier Substrate oligos EAS1 and EAS2 are complementary over at least a portion of their length such that the complementary portions of the first and second EAS oligos can hybridise to form a partially double stranded restriction enzyme recognition sequence and/or restriction enzyme cleavage sequence. With reference to FIGS. 4 and 5, the second EAS (EAS2) may contain a quencher portion which upon binding to EAS1 may quench a detectable portion located on EAS1. Alternatively, EAS2 may contain a detectable portion, the fluorescence of which is quenched by a quencher portion located on EAS1. Complexes formed by hybridization of EAS1 and EAS2 are referred to as Partial Enzyme Signal Amplifier (PESA) complexes.

A PESA complex is a multi-oligonucleotide complex that comprises at least two Enzyme Amplifier Substrate (EAS) oligonucleotides, wherein at least a portion of one EAS oligonucleotide is complementary to at least a portion of another EAS oligonucleotide in the complex. In addition, at least a portion of one of said EAS oligonucleotides is also complementary to at least a portion of at least one DF. Despite having the capacity to hybridise to a DF, the DF is not hybridised to and thus not a component of the PESA complex. A PESA complex comprises at least a partial recognition sequence/site and/or at least a partial cleavage sequence/site for an enzyme, and may contain a full recognition sequence/site and/or a full cleavage sequence/site for an enzyme. Exemplary PESAs are illustrated in FIGS. 1C, 3C, 4, 5B, 7A, 7B, 8 (both left and right panels), 14C, 17A, 18A, 19A, 20 and 22.

A Driver Fragment (DF) produced by cleavage of an MNAzyme substrate by an MNAzyme, or by cleavage of SIO/target duplexes by other nucleases including protein exonucleases and endonucleases, may be required to complete the restriction enzyme recognition sequence (represented as a hatched box in FIG. 2) and/or it may provide additional sequence adjacent to the restriction enzyme recognition sequence which is required for cleavage by the restriction enzyme. With reference to FIG. 2, the cleavage site(s) are represented by solid black vertical arrows. At least a portion of the Driver Fragment is complementary to at least a portion of the first Enzyme Amplifier Substrate oligo EAS1. With reference to FIGS. 1, 2 and 3, the Driver Fragment and first EAS1 are complementary over at least a portion of their length such that the complementary portions of the Driver Fragment and first Enzyme Amplifier Substrate oligo can assemble, for example by hybridisation to form a double stranded sequence containing a complete or partial restriction enzyme recognition. A complete or partial double stranded restriction enzyme cleavage sequence incorporated into a CESA may also be formed in this way. The CESA assembled by hybridization of EAS1, EAS2 and the DF contains all sequences required for both recognition and cleavage by a RE.

In one embodiment, cleavage of a CESA by the appropriate RE results in cleavage of the first Enzyme Amplifier Substrate oligo EAS1 between the detectable portion and the quencher portion allowing the two portions to separate thereby allowing the detectable signal to appear or increase as the quencher portion is distanced from, or effectively removed from the local environment of the detectable portion. In other embodiments cleavage of the CESA may result in generation of new Driver Fragments capable of hybridizing to additional PESAs to form additional CESAs (e.g. FIGS. 7, 17A, 18A, 19A, 20, and 22). The additional CESAs may be amenable to cleavage with the same RE or a different RE.

With reference to FIGS. 2 and 15, in some embodiments the fully assembled CESA may have different designs. The DF (black lines with white centers) may be required to complete the recognition sequence of the restriction enzyme and/or it may provide additional sequence adjacent to the restriction enzyme recognition site which is required for cleavage by the restriction enzyme. Cleavage by the restriction enzyme may result in either a 5' overhang, a 3' overhang, or it may generate blunt ends. The restriction enzyme may cleave one or both strands of the double stranded assembled complex of EAS1, EAS2 and DF. The position where EAS2 and the DF are abutted may be at a position where the RE would normally cleave a continuous double stranded duplex or it may be elsewhere with the sequences required for recognition and cleavage by the restriction enzyme. The end of the DF which abuts with the EAS2 must be resultant from cleavage of a longer molecule in a previous step. For example, if the Driver Fragment is generated by cleavage of an MNAzyme substrate by an MNAzyme into a 5' and a 3' fragment then the end which abuts must be the 5' end of the 3' fragment or the 3' end of the 5' fragment of the cleaved MNAzyme substrate. In another example, if the Driver Fragment is generated by cleavage of a SIO by Exonuclease III (FIG. 10) thus creating a 5' fragment then the end which abuts must be the 3' end of this 5' fragment.

With reference to FIG. 1B, an "Enzyme Inhibitory Complex" or "EIC" is a complex formed by multiple oligonucleotides which may comprise EAS1, EAS2 and an Inhibitory Fragment (InF). The EIC contains sequence for an enzyme recognition site and a cleavage site present on multiple oligos but also contains additional sequence which causes inhibition of cleavage by a restriction enzyme or other nuclease.

In embodiments where the EIC comprises a PESA and an InF, its conversion to a CESA requires the cleavage of the Inhibitory Fragment (InF) thus producing a smaller fragment which can function as a Driver Fragment (DF) to complete the CESA. Cleavage of the InF may be achieved by several means. The InF may be a substrate for an MNAzyme which assembles in the presence of the target analyte and which cleaves the InF/MNAzyme substrate to generate a DF. Alternatively the InF can be a Synthetic Initiator Oligonucleotide (SIO) which hybridises to a target sequence to form a duplex which is recognized by a protein exonuclease or endonuclease such that paired or unpaired bases of InF/target complex are cleaved to generate a DF which completes the CESA.

In certain embodiments, PESA complexes and CESA complexes are provided in the form of hairpin structures. By way of non-limiting example, a PESA complex may comprise a double stranded stem portion arising from sequence complementarity between at least a portion of each EAS oligo in the complex, and a hairpin loop portion at one end of the stem within which loop bases are not complementary. The hairpin PESA complex may have extra sequence extending from the stem at either the 5' or the 3' termini thereby forming a 5' or 3' overhang of single stranded sequence. The hairpin PESA complex may contain sequence which is complementary to another oligonucleotide such as, for example, a DF. A hairpin CESA complex may be formed upon binding of a DF to a hairpin PESA complex. FIG. 18 provides a non-limiting example of a hairpin PESA complex and a hairpin CESA complex.

Figure 22D:
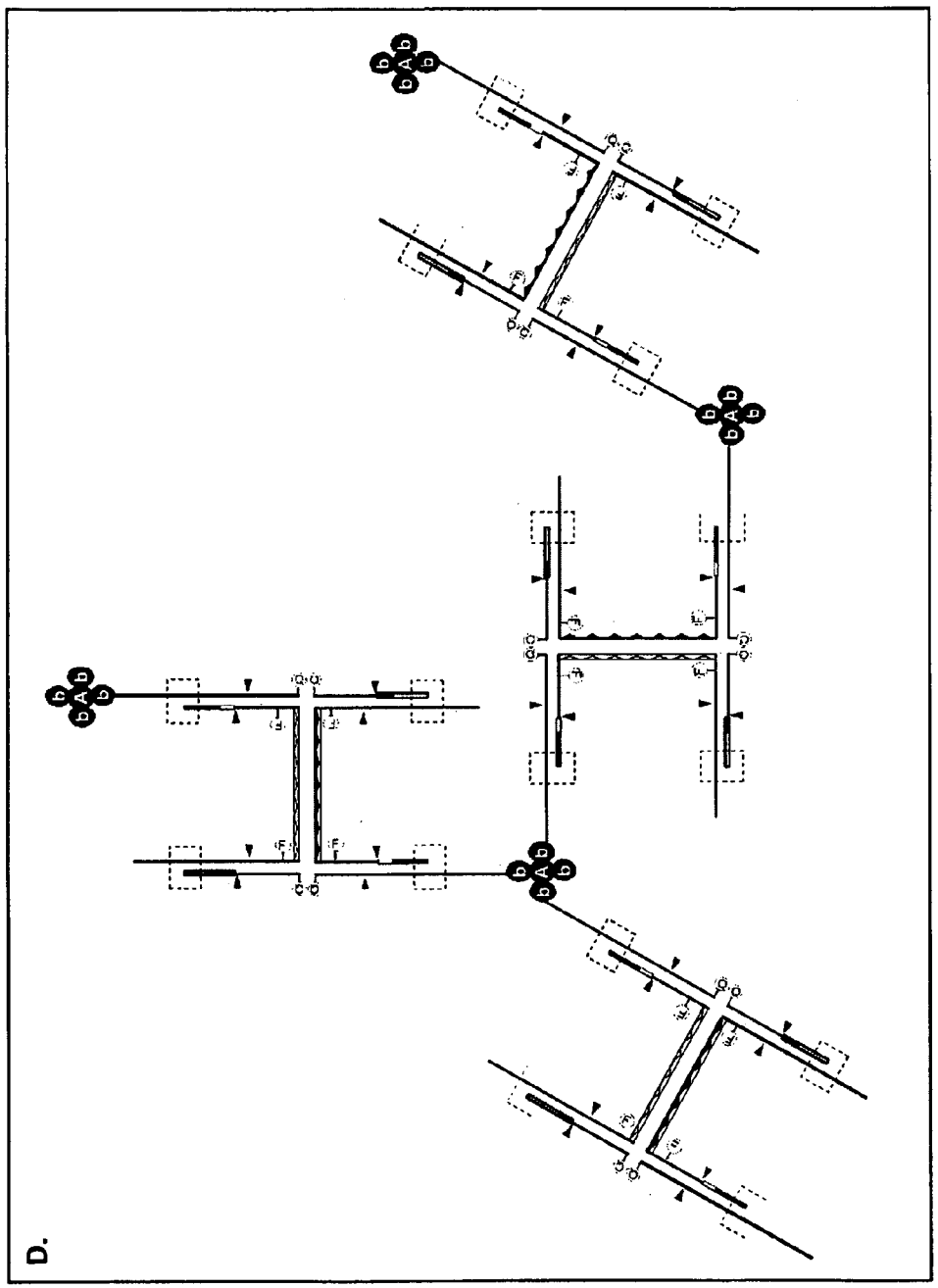

PESA complexes with the potential to form CESA complexes may be incorporated into composite structures to localise and improve the transfer of components such as driver fragments between multiple complexes. FIG. 22 illustrates an exemplary method for localising EzyAmp components by incorporating PESA complexes into branched structures. A first complex is provided comprising a backbone oligonucleotide, an EAS1, an EAS2, an EAS3, and an EAS4. The backbone oligonucleotide comprises the EAS1, the EAS3 and an intervening portion separating EAS1 and EAS3. A portion of EAS1 is complementary to a portion of EAS2 (to which it is hybridised), a portion of the EAS2 is complementary to a portion of a first DF, and a portion of the EAS1 or EAS2 comprises a second DF. A portion of EAS3 is complementary to a portion of EAS4 (to which it is hybridised), a portion of the EAS3 is complementary to a portion of the second DF, and a portion of the EAS3 or EAS4 comprises a second DF. The first complex adopts a C-shape with the intervening portion separating EAS1 and EAS3 positioned for hybridisation with the corresponding portion of a second complex comprising complementary sequence. As shown in panel B of FIG. 22, this allows the formation of a double complex with four separate PESA complexes. One or more arms of each single or double complex may be linked with one or more arms of another single or double complex using any suitable reagents (e.g. biotin/avidin, chemical reagents, antibodies, peptide linkers and the like), as illustrated in FIG. 22D. The bringing of various PESA complexes into proximity with each other allows for the efficient transfer of driver fragments between various PESA complexes upon the formation and cleavage of CESA complexes.

1.6 Oligonucleotides

Driver Fragments, Inhibitor Fragments, Synthetic Initiator Oligonucleotides and Enzyme Amplifier Substrates are oligonucleotides and may contain one or more substitutions such as analogues (e.g. those listed in Table 1), derivatives, modified or altered bases, ribonucleotides, alterations of the sugar or phosphate backbone, various deletions, insertions, substitutions, duplications or other modifications, or any combination of these, well known to those skilled in the art. Such modifications, substitutions, deletions, insertions, etc may be made at any position in the oligonucleotide provided that it substantially retains its function. Substitutions and modifications to the oligonucleotides may be well tolerated and allow tailoring of the molecules to function under certain conditions or for improvement of the efficiency of reaction involving the Complete Enzyme Signal Amplifier complex. For example, modification of an Enzyme Amplifier Substrate or Driver Fragment by inclusion of one or more nucleotide analogues may facilitate the assembly of a more labile Complete Enzyme Signal Amplifier complex thereby improving the efficiency of, for example, cleavage of a Complete Enzyme Signal Amplifier complex by a nuclease.

The skilled artisan will appreciate that oligonucleotides of the present invention such as, for example, Driver Fragments, Synthetic Initiator Oligonucleotides, inhibitory fragments, substrates, apatamers, and Enzyme Amplifier Substrate oligos may comprise either deoxyribonucleotides or ribonucleotides, or both. In certain embodiments, the oligonucleotides comprise at least one deoxyribonucleotide. In preferred embodiments, the oligonucleotides comprise predominantly deoxyribonucleotides, and still more preferably only deoxyribonucleotides.

1.7 Restriction Enzymes

Compositions and kits of the present invention may comprise one or more restriction enzymes, exonucleases, endonucleases, or a combination thereof. Restriction enzymes useful in compositions, methods and kits of the invention may be Type I, Type II, Type III or Type IV restriction enzymes. Restriction enzymes are generally classified into these types based on subunit composition, cleavage position, sequence specificity and cofactor requirements (see Table 2).

TABLE 2

Types of Restriction Enzymes

| Type | Attributes |
|---|---|
| Type I | Complex, multi-subunit enzymes<br>Cleave DNA at random at a position distant from their recognition sequence<br>e.g. Eco606ORF4215P (TGANNNNNNNNNTGCT) |
| Type II | Cleave DNA at defined positions near or within their recognition sequences to produce discrete restriction fragments e.g. HhaI, HindIII, Not I<br>Cleavage creates a 3'-hydroxyl and a 5'-phosphate<br>Only require magnesium for activity<br>Structure & Recognition sequences<br>Many are homodimers which recognize palindromic sequences |

TABLE 2-continued

Types of Restriction Enzymes

| Type | Attributes |
|---|---|
| | Some are heterodimers which recognize asymmetric DNA sequences (e.g., Bbv CI: CCTCAGC) Some recognize continuous sequences (e.g., EcoR I: GAATTC) Others recognize discontinuous sequences (e.g., Bgl I: GCCNNNNNGGC) where the half-sites are separated |
| Type IIS | Cleave at defined positions near their recognition sequences to produce discrete restriction fragments. Recognize sequences that are continuous and asymmetric and cleave outside of their recognition sequence e.g. Fok I and Alw I Comprise two distinct domains for DNA binding and for DNA cleavage Generally thought to bind as monomers but to cleave cooperatively through dimerization |
| Type IIG | Large combination restriction-and-modification enzymes, in which the two enzymatic activities reside in the same protein chain Cleave outside of their recognition sequences Some recognize continuous sequences (e.g., Acu I: CTGAAG) and cleave on only one side (nicking) Some recognize discontinuous sequences (e.g., Bcg.I: CGANNNNNNTGC) and cleave on both sides (thus releasing a small fragment containing the recognition sites) When they bind their substrates, they switch into either restriction mode to cleave the DNA, or modification mode to methylate it |
| Type III | Large combination restriction-and-modification enzymes Cleave outside of their recognition sequences and require two such sequences in opposite orientations within the same DNA molecule to accomplish cleavage outside of their recognition sequences |
| Type IV | Enzymes recognize modified, typically methylated DNA and are exemplified by the McrBC and Mrr systems of *E. coli* |

The restriction enzymes listed in Table 2 are provided solely for the purpose of exemplification and are not in any way restrictive on the scope of the invention. One skilled in the art will appreciate that a wide range of restriction enzyme will be compatible with the development of CESAs and EzyAmp reactions. For example, many restriction enzymes listed in the Restriction Enzyme Database, REBASE (http://rebase.neb.com/rebase/rebase.html) will be compatible with the development of CESAs and EzyAmp reactions. Table 3 below provides examples of restriction enzymes of the varied specificities and characteristics in the present invention.

TABLE 3

Examples of Restriction Enzymes (Groups are not mutually exclusive)

| Group | # in REBASE | Name | Recognition Sequence (/ or ↓ indicate cleavage site(s)) N = any nucleotide |
|---|---|---|---|
| Type 1 | 240 | CfrAI, M. CfrAI, S. CfrAI | GCANNNNNNNGTGG |
| | | Eco37I, M. Eco37I, S. Eco37I, Eco377I, M. Eco377I, S.Eco377I | GGANNNNNNNATGC |
| | | EcoprrI, M. EcoprrI, S. EcoprrI | CCANNNNNNNRTGC |
| | | KpnBI, M. KpnBI, S. KpnBI | CAAANNNNNNRTCA |
| | | StySBLI,, M. StySBLI, S. StySBL | CGANNNNNNTACC |
| | | StySQI, M. StySQI, S. StySQI | AACNNNNNNRTAYG |
| Type II | | Acc III | T↓CCGGA |
| | | Bam HI | G↓GATCC |
| | | Bgl I | GCCNNNN↓NGGC |
| | | Bgl II | A↓GATCT |
| | | Hpa II | C↓CGG |
| | | Hae III | GG↓CC |
| | | Mal I | G6mA↓TC |
| | | Pst I | CTGCA↓G |
| | | Sau 3AI | ↓GATC |
| | | Tsp 509I | ↓AATT |

TABLE 3-continued

Examples of Restriction Enzymes (Groups are not mutually exclusive)

| Group | # in REBASE | Name | Recognition Sequence (/ or ↓ indicate cleavage site(s)) N = any nucleotide |
|---|---|---|---|
| Type IIS | 367 | Abe I | CCTCAGC (-5/-2) |
| | | Aci I | CCGC (-3/-1) |
| | | Acc 36I | ACCTGC (4/8) |
| | | Asp 26HI | GAATGC (1/-1) |
| | | Bau I | CACGAG (-5/-1) |
| | | Bbs I | GAAGAC (2/6) |
| | | Bbv CI | CCTCAGC (-5/-2) |
| | | Bpu 10I | CCTNAGC (-5/-2) |
| | | Bsm DI | ACNNNNNCTCC |
| | | Bsp ACI | CCGC (-3/-1 |
| | | Btr I | CACGTC (-3/-3) |
| | | Mnl I | CCTC (7/6) |
| | | Taq II | GACCGA (11/9) |
| Type IIG | 1445 | Acu I | CTGAAG (16/14) |
| | | Bmu SORF1564P | GAGNNNNNGT |
| | | Eli ORF730P | CTGGAG |
| | | Nha XI | CAAGRAG |
| Nicking Enzymes | 333 | Nt. Alw I | GGATC (4/none) |
| | | Nb. Bsm AI | GTCTC (none/5) |
| | | Nt. Bbv CI | CCTCAGC (-5/none) |
| | | Nt. Bha III | GAGTC (4/none) |
| | | Nt. Bsm AI | GTCTC (1/none) |
| | | Nt. Cvi PII | CCD (-3/none) |
| | | Nb. Mva 1269I | GAATGC (none/-1) |
| Type IIB | 23 | Aju I | (7/12) GAANNNNNNNTTGG (11/6) |
| | | Bsa XI | (9/12) ACNNNNNCTCC (10/7) |
| | | Nme DI | (12/7) RCCGGY (7/12) |
| | | Tst I | (8/13) CACNNNNNNTCC (12/7) |
| Type III | 34 | Bce SI | MMCGAAG (25/27) |
| | | Eco P15I | CAGCAG (25/27) |
| | | M. Hpy AX | TCGA |
| Type IV | 10 | Eco KMcrA | Y5mCGR |
| | | Eco KMcrBC | — |
| Thermo-stable Enzymes (Optimal Temp) | Not listed as a separate group in REBASE | Acc III (65 °C.) | TCCGGA |
| | | Bsc BI (55 °C.) | GGNNCC |
| | | Bsi XI (65 °C.) | ATCGAT |
| | | Bsl I (55 °C.) | CCNNNNNNNGG |
| | | Bst BI (65 °C.) | TTCGAA |
| | | Mwo I (60 °C.) | GCNNNNNNNGC |
| | | Taq I (65 °C.) | TCGA |
| | | Tsp RI (65 °C.) | NNCASTGNN |

Again by way of example only, Mnl I is a particularly useful enzyme for use in EzyAmp reactions. Mnl I requires a four nucleotide double-stranded recognition sequence. The cleavage site is at a distance from RERS and the enzyme does not require any specific sequence in the intervening space. Each strand of DNA provides a partial recognition sequence that must be hybridized with its complement to provide the complete, double stranded recognition sequence. The recognition sequence, intervening sequence and cleavage site can be depicted as follows (where N can be any deoxyribonucleotide and "/" indicates the cleavage site:

```
5' CCTCNNNNNNN/ 5'

3' GGAGNNNNNN/ 3'
```

In the case where one strand of a double-stranded sequence is non-contiguous (i.e. adjacent deoxyribonucleotides are not linked with a phosphodiester bond) the DNA duplex is said to contain a "nick". The canonical recognition sequence of Mnl I is composed of contiguous double-stranded DNA without any nicks.

Extensive investigations were undertaken to characterize the ability of Mnl I to cleave various duplex structures including those with nicks at different positions within the RERS, and structures containing mismatched nucleotides, thio groups and ribonucleotides. The intent of these investigations was to determine the level of flexibility to allow design of a range of PESAs and DFs containing partial Mnl I recognition sites (Table 4). Such an extensive characterization performed on other RE would provide information for using other REs in EzyAmp reactions.

TABLE 4

Structures tested for capacity to be cleaved by Mnl I

| Sequence Tested* | Cleavable under conditions tested in the examples |
|---|---|

A. (canonical, contiguous recognition sequence as part of a larger DNA duplex)  
                            ↓  
...N N N N C C T C N N N N N N N...  
...N' N' N' N' G G A G N' N' N' N' N' N' N'...  
                            ↑

Yes  
Example not shown

B. (DF binding results in a nick immediately adjacent to the 3' end of partial RERS GAGG)  
                            ↓  
...N N N N C C T C N N N N N N N...  
...N' N' N' N' G G A G N' N' N' N' N' N' N'...  
                            ↑

Yes  
FIG. 15.1

C. (DF binding results in a nick one nucleotide into the 3' end of the partial RERS GAGG  
↓  
...N N N N C C T C N N N N N N N...  
...N' N' N' N' G G A G N' N' N' N' N' N' N'...  
                          ↑

Yes  
FIG. 15.2

D. (DF binding results in a nick two nucleotides into the 3' end of the partial RERS GAGG  
↓  
...N N N N C C T C N N N N N N N...  
...N' N' N' N' G G A G N' N' N' N' N' N' N'...  
                       ↑

Yes  
FIG. 15.3

E. (DF binding results in a nick and a ribonucleotide two nucleotides into the 3' end of the partial RERS GAGG  
↓  
...N N N N C C  T C N N N N N N...  
...N' N' N' N' G rG A G N' N' N' N' N' N' N'...  
                     ↑

Yes  
FIG. 15.4

F. (DF binding results in a nick three nucleotides into the 3' end of the partial RERS GAGG)  
                        ↓  
...N N N N C C T C N N N N N N N...  
...N' N' N' N' G G A G  N' N' N' N' N' N' N'...  
                       ↑

Yes  
FIG. 15.5

G. (DF binding results in a nick immediately adjacent to the 5' end of partial RERS GAGG the DF forms part of the cleavage site.  
↓  
...N N N N C C T C N N N N N N N...  
...N' N' N' N' G G A G N' N' N' N' N' N' N'...  
             ↑

No  
FIG. 15.6

H. (DF binding results in a nick two nucleotides to the 5' end of a partial RERS GAGG) The DF forms part of the cleavage site.  
                       ↓  
...N N N N C C T C N N N N N N N...  
...N' N' N' N' G G A G N' N'  N' N' N' N' N'...  
               ↑

Yes  
FIG. 15.7

I. (DF binding results in a nick two nucleotides into the 5' end of the partial RERS CTCC)  
              ↓  
...N N N N C C  T C N N N N N N N...  
...N' N' N' N' G G  A G N' N' N' N N' N' N...  
                          ↑

Yes  
FIG. 15.8

J. (InF binding results in a nick two nucleotides into the partial RERS GAGG and leaves an overhang at the nick site  
↓  
...N N N N C C T C N N N N N N N...  
...N' N' N' N' G G A G N' N' N' N' N' N' N'...  
                     ↑  
     |  
   N N N N Yes  
FIG. 14.B TABLE 4-continued Structures tested for capacity to be cleaved by Mnl I

| Sequence Tested* | Cleavable under conditions tested in the examples |
|---|---|
| K. (canonical, contiguous recognition sequence as part of a larger DNA duplex with mismatches between recognition and cleavage site) Same as I)<br>↓<br>. . . N N N N C C T C N N N N  N N  N N . . .<br>. . . N' N' N' N' G G A G N N N N'  N N'  N N . . .<br>↑ | Yes<br><br>(mismatches)<br>Example 10) |

*Where: -CCTC or GAGG are the partial sequences that make up the Mnl I recognition site
N is any nucleotide and N' is complementary to N
rN is a ribonucleotide
↓↑ are sites of RE directed cleavage
indicates a nick

1.8. Enzymes with Exonuclease or Endonuclease Activity.

Compositions and kits of the present invention may comprise one or more enzymes with exonuclease or endonuclease activity.

In addition to restriction enzymes and catalytic nucleic acid enzymes, other protein enzymes with the ability to cleave nucleic acid sequences are useful in the compositions, methods and kits described herein. Some of these enzymes have exonuclease activity which results in removal of nucleotides from the termini of single or double stranded nucleic acids. Other enzymes have endonuclease activity and cleave the sequence at internal bonds to produce smaller fragments.

Non-limiting examples of suitable exonucleases include Nuclease BAL-31, Exonuclease I (*E. Coli*), Exonuclease III (*E. coli*), T7 Exonuclease, T7 Exonuclease I, Exonuclease T, and Nuclease BAL-31. Non-limiting examples of suitable endoncleases include T7 Endonuclease I, RNase H, Flap Nuclease, Mung Bean Nuclease, and MNAzymes.

Properties of a subset of suitable nucleases are listed in Table 5.

TABLE 5

Nuclease Properties

| Enzyme | Examples of potential activities which could be exploited in the current invention<br>ss—single stranded; ds—double stranded |
|---|---|
| Nuclease BAL-31 | This exonuclease degrades both 3' and 5' termini of duplex DNA. It is also a highly specific ss endonuclease which cleaves at nicks, gaps and ss regions of duplex DNA and RNA |
| Exonuclease I (*E Coli*) | This 3' to 5' exonuclease removes nucleotides from ss DNA and thus will cleave ss overhangs from ds DNA. |
| Mung Bean Nuclease | This endonuclease removes ss extensions (3'and 5') from the ends of ds DNA or ds RNA leaving blunt ends. |
| Exonuclease III (*E. coli*) | This exonuclease removes nucleotides from 3' termini of duplex DNA with blunt or recessed 3'-termini, and also at nicks in duplex DNA to produce ss gaps |
| T7 Endonuclease I | This endonuclease cleaves non-perfectly matched DNA, cruciform DNA structures, Holliday structures or junctions, heteroduplex DNA and more slowly, nicked ds DNA. It has been used previously to detect or cleave heteroduplex and nicked DNA. |
| T7 Exonuclease | This exonuclease removes 5' nucleotides from duplex DNA in the 5' to 3' direction. It can initiate nucleotide removal from the 5' termini at gaps and nicks of ds DNA. It has also been reported to degrade RNA and DNA from RNA/DNA hybrids in the 5' to 3' direction but is unable to degrade ds or ss RNA. |
| Exonuclease T | This exonuclease is a ss RNA or ss DNA specific nuclease that requires a free 3'terminus and removes nucleotides in the 3' to 5' direction. It can generate blunt ends from dsRNA or ds DNA molecules that have 3' extensions. |
| Flap Endonucleases | These are structure-specific 5' endonucleases that recognize bifurcated ends of double stranded oligonucleotides and remove single stranded 5' arms after the first overlapping base leaving a 3' hydroxyl nick between the two oligonucleotides. |

1.9 Aptamers

Compositions and kits of the present invention may comprise one or more aptamers. An aptamer is a nucleic acid or peptide sequence that has the ability to recognize one or more ligands with great affinity and specificity due to their higher level structure, for example, a 3-D binding domain or pocket. For example, aptamers may bind to proteins, polypeptides, peptides, nucleic acids, glycoproteins, lipids, lipoproteins, cells, viruses, bacteria, archaea, fungi, antibodies, metabolites, pathogens, toxins, contaminants, poisons, entire organisms, small molecules; polymers, metal ions, metal salts, prions or any derivatives, portions or combinations thereof, or any other entity.

In some embodiments, aptamers may comprise a nucleic acid, protein, polypeptide, peptide, or combination thereof which has the ability to recognize one or more ligands. Preferred aptamers herein include short single-strand DNA, RNA oligomers, or peptides. These may be isolated from complex libraries of synthetic nucleic acids by an iterative process of adsorption, recovery, and reamplification. Aptamers may be generated against almost any target, ranging from small molecules such as amino acids, or antibiotics to protein and nucleic acid structures. Preferably, aptamers may comprise DNA or RNA molecules, or a combination of both, including but not limited to the nucleotide analogues as per, for example, Table 1 above.

One skilled in the art will appreciate that aptamers may be incorporated into any other component used in the methods of the present invention (e.g. MNAzyme components).

1.10 Kits

The present invention also provides kits for practising the methods disclosed herein. Typically, kits for carrying out the methods of the present invention contain all the necessary reagents to carry out the method.

The kits may comprise any one or more compositions of the present invention, and/or any one or more components of a composition of the present invention. For example, in one embodiment a kit may comprise a first container with MNAzyme components, a second container with an MNAzyme substrate and a third container with PESA components and a fourth container with a restriction enzyme. Self-assembly of the MNAzyme requires association of an assembly facilitator or target present in a test sample. Accordingly, in such an embodiment, on combining the components of the kit the MNAzyme assembles in the presence of an assembly facilitator or target present in a test sample and cleaves the substrate to form a DF. The DF then assembles with the PESA components to provide a CESA containing a recognition and cleavage site for the restriction enzyme.

In other embodiments a kit may comprise a first container with an SIO, a second container with PESA components and a third container with a nuclease capable of cleaving when a duplex is formed between an SIO and a target and a fourth container containing a restriction enzyme. During use, duplexes are formed by association of the SIO and the target present in a test sample. Accordingly, in such an embodiment, on combining the components of the kit the SIO forms a duplex in the presence of a target present in a test sample and the nuclease cleaves when the duplex is formed to form a DF. The DF then assembles with the PESA components to provide a CESA containing a recognition and cleavage site for the restriction enzyme.

Typically, the kits of the present invention will also comprise one or more other containers, containing for example, wash reagents, and/or other reagents as required in the performance of the methods of the invention.

In the context of the present invention, a kit may include any kit in which reagents are contained in separate containers, and may include small glass containers, plastic containers or strips of plastic or paper. Such containers may allow the efficient transfer of reagents from one compartment to another compartment whilst avoiding cross-contamination of the samples and reagents, and the addition of agents or solutions of each container from one compartment to another in a quantitative fashion. Such kits may also include a container which will accept the test sample, a container which contains the reagents used in the assay, containers which contain wash reagents, and containers which contain a detection reagent. Typically, a kit of the present invention will also include instructions for using the kit components to conduct the appropriate methods. Kits and methods of the invention may be used in conjunction with automated analysis equipment and systems, for example, including but not limited to, real time PCR machines.

For application to detection, identification or quantitation of different targets, a single kit of the invention may be applicable, or alternatively different kits, for example containing reagents specific for each target, may be required. Methods and kits of the present invention find application in any circumstance in which it is desirable to detect, identify or quantitate any entity.

2. Detection and Signal Amplification

The present invention provides various methods for the detection, identification, and/or quantification of at least one target. Further the present invention provides various methods for the amplification of a signal arising from the detection of a target.

The methods may be performed using compositions and kits of the invention, and components thereof, including those described in section 1 above.

2.1 Initiator Driver Fragments

The detection, quantification and or amplification of a target in accordance with the methods of the present invention typically relies on the use of one or more Driver Fragments (DFs). In particular, the methods typically rely on the production of an initial DF, (also referred to herein as an "initiator DF") which arises upon the detection of a target molecule. Once generated, the initiator DF can initiate the generation of a signal, for example, by hybridizing with a PESA complex to form a CESA complex capable of recognition and modification by an enzyme. Modification of the CESA complex (e.g. cleavage) by the enzyme (e.g. a nuclease) provides a detectable effect, and may release further DF capable of binding to additional PESA complexes thereby facilitating signal amplification.

In preferred embodiments, the initiator DF is distinct from the target, although in some embodiments an initiator. DF may comprise a portion of the target, and in other embodiments an initiator DF may be the target.

In preferred embodiments, generation of the initiator DF does not involve the enzymatic cleavage of the target by a restriction enzyme although this possibility is not necessarily excluded. An initiator DF may be produced by a target-specific event and this serve as a trigger to activate the signal detection and signal amplification pathways of the present invention. In general, the production of an initiator DF involves the binding of a target molecule to an oligonucleotide of the present invention (e.g. an SIO, MNAzyme or a PESA complex) to form a complex capable of modification by an enzyme such as a nuclease. For example, binding of the target to the oligonucleotide may complete a partial enzyme recognition and/or cleavage site. In some embodiments, the oligonucleotide to which the target binds comprises the DF and enzymatic modification of the complex so formed serves to release the initiator DF from the oligonucleotide (see, for example, FIGS. 8B, 9B, 10, 11 and 23). In other embodiments, binding of the target to the oligonucleotide facilitates enzymatic modification of the target to form an initiator DF directly from the target (see, for example, FIGS. 8A and 9A). In still other embodiments the oligonucleotide becomes catalytically active upon binding to the target and modifies one or more substrates to form the DF (see for Example, FIGS. 5, 13, 19 and 24).

By way of non-limiting example only, an initiator DF may be generated by cleavage or ligation of substrates by MNAzymes, as described above in subsection 1.3. The substrate may be a substrate-blocker oligonucleotide (see subsection 1.3, FIGS. 19 and 24 B, 24C, 24D and Examples 9 and 14).

In other embodiments, an initiator DF may be generated by restriction enzyme cleavage of a target (e.g. genomic DNA), cleavage of Synthetic Initiator Oligonucleotides (SIO) complexed with a target (see, for example, subsection 1.4 above, FIGS. 8-11 and FIG. 23), or by using an enzyme or chemical which recognizes and cleaves either a mismatch heteroduplex sequence or a DNA/RNA duplex sequences. The mismatch could be a natural mismatch relating to the sequence which is being interrogated and could be, for example, an acquired mutation or an inherited SNP.

The skilled addressee will recognize that the methods for generating initiator driver fragments referred to above are provided for the purpose of exemplification only, and that other suitable methods may also be utilized.

2.2 Target Detection

Methods of the present invention may be used to provide a signal indicative of the presence of a target.

In certain embodiments the generation of an initiator DF may provide a detectable effect. As noted in subsection 2.1 above, an initiator DF may be generated by the enzymatic modification (e.g. cleavage) of a complex formed by the binding of the target to an oligonucleotide of the invention. For example, the binding of a target to an SIO labeled with fluorophore and quencher moieties may facilitate enzymatic modification of the SIO in a manner that separates the moieties thus providing a detectable effect during release of the initiator DF (see for example, FIG. 23). Additionally or alternatively, the presence of the target may be detected and potentially quantified on the basis of characteristics such as the size and sequence of products arising from enzymatic modification of the oligonucleotide/target complex.

2.2.1 Linear Cascades

In preferred embodiments, an initiator DF generated upon a target recognition event is used to generate a signal via completion of a PESA complex to form a CESA complex. Enzymatic cleavage of the CESA complex may be used to generate a detectable effect and/or provide one or more additional DF capable of binding to another PESA complex to form a further CESA complex capable of enzymatic cleavage and signal generation, thus providing a linear cascade.

This process is illustrated in FIG. 4, wherein a Driver Fragment (e.g. an initiator DF), generated in a previous step, assembles with PESA complexes comprising a first Enzyme Amplifier Substrate (EAS1) oligo and a second Enzyme Amplifier Substrate (EAS2) oligo. When the DF assembles with a PESA complex a CESA is created which contains a restriction endonuclease recognition site (dashed box in FIG. 4) and restriction endonuclease cleavage site(s) (vertical filled arrows in FIG. 4). In one embodiment the first EAS1 is labeled with a quencher (Q) and the second EAS2 is labeled with a fluorophore (F). Cleavage of the assembled CESA followed by subsequent dissociation of the components results in separation of the fluorophore and quencher and concomitant generation of a fluorescent signal and release of the intact DF (FIG. 4). The DF is then free to associate with another PESA to form another CESA which leads to further restriction endonuclease cleavage and increase in fluorescence. The process thus continues and results in signal amplification whereby a fluorescent signal is produced by the restriction enzyme mediated cleavage of further EAS1 as illustrated in FIG. 4. In yet other embodiments the enzyme which cleaves the CESA is a nuclease which is not a restriction endonuclease.

In another embodiment, illustrated in FIG. 5, first and second partzymes self-assemble into a catalytically active MNAzyme when contacted with a sample containing an assembly facilitator. The MNAzyme binds to an MNAzyme substrate and facilitates modification of the MNAzyme substrate, said modification thereby indicating the presence of the assembly facilitator, wherein the assembly facilitator is the target (FIG. 5A). In other embodiments, such as for example those involving an aptamer, the assembly facilitator may not be the target, and thus may comprise only an element required for self-assembly of the MNAzyme.

Cleavage of the MNAzyme substrate by the catalytically active MNAzyme (FIG. 5A, step 1) Produces a Driver Fragment (DF) which can assemble with an PESA (FIG. 5B) (FIG. 5, step 2) to create a CESA (FIG. 5C) comprising a first EAS (EAS1) and a second EAS (EAS2) and the DF which forms a restriction enzyme recognition site (dashed box) and restriction enzyme cleavage sites (vertical black arrows). In one embodiment the first Enzyme Amplifier Substrate oligo is labeled with a fluorophore (F) and a quencher (Q) and the EAS2 is labeled with a quencher (Q). Cleavage of this assembled structure (FIG. 5, step 3) by the restriction enzyme and subsequent dissociation of the components (FIG. 5, step 4) results in generation of a fluorescent signal and release of the DF. The DF is then free to associate with another PESA to form another CESA (FIG. 5, step 5) which leads to further restriction enzyme cleavage (FIG. 5, step 6, as in step 3). The process thus continues and results in signal amplification whereby a fluorescent signal is produced by the restriction enzyme mediated cleavage of further EAS1 as illustrated in steps 4, 5, and 6 of FIG. 5.

Due to the nature of the MNAzymes, and the diverse properties of nucleases including REs, reactions can be performed over a wide range of temperatures, subject only to the requirements for the assembly of MNAzyme, catalytic modification (e.g. cleavage) of the MNAzyme substrate and the requirements for assembly of the CESA from a PESA and a DF and the activity of the nuclease. Each stage of the method may be performed at a different temperature, for example formation of the MNAzyme in the presence of a target and subsequent cleavage of the MNAzyme substrate may be achieved at a temperature and formation of the CESA comprising the DF and subsequent cleavage by a restriction enzyme to generate signal amplification may occur at a different temperature. Alternatively all steps can be performed at a single temperature in a milieu that supports catalytic activity of both the MNAymes and the nucleases, including restriction enzymes.

In other embodiments where the Driver Fragment is generated by target-directed cleavage using protein exoncleases or endonuclease, then reaction conditions compatible with all protein enzymes required for EzyAmp can be easily determined by one skilled in the art.

As further provided herein, some methods for target detection employing nucleases including restriction enzymes, either alone or in combination with MNAzymes, do not require thermocycling and/or denaturation of a target. Isothermal methods are more flexible than methods requiring thermocycling and can also enable differentiation between targets comprising single stranded and double-stranded nucleic acid. Further, the lack of a need for thermocycling may make such methods easier and less expensive. Provided in accordance with the methods herein are simple, fast, cost effective, isothermal, and procedurally-flexible methods of detecting targets of interest in a sample, which may be synthetic or natural.

2.2.2 Feedback Cascades

In preferred embodiments of the invention, an initiator DF generated upon a target recognition event is used to produce a signal in a feedback cascade involving multiple PESA and CESA complexes.

Figure 17A:
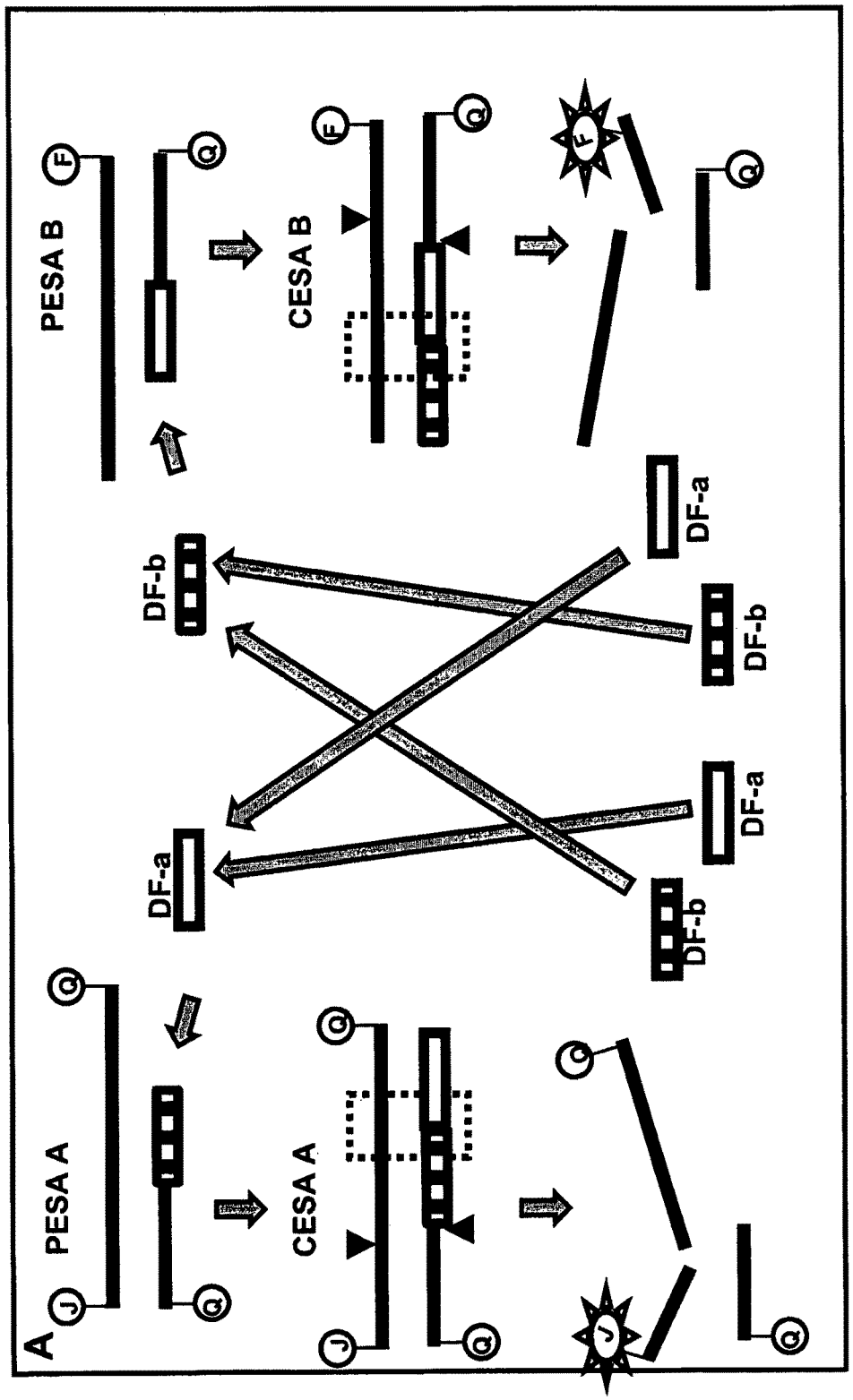

By way of non-limiting example only, and referring to FIGS. 17A and 18A, an initiator DF (DF-a) may bind to a first PESA complex (PESA A) thereby forming a first CESA complex (CESA A) having a recognition site and a cleavage site for a nuclease. PESA A may comprise first and second EAS oligos (EAS1 and EAS2) wherein a portion of EAS1 is complementary to EAS2, and a portion of EAS1 is complementary to DF-a. EAS1 may also labelled with fluorophore and quencher moieties positioned close enough together to prevent or substantially prevent any signal being generated whilst EAS1 is intact. The EAS2 may comprise a second DF (DF-b) that is distinct from DF-a. Cleavage of PESA A by a nuclease cleaves EAS1 thereby separating the fluorophore and quencher moieties providing a detectable signal, and also cleaves EAS2 releasing DF-b such that it can complex with PESA B and form CESA B. CESA B may comprise third and fourth EAS oligos (EAS3 and EAS4) wherein a portion of EAS3 is complementary to EAS4, and a portion of EAS3 is complementary to DF-b. EAS3 may also labelled with fluorophore and quencher moieties positioned close enough together to substantially prevent any signal being generated whilst EAS3 is intact. The EAS4 may comprise DF-a. Cleavage of PESA B by a nuclease cleaves EAS3 thereby separating the fluorophore and quencher moieties providing a detectable signal, and also cleaves EAS4 releasing DF-a such that it can complex with a new PESA A and form a new CESA A, thereby providing a feedback signal amplification loop. Subsequent rounds of CESA A and CESA B cleavage fuelled by the continued generation of new DF-a and DF-b serve to amplify the signal generated from the initial binding of the initiator DF (DF-a) to PESA A, and does so irrespective of the presence of additional target molecules. Nonetheless, new initiator DF oligos (i.e. DF-a) may also enter the system upon recognition of additional target molecules. Thus, the method may be used to amplify a signal arising from a minimal number of target molecules, and serve as a means of both detecting and quantifying the amount of target molecules present. In certain embodiments, PESA A and/or PESA B is/are hairpin oligonucleotides (see FIG. 18A).

FIG. 19 provides another example of a feedback signal amplification cascade involving MNAzymes. In this example, the initiating DF sequence is not part of an MNAzyme substrate sequence. Oligonucleotide partzymes assemble upon recognition of a target present within a loop portion of a substrate blocker-DF-a oligonucleotide, forming an MNAzyme capable of cleaving the loop. In this embodiment, the initiating DF (DF-a) is present on the opposing strand of the substrate-blocker oligo (relative to the loop). Cleavage of the loop by the MNAzyme results in dissociation of a portion of the substrate-blocker oligo that is complementary to DF-a, thereby allowing DF-a to hybridize to PESA A and form CESA A. Subsequent cleavage of CESA A may generate a detectable signal (e.g. by separation of fluorophore and quencher moieties), and release DF-b. The released DF-b can associate with PESA B to form CESA B which may be cleaved by an RE. Cleavage of CESA B may generate a detectable signal (e.g. by separation of fluorophore and quencher moieties) and results in release of an oligo which can function as DF-a. Thus, a feedback cascade is formed whereby CESA A and CESA B are continually formed and cleaved to release more DF-a and DF-b resulting in the formation of more CESA A and CESA B. In more complex reactions there may be multiple double stranded oligo complexes each containing unique initiating DFs designed to be released by unique MNAzymes.

A further non-limiting example of a feedback signal amplification cascade is provided in FIG. 22. As set out in the various descriptions of FIG. 22 above (see subsection 1.5 and "Brief Description of the Drawings"), the localisation of EzyAmp components by incorporating PESA complexes into branched structures may enhance the efficiency of feedback cascade systems. These structures bring multiple PESA complexes into proximity with each other allowing for the more efficient transfer of Driver Fragments between various PESA complexes upon the formation and cleavage of CESA complexes. For example, as indicated in the embodiment shown in FIG. 22A a single branch structure may comprise at least two PESA complexes (PESA A and PESA B), each complex capable of nuclease cleavage upon the binding of distinct DF (DF-a or DF-b). Nuclease cleavage of a CESA complex (CESA A) formed upon binding of DF-a to PESA A may provide a detectable effect and release DF-b. DF-b can bind PESA B to from CESA B, which can be cleaved by a nuclease providing a further detectable effect and releasing further DF-a which can bind to further PESA A, thus forming a feedback loop. As indicated in the embodiment shown in FIG. 22B, single branched structures may be hybridised via their respective backbone portions to form dual branched structures, thus effectively doubling the number of PESA A and PESA B complexes present in the structure. Single branched structures and double branched structures may be linked to other single branched structures and/or other double branched structures using one or more linking reagents to form a network of branched structures. For example, one or more arms of single branched structures and/or double branched structures may be linked with one or more arms of other single branched structures and/or double branched structures using any suitable reagent's (e.g. biotin/avidin, chemical reagents, antibodies, peptide linkers and the like), as indicated in the embodiment shown in FIG. 22D.

FIG. 23 illustrates another embodiment in which a feedback cascade is generated using a single PESA structure and an SIO. In this example, signal amplification is initiated and mediated by a suitable exonuclease such as Exonuclease III (Exo III). Exo III can remove nucleotides from 3' hydroxyl termini of DNA duplexes when the termini are either blunt or recessed, and does not digest single stranded oligos, including duplexes with a 3' overhang with at least 5 nucleotides. Phosphorothioate nucleotides are also known to block exonuclease activity. The SIO, which could be labeled with a fluorophore (F) and a quencher (Q), is represented in a hairpin conformation with an overhanging 3' terminus. Exo III cannot digest the SIO prior to a target binding as the SIO contains a 3' overhang of more than five nucleotides. The phosphorothioate nucleotide in the SIO prevents hydrolysis beyond that point in the SIO, thus leaving the DF intact.

The SIO may bind to a complementary region of the target forming a recessed 3' end in the SIO capable of being hydrolyzed by Exo III up to the phosphorothioate base, thus releasing an intact DF and causing an increase in fluorescence. In this example, the DF corresponds to the 5' portion of the SIO (i.e. sequence 5' to the phosphorothioate nucleotide) which is not complementary to the target. The target, which is no longer bound to the SIO, is then free to be recycled to bind with another SIO and thus generate another DF. DF so generated can bind to EAS1 of the PESA forming a CESA in which 3' end of the EAS1 is recessed. The Exo III can then hydrolyze the EAS1 strand of the CESA causing an increase in fluorescence and release of the DF which can be recycled to convert more PESA to CESA.

2.2.3 Multiplexing

The methods of the present invention may be used to detect multiple targets in a single EzyAmp reaction and individual signals arising from the detection of distinct targets may be amplified simultaneously.

In general, multiplex detection/signal amplification of different targets using the methods described herein may be achieved by generating a series of different initiator Driver Fragments, each derived from a specific target. A corresponding PESA complex may be provided for each specific type of initiator DF, each PESA complex comprising a distinct detectable element (e.g. a unique fluorophore) that is capable of being distinguished from that of the other PESA complexes. Initiator Driver Fragments for such reactions may be generated in any suitable manner, including any one or more of the methods referred to in subsection 2.1 above.

In certain embodiments, multiple distinct initiator Driver Fragments, each derived from a different target, may be generated using two or more Synthetic Initiator Oligonucleotides having different target specificity and comprising distinct Driver Fragments, two or more MNAzymes having distinct target specificities and capable of producing distinct Driver Fragments by catalytic modification of one or more MNAzyme substrates, or a combination of one or more Synthetic Initiator Oligonucleotides and one or more MNAzymes each having a different target specifcity and each capable of producing a distinct DF.

The skilled person will thus recognize that the compositions and methods provided herein can be used to detect a single target per reaction, or to detect multiple targets in a single reaction. When detecting multiple targets, one or more MNAzymes may be used depending on the assay and what is to be detected. For example, a single MNAzyme may suffice where detecting multiple related structures, for example a group of sequences sharing a critical sequence (recognized by the MNAzyme) and varying only for example, in length, or in sequence outside of the critical sequence. Any sequence with the critical sequence could be detected. Multiple MNAzymes are contemplated to be useful where detecting related sequences differing by as little as a single nucleotide or even where vastly different targets are being detected, and it is desirable to know the presence or absence of each. Similarly, in some embodiments a single MNAzyme substrate will suffice, while in others a unique MNAzyme substrate is required to form a unique DF to allow detection of each of several targets.

In some cases, multiplexing the method requires the formation of a distinct or unique MNAzyme which will to facilitate the design of the method. A distinct or unique DF may not be required when the substrates are affixed to a support or supports and can be distinguished by virtue of their localization on the support or supports. These design features will be readily understood by one skilled in the art.

In some embodiments, the methods allow detection of a variety of different types of target in one reaction, e.g. a nucleic acid target and a protein.

Similarly reaction which use multiple SIO directed towards multiple targets would allow multiple assay analysing multiple targets simultaneously to be developed. In this scheme or others the CESA may be cleaved by a restriction enzymes or another nuclease to facilitate signal amplification.

By way of non-limiting example only, multiple targets may be detected using multiple MNAzymes which modify a series of universal substrates, the modification of each substrate resulting in a distinct DF that will assemble with a distinct PESA to produce a CESA for a distinct restriction enzyme thereby resulting in distinctly detectable signal (e.g. different fluorescence).

An exemplary strategy for a multiplex EzyAmp system is illustrated in FIG. 13, in which various distinct initiator Driver Fragments are generated in a target-specific manner using a series of three MNAzymes with different target specificities. Each different DF generated binds to a distinct PESA complex each distinct PESA complex containing a distinct fluorophore. The three CESA complexes so formed can be cleaved by a nuclease, in each case generating a distinct signal by virtue of the three different fluorphores. FIG. 25 shows the results of a multiplex analysis where two EzyAmp reactions occur simultaneously in a single tube and are monitored independently in this manner.

It will be understood that distinct signals arising from the recognition of different targets as described above may be independently amplified in a simultaneous or substantially simultaneous manner. For example, CESA complexes arising from detection of distinct targets and formed with distinct initiator Driver Fragments may each be incorporated into separate linear and/or feedback cascades to amplify each distinct signal, for example, using methods described in subsections 2.2.2 and/or 2.2.3 above. The linear and/or feedback cascades may be run together for the independent amplification of different signals.

Multiple regions within a single target may also be detected simultaneously or substantially simultaneously using the methods of the present invention. In such cases, a series of distinct or identical initiating Driver Fragments may generated from a series of target recognition events based on different regions within a given target. For example, multiple different MNAzymes with specificity for different regions within the target may be used for this purpose. The MNAzymes may utilise a single universal subtrate to generate multiple copies of a single type of DF each of which binds to a single type of PESA forming a series of identical CESA to generate an identical detectable effect. Alternatively, the MNAzymes may catalytically modify a series of different universal substrates, the modification of each substrate resulting in a distinct DF that will assemble with a distinct PESA to produce a distinct CESA producing distinct detectable signals.

2.2.4 Methods Using Insoluble and Solid Supports

It is also to be understood that generally the methods of the present invention, whether multiplexed or not, are applicable in solution, or combined with an insoluble support or solid support on which one or more assay components including, for example, an MNAzyme substrate, partzyme, PESA, CESA, EAS, DF, EIC, InF, SIO, restriction enzyme, nuclease, exonuclease, endonuclease, aptamer, hairpin oligonucleotide, MNAzyme assembly facilitator, and/or target are bound, attached or tethered. The features of such systems will be generally understood by the skilled artisan provided with the methods and variations discussed herein. Thus, the invention is not to be considered limited to the literal teachings herein, but is capable of being modified and varied consistent with the principles and scope of the teachings provided herein and the knowledge in the art.

Preferably the support is an insoluble material, or a matrix which retains the substrate and excludes it from freely moving in the bulk of the reaction mixture. Such supports are known in the art for immobilizing or localizing substrates, including nucleic acid oligonucleotides. The skilled artisan will appreciate that the support can be selected from a wide variety of matrices, polymers, and the like in a variety of forms including beads convenient for use in microassays, as well as other materials compatible with the reaction conditions. In certain preferred embodiments, the support can be a plastic material, such as plastic beads or wafers, or that of the well or tube in which a particular assay is conducted. In certain embodiments the support may be microcarriers or nanocarriers. In certain embodiments the support may be encoded.

For example, methods for detecting targets using an MNAzyme, MNAzyme substrate, CESA, and/or PESA anchored to a support are contemplated. In a preferred embodiment, the PESA is preferably attached to a support. In another preferred embodiment, the SIO is attached to a support. The attachment of the PESA or components thereof to the support is designed such that upon assembly of the Driver Fragment with the PESA and subsequent cleavage of the CESA labeled with a fluorophore (F) and quencher (Q) by the restriction enzyme, the fluorophore is released into the bulk of the reaction mixture, away from the quencher which remains attached to the support. Thus, the detectable signal vastly increases as the quencher portion and the detectable portion are separated upon cleavage. In an alternate embodiment the fluorophore-containing detectable portion may remain attached after cleavage. This allows localization of the signal on the support. In certain instances it is contemplated that the fluorophore may be free in solution.

In certain embodiments, reactions may be set up to occur in solution and/or may comprise component/s which are attached to a solid support. The reaction illustrated in FIG. 20 shows an exemplary schema for an assay using tethered components. In this figure Station 1 is depicted as having a tethered oligonucleotide which, when cleaved in a target dependent manner (step 1), would release a first DF (striped line). This DF could then migrate to the tethered PESA A at Station 2 and hybridize with this to form CESA A (step 2). Cleavage of CESA A (step 3) would release a second driver fragment (solid black line) which could migrate to PESA B at Station 3. When the second DF hybridizes with PESA B, CESA B could be formed (step 4). Cleavage of CESA B would result in release of a sequence equivalent to the first DF (striped line). This first DF could then migrate to Station 2 (step 5) and form more CESA A which could be cleaved to release more of the second DF. In this way a cascade reaction could be initiated thus allowing continual formation and cleavage of CESA (steps 3, 4 and 5). In assays where each PESA is labeled with a fluorophore (F) and a quencher (Q) cleavage between these moieties could generate of fluorescent signal. This signal could be retained on the solid surface 2 or 3 (as illustrated) or could be released in solution, for example, if the location of the fluorophore and quencher were reversed.

The stations may be separate chambers or they may be, for example, on separate solid surfaces such as on chips or microcarriers. This strategy would increase the number of restriction enzymes useful in developing EzyAmp cascades.

In this scenario the only requirement would be that the driver fragment, generated by target-dependent cleavage, completes the sequence required for recognition and cleavage by a RE. The scenario would no longer have the requirement that RE is inhibited by the full length oligonucleotide that contains the driver fragment prior to its target dependent cleavage. The uncleaved longer fragment would now be physically separated from the PESA and could only come in contact with a PESA following cleavage in a target-dependent manner. Therefore RE which are not inhibited by the presence of additional sequence at the junction of the PESA fragment and target specific fragment can be used in EzyAmp assays to create cascade reactions.

2.2.5. Aptamers

Persons skilled in the art will readily appreciate that the methods described herein may be performed with aptamers, wherein said aptamers may facilitate the detection, identification and/or quantification of targets including targets other than nucleic acids. Non-limiting examples of aptamers suitable for use in the methods of the present invention include those described in subsection 1.8 above.

For example, methods of using MNAzymes and restriction enzymes to detect targets, including non-nucleic acid entities are contemplated. One skilled in the art will appreciate that the aptamer may be incorporated into any of the MNAzyme components. Further it will be appreciated that multiple aptamers could be incorporated into one or more of the partzyme oligonucleotide components.

In embodiments where the target is not required for the assembly of an MNAzyme an aptamer may be incorporated into an assembly facilitator. A related strategy is also envisaged where an aptamer sequence is incorporated at the end of a partzyme (apta-partzyme) in a configuration whereby an active MNAzyme is only formed in the presence of the target. The oligonucleotide components required for such a detection strategy include; a standard partzyme; an apta-partzyme which is a partzyme with an aptamer incorporated into one of its ends; an assembly facilitator which binds to both the apta-partzyme and the partzyme enabling assembly of an active MNAzyme (in the presence of target); an MNAzyme substrate; and an assembly inhibitor which hybridises to the apta-partzyme in a region which spans at least part of the aptamer sequence and part of the substrate binding arm of the partzyme sequence. In the absence of a target, the assembly inhibitor binds to the apta-partzyme thus blocking binding (and cleavage) of the MNAzyme substrate. In the presence of a target, the target binds to the aptamer sequence of the apta-partzyme, preventing the binding of the assembly inhibitor and allowing the binding and cleavage of the MNAzyme substrate. As such, an active MNAzyme can only form and produce fluorescent signal generation in the presence of a target.

It will be appreciated by one skilled in the art that in the above strategy an inhibitor sequence can be a separate molecule or can be incorporated into one of the components that participate in the MNAzyme complex. It will also be appreciated that one or more aptamers could be incorporated into any of the oligonucleotide components, including the partzymes, the assembly facilitator or the substrate. Further the aptamer could be incorporated into either end of any one of these oligonucleotides.

2.2.6. Optimization of Methods

The skilled artisan will readily understand that the methods described herein may be optimized using a variety of experimental parameters in order to optimize the detection, identification and/or quantification of a target. The particular experimental parameters that are optimized, and the level of such optimization, will depend upon the particular method being employed and the particular target being sought to be detected, identified and/or quantified. Such parameters include, but are not limited to time, temperature, pH, concentration of salts, concentrations of oligonucleotides, type and concentration of buffers, concentration of restriction enzyme co-factors, detergents, cations and other reagents including, but not limited to, dimethylsulfoxide (DMSO), EDTA, ATP, glycerol, length of complementarity, GC content and melting point (Tm) of nucleic acids components of MNAzymes and/or CESA.

In some embodiments, for example, those methods involving detection of specific nucleic acid sequences, the experimental parameters, preferably including the temperature at which the method is performed, may be optimized so as to discriminate between binding of an MNAzyme component to a target nucleic acid that does or does not comprise a sequence variation. The temperature at which such methods may be performed may be in the range of about 20° C. to about 96° C., about 20° C. to about 75° C., about 20° C. to about 60° C., or about 20° C. to about 55° C.

In one preferred embodiment, optimized reactions for practicing the methods described herein are provided. In such optimized reactions, the signal detected is increased by up to 10%, 20%, or 30% above unoptimized reactions. More preferred reaction conditions improve signal detected by at least 35%, or 40%, and preferably up to 50% or more. In still more preferred embodiments, optimized reactions have an increase of catalytic activity of more than 50%, and up to 66%, 75% or even 100%. In yet more preferred embodiments, a fully optimized reaction method will offer a 100%, 200% or even 300% or more increase in signal detection. Other preferred reaction conditions can improve the catalytic activity by up to 1000% or more over methods practiced with unoptimized reaction conditions. A highly preferred reaction condition for optimizing the methods provided herein is the inclusion of certain divalent cations. The catalytic activity of most nucleic acid enzymes and protein enzymes may be influenced in a concentration-dependent fashion by the concentration of divalent cations. Preferred optimized reactions are optimized for one or more of $Ba^{2+}$, $Sr^{2+}$, $Mg^{2+}$, $Ca^{2+}$, $Ni^{2+}$, $Co^{2+}$, $Mn^{2+}$, $Zn^{2+}$, and $Pb^{2+}$.

2.2.7 Applications of Methods

One skilled in the art would recognise that MNAzymes, CESA and restriction enzymes can be used in strategies for detection, identification or quantification of targets over a broad range of application areas. These areas include, but are not limited to, medical, veterinary, agricultural, food technology, quality control, environmental testing, life science research, forensics, identity testing, imaging, and bioterrorism applications.

A non-limiting example of a medical application is the diagnosis of a particular disease or condition or the risk of developing such a disease or condition, and/or obtaining a prognosis for a disease or condition.

For biological applications it will be understood that although not excluding the possibility, there is no particular requirement for the methods of the present invention to be carried out on the body of a living animal or human, and that the methods may be performed in vitro/ex vivo. For example, the methods may be conducted on a biological sample (e.g. a blood or tissue sample), on cells or nucleic acids previously isolated from a subject, including frozen samples of such cells and nucleic acids, paraffin embedded samples, and on cultured cells.

It will also be readily apparent that the methods described herein can be used to detect, identify and/or quantify targets in solution. For example, strategies involving detecting, identifying and/or quantifying single targets using a single substrate are applicable to such detection. In some embodiments this may involve the use of a universal substrate.

The present invention will now be further described in greater detail by reference to the following specific examples, which should not be construed as in any way limiting the scope of the invention.

EXAMPLES

Example 1

The following example demonstrates the capacity for oligonucleotides to form various duplex structures which are either cleavable or uncleavable by nucleases. Structures which are cleavable by a nuclease are duplex substrates such as CESA complexes and the nuclease in this example is a restriction enzyme (RE).

1.1. Oligonucleotides

For the following reactions, oligonucleotide fragments were combined and tested for their ability to form cleavable duplex substrates. Exemplary structures are illustrated in FIG. 3. In this example, duplexes contain one strand which includes all nucleotides required to form one strand of the double stranded restriction enzyme recognition site (RERS) for the enzyme Mnl I.

RE cleavage activity was monitored by cleavage of a dual labelled DNA complex. In the current example, Enzyme Amplifier Substrate oligo 1 (EAS1) was end labelled with an Iowa Black FQ ("IAbFQ") moiety at the 5' end, and a 6-fluorescein ("6-FAM") moiety at the 3' end and was designated, EAS1-5(23)-BF. The second Enzyme Amplifier Substrate oligo EAS2, designated EAS2-5(16)-B, was also end labelled with an Iowa. Black FQ ("IAbFQ") moiety at the 5' end, and anneals to EAS1-5(23)-BF to produce a PESA. Cleavage by the RE of fully assembled cleavable duplex substrates, termed Complete Enzyme Signal Amplifier (CESA) complexes, was monitored at 530 nm (FAM emission wavelength) with excitation at 485 nm (FAM excitation wavelength). The sequences of these oligonucleotides are listed below from 5' to 3' where the bases that are are bold and underlined form at least part of the recognition sequence for Mnl I. The bases which contribute to the recognition sequence are underlined for this enzyme, and are top strand 5' NNCCTCN$_7$/3' and bottom strand 3'NN GGAGN$_6$/5' where/indicates the cleavage site. Regions which are common to the inhibitory fragment (Sub1(8:9)-TRB2) and to the DF are italicised and underlined. Upper case letters indicate DNA and lowercase letters indicate RNA.

```
EAS 1-5(23)-BF (EAS1; FIG. 3)
CTCTTCCTCGTCTTCACATCCTA

EAS2-5(16)-B (EAS2; FIG. 3)
TAGGATGTGAAGACGA

Sub1(8:9)-TRB2 (InF; FIG. 3)
CTCACTATa*GG*AAGAGAT

DF1 (DF; FIG. 3)
*GG*AAGAGAT
```

1.4. Reaction Components

Reaction A, B, C and D were set up to contain the following oligonucleotide fragments as listed in Table 6, with reference to oligonucleotides and structures illustrated in FIG. 3.

TABLE 6

Components for cleavable and uncleavable structures

|  | Reaction A (CESA) | Reaction B (EIC) | Reaction C (PESA) | Reaction D (Control) |
|---|---|---|---|---|
| EAS1 | EAS1-5(23)-BF | EAS1-5(23)-BF | EAS1-5(23)-BF | EAS1-5(23)-BF |
| EAS2 | EAS2-5(16)-B | EAS2-5(16)-B | EAS2-5(16)-B |  |
| DF | DF1 |  |  |  |
| InF |  | Inhibitory Fragment Sub1(8:9)-TRB2 |  |  |

Formation of the CESA by the EAS1, EAS2 and the DF was measured by an increase in fluorescent signal caused by cleavage of the fluorescently labelled EAS1 (EAS1-5(23)-BF) by the RE (10U Mnl I). All reactions A, B, C and D were conducted at 37° C. in a SmartCycler® System thermocycler (Cepheid) and the total volume of all reactions was 25 µL. Fluorescence for each reaction was read every 36 seconds for a total of, 60 minutes. All reactions contained 100 nM of EAS1-5(23)-13F in 1×BSA (New England Biolabs), 1.25× NEBuffer 4 (New England Biolabs) and 10 units of Mnl I. In addition, reaction A contained 100 nM of EAS2-5(16)-B and 100 nM DF1, reaction B contained 100 nM of EAS2-5(16)-B and 100 nM Sub1(8:9)-TRB2, reaction C contained 100 nM of EAS2-5(16)-B while reaction D contained only EAS1.

1.5. Results: Detection of Cleavage by RE

In reaction A, the addition of EAS1 (EAS1-5(23)-BF), EAS2-5(16)-B and DF1 resulted in the formation of a cleavable CESA duplex substrate for the RE Mnl I as indicated by an increase in FAM fluorescence over time (FIG. 14A; +RE). This observation is consistent with the ability for restriction enzymes to recognise and cleave double stranded complexes which contain breaks or nicks in at least one of the two strands within the region which is required for recognition and cleavage by the RE. In other words, the cleavable duplex substrate is not necessary formed from two unbroken continuous complementary strands but rather can be made up from multiple oligos which form complementary duplexes.

In contrast, in reaction B, which lacked the DPI fragment but included Sub 1(8:9)-TRB2, the duplexes that formed were not cleaved because Sub-1(8:9)-TRB2 act as an InF and hence the fluorescence did not increase over time (FIG. 14B; +RE). This occurred despite the fact that Sub1(8:9)-TRB2 included the entire sequence of DF1. The sequence present in the Inf Sub1(8:9)-TRB2, which is additional to that specific sequence which is also present in the DF, inhibited the formation of cleavable duplex substrates. Indeed the additional sequence resulted in formation of non-cleavable complexes, termed Enzyme Inhibitory Complexes (EICs).

In reaction C, which contained only EAS1-5(23)-BF and EAS2-5(16)-B and lacked both the DF1 and Sub1(8:9)-TRB2, no increase in fluorescence was observed indicating that these two oligos alone (EAS1 and EAS2) are insufficient for recognition and cleavage of the duplex by the RE (FIG. 14C; +RE). The oligos EAS1 and EAS2 hybridize to form a Partial Enzyme Signal Amplifier (PESA) complex, however, an additional oligo namely the DF, is required to convert the non-cleavable PESA to a cleavable CESA.

Finally, no increase in fluorescence over time was observed in control reaction D which contained EAS1 only indicating that this structure is not amenable to cleavage despite the fact that this structure contains one strand of the recognition sequence for Mnl I. Cleavage cannot occur because complementary sequence is required to form a cleavable duplex incorporating EAS1.

Example 2

The following example was based on using multiple oligonucleotide fragments to create restriction enzyme recognition sites in CESA that resulted in cleavage of a fluorescently labeled oligo, leading to nuclease (restriction enzyme) mediated signal amplification. Reactions where nucleases cleavage result in signal amplification are termed EzyAmp reactions.

2.1. EzyAmp Oligonucleotides

For this EzyAmp reaction, two oligonucleotides EAS1 and EAS2 are required in combination with a Driver Fragment to form the restriction enzyme recognition site. In this example, EzyAmp system 1 is used to form a restriction enzyme recognition site (RERS) for the enzyme Mnl I. EzyAmp system 1 (EzyAmp 1) is composed of Enzyme Amplifier Substrate oligo 1 (EAS1-1(20)-JB), Enzyme Amplifier Substrate oligo 2 (EAS2-1(13)) and the Driver Fragment 1 (DF1) which is created by cleavage of the MNAzyme substrate Sub1 (Sub1(8:9)-FB). The strategy is as illustrated in FIG. 5.

EzyAmp activity is monitored by cleavage of a dual labelled fragment. In the current example, EAS1 (EAS1-1 (20)-JB) was end labelled with JOE moiety at the 5' end, and a Black Hole Quencher 1 ("BHQ1") moiety at the 3' end. The EAS2 (EAS2-1(13)) anneals to EAS1-1(20)-JB. RE cleavage of the fully assembled CESA was monitored at 548 nm (JOE emission wavelength) with excitation at 520 nm (JOE excitation wavelength). The sequences of these oligonucleotides are listed below from 5' to 3' where the bases underlined form at least part of the recognition sequence for MnlI (top strand 5' NN<u>CCTC</u>N$_7$/3' and bottom strand 3'NN <u>GGAG</u>N$_6$/5').

```
EzyAmp system 1-EAS 1; EAS1-1(20)-JB:
CTCTTCCTCAGCAGTTCATC

EzyAmp system 1: EAS2; EAS2-1(13):
GATGAACTGCTGA
```

2.2. Partzyme Oligonucleotides and Assembly Facilitator

To create the Driver Fragment 1 (DF1) the MNAzyme substrate, Sub1(8:9)-FB, is cleaved by the catalytically active MNAzyme that forms in the presence of the synthetic target, namely the assembly facilitator, AF-PD1. The sequences of the assembly facilitator and partzymes A and B are listed below from 5' to 3' where the bases underlined form at least part of the active catalytic core of the assembled MNAzyme, bases in bold hybridize with the target assembly facilitator, and bases in italics hybridize to the MNAzyme substrate.

```
Partzyme A PD1A2/1 (8):
GCTCCTCATCCAGCAGCGGTCGAAATAGTGAG

Partzyme B PD1B3/1(9):
ATCTCTTCTCCGAGCGTGTACGACAATGGC

Target Assembly Facilitator AF-PD1:
GCCATTGTCGTACACCTGCTGGATGAGGAGC
```

2.3. MNAzyme Substrate

MNAzyme activity is monitored by cleavage of a dual labelled nucleic acid reporter MNAzyme substrate (Sub1(8:9)-FB). The MNAzyme substrate sequence is a chimeric sequence containing both RNA and DNA bases in which a longer version has been used previously as an 8:17 DNAzyme substrate (Li et al., 2000). In the current example, the reporter MNAzyme substrate was designated Sub1(8:9)-FB and was end-labelled with 6-carboxyfluorescein ("6-FAM") moiety at the 5' end, and a Black Hole Quencher 1 ("BHQ1") moiety at the 3' end. Cleavage of Sub1(8:9)-FB by MNAzymes was monitored at 530 nm (FAM emission wavelength) with excitation at 485 nm (FAM excitation wavelength). The labelled sequence of Sub1(8:9)-FB is as follows, 5' to 3'. The lower case base represents RNA and the upper case bases represent DNA. The italicized bases correspond to the protion which acts as a DF following cleavage.

```
Sub 1(8: 9)-FB:
CTCACTATaGGAAGAGAT
```

2.4. Reaction Components

Formation of the CESA by the EAS1, EAS2 and the Driver Fragment was measured by an increase in fluorescent signal caused by cleavage by the RE (20U Mnl I; New England Biolabs) of the fluorescently labelled EAS1-1(20)-JB. Test reactions were initiated by the addition of 20 nM target assembly facilitator AF-PD1 and control reactions were initiated by the addition of H₂O. All reactions were conducted at 35° C. in a SmartCycler® System thermocycler (Cepheid) and the total volume of all reactions was 25 µL. Fluorescence for each reaction was read every 72 seconds for a total of 120 minutes in Channel 1 (FAM) and Channel 2 (Cy3) to monitor FAM and JOE respectively. All reactions contained the bulk mix of 50 nM of partzyme A (PD1A2/1(8)), 50 nM partzyme B (PD1B3/1(9)), 50 nM Sub1(8:9)-FB, 100 nM EAS1-1(20)-JB and 100 nM EAS2-1(13) in 50 mM MgCl₂ (Ambion), 1×BSA (New England Biolabs) and 1×NEBuffer 4 (New England Biolabs).

2.5. Results: Detection of Cleavage of EAS1

The addition of the target assembly facilitator to the test reaction allowed partzymes A and B to assemble into a catalytically active MNAzyme that cleaved the reporter MNAzyme substrate Sub1(8:9)-FB which resulted in (i) creation of the Driver Fragment, DF1, (DF1: GGAAGA-GAT) and (ii) a detectable signal that increased over time and could be monitored in real time in the FAM channel indicating MNAzyme cleavage of Sub1(8:9)-FB (FIG. 6 (i) Target AF-PD1). The DF could then bind to the PESA complex (formed by EAS1 and EAS2) to form a CESA complex which functioned as a duplex substrate that was cleaved by Mnl I. This resulted in detectable signal that increased over time in the JOE indicating RE cleavage of EAS1 present within the CESA complex which in turn is indicative of the presence of the target AF-PD1 (FIG. 6 (iii) Target AF-PD1).

In Control reactions where no target assembly facilitator was added to the mix, the catalytically active MNAzyme did not form and thus the reporter MNAzyme substrate Sub1(8:9)-FB was not cleaved, no DF was generated and no CESA was created. Therefore there was no increasing signal in either the FAM or JOE signal over time (FIG. 6 (ii) and (iv) No Target Controls). This indicates that cleavage of Sub1(8:9)-FB by the MNAzyme is required to supply the DF for the formation of the CESA. In contrast, in these no target reactions, an EIC was formed by hybridization between the PESA and Sub1(8:9)-FB which in its uncleaved state functions as an InF.

Example 3

This example provides a strategy for design of Complete Enzyme Signal Amplifier (CESA) complexes and associated oligonucleotides.

By way of example, an MNAzyme substrate suitable for cleavage by an MNAzyme based on an 8-17 DNAzyme may have the following sequence; 5' CTCACTATaGGAAGA-GAT 3' (where upper case indicates DNA and lower case indicates RNA). Once cleaved by an MNAzyme in the presence of an appropriate assembly facilitator, this MNAzyme substrate produces two fragments namely CTCAC-TATa and GGAAGAGAT. Examples of how to use the 3' oligonucleotide fragment 5' GGAAGAGAT 3' (3' TAGA-GAAGG 5') as a Driver Fragment to produce a CESA complex are demonstrated in the following tables. In the following examples N is any nucleotide and N' is its complement. The sequences of EAS1 and the 3' cleavage fragment of Sub1(8:9) (see below) can be amended slightly to provide many different PESA, and subsequent CESA, designed to be used with a range of different restriction enzymes with different recognition sequences.

|      |    | 1 | 2 | 3 | 4 | 5 | 6 | 7 | 8 | 9 | 10 | 11 | 12 | 13 | 14 | 15+ |
|------|----|---|---|---|---|---|---|---|---|---|----|----|----|----|----|-----|
| EAS1 | 5' | . | . | . | T | C | T | C | T | T | C  | C  | N  | N  | N  | N N N . . . |
| EAS2 | 3  |   |   |   |   |   |   |   |   |   |    |    | N' | N' | N' | N' N' N' N' . . . |
| DF   | 3  | T |   |   | A | G | A | G | A | A | G  | G  |    |    |    |     |

The oligonucleotide EAS1 may contain sequences where the restriction recognition site for a restriction enzyme begins for example at various positions along the universal or generic ESA1 sequence shown above.

By way of example, if the RE site begins at position 6 the recognition sequence for BsaW1 (TCCGGA) could be incorporated into EAS1, EAS2 and the Driver Fragment as illustrated below where the RER site is underlined.

|   | 1 2 3 4 5 6 7 8 9 10 | 11 | 12 | 13 | 14 | 15+ |
|---|---|---|---|---|---|---|
| EAS1 5' | . . .T C T C T T C C G G | A | N | N | N | N . . . |
| EAS2 3' |                  C C | T | N' | N' | N' | N' |
|   |   |   |   |   |   | . . . |
| DF 3' T |   A G A G A A G G |   |   |   |   |   |

Alternatively, if the RE site begins at position 7 the recognition sequence for Mnl 1 (CCTC) could be incorporated into EAS1, EAS2 and the Driver Fragment as illustrated below where the RER site is underlined.

|   | 1 2 3 4 5 6 7 8 9 10 | 11 | 12 | 13 | 14 | 15+ |
|---|---|---|---|---|---|---|
| EAS1 5' | . . .T C T C T T C C T C | N | N | N | N | N . . . |
| EAS2 3' |                 A G | N' | N' | N' | N' | N' |
|   |   |   |   |   |   | . . . |
| DF 3' T |   A G A G A A G G |   |   |   |   |   |

In a further example, if the RE site begins at position 8 the recognition sequence for Ear1 (CTCTTC) could be incorporated into EAS1, EAS2 and the Driver Fragment as illustrated below where the RER site is underlined.

|   | 1 2 3 4 5 6 7 8 9 10 | 11 | 12 | 13 | 14 | 15+ |
|---|---|---|---|---|---|---|
| EAS1 5' | . . .T C T C T T C C T C | T | T | C | N | N . . . |
| EAS2 3' |                 A G | A | A | A | N' | N' |
|   |   |   |   |   |   | . . . |
| DF 3' T |   A G A G A A G G |   |   |   |   |   |

Using this general strategy candidate REs for use with this DF would include REs which have a recognition sequence which has at its 5' end either C or CC or TCC. As such REs in the following table (along with many others) could be tested for use with this Driver Fragment.

| Enzyme | Top strand of the RERS (5' to 3') |
|---|---|
| Aci I | CCGC(-3/-1) |
| Acu I | CTGAAG(16/14) |
| Afl II | C/TTAAG |
| Alw NI | CAGNNN/CTG |
| Ava I | C/YCGRG |
| Avr II | C/CTAGG |
| Bbv CI | CCTCAGC(-5/-2) |
| Bcc I | CCATC(4/5) |
| Bfa I | C/TAG |
| Bmg BI | CACGTC(-3/-3) |
| Bpm I | CTGGAG(16/14) |
| Bpu EI | CTTGAG(16/14) |
| Bsa WI | W/CCGGW |
| Bsi EI | CGRY/CG |
| Bsi WI | C/GTACG |
| Bsl I | CCNNNNN/NNGG |
| Bsm BI | CGTCTC(1/5) |
| Bso BI | C/YCGRG |
| Bsp CNI | CTCAG(9/7) |
| Bsp EI | T/CCGGA |

Other examples illustrated show the use of the same Driver Fragment in the opposite orientation to those examples above. In these cases candidate REs can have an RERS that ends with G or GG or GGA. The generic sequences of EAS1, EAS2 and the DF for use in such systems are as follows.

|   | 1 | 2 | 3 | 4 | 5 | 6 7 8 9 10 | 11 | 12 | 13 | 14 | 15 |
|---|---|---|---|---|---|---|---|---|---|---|---|
| DF 5' |   |   |   |   |   | G G A A | G | A | G | A | T |
| EAS2 5' | N' | N' | N' | N' | N' |   |   |   |   |   |   |
| EAS1 3' | N | N | N | N | N | N C C T T | C | N | N | N |   |

By way of example, if the RE site begins at position 4, the RERS for BstU1 (CGCG) could be incorporated into EAS1, EAS2 and the Driver Fragment as illustrated below where the site is underlined.

|   | 1 | 2 | 3 | 4 5 6 7 8 9 10 | 11 | 12 | 13 | 14 | 15 |
|---|---|---|---|---|---|---|---|---|---|
| DF 5' |   |   |   | G G A A | G | A | G | A | T |
| EAS2 5' | N' |   | N' | N' C G C |   |   |   |   |   |
| EAS1 3' | N |   | N | N G C G C C T T | C | N | N | N |   |

The range of useful restriction enzymes which can be used with any specific DF may be extended by taking advantage of the requirement by some REs for additional sequence either 5' or 3' of the recognition sequence to be present to allow cleavage.

Example 4

The following example was based on using multiple oligonucleotide fragments to create restriction enzyme recognition sites in CESA that resulted in cleavage of a fluorescently labeled oligo, leading to nuclease (restriction enzyme) mediated signal amplification. Reactions where nucleases cleavage result in signal amplification are termed EzyAmp reactions.

4.1. EzyAmp Oligonucleotides

For this EzyAmp reaction, two oligonucleotides EAS1 and EAS2 are required in combination with a Driver Fragment to form the restriction enzyme recognition site. In this example, EzyAmp system 1 is used to form a restriction enzyme recognition site (RERS) for the enzyme MnlI. EzyAmp system 1 (EzyAmp 1) is composed of Enzyme Amplifier Substrate oligo 1 (EAS1-1(20)), Enzyme Amplifier Substrate oligo 2 (EAS2-1(13)) and the Driver Fragment 1 (DF1) which is created by cleavage of the MNAzyme substrate Sub1. The strategy is as illustrated in FIG. 5.

EzyAmp activity is monitored by cleavage of a dual labelled fragment. In the current example, EAS1 (EAS1-1 (20)-BJ) was end labelled with an Iowa Black FQ ("IAbFQ") moiety at the 5' end, and a JOE moiety at the 3' end. The EAS2 (EAS2-1(13)) is end labelled with an Iowa Black FQ ("IAbFQ") and anneals to EAS1-1(20)-BJ. RE cleavage of the fully assembled CESA was monitored at 548 nm (JOE emission wavelength) with excitation at 520 nm (JOE excitation wavelength). The sequences of these oligonucleotides are listed below from 5' to 3' where the bases underlined form at least part of the recognition sequence for MnlI (CCTC).

```
EzyAmp system 1a EAS1; EAS1-1(20)-BJa:
CTCTTCCTCAGCAGTTCATT

EzyAmp system 1a EAS2; EAS2-1(13)-Ba:
AATGAACTGCTGA
```

4.2. Partzyme Oligonucleotides and Assembly Facilitator

To create the Driver Fragment 1 (DF1) the MNAzyme substrate, Sub1(8:9)-TRB2, is cleaved by the catalytically active MNAzyme that forms in the presence of the synthetic target, namely the assembly facilitator, AF-PD1. The sequences of the assembly facilitator and partzymes A and B are listed below from 5' to 3' where the bases underlined form at least part of the active catalytic core of the assembled MNAzyme, bases in bold hybridize with the target, and bases in italics hybridize to the MNAzyme substrate.

```
Partzyme A PD1A2/1 (8):
GCTCCTCATCCAGCAGCGGTCGAAATAGTGAG

Partzyme B PD1B3/1(9):
ATCTCTTCTCCGAGCGTGTACGACAATGGC

Target Assembly Facilitator AF-PD1:
GCCATTGTCGTACACCTGCTGGATGAGGAGC
```

4.3. MNAzyme Substrate

MNAzyme activity is monitored by cleavage of a dual labelled nucleic acid reporter MNAzyme substrate (Sub1(8:9)-TRB2). The MNAzyme substrate sequence is a chimeric sequence containing both RNA and DNA bases in which a longer version has been used previously as an 8:17 DNAzyme substrate (Li et al., 2000). In the current example, the reporter MNAzyme substrate was designated Sub1(8:9)-TRB2 and was end-labelled with sulforhodamine ("TXR") moiety at the 5' end, and a Black Hole Quencher 2 ("BHQ2") moiety at the 3' end. Cleavage of Sub1(8:9)-TRB2 by MNAzymes was monitored at 617 nm (TXR emission wavelength) with excitation at 598 nm (TXR excitation wavelength). The labelled sequence of Sub1(8:9)-TRB2 is as follows, 5' to 3'. The lower case base represents RNA and the upper case bases represent DNA. The bases in italics correspond to the portion which can act as the DF.

```
Sub1(8: 9)-TRB2:
CTCACTATaGGAAGAGAT
```

4.4. Reaction Components

Formation of the CESA by the EAS1, EAS2 and the Driver Fragment was measured by an increase in fluorescent signal caused by cleavage by the RE (MnlI) of the fluorescently labelled EAS1-1(20)-BJ. Reactions were initiated by the addition of 10U Mnl I (New England Biolabs). All reactions were conducted at 35° C. in a SmartCycler® System thermocycler (Cepheid) and the total volume of all reactions was 25 µL. Fluorescence for each reaction was read every 72 seconds for a total of 120 minutes. All reactions contained the bulk mix of 50 nM partzyme A (PD1A2/1(8)), 50 nM partzyme B (PD1B3/1(9)), 100 nM of Sub1(8:9)-TRB2, 100 nM EAS1-1(20)-BJ and 100 nM EAS2-1(13)-B, in 50 mM MgCl$_2$ (Ambion), 1×BSA (New England Biolabs) and 1.2×NEBuffer 4 (New England. Biolabs). In addition, test reactions contained 20 nM target assembly facilitator (AF-PD1) and control reactions contained H$_2$O.

4.5. Results: Detection of Cleavage of EAS1

The addition of the target assembly facilitator to the test reaction allowed partzymes A and B to assemble into a catalytically active MNAzyme that cleaved the reporter MNAzyme substrate Sub1(8:9)-TRB2 which resulted in (i) creation of the Driver Fragment, DF1, (DF1: GGAAGAGAT) and (ii) a detectable signal that increased over time and could be monitored in real time in the TXR channel indicating MNAzyme cleavage of Sub1(8:9)-TRB2. The DF could then bind to the PESA complex (formed by EAS1 and EAS2) to form a CESA complex which functioned as a duplex substrate that was cleaved by Mnl I. This resulted in detectable signal that increased over time in the JOE channel indicating RE cleavage of EAS1 present within the CESA complex which in turn was indicative of the presence of the target AF-PD1 (FIG. 12).

In Control reactions where no target assembly facilitator was added to the mix, the catalytically active MNAzyme did not form and thus the reporter MNAzyme substrate Sub1 (8:9)-TRB2 was not cleaved, no DF was generated and no CESA was created. Therefore there was no increase in signal in either the TXR or JOE channels over time (FIG. 12). This indicates that cleavage of Sub1(8:9)-TRB2 by the MNAzyme is required to supply the DF for the formation of the CESA. In contrast, in this reaction, an EIC was formed by hybridization between the PESA and Sub1(8:9)-TRB2, which in its uncleaved state, functions as an InF.

Example 5

The following examples demonstrate the ability of Mnl I to (i) tolerate nicks at various points adjacent to, and within, the specific bases of the recognition sequence, (ii) tolerate non-complementary bases adjacent to the specific bases in the recognition sequence, (iii) tolerate non-complementary bases between the recognition sequence and the cleavage site and (iv) tolerate the presence of ribonucleotides adjacent to, or within, the recognition sequence.

5.1. Oligonucleotides 5.1.1 Reaction 1: DF Binding Results in a Nick Immediately Adjacent to the 3' End of the RERS "GAGG"

In the following reaction, the PESA was composed of EAS1 (EAS1_10_2) and EAS2 (EAS2_11_2(16)). EAS1 was labelled with an Iowa Black FQ ("IAbFQ") moiety at the 5' end and a 6-fluorescein ("6-FAM") moiety at the 3' end, and contained a partial Mnl I recognition sequence of 5'CCTC3'. EAS2 was designed to anneal to EAST and was labelled with an Iowa Black FQ ("IAbFQ") moiety at the 5' end. EAS2 contained a partial Mnl I recognition sequence of 5'GAGG3' at its 3' end. The DF (DF1(8)) was designed to hybridize to EAS1 as the 3' sequence immediately before the 5'GAGG3' partial Mnl I recognition sequence in EAS2

(Table 4B). The DF did not contain any part of the Mnl I recognition sequence. The sequences of these oligonucleotides are listed below from 5' to 3' where the bases underlined form at least part of the recognition sequence for Mnl I. The bases which contribute to the recognition sequence for Mnl I are 5' CCTC(N)$_7$/3' and 3' GAGG(N)$_6$/5' where/indicates the cleavage site.

```
EAS1_10_2 (EAS1)
CATCTCTTCCTCAGAGCCTGACTT

EAS2_11_2 (16) (EAS2)
AAGTCAGGTCTGAGG

DF1 (8) (DF)
AAGAGATG
```

5.1.2 Reaction 2: DF Binding Results in a Nick One Base into the 3' End of the Partial RERS "GAGG".

In the following reaction, the PESA was composed of EAS1 (EAS1_10_2) and EAS2 (EAS2_11_2(15)). EAS1 was labelled with an Iowa Black FQ ("IAbFQ") moiety at the 5' end and a 6-fluorescein ("6-FAM") moiety at the 3' end, and contained a partial Mnl I recognition sequence of 5'CCTC3'. EAS2 was designed to anneal to EAS1 and was labelled with an Iowa Black FQ ("IAbFQ") moiety at the 5' end. EAS2 contained a fragment (5'GAG3') of the partial Mnl I recognition sequence of 5'GAGG3' at its 3' end. The DF (DF1(9)) was designed to hybridize to EAS1 adjacent to EAS2. The DF contained a fragment (the 3' G) of the partial Mnl I recognition sequence of 5'GAGG3', completing it by adding the one base missing from EAS2 (Table 4C). The sequences of these oligonucleotides are listed below from 5' to 3' where the bases underlined form at least part of the recognition sequence for Mnl I. The bases which contribute to the recognition sequence for Mnl I are 5' CCTC(N)$_7$/3' and 3' GAGG(N)$_6$/5' where / indicates the cleavage site.

```
EAS1_10_2 (EAS1)
CATCTCTTCCTCAGAGCCTGACTT

EAS2_11_2(15) (EAS2)
AAGTCAGGTCTGAG

DF1(9) (DF)
GAAGAGATG
```

5.1.3 Reaction 3: DF Binding Results in a Nick Two Bases into the 3' End of the Partial RERS "GAGG".

In the following reaction, the PESA was composed of EAS1 (EAS1_10) and EAS2 (EAS2_11).

EAS1 was labelled with an Iowa Black FQ ("IAbFQ") moiety at the 5' end and a 6-fluorescein ("6-FAM") moiety at the 3' end, and contained a partial Mnl I recognition sequence of 5'CCTC3'. EAS2 was designed to anneal to EAS1 and was labelled with an Iowa Black FQ ("IAbFQ") moiety at the 5' end. The 3' end of EAS2 contained a fragment (5'GA3') of the partial Mnl I recognition sequence of 5'GAGG3'. The DF (DF1) was designed to hybridize on EAS1 adjacent to EAS2 and contained a fragment (5'GG3') of the partial Mnl I recognition sequence of 5'GAGG3', completing it by adding the two bases (GG) missing from EAS2 (Table 4D). The sequences of these oligonucleotides are listed below from 5' to 3' where the bases underlined form at least part of the recognition sequence for Mnl I. The bases which contribute to the recognition sequence for Mnl I are 5' CCTC(N)$_7$/3' and 3' GAGG(N)$_6$/5' where/indicates the cleavage site.

```
EAS1_10 (EAS1)
CTCTTCCTCAGCACCTGATT

EAS2_11 (EAS2)
AATCAGGTGCTGA

DF1 (DF)
GGAAGAGAT
```

5.1.4 Reaction 4: DF Binding Results in a Nick and a Ribonucleotide Base Two Bases into The Partial RERS "GAGG".

In the following reaction, the PESA was composed of EAS1 (Re1F1(20T)(20)-BJ) and EAS2 (Re1S1(1A)(13)-5-B). EAS1 was labelled with an Iowa Black FQ. ("IAbFQ") moiety at the 5' end and a Joe_N ("JOE") moiety at the 3' end, and contained a partial Mnl I recognition sequence of 5' CCTC 3'. EAS2 was designed to anneal to EAS1 and was labelled with an Iowa Black FQ ("IAbFQ") moiety at the 5' end. EAS2 contained a fragment (5'GA3') of the partial Mnl I recognition sequence of 5'GAGG3'. The DF (rRe1S1(9)-3) was designed to anneal to EAS1 adjacent to EAS2. The 5' end of the DF contained a fragment (5'GG3') of the partial Mnl I recognition sequence of 5'GAGG3', completing it by adding the two bases missing from EAS2. The DF also contained a ribonucleotide (Gg) to introduce a ribonucleotide into the recognition sequence (Table 4E). The sequences of these oligonucleotides are listed below from 5' to 3' where the bases underlined form at least part of the recognition sequence for Mnl I, and the ribonucleotide base is indicated as a lower case g. The bases which contribute to the recognition sequence for Mnl I are 5' CCTC(N)$_7$/3' and 3' GAGG(N)$_6$/5' where / indicates the cleavage site.

```
Re1F1 (20)-BJ (EAS1)
CTCTTCCTCAGCAGTTCATT

Re1S1 (13)-5-B (EAS2)
AATGAACTGCTGA rRe1S1(9)-3 (DF)
gGAAGAGAT
```

5.1.5 Reaction 5: DF Binding Results in a Nick Three Bases into the 3' End of the Partial RERS GAGG.

In the following reaction, the PESA was composed of EAS1 (EAS1_10_2) and EAS2 (EAS2_11_2(13)). EAS1 was labelled with an Iowa Black FQ ("IAbFQ") moiety at the 5' end and a 6-fluorescein ("6-FAM") moiety at the 3' end, and contained a partial Mnl I recognition sequence of 5'CCTC3'. EAS2 was designed to anneal to EAS1 and was labelled with an Iowa Black FQ ("IAbFQ") moiety at the 5' end. EAS2 contained fragment (5'G3') of the partial Mnl I recognition sequence of 5'GAGG3' at its 3' end. The DF (DF1(11)) was designed to hybridize to EAS1 adjacent to EAS2. The 5' end of the DF contained a fragment (5'GGA3') of the partial Mnl I recognition sequence of 5'GAGG3', completing it by adding the three bases missing from EAS2 (Table 4F). The sequences of these oligonucleotides are listed below from 5' to 3' where the bases underlined form at least part of the recognition sequence for Mnl I. The bases which contribute to the recognition sequence for Mnl I are 5' CCTC(N)$_7$/3' and 3' GAGG(N)$_6$/5' where/indicates the cleavage site.

```
EAS1_10_2 (EAS1)
CATCTCTTCCTCAGAGCCTGACTT

EAS2_11_2(13) (EAS2)
AAGTCAGGTGCTG

DF1(11) (DF)
AGGAAGAGATG
```

5.1.6 Reaction 6: DF Binding Results in a Nick Immediately Adjacent to the 5' End of RERS "GAGG".

The DF forms part of the recognition and cleavage sequence. In the following reaction, the PESA is composed of EAS1 (Mnl I/DFS_F1-BF) and EAS2 (Mnl I/DFS_F2). EAS1 was labelled with an Iowa Black FQ ("IAbFQ") moiety at the 5' end and a 6-fluorescein ("6-FAM") moiety at the 3' end, and contained a partial Mnl I recognition sequence of 5'CCTC3'. EAS2 was designed to hybridize to EAS1. The 5' end of EAS2 contained a partial Mnl I recognition sequence of 5'GAGG3'. The DF (Mnl I/DFS_DF) was designed to anneal to EAS1 as the 5' sequence immediately upstream of the 5'-GAGG3' Mnl I recognition site in EAS2. The DF did not contain any portion of the Mnl I recognition sequence, but did contain a cleavage site (Table 4G). The sequences of these oligonucleotides are listed below from 5' to 3' where the bases underlined form at least part of the recognition sequence for Mnl I. The bases which contribute to the recognition sequence for Mnl I are 5' CCTC(N)$_7$/3' and 3' GAGG(N)$_6$/5' where/indicates the cleavage site.

```
Mnl I/DFS_F1-BF (EAS1)
TCCGCAGCCTCCCTTCTCTAC

Mnl I/DFS_F2 (EAS2)
GAGGCTGCGGA

Mnl I/DFS_DF (DF)
GTAGAGAAGG
```

5.1.7 Reaction 7: DF Binding Results in a Nick 2 Bases Upstream from the 5' End of Partial RERS GAGG. The DF Forms Part of the Cleavage Site.

In the following reaction, the PESA was composed of EAS1 (Mnl IDFS_F1-BF) and EAS2 (Mnl I/DFS_F2(13)). EAS1 was labelled with an Iowa Black FQ ("IAbFQ") moiety at the 5' end and a 6-fluorescein ("6-FAM") moiety at the 3' end, and contained the partial Mnl I recognition sequence of 5'CCTC3'. EAS2 was designed to hybridize to EAS1 and contained the partial Mnl I recognition sequence of 5GAGG3' plus a two extra bases 5' to this sequence. The DF (Mnl I/DFS_DF(8)) was designed to hybridize to EAS1 two bases upstream from the 5' end of EAS2. This DF did not contain any portion of the Mnl I recognition sequence, but did contain a cleavage site (Table 4H). The sequences of these oligonucleotides are listed below from 5' to 3' where the bases underlined form at least part of the recognition sequence for Mnl I. The bases which contribute to the recognition sequence for Mnl I are 5' CCTC(N)$_7$/3' and 3' GAGG(N)$_6$/5' where/indicates the cleavage site.

```
Mnl I/DFS_F1-BF (EAS1)
TCCGCAGCCTCCCTTCTCTAC

Mnl I/DFS_F2(13) (EAS2)
GGGAGGCTGCGGA

Mnl I/DFS_DF(8) (DF)
GTAGAGAA
```

5.1.8 Reaction 8: DF Binding Results in a Nick Two Bases into the 5' End of the Partial RERS "CCTC".

In the following reaction, the PESA was composed of EAS1 (EAS1_28) and EAS2 (EAS2_27). EAS1 was labelled with an Iowa Black FQ ("IAbFQ") moiety at the 5' end and contained the partial Mnl I recognition sequence of 5'GAGG3'. EAS2 was designed to hybridize to EAS1 and was labelled with a 6-fluorescein ("6-FAM") moiety at the 3' end. EAS2 contained a fragment (5'TC3') of the partial Mnl I recognition sequence of 5'CCTC3'. EAS2 was designed to create a single non-complementary base pair between the recognition sequence and the cleavage site. The DF (DF-3EAS2_26) was designed to hybridize to EAS1 and contained a fragment (5'CC3') of the partial Mnl I recognition sequence of 5'CCTC3, completing it by adding the two bases missing from EAS2 (Table 4I). The sequences of these oligonucleotides are listed below from 5' to 3' where the bases underlined form at least part of the recognition sequence of Mnl I. The bases which contribute to the recognition sequence for Mnl I are 5' CCTC(N)$_7$/3' and 3' GAGG(N)$_6$/5' where/indicates the cleavage site.

```
EAS1_28 (EAS1)
TGGTTGAGCAGAGAGGGATCATC

EAS2_27 (EAS2)
TCTCTGCTCAACCA

DF-3EAS2_26
GATGATCCC
```

5.2 Reaction Components

Cleavage of a candidate CESA composed of EAS1, EAS2 and a DF by the RE Mnl I was monitored by measuring changes in fluorescent signal produced in response to separation of fluorophore and quencher moieties. Test reactions were initiated by the addition of 100 nm of the DF, and control reactions were initiated by the addition of water (control reactions did not contain any DF). The reactions were performed in a CFX96™ Real-Time PCR Detection System (Bio-Rad) and the total volume of the reaction was 25 μL. Reactions were performed in duplicate. All oligonucleotides were purchased from Integrated DNA Technologies (IDT). The reactions each contained 100 nM of EAS1, 100 mM of EAS2, 1×BSA (New England Biolabs), 1×NEBuffer 4 (New England Biolabs) and nuclease free water (Ambion). Variations between each reaction are listed in Table 7.

TABLE 7

Variations in reaction conditions for experiments in Example 5

| Reaction Number | Mnl I (U) | Additional MgCl$_2$ (mM) | Temperature (° C.) | Detection Channel | Programmed Read Time (seconds) | Reaction Time (minutes) |
|---|---|---|---|---|---|---|
| 1 | 0.75 | 15 | 35 | 1 (FAM) | 1 | 17 |
| 2 | 2 | 10 | 35 | 1 (FAM) | 1 | 17 |
| 3 | 2 | 10 | 35 | 1 (FAM) | 1 | 23 |
| 4 | 2 | 10 | 35 | 2 (HEX) | 8 | 40 |
| 5 | 2 | 10 | 35 | 1 (FAM) | 1 | 17 |
| 6 | 2 | 0 | 30 | 1 (FAM) | 1 | 17 |
| 7 | 2 | 0 | 30 | 1 (FAM) | 1 | 17 |
| 8 | 2 | 0 | 35 | 1 (FAM) | 1 | 17 |

5.3 Results: Detection of Cleavage of CESA

The addition of DF to the test reactions allowed the DF to bind to the PESA complex (formed by EAS1 and EAS2). This formed a CESA complex which contained a complete restriction site for the RE, Mnl I. An increase in fluorescent signal was indicative of cleavage of the candidate CESA complexes.

5.3.1: DF Binding Results in a Nick Immediately Adjacent to the 3' End of the RERS "GAGG".

The addition of DF to Reaction 1 resulted in increasing fluorescence over time (FIG. 15.1(i)). This indicates that a CESA that is cleavable by Mnl I can be formed when the DF binds to form a nick immediately adjacent to the 3' end of the Mnl I RERS of 5' GAGG 3'. In this example the PESA contains the entire RERS, as well as the cleavage site, and hence is also cleaved by Mnl I, albeit at a lower efficiency. As such, in the absence of DF, the fluorescence still increased, but at a slower rate than the reaction containing DF (FIG. 15.1(ii)).

5.3.2: DF Binding Results in a Nick One Base into the 3' End of the Partial RERS "GAGG".

The addition of DF to Reaction 2 resulted in increasing fluorescence over time (FIG. 15.2(i)). In contrast, no increase in signal was observed over time where no DF was added (FIG. 15.2(ii)). This indicates that a CESA cleavable by Mnl I can be formed when the DF completes the 5' GAGG 3' partial Mnl I recognition sequence by supplying the last 3' base (G) of this sequence within the PESA.

5.3.3: DF Binding Results in a Nick Two Bases into the 3' End of the Partial RERS "GAGG".

The addition of DF to Reaction 3 resulted in increasing fluorescence over time (FIG. 15.3(i)). In contrast, no increase in signal was observed over time where no DF was added (FIG. 15.3(ii)). This indicates that a CESA cleavable by Mnl I can be formed when the DF completes the 5' GAGG 3' partial Mnl I recognition sequence by supplying the last two 3' bases (GG) of this sequence within the PESA.

5.3.4: DF Binding Results in a Nick and a Ribonucleotide Base Two Bases into the Partial RERS "GAGG".

The addition of DF to Reaction 4 resulted in increasing fluorescence over time (FIG. 15.4(i)). In contrast, no increase in signal was observed over time where no DF was added (FIG. 15.4(ii)). This indicates that a CESA cleavable by Mnl I can be formed when the DF completes the 5' GAGG 3' partial Mnl I recognition sequence by supplying the last two 3' bases (GG) of this sequence within the PESA, even when the second base is a ribonucleotide (Gg).

5.3.5: DF Binding Results in a Nick Three Bases into the 3' End of the Partial RERS "GAGG".

The addition of DF to Reaction 5 resulted in increasing fluorescence over time (FIG. 15.5(i)). In contrast, no increase in signal was observed over time where no DF was added (FIG. 15.5(ii)). This indicates that a CESA cleavable by Mnl I can be formed when the DF completes the 5' GAGG 3' partial Mnl I recognition sequence by supplying the last three 3' bases (GGA) of this sequence within the PESA.

5.3.6: DF Binding Results in a Nick Immediately Adjacent to the 5' End of RERS "GAGG".

The DF forms part of the recognition and cleavage sequence. There was no increase in fluorescence over time in the presence (FIG. 15.6(i)) or absence of DF (FIG. 15.6(ii)), indicating no cleavable CESA was formed when the DF bound to the 3' end of EAS1 immediately upstream from the partial Mnl I recognition sequence of 5' GAGG 3'. Addition of the DF appears to have a quenching effect on the PESA, possibly due to hybridization of DF to EAS1 inducing a less flexible and better quenched structure.

5.3.7: DF Binding Results in a Nick 2 Bases Upstream from the 5' End of RERS "GAGG".

The DF forms part of the recognition and cleavage sequence. In Reaction 7, the addition of DF resulted in increasing fluorescence over time (FIG. 15.7(i)). In contrast, no signal increase was observed, over time where no DF was added (FIG. 15.7(ii)). This indicates that a CESA cleavable by Mnl I can be formed when the DF binds to the sequence two bases upstream of the 5' GAGG 3' partial Mnl I recognition site within the PESA, and provides one of the cleavage sites.

5.3.8: DF Binding Results in a Nick Two Bases into the 5' End of the Partial RERS "CCTC".

In Reaction 8, the addition of DF resulted in increasing fluorescence over time (FIG. 15.8(i)). In contrast, no increase in signal increase was observed over time where no DF was added (FIG. 15.8(ii)). This indicates that a CESA cleavable by Mnl I can be formed when the DF completes the partial Mnl I recognition sequence of 5'CCTC3' by two bases from the 5' end (CC).

Overall the results from Reactions 1 to 8 demonstrate that there is considerable flexibility in how one skilled in the art can design PESA's and corresponding DFs such that they produce cleavable CESA structures. Of particular note is the ability to include ribonucleotides in the DF which can convert a PESA to a CESA (FIG. 15.4(i)). The ability to use DFs containing ribonucleotides extends the ability to use a variety of MNAzymes to initiate an EzyAmp reaction. In formats which use an MNAzyme derived from a 10:23 DNAzyme to cleave a substrate in a target-specific manner to directly generate a DF or DFs, both cleaved fragments will both contain a ribonucleotide at their cleaved termini.

These cleaved fragments would be useful as DFs in EzyAmp reactions since ribonucleotides can be tolerated within the RERS.

Example 6

The following example demonstrates the capacity for oligonucleotides to form various duplex structures which are either cleavable, or not cleavable, by specific enzymes. Structures which are cleavable by a nuclease are duplex substrates such as CESA complexes and the nuclease in this example is a restriction enzyme (RE).

6.1. Oligonucleotides

For the following reactions, oligonucleotide fragments were combined and used as substrates to test the ability of various REs to cleave duplex substrates. Exemplary structures of CESA, PESA and EIC are illustrated in FIG. 1. In this example, the various duplexes contained one oligonucleotide which included all bases required to form one strand of the RERS for the specific REs which were screened.

RE cleavage activity was monitored by cleavage of labelled complexes, where a fluorophore and quencher were positioned on the complex in such a way that physical separation between the fluorophore and quencher would produce a detectable signal. In the current example, an Enzyme Amplifier Substrate oligo 1, designated EAS1, was labelled with a fluorophore and a quencher and in addition contained sequence corresponding to all of the bases required to form one strand of the RERS for each RE. RE1F1(20)-JB was labeled with a JOE on the 5' end and a BHQ on the 3' end. EAS7-1(21)-FB was labeled with a 6-FAM on the 5' end and an IaBFQ on the 3' end. REF4F1-F1B was labeled internally in positon 4 with a fluorescein and internally on positon 15 with an IaBFQ. EAS1-4(16)-BF was labeled with an IaBFQ on the 5' end and a 6-FAM on the 3' end. EAS5-1(18)-BF was labeled with an IaBFQ on the 5' end and a 6-FAM on the 3' end. EAS3-1(18)-BF was labeled with an IaBFQ on the 5' end and a 6-FAM on the 3' end.

The second Enzyme Amplifier Substrate oligo, designated EAS2, contained a partial RERS, and anneals to EAS1 and in some instances was labelled with a quencher moiety, for example, EAS6-1(10)-B was labeled with an IaBFQ on the 5' end. Together EAS1 and EAS2 form the structural equivalent of PESA complexes (FIG. 1C). Hybridization of a third fragment, which corresponds to the structural equivalent of the Driver Fragment (DF), results in the formation of duplex structures which are equivalent in structure, but not necessarily function, to Complete Enzyme Signal Amplifier (CESA) complexes (FIG. 1A). Alternatively, hybridization of a third fragment, which corresponds to the structural equivalent of the Inhibitory Fragment (InF), results in the formation of duplex structures which are equivalent in structure, but not necessarily in function, to Enzyme Inhibitory Complexes (EICs) (FIG. 1B). In some instances the InF was labeled with a fluorophore and/or quencher moiety. Sub1(8:9)TRB2 was labeled with a Texas red fluorophore on the 5' end and a BHQ2 on the 3' end; RE1S1(1A)(13)-5-B was labeled with an IaBFQ on the 5' end. Finally, an Antisense Control strand (ASC), which contained all of the fully complement RE recognition sequence of EAS1, was included as a positive control for RE cleavage of an intact duplex. In some instances the ASC was labelled with a quencher moiety, for example ASC-EAS6-1(8)-B was labeled with an IaBFQ on the 5' end.

The ability, or lack thereof, for various REs to cleave fully assembled duplex structures described above was monitored in the appropriate channel for the fluorophore present on the EAS1. The names of these oligonucleotides present in each reaction are listed below from 5' to 3' in Table 8. The bases which contribute to the recognition sequences of the REs are provided in Table 9, where '/' indicates the cleavage site.

TABLE 8

REs and Oligos used in Screening REs for EzyAmp

| RE; RERS | Oligonucleotides P = present in mix, Rn = Reaction Rn A = CESA structural equivalent; Rn B EIC structural equivalent; Rn C PESA structural equivalent; Rn D - Labelled EAS1 Oligo only; Rn E and F = Double stranded duplex (without nicks) | | | | | | |
|---|---|---|---|---|---|---|---|
| | Type | Name | A | B | C | D | E/F |
| EarI; | EAS1 | RE1F1(20)-JB | P | P | P | P | P |
| 5'CTCTTC(N)$_1$/3' | EAS2 | RE1S1(13)-5 | P | P | P | | |
| 3'GAGAAG(N)$_4$/5' | DF | D1F-3Sub1 | P | | | | |
| | InF | Sub1(8:9)-TRB2 | | P | | | |
| | ASC | ASC-RE1S1)22)-5 | | | | | P |
| | ASC | ASC-RE5F2(25) | | | | | P |
| AlwI; | EAS1 | EAS7-1(21)-FB | P | P | P | P | P |
| 5'GGATC(N)$_4$/3' | EAS2 | EAS8-1(14) | P | P | P | | |
| 3'CCTAG(N)5/5' | DF | D1F-3Sub1 | P | | | | |
| | InF | Sub1(8:9) | | P | | | |
| | ASC | ASC-EAS8-1(23) | | | | | P |
| BssKI; | EAS1 | RE4F1-FIB | P | P | P | P | P |
| 5'/CCNGG3' | EAS2 | RE4F2(12) | P | P | P | | |
| 3'GGNCC/5' | DF | D1F-3Sub1 | P | | | | |
| | InF | Sub1(8:9)-TRB2 | | P | | | |
| | ASC | ASC-RE4F2(21) | | | | | P |

TABLE 8-continued

REs and Oligos used in Screening REs for EzyAmp

| | | | | | | | | |
|---|---|---|---|---|---|---|---|---|
| MspI; | EAS1 | EAS1-4(16)-BF | P | P | P | P | P | |
| 5'C/CGG3' | EAS2 | EAS2-4(9) | P | P | P | | | |
| 3'GGC/C5' | DF | D1F-3Sub1 | P | | | | | |
| | InF | Sub1(8:9)-TRB2 | | P | | | | |
| | ASC | ASC-EAS2-4(18) | | | | | P | |
| | | | | | | | | |
| PmeI; | EAS1 | EAS5-1(18)-BF | P | P | P | P | P | |
| 5'GTTT/AAAC3' | EAS2 | EAS6-1(10)-B | P | P | P | | | |
| 3'CAAA/TTTG5' | DF | D2F-3RE1S1(9) | P | | | | | |
| | InF | RE1S1(1A)(13)-5-B | | P | | | | |
| | ASC | ASC-EAS6-1(18)-B | | | | | P | |
| | | | | | | | | |
| Hpy8I; | EAS1 | EAS3-1(18)-BF | P | P | P | P | P | |
| 5'GTN/NAC3' | EAS2 | EAS4-1(10) | P | P | P | | | |
| 3'CAN/NTG5' | DF | D2F-3RE1S1(9) | P | | | | | |
| | InF | RE1S1(1A)(13)-5-B | | P | | | | |
| | ASC | ASC-EAS4-1(18) | | | | | P | |
| | | | | | | | | |
| RsaI; | EAS1 | EAS3-1(18)-BF | P | P | P | P | P | |
| 5'GT/AC3' | EAS2 | EAS4-1(10) | P | P | P | | | |
| 3'CA/TG5' | DF | D2F-3RE1S1(9) | P | | | | | |
| | InF | RE1S1(1A)(13)-5-B | | P | | | | |
| | ASC | ASC-EAS4-1(18) | | | | | P | |
| | | | | | | | | |
| StyD4I; | EAS1 | RE4F1-FIB | P | P | P | P | P | |
| 5'/CCNGG3' | EAS2 | RE4F2(12) | P | P | P | | | |
| 3'GGNCC/3' | DF | D1F-3Sub1 | P | | | | | |
| | InF | Sub1(8:9)-TRB2 | | P | | | | |
| | ASC | ASC-RE4F2(21) | | | | | P | |

The sequences for each of the oligos in Table 8 are provided in Table 9.

TABLE 9

| Oligo Name | Oligo Sequence Bases in capitals are DNA, bases in lower case are RNA |
|---|---|
| RE1F1(20)-JB | CTCTTCCTCAGCAGTTCATC |
| RE1S1(13)-5 | GATGAACTGCTGA |
| D1F-3Sub1 | GGAAGAGAT |
| Sub1(8:9)-TRB2 | CTCACTATaGGAAGAGAT |
| ASC-RE1S1(22)-5 | GATGAACTGCTGAGGAAGAGAT |
| ASC-RE5F2(25) | CAGGATGTGAAGACGAGGAAGAAGAT |
| EAS7-1(21)-FB | CTCTTCCACTTGATCCCGTAT |
| EAS8-1(14) | ATACGGGATCAAGT |
| ASC-EAS8-1(23) | ATACGGGATCAAGTGGAAGAGAT |
| RE4F1-FIB | CTCTCCAGGCAAGAGGT |
| RE4F2(12) | ACCTACTTGCCT |
| ASC-RE4F2(21) | ACCTACTTGCCTGGAAGAGAT |
| EAS1-4(16)-BF | CTCTTCCGGAGTTGCT |
| EAS2-4(9) | AGCAACTCC |
| ASC-EAS2-4(18) | AGCAACTCCGGAAGAGAT |
| EAS5-1(18)-BF | TCAGCAGTTTAAACAACC |
| EAS6-1(10)-B | GGTTGTTTAA |
| D2F-3RE1S1(9) | ACTGCTGAG |
| RE1S1(1A)(13)-5-B | AATGAACTGCTGA |
| ASC-EASE-1(18)-B | GGTTGTTTAAACTGCTGA |
| EAS3-1(18)-BF | TCAGCAGTACACAGAACC |
| EAS4-1(10) | GGTTCTGTGT |
| ASC-EAS4-1(18) | GGTTCTGTGTACTGCTGA |

6.2. Reaction Components

Reaction A, B, C, D, E and F were set up to contain the following oligonucleotide fragments as listed in Table 10.

TABLE 10

Oligonucleotide Components of Reaction A to F

| CESA structural equivalent Reaction A | EIC structural equivalent Reaction B | PESA structural equivalent Reaction C | EAS1 only Reaction D | Double stranded duplex with no nick at RER | |
|---|---|---|---|---|---|
| | | | | Reaction E Positive Control | Reaction F Negative Control |
| RE present EAS1 EAS2 DF | RE present EAS1 EAS2 InF | RE present EAS1 EAS2 | RE present EAS1 | RE present EAS1 ASC | RE absent EAS1 ASC |

All reactions contained 100 nM of EAS1 in 1×NEB buffer (Table 11) and a specified number of units of RE (Table 11). In addition, Reaction A contained 100 nM of each of EAS2 and DF; Reaction B contained 100 nM of each of EAS2 and InF; Reaction C contained 100 nM of EAS2; Reaction D contained only EAST; while Reactions E and F contained 100 nM of ASC. Oligonucleotides were purchased from IDT. Some reactions also included the addition of 1×BSA (New England Biolabs) as directed by the manufacturers recommendations with use for that particular RE. Specific reaction conditions for Reactions A to E are shown in Table 11. Each Reaction F was identical to Reactions E except no RE was added to the mix. Cleavage, or lack therefore, of the various oligo structures was measured by monitoring changes in fluorescent signal associated with modification of the fluorescently labelled EAS1 due to its cleavage by a RE. All reactions A, B, C, D, E and F were conducted at a specified temperature in a CFX96™ Real-Time PCR Detection System (Bio-Rad) and the total volume of all reactions was 25 μL. Fluorescence for each reaction was programmed to be read every 1 second for a total of 100 cycles. All reactions were performed in duplicate.

TABLE 11

Reaction conditions for each specific RE

| RE | Amount of RE | Temperature (° C.) | Buffer (1x) | BSA | Reaction Time (min) | Fluorophore* |
|---|---|---|---|---|---|---|
| PmeI | 2 U | 30 | NEBuffer 4 | 1x | 17 | FAM |
| RsaI | 2 U | 30 | NEBuffer 4 | 1x | 17 | FAM |
| Hpy8I** | 2 μL*** | 30 | FD Buffer* | 1x | 17 | FAM |
| BssKI | 8 U | 37 | NEBuffer 3 | 1x | 27 | FAM |
| StyD4I | 2 U | 30 | NEBuffer 2 | | 27 | FAM |
| EarI | 2 U | 35 | NEBuffer 4 | | 27 | JOE |
| MspI | 2 U | 37 | NEBuffer 4 | 1x | 27 | FAM |
| AlwI | 10 U | 37 | NEBuffer 4 plus 15 mM MgCl$_2$ (Ambion) | | 27 | FAM |

*Increases in fluorescence for reactions containing 6-fluorescein (FAM) moieties or a 6-JOE (JOE) moieties were detected in the FAM or JOE channels (channel 1 or 2) respectively) of the CFX96 ™ Real-Time PCR Detection System (Bio-Rad). In reactions reactions that used scan mode FAM/Sybr the run time was 17 minutes, in reactions that used the scan mode all channels the reaction time was 24 minutes.

**Supplied by Fermentas (remaining RE and buffers supplied by New England Biolabs),

***Concentration not disclosed by supplier, therefore, these reactions were performed based on μL per reaction.

6.3. Results: Detection of Cleavage

For Reactions A-F, if an increase in fluorescence was detected, which indicated separation of the fluorophore and quencher, this was recorded as 'Cleavage' in Table 12. Where no increase in fluorescence was detected, this indicated of no separation of fluorophore and quencher, and this was recorded as 'No cleavage' in Table 12.

TABLE 12

Results

| RE | Reaction A | Reaction B | Reaction C | Reaction D | Reaction E | Reaction F |
|---|---|---|---|---|---|---|
| PmeI | Cleavage | No cleavage | No cleavage | No cleavage | Cleavage | No cleavage |
| RsaI | Cleavage | No cleavage | No cleavage | No cleavage | Cleavage | No cleavage |
| Hpy8I | Cleavage | No cleavage | No cleavage | No cleavage | Cleavage | No cleavage |
| BssKI | Cleavage | Cleavage | Cleavage | Cleavage | Cleavage | No cleavage |
| Styd4I | No cleavage | No cleavage | No cleavage | No cleavage | Cleavage | No cleavage |
| EarI | Cleavage | Cleavage | No cleavage | No cleavage | Cleavage | No cleavage |
| MspI | Cleavage | Cleavage | No cleavage | No cleavage | Cleavage | No cleavage |
| AlwI | Cleavage | Cleavage | Cleavage | No cleavage | Cleavage | No cleavage |

An increase in fluorescent signal over time was observed in all positive control reactions E, which contained EAS1 with its full complementary strand, ASC, indicating that this structure is amenable to cleavage. Cleavage can occur because each of the REs could recognize and cleave the double stranded complex. Conversely, as anticipated, no increase in fluorescent signal was observed for negative control reactions F, which contained EAS1 with its full complementary strand, ASC, but lacked any REs.

With regards to cleavage of various complete and partial duplex structures the REs fell into one of four basic patterns (I to IV) depending on the oligo structures that were cleaved by the various RE. One example of an enzyme which behaved according to each pattern is illustrated in FIG. 16. The significance of the above results presented in Table 12 is summarized in Table 13.

TABLE 13

| Pattern | Example | Behaviour under the specific screening conditions for these experiments. Usefulness in EzyAmp (under same conditions) |
|---|---|---|
| I | StyD4 I | This enzyme did not cleave a double stranded structure containing a nicked RERS (i.e. did not cleave a CESA) and therefore would not be useful for an EzyAmp assay under the reaction conditions tested in this example. |
| II | Pme I, Rsa I, Hpy8 I | These enzymes did recognize and cleave a double stranded structure containing a nicked RERS (i.e. did cleave a CESA complex), but did not cleave a structure using an InF to complete the RERS (i.e. did not cleave an EIC complex) and therefore would be useful for EzyAmp assays including single tube, in-solution assays. |
| III | Ear I, Msp I | These enzymes did recognize and cleave across a double stranded structure containing nicked RERS (i.e. did cleave CESAs) but also cleaved a structure using an InF to complete the RERS (i.e. they did cleave a structure equivalent to an EIC complex). Under the reaction conditions tested they would be useful in EzyAmp systems where the initiating fragment is physically separate from the first PESA, for example, in assays where components are either tethered (e.g. FIG. 20) or in separate chambers. |
| IV | BssK I, Alw I | These enzymes cleave CESA, EIC and PESA complexes and would not be suitable for inclusion in an EzyAmp reaction using the buffer system and conditions under which these enzymes were screened. |

It should be noted, however, that the behaviour of each RE is highly dependent on many factors including ionic strength, pH, Mg concentration and RE concentration and as such these groupings and patterns may only pertain to these REs under these reaction conditions only. None-the-less these experiments show a process whereby one can set up a screening assay to find combinations of nucleases with suitable reaction conditions such that the nucleases cleave duplex structures in such a pattern so as to make them suitable to be exploited to develop EzyAmp reactions.

Example 7

The following example demonstrates the capacity of two different CESA complexes (CESA A and CESA B) to be cleaved by a single restriction enzyme within one reaction tube following completion of these CESA complexes in response to initiation by either of their respective DFs. The strategy for this reaction is illustrated in FIG. 17A. The CESA in this example were designed such that cleavage of each CESA generated a new DF for the other CESA. In this example, CESA A and CESA B were labeled with different fluorophores so that fluorescent signal generated by cleavage of each CESA could be independently monitored.

7.1 Oligonucleotides

In the following reaction, CESA A is composed of PESA A and DF-a (DF1) whereas CESA B is composed of PESA B and DF-b (DF-3EAS1_11). In turn, PESA A is composed of EAS1A (EAS1_10) and EAS2A (EAS2_11) and PESA B is composed of EAS (EAS1_12) and EAS2B (EAS2_13) EAS2A of PESA A contains a region within it which is equivalent to the sequence of DF-b and EAS2B of PESA B contains a region within it which is equivalent to the sequence of DF-a. As such, this experiment was designed so that DF-a or DF-b could either be added at the initiation of the reaction and then each DF could be generated by cleavage of the CESA B or CESA A respectively during the reaction. A schematic diagram of the process is illustrated in FIG. 17A.

RE activity was monitored by changes in fluorescence corresponding to the separation of fluorophore and quencher. In the current example, EAS1A was end labeled with an Iowa Black FQ ("IAbFQ") moiety at the 5' end, and a JOE moiety at the 3' end. EAS2A was also labeled by an Iowa Black FQ ("IAbFQ") moiety at the 5' end and anneals to EAS1A. EAS1B was end labeled with a 6-fluorescein (6"FAM") moiety at the 5' end. EAS2B was labeled by an Iowa Black FQ ("IAbFQ") moiety at the 3' end and anneals to EAS1B. The sequences of these oligonucleotides are listed below from 5' to 3' where the bases underlined form at least part of the recognition sequence for Mnl I (CCTC or GAGG) and where italicized bases represent those that are equivalent to DFs present in the context of longer oligonucleotides

```
EAS1_10 (EAS1A)
CTCTTCCTCAGCACCTGATT

EAS2_11 (EAS2A)
AATCAGGTGCTGA

EAS1_12 (EAS1B)
TCAGTCCCACGTGTGA
```

-continued

EAS2_13 (EAS2B)
TCAGCA<u>CCTC</u>ACACGTG<i>GGAAGAG</i>

DF-3EAS1_11 (DF-b)
<u>GG</u>TGCT<u>GA</u>

DF1 (DF-a)
<u>GG</u>AAGAGAT 7.2 Reaction Conditions

Oligonucleotides were purchased from Integrated DNA Technologies (IDT). All reactions contained a bulk mix of 100 nM each of EAS1_10, EAS2_11, EAS1_12, EAS2_13 and 10 mM $MgCl_2$(Ambion), 1×BSA (New England Biolabs), 1×NEBuffer 4 (New England Biolabs) nuclease free water (Ambion) and 0.75 U Mnl I (New England Biolabs). Reaction A was initiated by the addition of 100 nM DF1(I) or an equivalent volume of water (II), and Reaction B was initiated by the addition of 100 nM DF3ESA1_11 (III) or an equivalent volume of water (IV). All reactions had a total reaction volume of 25 µl. Fluorescence signal was measured simultaneously in both Channel 1 (FAM) and Channel 2 (HEX) to monitor FAM and JOE respectively. The reaction was conducted at 35° C. in a CFX96™ Real-Time PCR Detection System (BioRad). Fluorescence for each sample was programmed to be read after every 1 second for 150 cycles (Scan Mode: All channels). The total run time was 40 minutes. All reactions were performed in duplicate.

7.3 Results: Detection of Cleavage of CESAA and CESAB

Figure 17B:
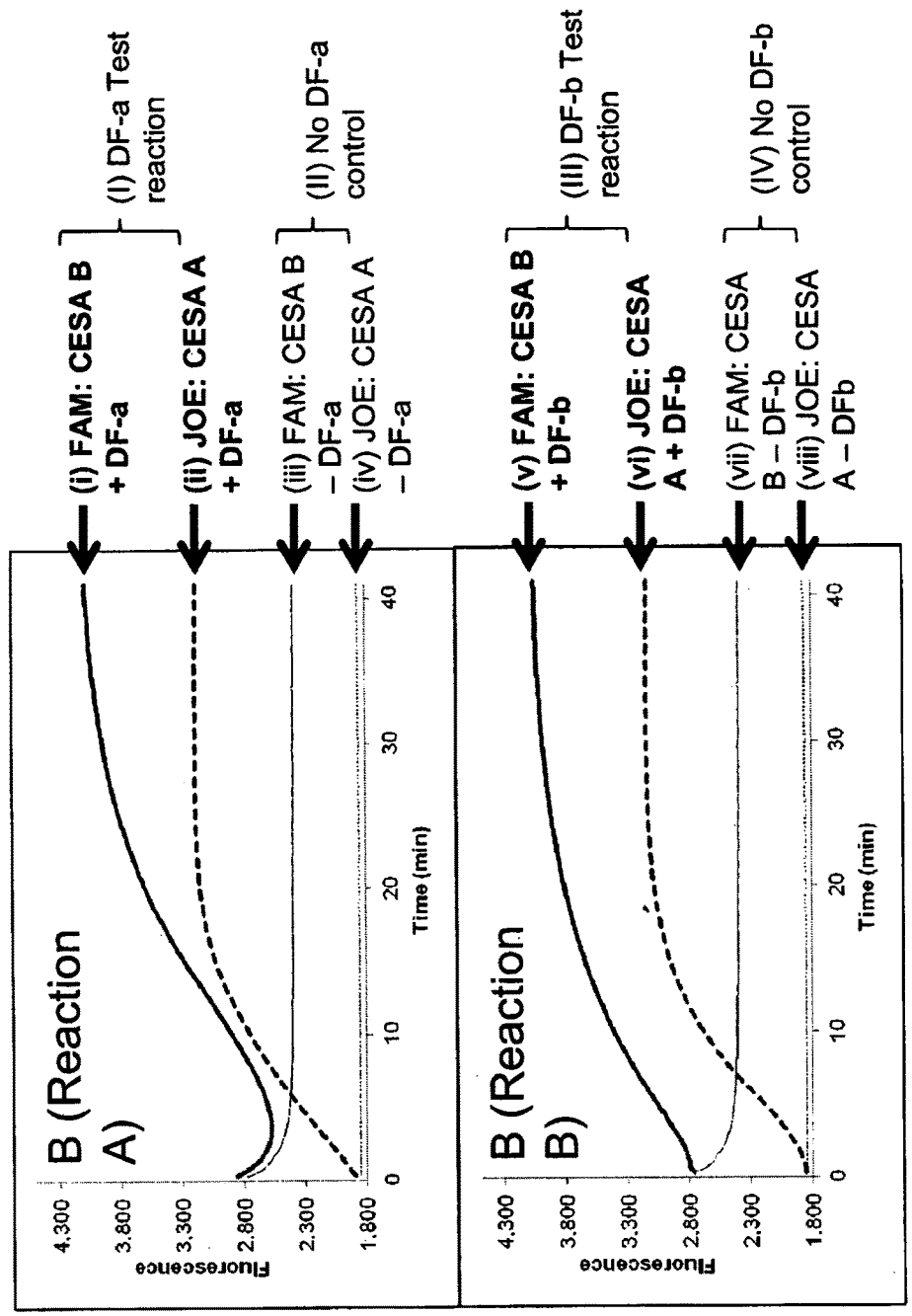

The changes in fluorescence in each reaction were plotted against time and shown in FIG. 17B. In Reaction A, the addition of DF-a resulted in the formation of a cleavable CESA A duplex substrate for the RE Mnl I as indicated by the increase in JOE fluorescence over time (Reaction A(ii) JOE: CESA A+DF-a). At the same time, an increase in FAM fluorescence was also observed over time in this reaction, indicative of the production of DF-b from CESA A cleavage to form cleavable CESA B duplex substrate for the same RE Mnl I (Reaction A(i) FAM: CESA B+DF-a). In contrast, no increase in JOE or FAM fluorescence was observed in the control reactions where DF-a was not added (Reactions A(II) No DF-a controls indicating that neither CESA A or CESA B was formed in the absence of initiating DF-a.

In Reaction B, the addition of DF-b resulted in the formation of cleavable CESA B duplex substrate for the RE Mnl I as indicated by the increase in FAM fluorescence over time (Reaction B(v) FAM: CESA B+DF-b). At the same time, an increase in JOE fluorescence was also observed over time in this reaction indicative of the production of DF-a from CESA B cleavage to form cleavable CESA B duplex substrate for the same RE Mnl I (Reaction B(vi) JOE: CESA A+DF-b). In contrast, no increase in JOE or FAM fluorescence was observed in the control reactions where DF-b was not added (Reactions B(IV) No DF-b control) indicating that neither CESA A or CESA B was formed in the absence of initiating DF-b.

Additional non-cleavable EIC complexes would also have been expected to be formed by hybridization between PESA A (EAS1A and EAS2A) and EAS2B (in this context acting as an InF) and/or between PESA B (EAS1B and EAS2B) and EAS2A (in this context acting as an InF).

Overall, the experiment demonstrates that addition of DF-a can form CESA A resulting in its cleavage by Mnl I which further causes a) an increase in JOE fluorescence and b) generation of a DF-b fragment by cleavage of the EAS2A oligonucleotide which in turn can form CESA B resulting in its cleavage by Mnl I and the concomitant c) increase in FAM fluorescence and d) generation of a DF-a fragment by cleavage of the EAS2B oligonucleotide. Further, the experiment demonstrates that addition of DF-b to reaction B can form CESA B resulting in its cleavage by Mnl I which further causes a) an increase in FAM fluorescence and b) generation of a DF-a fragment by cleavage of the EAS2B oligonucleotide which in turn can form CESA A resulting in its cleavage by Mnl I and the concomitant c) increase in JOE fluorescence and d) generation of a DF-b fragment by cleavage of the EASIB oligonucleotide. As such both CESA A and CESA B can be formed by addition of their respective driver fragments and cleavage of each CESA is capable of generating a driver fragment that can complete the other PESA.

Example 8

The following example demonstrates the capacity of two different hair-pinned CESA complexes (CESA A and CESA B) to be cleaved by a single restriction enzyme within one reaction tube following completion of these complexes by either of their respective DFs. In this example the PESA A and PESA B are composed of single oligonucleotides containing, from 5' to 3', EAS1, linking sequence and EAS2. PESA A and PESA B are capable of forming intramolecular hairpins. The strategy is illustrated in FIG. 18 Panel A. Further, the hair-pinned CESA in this example were designed such that cleavage of each CESA generated a new DF for the other CESA. In this example, both PESA A and PESA B were labeled with the same fluorophore so that the fluorescent signal generated by cleavage of resultant CESA would be additive.

8.1. Oligonucleotides

In the following reaction, CESA A is composed of PESA A (PESA_35) and DF-a (D1F-3Sub1); and CESA B is composed of PESA B (PESA_36) and DF-b (DF-3PESA_35).

PESA A (PESA_35) can form a hairpin and it contains a region within it which is equivalent to the sequence of DF-b. PESA B (PESA_36) can also form a hairpin and it contains a region within it which is equivalent to the sequence of DF-a. As such, this experiment was designed so that either DF-a or DF-b could be added to initiate the reaction and then both DFs could be generated by cleavage of CESA A or CESA B respectively during the reaction in a feedback cascade reaction.

In the current example RE activity was monitored by the change in fluorescence associated with cleavage of each dual labeled PESA. In this example, PESA A (PESA_35) was end labeled with an Iowa Black FQ ("IAbFQ") moiety and internally labelled with a Fluorescein moiety (on a T base in position 22) and PESA B (PESA_36) was 5' end labeled with an Iowa Black FQ ("IAbFQ") moiety and internally labelled with a Fluorescein moiety (on a T base in position 21).

The sequences of these oligonucleotides are listed below from 5' to 3' where the bases underlined form at least part of the recognition sequence for Mnl I (CCTC or GAGG) and where italicized bases represent those that are equivalent to DFs present in the context of longer oligonucleotides. The position of the internal Fluorescein is indicated in bold. The boxed bases on the 5' end indicates EAS1, the boxed bases on the 3' side indicates EAS2.

```
PESA_35 (PESA A)
ATCTCTTCCTCTACACCTTTTTTTTTTTTTTTTAGGTGTGGA

PESA_36 (PESA B)
TCCACACCTCTCTTCCTTTTTTTTTTTTTTTTTTTGGAAGAGA

D1F-3Sub1 (DF-a)
GGAAGAGATG

DF-3PESA_35 (DF-b)
GGTGTGGA
```

8.2. Reaction Components

Oligonucleotides were purchased from integrated DNA technologies. All reactions contained a bulk mix of nuclease free water (Ambion), 1×NEBuffer 4, 1×BSA and 0.75U Mnl I (all New England Biolabs). Reactions were made up to a final volume of 25 µL and performed in duplicate.

Reaction (i) contained 100 nM PESA_35 & 10 nM DF1; Reaction (ii) contained 100 nM PESA_35; Reaction (iii) contained 100 nM PESA 36 and 10 nM DF-3PESA_35; Reaction (iv) contained 100 nM PESA_36; Reaction (v) contained 100 nM PESA_35, 100 nM PESA_36 & 10 nM DF1; Reaction (vi) contained 100 nM PESA_35, 100 nM PESA_36 & 10 nM DF-3PESA_35; Reaction (vii) contained 100 nM PESA_35 & 100 nM PESA_36; Reaction (viii) contained 100 nM PESA_35, 100 nM PESA_36, 100 nM DF1 and 100 nM DF-3PESA_35.

The reactions were performed at 33° C. on a CFX96™ Real-Time PCR Detection System (BioRad). Fluorescence for each reaction was read after every 5 seconds for 60 cycles (scan mode FAM/SYBR; channel 1 FAM) then after every 25 seconds for 100 cycles (scan mode FAM/SYBR; channel 1 FAM). The total run time was 65 minutes. The fluorescence was normalized to cycle 1 of each corresponding reaction which contained the same number, type and concentration of PESA but which lacked an initiating DF.

8.3. Results: Detection of Cleavage of PESA_35 and PESA_36

In Reaction (i) the addition of DF-a together with hairpin PESA A resulted in the formation of a cleavable CESA A duplex substrate for the RE Mnl I, as indicated by the increase in fluorescence over time (FIG. 18B; Reaction (i)). In contrast, in Reaction (ii) where no DF-a was added with PESA A, no cleavable CESA A duplex substrate was formed, as indicated by the lack of increase in fluorescence over time (FIG. 18B; Reaction (ii)).

In Reaction (iii), the addition of DF-b together with hairpin PESA B resulted in the formation of a cleavable CESA B duplex substrate for the RE Mnl I, as indicated by the increase in fluorescence over time (FIG. 18B; Reaction (iii)). In contrast, in Reaction (iv) where no DF-b was added with PESA B, no cleavable CESA B duplex substrate was formed, as indicated by the lack of increase in fluorescence over time (FIG. 18B; Reaction (iv)).

In Reaction (v), the addition of DF-a to a mix containing both PESA A and PESA B resulted in an almost doubling of the increase in fluorescence over time compared to reaction (i) (FIG. 18B; Reaction (v)). This is indicative of the release of DF-b following CESA A cleavage, which then hybridized to PESA B to form CESA B which in turn can be cleaved resulting in the release of more DF-a. In Reaction (vi), the addition of DF-b to a mix containing both PESA A and PESA B also resulted in an almost doubling of the increase in fluorescence over time compared to Reaction (iii) (FIG. 18B; Reaction (vi)). This is indicative of the release of DF-a following cleavage of CESA B, which then hybridized to PESA A to form CESA A which in turn can be cleaved resulting in the release of more DF-b. A control Reaction (vii) containing a mix of PESA A and PESA B, without the addition of either DF, showed no increase in fluorescence over time (FIG. 18B; Reaction (vii)). This indicates that no cleavable CESA structures can be formed between PESA A and PESA B in the absence of any DF.

Finally, Reaction (viii) (FIG. 18 B) was designed as a positive control where DF-a, DF-b, PESA A and PESA B were mixed at equal concentrations (100 nM of each) such that all of both PESAs have available DF. As such, all PESAs should form CESAs and be cleaved to produce the maximum change in florescence obtainable in this system. Reaction (viii) displayed a faster reaction rate compared to Reactions (v) & (vii), however the final fluorescence was similar to that observed in Reactions (v) and (vii). This provides additional evidence that either 10 nM of either DF-a (Reaction v) or DF-b (Reaction vii) can initiate a cascade reaction which ultimately results in cleavage of 100 nM of each of CESA A and CESA B, driven by the generation of more DF-a when CESA B is cleaved and by generation of more DF-b when CESA A is cleaved. This indicates that initiating the reaction with inclusion of either DF-a or DF-b with PESA A and PESA B results in full cleavage of both PESA A and PESA B oligonucleotides within the time frame the reaction was observed.

In summary, the experiment demonstrates that (a) addition of a DF (DF-a or DF-b) to its matching hairpin PESA (PESA A or PESA B, respectively) can form a cleavable CESA A or CESA B, duplex substrate for the RE Mnl I and results in an increase in fluorescence.

(b) Addition of DF-a to a mixture of PESA A and PESA B, results in the formation and subsequent cleavage of CESA A, which generates a DF-b that can hybridize with PESA B to form CESA B, which in turn, is cleaved and releases DF-a. Similarly, addition of DF-b to a mixture of PESA A and PESA B, results in the formation and subsequent cleavage of CESA B, which generates a DF-a that can hybridize with PESA A to form CESA A, which in turn, is cleaved and releases DF-b. This feedback continues to occur until all of PESA A and PESA B are cleaved.

This amplification cascade can be used to amplify a signal, allowing detection of any target provided a DF can be generated in a target specific manner. The specific sequence of the hairpin PESA can be altered so as to create additional PESA which may be activated by one of the DFs in this example or a different DF which is complementary to the new PESA.

Example 9

The following example demonstrates an MNAzyme-initiated EzyAmp reaction using a strategy where DF sequence is not part of MNAzyme substrate sequence. The strategy demonstrated in this example is illustrated in FIG. 19A. In this example, the substrate sequence was flanked by a sequence complementary to the DF, and a sequence complementary to the DF extension. The sequence of the substrate itself is not complementary to any of these regions such that a single stranded substrate loop was created when the substrate containing oligo binds to the DF. The binding of the full substrate blocked the DF rendering it unavailable to hybridize with a PESA. The system was designed such that the DF would only be released from this complex when the looped substrate is cleaved by an MNAzyme formed in the presence of a specific target. MNAzyme cleavage of the substrates loop releases the DF and allows initiation of an EzyAmp signal amplification reaction.

9.1 EzyAmp Oligonucleotides

For this EzyAmp reaction, two different PESA complexes (PESA A and PESA B) were present within one reaction. Hybridization of PESA A and DF-a (DF-3EAS2_11(22)) results in formation of CESA A, whereas hybridization of PESA B and DF-b results in formation of CESA B. PESA A is composed of EAS1A (EAS1_12) and EAS2A (EAS2_13) and PESA B is composed of EAS1B (EAS1_10) and EAS2B (EAS2_11). EAS2A of PESA A contains a region within it which is equivalent to the sequence of DF-b. EAS2B of PESA B contains a region within it which is equivalent to the sequence of DF-a. As such, this experiment was designed so that DF-a or DF-b could either be generated by the cleavage of the substrate-blocker, or by cleavage of the CESA B or CESA A respectively during the reaction. A schematic diagram of the process is illustrated in FIG. 19 Panel A.

RE activity was monitored by changes in fluorescence corresponding to the separation of fluorophore and quencher when the oligos were cleaved. In the current example, EAS was end labeled with a 6-fluorescein ("6-FAM") moiety at the 5' end, and EAS2A was end labeled with an Iowa Black FQ ("IAbFQ") moiety at the 3' end. EAS and EAS2A annealed to each other to form PESA A. EAS was end labeled with an Iowa Black FQ ("IAbFQ") moiety at the 5' end and a 6-fluorescein ("6-FAM") moiety at the 3' end. EAS2B was labeled with an Iowa Black FQ ("IAbFQ") moiety at the 3' end. EAS1B and EAS2B annealed to each other to form PESA B.

The sequences of these oligonucleotides are listed below from 5' to 3' where the bases underlined form at least part of the recognition sequence for Mnl I (CCTC or GAGG) and where italicized bold bases represent those that are equivalent to DFs, or shorter versions thereof, that are present in the context of longer oligonucleotides.

```
ESA1_12 (EAS1A):
TCAGTCCCACGTGTGA

ESA2_13 (EAS2A):
TCAGCACCTCACACGTGGGAAGAG

EAS1_10 (EAS1B):
CTCTTCCTCAGCACCTGATT

EAS2_11 (EAS2B):
AATCAGGTGCTGA

DF-3ESA1_11(22) (DF-a):
GGTGCTGATACTGCGCTCTGGG
```

9.2 Partzyme Oligonucleotides and the Assembly Facilitator

Partzymes were designed such that catalytically active MNAzyme would be formed in the presence of the synthetic target, namely the assembly facilitator, AF-RO5. The sequences of the assembly facilitator, partzyme A (RO5A4/3(8)) and partzyme B (RO5B5/3(7)) are listed below from 5' to 3' where the bases underlined form at least part of the active catalytic core of the assembled MNAzymes, bases in bold hybridize with the target and bases in italics hybridize to the MNAzyme substrate.

```
Partzyme A RO5A4/3(8):
CAAACGAGTCCTGGCCTTGTCTACAACGAGGTTGTGC

Partzyme B RO5B5/3(7):
TTGGTGAGGCTAGCTGTGGAGACGGATTACACCTTC
```

```
Target Assembly Facilitator AF-RO5:
GAAGGTGTAATCCGTCTCCACAGACAAGGCCAGGACTCGTTTG
```

9.3 MNAzyme Substrate-Blocker

The MNAzyme substrate sequence was a chimeric sequence containing both RNA and DNA bases in an oligo which constitutes an extension of a sequence which has been previously used as a substrate for an MNAzyme derived from a10:23 DNAzyme. In the current example, the reporter MNAzyme substrate was designated Sub3(8:7) and it was flanked by a sequence complementary to DF-a, and a sequence complementary to the DF extension. The sequence of the MNAzyme substrate itself is not complementary to any of these regions such that a single stranded substrate loop was created when it binds to the DF. The sequence of the substrate-blocker is as follow in 5' to 3' direction. The lower case base represents RNA and the upper case bases represent DNA, bases in bold hybridize with the partzymes and bases underlined binds to the DF-a.

```
14Sub3(8:7)_16)(21) Inh(D2F-3EAS2_11)
(substrate-blocker)
CCCAGAGCGCAGTCCACAACCguCACCAATCAGCACC
```

9.4 Reaction Components

The formation of a cleavable CESA in the presence of target was measured by detecting an increase in fluorescence. Test reactions were initiated by the addition of 100 nM target assembly facilitator AF-R05 and control reactions were initiated by the addition of H$_2$O. All reactions were conducted at 35° C. in a CFX96™ Real-Time PCR Detection System (BioRad) with a total reaction volume of 25 µL. Fluorescence for each sample was programmed to be read after every 1 minute in Channel 1 (FAM) for 100 cycles (Scan Mode: FAM/SYBR only). The total run time was 115 minutes. All reactions contained bulk mix of 200 nM partzyme A (RO5A4/3(8)), 200 nM partzyme B (RO5B5/3(7)), 200 nM of substrate-blocker (14Sub3(8:7)_16)(21)Inh (D2F-3EAS2_11); 100 nM each DF-3ESA1_11(22), EAS1_10, EAS2_11, EAS1_12, and EAS2_13 in 15 mM MgCl$_2$ (Ambion), 1×BSA (New England Biolabs), 1×NEBuffer 4 (New England Biolabs), nuclease free water (Ambion) and 0.75 U Mnl I (New England Biolabs). All reactions were performed in duplicate. All oligonucleotides were purchased from Integrated DNA Technologies (IDT).

9.5 Results: Detection of Cleavage of CESA A and CESA B

An exponential increase in fluorescence was observed in the test reactions where the target was present (FIG. 19Panel B panel; Target). This indicates that the target assembly facilitator allowed partzyme A and B to assemble into a catalytically active MNAzyme that cleaved the MNAzyme substrate. The cleavage of the substrate leads to the dissociation of the fragment bonded to DF-a, thus allowing the DF-a to initiate the subsequent EzyAmp cascade reaction (composed of PESA A and PESA B). This reaction started when the released DF-a bound to PESA A (formed by EAS1A and EAS1B) to form a CESA A, which was then cleaved by Mnl I. This in turn released DF-b, and also generated a concomitant increase in fluorescence corresponding to the separation of fluorophore and quencher moieties. The DF-b then binds to the PESA B (formed by EAS1B and EAS2B) forms CESA B allowing its cleavage by Mnl I. This released more DF-a to complete a feedback cascade between other CESA A and CESA B, and also generated a concomitant increase in fluorescence corresponding to the separation of fluorophore and quencher moieties.

In the "No Target Control reaction where no target assembly facilitator was added, no exponential increased in FAM signal was observed with only a low level of fluorescent drift observed after 80 minutes (FIG. 19 Panel B; No Target Control). This indicates that presence of target is required to initiate MNAzyme cleavage of substrate in order to release the DF-a to initiate the subsequent EzyAmp reaction.

The results demonstrate that the EzyAmp reactions can be designed to be initiated by a target-dependent MNAzyme cleavage step whereby the sequence of the DF does not have to be part of the MNAzyme substrate sequence. In this reaction, EIC complexes would also have been expected to form by hybridization between PESA A and EAS2B, and between PESA B and EAS1A which in its uncleaved state functions as an InF.

Example 10

The following example demonstrates the ability of the restriction enzyme to cleave two partially complementary oligonucleotides containing a complete restriction site.
10.1 Oligonucleotides In the following reaction, Oligonucleotide 1 (EAS1_1) and Oligonucleotide 2 (ASC-RE5F2(22)-FB) could potentially hybridize in two orientations both of which would result in partially complementary duplexes which would contain the complete recognition sequence for Mnl I; however, both duplexes would have several unpaired bases between the recognition site and the and cleavage site.

The potential for the RE Mnl I to cleave partially non-complementary duplexes was examined by monitoring changes in fluorescence due to the separation of fluorophore and quencher moieties following cleavage of a dual labeled fragment. Oligonucleotide 1 was end labeled with an Iowa Black FQ ("IAbFQ") moiety at the 5' end and an Iowa Black FQ ("IAbFQ") at its 3' end. Oligonucleotide 2 was end labeled with a 6-fluorescein (6"FAM") moiety at the 5' end, and anBlack Hole Quencher ("BHQ_1") moiety at the 3' end. The sequences of the oligonucleotides are listed below from 5' to 3' where the bases underlined form one strand of the recognition sequence for Mnl I (CCTC or GAGG).

```
EAS1_1 (Oligonucleotide 1)
CTCTTCCTCTCTTCCCGGATGTCGGCCTCCTAGTACAGCG

ASC-RE5F2(25)-FB (Oligonucleotide 2)
TAGGATGTGAAGACGAGGAAGAGAT
```

10.2 Reaction Components

All reactions were performed in duplicates and contained 100 nM Oligonucleotide 2 and 2 U of Mnl I in nuclease free water (Ambion), 1×BSA (New England Biolabs) and 1×NEBuffer 4 (New England Biolabs) with the addition of (i) 100 nM Oligonucleotide 1 or (ii) H$_2$O. Fluorescence signal was measured in Channel 1 (FAM). The reaction was conducted at 35° C. in a CFX96™ Real-Time PCR Detection System (BioRad) with a total reaction volume of 25 µL. Fluorescence for each sample was programmed to be read after every 8 second for 100 cycles (Scan Mode: FAM/SYBR only). The total run time was 40 minutes.
10.3 Results: Detection of Cleavage of Oligonucleotide 1 and 2

In reaction (i), the presence of both Oligonucleotide 1 and 2 resulted in increasing fluorescence, indicative of Mnl I cleavage separating the fluorophore from quenchers in Oligonucleotide 2. In contrast, no increasing fluorescence was observed in the absence of Oligonucleotide 1 (reaction (ii)), indicating that cleavage of Oligonucleotide 2 is dependent on the formation of partial duplex with Oligonucleotide 1 and that the signal in the presence of Mnl I is not due to cleavage of single stranded Oligonucleotide 2.

The results demonstrate that certain REs such as Mnl I can cleave partially complementary duplexes which may contain complete, double stranded recognition sequences, but which are not fully complementary across the entire region encompassing the recognition and cleavage site. This observation provides a new tool for designing PESA complexes consisting of one or more oligonucleotides which include mismatches in the intervening sequence between the recognition and cleavage site, thus allowing manipulation of the temperature and rate of dissociation of cleavage fragments which can function as DFs.

Example 11

The following example illustrates the detection and quantification of a specific target at various concentrations with the following steps occurring concurrently in a single reaction; Step (i) MNAzymes form in the presence of target and cleave an MNAzyme substrate to generate a first DF; Step (ii) this DF hybridizes to a PESA to create a CESA which when cleaved by a RE generates another DF and concomitantly causes separation of a fluorophore and a quencher resulting in the generation of a fluorescent signal; Step (iv) the DF generated by cleavage of the first CESA hybridizes to a second PESA to create a second CESA which when cleaved by a RE generates a fluorescent signal and releases a DF which can fulfill the same function as the first DF; Step (v) a feedback loop is created as steps (iv) and (v) are repeated. Reactions where nuclease cleavage results in signal amplification are termed EzyAmp reactions. In the current example, the EzyAmp reactions are composed of two different CESA complexes (CESA A and CESA B) which are cleaved by a single RE within one reaction tube. In this example both PESA complexes are labeled with the same fluorophore, and as such the signal generated by cleavage of resultant CESA A and CESA B are additive.
11.1 EzyAmp Oligonucleotides For this EzyAmp reaction, two different CESA complexes (CESA A and CESA B) are present within one reaction. CESA A is composed of PESA A and DF-a whereas CESA B is composed of PESA B and DF-b. In turn, PESA A is composed of EAS1A (EAS1_10) and EAS2A (EAS2_11) and PESA B is composed of EAS1B (EAS1_12) and EAS2B (EAS2_13). EAS2A of PESA A contains a region within it which is functionally equivalent to the sequence of DF-b. EAS2B of PESA B contains a region within it which is functionally equivalent to the sequence of DF-a. As such, this experiment was designed so that DF-a could be generated at the initiation of the reaction in the presence of target and then each DF could be generated by cleavage of the CESA B or CESA A respectively during the reaction. Exemplary schematic diagrams of the process of CESA complexes which can feedback are illustrated in FIGS. 17A, 18A, 19A and 27A.

RE activity was monitored by changes in fluorescence corresponding to the separation of fluorophore and quencher. In the current example, EAS1A was end labeled with an Iowa Black FQ ("IAbFQ") moiety at the 5' end, and a 6-fluorescein ("6-FAM") moiety at the 3' end. EAS2A was also labeled by an Iowa Black FQ ("IAbFQ") moiety at the 5' end and anneals to EAS1A. EAS was end labeled with a 6-fluorescein ("6-FAM") moiety at the 5' end whereas EAS2B was labeled by an Iowa Black FQ ("IAbFQ") moiety at the 3' end and anneals to EAS1A.

The sequences of these oligonucleotides are listed below from 5' to 3' where the bases underlined form at least part of the recognition sequence for Mnl I (CCTC or GAGG) and the bases in italics represent those that are equivalent to DFs present in the context of longer oligonucleotides.

```
EAS1_10 (EAS1A)
CTCTTCCTCAGCACCTGATT

EAS2_11 (EAS2A)
AATCAGGTGCTGA

ESA1_12 (EAS1B)
TCAGTCCCACGTGTGA

ESA2_13 (EAS2B)
TCAGCACCTCACACGTGGGAAGAG
```

11.2 Partzyme Oligonucleotides and Target Assembly Facilitator

To create the DF-a, the substrate (Sub1i-FIB), was designed to be cleaved by the catalytically active MNAzyme that forms in the presence of the synthetic target, namely the target assembly facilitator, AF-TL5. The sequences of the target assembly facilitator, partzyme A (TL5A2(12)/1) and partzyme B (TL5B5(12)/1) are listed below from 5' to 3' where the bases underlined form at least part of the active catalytic core of the assembled MNAzymes, bases in bold hybridize with the target and bases in italics hybridize to the MNAzyme substrate.

```
Partzyme A TL5A2(12)/1:
TGCTCATCTCAGCGGTCGAAATAGTGAGT

Partzyme B TL5B3(12)/1:
CATCTCTTCTCCGAGCGTCTACGACAAT

Target Assembly Facilitator AF-TL5:
ATTGTCGTAGACCTGAGATGAGCA
```

11.3 MNAzyme Substrate

MNAzyme activity is monitored by cleavage of a dual labeled reporter MNAzyme substrate. The MNAzyme substrate sequence is a chimeric sequence containing both RNA and DNA bases that has been used previously as an 8:17 DNAzyme substrate (Li et al., 2000). In the current example, the reporter MNAzyme substrate was designated Sub1i-FIB and was labeled with an internal fluorescein dT ("iFluorT") moiety and an Iowa Black FQ ("IAbFQ") moiety at the 3' end. The labeled sequence of Sub1i-FIB is as follows, from 5' to 3' where the lower case base represents RNA and the upper case bases represent DNA. The bases in italics represent those which function as DFs that are present in the context of longer oligonucleotides.

```
Substrate, Sub1i-FIB;
ACTCACTATaGGAAGAGATG
```

11.4 Reaction Components

The cleavage of MNAzyme substrate by a catalytically active MNAzyme was measured by an increase in fluorescence (although this fluorescence was not distinguishable from the fluorescence generated by the cleavage of EAS oligos since both MNAzyme substrate cleavage and CESA cleavage released fluorophore that was detected in the same channel). The oligos were designed such that CESA A is formed by the hybridization of EAS1_10, EAS2_11 and DF-1a, and CESA B is formed by the EAS_12, EAS2_13 and DF-b. Cleavage of the fluorescently labeled CESA components, EAS1_10 and EAS1_12, was also measured by an increase in fluorescence. Duplicate test reactions were initiated by the addition of target assembly facilitator AF-TL5 in the concentrations of (i) 1 nM, (ii) 800 µM, (iii) 600 µM, (iv) 400 µM, (v) 200 nM (vi) 100 nM or (vii) 50 nM. The "no target control" (NTC) duplicate reactions were initiated by the addition of H$_2$O. All reactions were conducted at 35° C. in a CFX96™ Real-Time PCR Detection System (BioRad) with a total reaction volume of 25 µL. Fluorescence for each sample was programmed to be read in Channel 1 (FAM) after every 1 minute for 110 cycles (Scan Mode: FAM/SYBR only). The total run time was 120 minutes. All reactions contained bulk mix of 300 nM partzyme A (TL5A2(12)/1), 150 nM partzyme B (TL5B3(12)/1), and 30 nM Sub1i-FIB; 100 nM each EAS1_10, EAS2_11, EAS1_12, and EAS2_13 with 0.75 U Mnl I in 10 mM MgCl$_2$ (Ambion), 1×BSA (New England Biolabs) nuclease free water (Ambion) and 1×NEBuffer 1 (New England Biolabs) adjusted to pH 8.3 using KOH. All oligonucleotides were purchased from Integrated DNA Technologies (IDT). A standard curve was plotted from the Ct value of concentration of the target added to the reaction against the logarithmic value of the target concentration. The Ct value is the amount of time (one cycle equals approximately 1 minute) it takes for a given amount of a target to generate a signal which corresponds to the threshold fluorescence. The threshold was set at the start of the exponential phase of the increase in fluorescence.

11.5 Results: Detection and Quantification of Target Nucleic Acid

FIGS. 21A and 21B shows increasing fluorescence signals (log and linear plots) that start at various time points corresponding to the amount of target added to the test reactions (i) to (vii). The amount of target determined the time required to generate a signal in an EzyAmp reaction. The less target present, the longer it took to produce DF-a to start the EzyAmp feedback reaction and hence the longer it takes to reach the threshold fluorescence. No increasing signal was observed after 120 minutess in the control reaction ((viii) NTC) where no target was added, suggesting that target dependent formation of catalytically active MNAzyme is required for DF-production and subsequent EzyAmp signal amplification. Additional lower concentrations of target were also analysed (data not shown) and as little as 1 µM was detectable above the no template control signal. This corresponds to approximately 25 amole or 10$^7$ copies of a target nucleic acid sequence in a 25 µL reaction.

FIG. 21C shows the quantitative ability of the assay by the observation that a linear standard curve can be produced within the range of the target concentrations tested. The DF production doubles per restriction enzyme cleavage event, resulting in an exponential increase in signal over time. This exponential increase allows the use of the PCR exponential cycle threshold method (described in 14.4 Reaction Components) to show the relationship between the Ct and target concentration in a linear curve with a regression value of 0.99. These results demonstrate the capacity for EzyAmp to allow the sensitive and quantitative detection of a target sequence.

Example 12

This example is hypothetical and provides a strategy utilizing the nuclease ability of Exonuclease III (ExoIII) to initiate and mediate a signal amplification cascade (FIG. 23). This enzyme removes nucleotides from 3' termini of DNA duplexes. It is active on blunt or recessed 3' ends but not active on single stranded DNA comprised of five or more nucleotides and hence will not cleave 3' protruding termini with at least five nucleotides or longer. It can also start hydrolysis from nicks in a duplex DNA to produce single stranded gaps. The presence of a phosphorothioate nucleotide within an oligo blocks the exonuclease activity.

This method includes an initiation step and a signal amplification step, which may be present within one or separate reaction chambers but utilizing the same nuclease, ExoIII.

12.1 Initiation Step; Creation of a Driver Fragment in a Target Dependent Manner A Synthetic Initiator Oligo (SIO) can be designed as a substrate for ExoIII whereby the SIO would only be hydrolyzed in the presence of a target nucleic acid (FIG. 23). The SIO may have at around 20 nucleotides at its 3' end which are complementary to the target to allow detection of a specific target. The SIO may also contain the sequence of a DF at the 5' end which is non-complementary to the target. Finally, the SIO may contain one or more phosphorothiolated nucleotides at the junction of the target binding portion and the DF portion and it may be dual-labeled with a fluorophore and quencher. In some embodiments the SIO may have a hairpin structure.

The steps in the reaction are illustrated in FIG. 23. Upon binding of the SIO to the target (step 1), the DF portion of the SIO would form a single stranded 5' overhang, while the target-binding region of the SIO would form a duplex whereby the SIO has a 3' recessed terminus which could serve as a suitable substrate for Exo III. Exo III could then hydrolyze the SIO back to the position of phosphorothioated nucleotide(s) thus releasing the DF portion of the SIO (Step 2). Concomitantly, hydrolysis would result in separation of the fluorophore and quencher, which would cause an increase in fluorescence. The target would remain intact and would be free to be recycled to bind additional SIOs (step 3).

12.2 Signal Amplification Step: Formation and Cleavage of CESA Complexes

The signal amplification step would contain similar fragments as in other variations of the EzyAmp reaction, namely the complementary oligonucleotides EAS1 and an EAS2. EAS1 could be labeled with a fluorophore and a quencher. Upon binding to each other, EAS1 and EAS 2 could form a PESA with 3' overhangs of at least five nucleotides at each terminus to prevent ExoIII degradation in the absence of DF. EAS1 could have a longer overhang which could serve as a binding site for the DF. The sequence at the 5' end of the DF could extend beyond that which is complementary to EAS1 and as such DF binding would create a CESA complex with 3' recessed terminus on EAS1.

When the DF is released from the SIO in the presence of target in the initiation step, it would then be free to bind to a PESA and create a CESA which could serve as a substrate for Exo III. The presence of phosphorothiolated bases at the 3' end of the DF would prevent nuclease degradation from the nick created when the DF binds to the PESA. However, the 3' recessed end of the EAS1 strand of the CESA would be hydrolyzed by Exo III (step 5) and this would result in increased fluorescence due to separation of the fluorophore and quenchers. In addition the DF would be released intact and would be free to be recycled (Step 6) and bind to another PESA to create another CESA. In this strategy both the initiation and amplification steps will rely on target and DF recycling for signal amplification to increase the sensitivity.

Many variants of the above scheme could be devised by one skilled in the art. As before the PESA may be formed from separate EAS1 and EAS2 oligos or EAS1 and EAS2 may be joined by linker sequence to create a PESA with a hairpin structure. Each step may be conducted within one chamber or in separate chambers. Further, there is flexibility in regard to the positions of the fluorophore and quencher labels.

Nonetheless this proposed strategy follows the basic steps of an EzyAmp reaction, namely, (i) conversion of an oligonucleotide (eg an SIO) to a DF in a target-dependent manner; (ii) providing a PESA, which on its own is not a substrate for a nuclease, (iii) hybridizing the DF to the PESA to create a CESA; and (iv) hydrolyzing the CESA with a nuclease to create a detectable signal and in addition release the DF so that it is capable of converting more PESA to CESA complexes.

Example 13

The following example demonstrates the capacity to multiplex EzyAmp systems such that the formation of two independent CESAs in the presence of two different DFs can be monitored simultaneously. In this example two different PESA complexes (PESA A and PESA B) were labeled with two different fluorophores so that they could be independently monitored. PESA A forms CESA A only in the presence of DF-a and PESA B forms CESA B only in the presence of DF-b. Formation of the fully assembled CESA A and CESA B complexes leads to the completion of the RERS for the RE, Mnl I.

13.1 Oligonucleotides

In the following reaction, CESA A is composed of PESA A and DF-a, whereas CESA B is composed of PESA B and DF-b. In turn, PESA A is composed of EAS1A and EAS2A and PESA B is composed of EAS and EAS2B. This experiment was designed so that only DF-a could bind PESA A to CESA A and only DF-b could bind PESA B to form CESA A.

RE activity is monitored by changes in fluorescence corresponding to the separation of fluorophore and quencher moieties. In the current example, EAS1A (RE1F1(20T)(20)-BJ) was end labeled with Iowa Black FQ ("IAbFQ") at the 5' end and JOE at the 3' end. EAS2A (REIS1(1A)(13)-5-B), which anneals to EAS1A, was also labeled with Iowa Black FQ ("IAbFQ") at the 5' end. EAS2B (ESA33) was end labeled with 6-fluorescein ("FAM") at the 5' end and EAS1B (ESA34_2), which anneals to EAS2B, was labeled with Iowa Black FQ ("IAbFQ") at the 3' end. The sequences of these oligonucleotides are listed below from 5' to 3' where the bases underlined form at least part of the recognition sequence for Mnl I (CCTC or GAGG).

```
EAS1A (RE1F1(20T)(20)-BJ)
CTCTTCCTCAGCAGTTCATT

EAS2A (RE1S1(1A)(13)-5-B)
AATGAACTGCTGA

EAS1B (ESA34_2)
CGACGTCCTCAACAGGCAACACC

EAS2B (ESA33)
TTCGTTGCCTGTTGA

DF-a (DF1-(10))
GGAAGAGATG
```

```
              -continued
       DF-b (D2F-3ESA31(22))
       GGACGTCGTACTGCGCTCTGGG
```

13.2 Reaction Conditions

Oligonucleotides were purchased from Integrated DNA Technologies (IDT). All reactions contained a bulk mix of 100 nM each of EAS1A (RE1F1(20T)(20)-BJ), EAS2A (RE1F1(20T)(20)-BJ), EAS1B (ESA34_2) and EAS2B (ESA33) in 15 mM $MgCl_2$ (Ambion), 1×BSA (New England Biolabs), nuclease free water (Ambion), 1×NEBuffer 4 (New England Biolabs) and 2 U Mnl I (New England Biolabs). Reactions were initiated by the addition of DF-a (DF1-(10)) and/or DF-b (D2F-3ESA31(22)), while control reactions were initiated by the addition of water in a total reaction volume of 25 µL. Concentrations of DF-a and/or DF-b used in each reaction are provided in Table 14. Fluorescent signal was measured simultaneously in both Channel 1 (monitors FAM) and Channel 2 (monitors JOE). The reaction was conducted at 35° C. in a CFX96™ Real-Time PCR Detection System (Bio-Rad). Fluorescence for each sample was programmed to be read after every 1 second for 100 cycles (scan mode: all channels). The total run time was 29 minutes.

TABLE 14

| Reaction | DF-a (nM) Resultant CESA A monitored by JOE | DF-b (nM) Resultant CESA B monitored by FAM | DF-a (% of total DF) | DF-b (% of total DF) |
|---|---|---|---|---|
| i   | 100 | 0   | 100% | —    |
| ii  | 90  | 10  | 90%  | 10%  |
| iii | 100 | 100 | 50%  | 50%  |
| iv  | 10  | 90  | 10%  | 90%  |
| v   | 0   | 100 | —    | 100% |

13.3 Results: Detection of Cleavage

The fluorescent signals for both JOE and FAM for each reaction are plotted against time in FIG. 25. Addition of DF-a resulted in an increase in JOE fluorescence over time. The increasing JOE signal is indicative of DF-a completing PESA A to become CESA A, which was then cleaved by Mnl I. In turn, dissociation of the oligo fragments of cleaved EAS1A and EAS2A lead to separation of the JOE fluorophore and the quencher. As observed in Reactions (i)-(v) (FIG. 25), the rate of increase in JOE fluorescent signal decreased as the percentage of DF-a present in each reaction was reduced.

The addition of DF-b resulted in an increase in FAM fluorescence over time. The increasing FAM signal is indicative of the DF-b completing PESA B to become CESA B. Cleavage of CESA B by Mnl I caused dissociation of the oligo fragments of cleaved EAS1B and EAS2B leading to separation of the FAM fluorophore and its quencher. As observed in Reactions (i) to (v) (FIG. 25), the rate of increase in fluorescent FAM signal decreased as the percentage of DF-b added to each reaction was reduced.

In control reactions where neither DF-a or DF-b were added, no increase was observed in either FAM or JOE fluorescence demonstrating that the duplex EzyAmp reaction is specific for the presence of one or more DFs.

In Reaction (i), where only DF-a was present, an increase in fluorescence was only observed for JOE and not for FAM indicating DF-a was specific for the formation of CESA A. Similarly in Reaction (v), where only DF-b was present, an increase in fluorescence was only observed for FAM and not for JOE indicating DF-b was specific for the formation CESA B. As the percentage of DF-a present in the total of DF-a plus DF-b changed from (i) 100% to (ii) 90% to (iii) 50% to (v) 10%, a corresponding decrease in JOE fluorescence was observed (FIG. 25). Similarly, as the percentage of DF-b present in the total of DF-a plus DF-b changed from (v) 100% to (iv) 90% to (iii) 50% to (ii) 10%, a corresponding decrease in JOE fluorescence was observed.

An exemplary strategy for a multiplex EzyAmp system is illustrated in FIG. 13. This experiment demonstrates the potential for multiplex detection of more than one target in a single multiplex EzyAmp reaction. For example, DF-a could be generated in a target-specific manner only in the presence of target A (e.g. by cleavage of a first MNAzyme substrate by a first MNAzyme) and DF-b could be generated in a target-specific manner only in the presence of target B (e.g. by cleavage of a second MNAzyme substrate by a second MNAzyme). If the presence of DF-a and/or DF-b were detected using the EzyAmp system demonstrated in this example, then an increase in JOE would indicate the presence of target A and increase in FAM would indicate the presence of target B. An increase in neither JOE nor FAM would indicate that neither target was present and an increase in JOE and FAM would indicate the presence of both targets.

Example 14

The following example demonstrates an MNAzyme-initiated EzyAmp reaction using a strategy where the DF sequence is not part of the sequence which is recognized by the MNAzyme as a substrate, although, it is still contained within the same molecule (FIG. 24D). In this example, the substrate and the DF are part of a long hair-pinned molecule termed a substrate—blocker-DF oligo. A single stranded loop within the hairpin contains the sequence recognized by the MNAzyme as a substrate. The stem of this hairpin contains the sequence of DF-a which can hybridize to a complementary blocker sequence. In this conformation, the DF is unavailable to hybridize with a PESA. The system was designed such that the DF would only be released when the MNAzyme substrate loop was cleaved by an MNAzyme formed in the presence of the target. MNAzyme initiated release of the DF allows initiation of an EzyAmp signal amplification reaction.

14.1 EzyAmp Oligonucleotides

For this EzyAmp reaction, two different PESA complexes (PESA A and PESA B) were present within one reaction. Hybridization of PESA A and DF-a results in formation of CESA A, whereas hybridization of PESA B and DF-b results in formation of CESA B. PESA A is composed of EAS1A (EAS1_1) and EAS2A (EAS2_13) and PESA B is composed of EAS1B (EAS1_10) and EAS2B (EAS2_11). EAS2A of PESA A contains a region within it which is equivalent to the sequence of DF-b. EAS2B of PESA B contains a region within it which is equivalent to the sequence of DF-a. As such, this experiment was designed so that the initiating DF-a could be generated in a target dependent manner by MNAzyme cleavage of the substrate-blocker-DF hairpin oligo. Later, during the EzyAmp cascade reaction, DF-a and DF-b could be generated by cleavage of the CESA B or CESA A respectively. A similar exemplary cascade reaction is illustrated in FIG. 19 A; however, the initiating step is as illustrated in FIG. 24D (as opposed to the step illustrated in FIG. 24C, which is similar to initiating structure in FIG. 19A).

RE activity was monitored by changes in fluorescence corresponding to the separation of fluorophore and quencher when the oligos were cleaved. In the current example, EAS1A was end labeled with a 6-fluorescein ("6-FAM") moiety at the 5' end, and EAS2A was end labeled with an Iowa Black FQ ("IAbFQ") moiety at the 3' end. EAS1A and EAS2A annealed to each other to form PESA A. EAS was The lower case base represents RNA and the upper case bases represent DNA, bases in bold hybridize with the partzymes, bases underlined forms the stem which also includes the sequence of DF-a (bold italics), and the stretch of T bases in italics forms the middle loop of the hairpin.

```
Hp5(Sub3(8:7))Inh(D2F-3EAS2_11)Hp5D2F-3EAS2_11(Sub3(8:7))(substrate-blocker-DF):
GGTGCTGATACTGCTTTTTTTTTTTTGCAGTCCACAACCguCACCAA

ATCAGCACC
``` end labeled with an Iowa Black FQ ("IAbFQ") moiety at the 5' end and a 6-fluorescein ("6-FAM") moiety at the 3' end. EAS2B was labeled with an Iowa Black FQ ("IAbFQ") moiety at the 3' end. EAS and EAS2B annealed to each other to form PESA B.

The sequences of these oligonucleotides are listed below from 5' to 3' where the bases underlined form at least part of the recognition sequence for MnlI (CCTC or GAGG) and where italicized bold bases represent those that are equivalent to DFs, or shorter version thereof, that are present in the context of longer oligonucleotides

```
ESA1_12 (EAS1A)
TCAGTCCCACGTGTGA

ESA2_13 (EAS2A)
TCAGCACCTCACACGTGGGAAGAG

EAS1_10 (EAS1B)
CTCTTCCTCAGCACCTGATT

EAS2_11 (EAS2B)
AATCAGGTGCTGA
```

14.2 Partzyme Oligonucleotides and Target Assembly Facilitator

Partzymes were designed such that catalytically active MNAzyme would form in the presence of the synthetic target, namely the assembly facilitator, AF-RO5. The sequences of the assembly facilitator, partzyme A (RO5A4/3(8)) and partzyme B (RO5B5/3(7)) are listed below from 5' to 3' where the bases underlined form at least part of the active catalytic core of the assembled MNAzymes, bases in bold hybridize with the target and bases in italics hybridize to the MNAzyme substrate.

```
Partzyme A RO5A4/3(8):
CAAACGAGTCCTGGCCTTGTCTACAACGAGGTTGTGC

Partzyme B RO5B5/3(7):
TTGGTGAGGCTAGCTGTGGAGACGGATTACACCTTC

Target Assembly Facilitator AF-RO5:
GAAGGTGTAATCCGTCTCCACAGACAAGGCCAGGACTCGTTTG
```

14.3 MNAzyme Substrate-Blocker-DF

The MNAzyme substrate sequence is a chimeric sequence containing both RNA and DNA bases in an oligo which constitutes an extension of a sequence which has been previously used as a substrate for an MNAzyme derived from a 10:23 DNAzyme. The substrate loops out from the stem of a hair-pinned substrate-blocker-DF molecule since the sequence is not complementary to any part of the sequence of the oligo. The stem also contains the sequence of DF-a. The (non-substrate) loop in the middle of this hairpin molecule is composed of a stretch of non-complementary dT bases. The sequence of the hair-pinned substrate-blocker-DF oligo is given below in 5' to 3' direction.

14.4 Reaction Components

The formation of a cleavable CESA in the presence of target was measured by monitoring fluorescence. Test reactions were initiated by the addition of 100 nM target assembly facilitator AF-RO5 and control reactions were initiated by the addition of H₂O. All reactions were conducted at 35° C. in a CFX96™ Real-Time PCR Detection System (BioRad) with a total reaction volume of 25 µL. Fluorescence for each sample was programmed to be read after every 1 minute in Channel 1 (FAM) for 100 cycles (Scan Mode: FAM/SYBR only). The total run time was 115 minutes. All reactions contained bulk mix of 200 nM partzyme A (RO5A4/3(8)), 200 nM partzyme B (RO5B5/3 (7)), 70 nM Hp5(Sub3(8:7))Inh(D2F-3EAS2_11), 100 nM of each EAS1_10, EAS2_11, EAS1_12, and EAS2_13 in 15 mM MgCl$_2$(Ambion), 1×BSA (New England Biolabs), 1×NEBuffer 4 (New England Biolabs), nuclease free water (Ambion) and 0.75U MnlI (New England Biolabs). All reactions were performed in duplicate. All oligonucleotides were purchased from Integrated DNA Technologies (IDT).

14.5 Results: Detection of Cleavage of CESA A and CESA B

An increase in fluorescence was observed in the test reaction where the target was present. This indicated that the target assembly facilitator allowed partzyme A and B to assemble into a catalytically active MNAzyme that cleaved the MNAzyme substrate portion of the substrate-blocker-DF hairpin oligo. Cleavage of the substrate led to the dissociation of the fragment bound to DF-a, and thus allowed DF-a to initiate the subsequent EzyAmp reaction (comprising PESA A and PESA B). This EzyAmp cascade started when released DF-a bound to PESA A (formed by EAS1A and EAS1B) formed CESA A. When CESA A was cleaved by MnlI, a DF-b was released. In addition, there was also a concomitant increase in fluorescence corresponding to the separation of fluorophore and quencher moieties present on CESA A. Next, the DF-b bound to the PESA B (formed by EAS1B and EAS2B) forming CESA B which was cleaved by MnlI. This released more DF-a to complete a feedback cascade between other CESA A and CESA B, and also generated a concomitant increase in fluorescence corresponding to the separation of fluorophore and quencher moieties present on CESA B.

In the "no target control" reaction where no target assembly facilitator was added, no exponential increased in FAM signal was observed. This indicates that the presence of target is required to initiate MNAzyme cleavage of the substrate portion within the hair-pinned substrate-blocker-DF-oligo in order to release the DF-a and initiate the subsequent EzyAmp reaction.

The results demonstrate that the EzyAmp reaction can be designed to be target dependent by the addition of an upfront MNAzyme step, and that the sequence of the initiating DF does not have to be part of the sequence recognized by the MNAzyme as its substrate.

Example 15

The following example illustrates the detection of cDNA (reverse transcribed from RNA) at two concentrations, using the following steps occurring concurrently in a single reaction; Step (i) MNAzymes form in the presence of target cDNA and cleave an MNAzyme reporter substrate to generate a first DF (DF-a); Step (ii) this DF-a hybridizes to a PESA A to create CESA A which, when cleaved by a RE, generates another DF (DF-b) and concomitantly causes separation of a fluorophore and a quencher resulting in the generation of a detectable fluorescent signal; Step (iv) DF-b hybridizes to a second PESA (PESA B) to create a CESA B which, when cleaved, generates a detectable fluorescent signal and releases a DF which can fulfill the same function as DF-a; Step (v) a feedback loop is created as steps (iv) and (v) are repeated. Reactions where nuclease cleavage results in signal amplification are termed EzyAmp reactions.

15.1 EzyAmp Oligonucleotides

For this EzyAmp reaction, two different CESA complexes (CESA A and CESA B) are present within one reaction. CESA A is composed of PESA A and DF-a (generated by cleavage of the MNAzyme substrate or by cleavage of CESA B), whereas CESA B is composed of PESA B and DF-b (generated by cleavage of EAS2A (EAS2_11)). In turn, PESA A is composed of EAS (EAS1_10) and EAS2A (EAS2_11) and PESA B is composed of EAS1B (EAS1_12) and EAS2B (EAS1_13). EAS2A of PESA A contains a region within it which is functionally equivalent to the sequence of DF-b and EAS2B of PESA B contains a region within it which is functionally equivalent to the sequence of DF-a. As such, each DF could be generated by cleavage of the CESA B or CESA A respectively during the reaction.

RE activity was monitored by measuring the fluorescence corresponding to the separation of fluorophore and quencher. In the current example, EAS1A was end labeled with an Iowa Black FQ ("IAbFQ") moiety at the 5' end, and a 6-fluorescein ("6-FAM") moiety at the 3' end. EAS2A was also labeled with an Iowa Black FQ ("IAbFQ") moiety at the 5' end and anneals to EAS1A. EAS was end labeled with a 6-fluorescein ("6-FAM") moiety at the 5' end whereas EAS2B was labeled with a Black Hole FQ ("BHQ1") moiety at the 3' end and anneals to EAS1A.

The sequences of these oligonucleotides are listed below from 5' to 3' where the bases underlined form at least part of the recognition sequence for Mnl I (CCTC or GAGG) and the bases in italics represent those that are equivalent to DFs present in the context of longer oligonucleotides.

```
EAS1_10 (EAS1A)
CTCTTCCTCAGCACCTGATT

EAS2_11 (EAS2A)
AATCAGGTGCTGA

EAS1_12 (EAS1B)
TCAGTCCCACGTGTGA

EAS2_13 (EAS2B)
TCAGCACCTCACACGTGGGAAGAG
```

15.2 Partzyme Oligonucleotides and Target

Partzymes were designed such that catalytically active MNAzyme would be formed in the presence of the target, cDNA of PPIA. The sequences of partzyme A (PPIAA2/1) and partzyme B (PPIAB3/1) are listed below from 5' to 3' where the bases underlined form at least part of the active catalytic core of the assembled MNAzymes, bases in bold hybridize with the target and bases in italics hybridize to the MNAzyme substrate.

```
Partzyme A PPIAA2/1:
TGGTTGGATGGGCAAGCATGTGCGGTCGAAATAGTGAGT

Partzyme B PPIAB3/1:
CATCTCTTCTCCGAGCGTGTTTGGCAAAGTGAAAGAAG
```

PPIA cDNA target was generated using a gene specific 3' primer (3PPIA). The sequence of the primer is listed below from 5' to 3'.

```
3PPIA
GCGCTCCATGGCCTCCAC
```

15.3 MNAzyme Substrate

MNAzyme activity was monitored by cleavage of a dual labeled nucleic acid reporter MNAzyme substrate. The MNAzyme substrate sequence is a chimeric sequence containing both RNA and DNA nucleotides that has been used previously as an 8:17 DNAzyme substrate (Li et al., 2000). In the current example, the reporter MNAzyme substrate was designated (Sub1i-FIB) and was labeled with an internal fluorescein dT ("iFluorT") moiety and an Iowa Black FQ ("IAbFQ") moiety at the 3' end. The labeled sequence of Sub1i-FIB is as follow, 5' to 3'. The lower case base represents RNA and the upper case bases represent DNA. Bases in italics form the DF-a, and the bases underlined will form part of the recognition sequence for the RE, Mnl I.

```
Substrate, Sub1i-FIB;
ACTCACTATaGGAAGAGATG
```

15.4 Generation of cDNA Target

Target cDNA was generated by reverse transcription of total RNA derived from the K562 cell line (Promega). Reverse transcription was performed using a Tetro cDNA synthesis kit according to the manufacturer's instructions (Bioline, Aust) except that 200 nM of gene specific 3' primer (3PPIA) was used to generate PPIA cDNA.

15.5 EzyAmp Reaction Components and Conditions

The cleavage of MNAzyme substrate by a catalytically active MNAzyme and cleavage of the fluorescently labeled CESA components, EAS1_10 and EAS1_12, by the RE, Mnl I, was measured by an increase in fluorescence. Test reactions were initiated by the addition of target, (PPIA cDNA; reaction (i) 115 pg, reaction (ii) 23 pg); the "no target control" reactions (reaction (iii)) were initiated by the addition of H$_2$O. All reactions were conducted in duplicate at 35° C. in a CFX96™ Real-Time PCR Detection System (Bio-Rad) in a total reaction volume of 25 µL. Fluorescent signal for each reaction was read in Channel 1 (FAM) after every minute for 150 cycles (Scan Mode: FAM/SYBR only). All reactions contained bulk mix of 300 nM partzyme A (PPIAA2/1), 150 nM partzyme B (PPIAB3/1), and 30 nM Sub1i-FIB; 100 nM each EAS1_10, EAS2_11, EAS1_12, and EAS2_13 with 0.75 U Mnl I in 10 mM MgCl$_2$ (Ambion), 1×BSA (New England Biolabs), nuclease free water (Ambion) and 1×NEBuffer 1 (New England Biolabs; adjusted to pH 8.5 with KOH). All oligonucleotides were purchased from Integrated DNA Technologies (IDT).

15.6 Results: Detection of Presence of Target cDNA

FIG. 26 shows an increase in fluorescence for reaction (i) containing 115 pg of cDNA and reaction (ii) containing 23 pg of cDNA. The amount of target determines the time required to generate a fluorescent signal in an EzyAmp reaction. The fewer target molecules present, the longer it took to produce detectable fluorescent signal. No increase in signal was observed for approximately the first 110 minutes of the 'No Target Control' reaction (reaction (iii)) (although some drift in fluorescence was observed after this time). This indicates that formation of catalytically active MNAzymes was required for DF-production and subsequent EzyAmp signal amplification and this was only initiated in the presence of a suitable target (PPIA cDNA in this example).

Example 16

The following example demonstrates the capacity for oligonucleotides to form various duplex structures which are either cleavable, or not cleavable, by a thermostable RE known as TspRI.

16.1. Oligonucleotides

For the following reactions, oligonucleotide fragments were combined to form duplexes which were tested for their ability to behave as substrates for the RE, TspRI. Exemplary structures of CESA, PESA and EIC are illustrated in FIG. 1. In this example, the various duplexes each contained one oligonucleotide which included all bases required to form one strand of the bouble stranded RERS for TspRI.

of either DF-1 (only comprised of deoxyribonucleotides) or DF-2 (comprised of deoxyribonucleotides and one ribonucleotide) with the PESA was designed to form a CESA containing a RERS with all DNA nucleotides or a RERS with one RNA nucleotide respectively (FIG. 1A). Alternatively, hybridization of an Inhibitory Fragment (InF) was designed to form an Enzyme Inhibitory Complex (EICs) (FIG. 1B). The InF was internally labeled with a Fluoroscein moiety on a T base in position 14 and 3' end labeled with an IaBFQ moiety. Finally, an Antisense Control strand (ASC), which contained a full continuous RERS was included as a positive control. The oligonucleotides present in each reaction are listed below from 5' to 3' in Table 15. The bases which contribute to the recognition and cleavage site of TspRI are 5'NNCASTGNN/3' and 3'/NNGTSACNN5' where "N" can be any base, "S" can be a C or a G, and "I" indicates the cleavage site.

TABLE 15

Oligonucleotide Components of Reaction A to F for TspRI

| RE; RERS | Oligonucleotides used in Reactions A, B, C, D, E and F. P indicates the oligo was present in the reactin (Rn). Rn A = CESA with DNA only DF-1; Rn B = CESA with RNA containing DF-2; Rn C = EIC; Rn D = PESA; Rn E and F = Double stranded duplex (without nicks) DF-1—DNA only; DF-2—contains a ribonucleotide | | | | | |
|---|---|---|---|---|---|---|
| | Type (Name) | A | B | C | D | E/F |
| TspRI; | EAS1 (EAS1-8(33)-B) | P | P | P | P | P |
| | EAS2 (EAS2-8(17)-F) | P | P | P | P | |
| 5'NNCASTGNN/3' | DF-1 (DF-(5Sub1i(20:10)_1)(16)) | P | | | | |
| 3'/NNGTSACNN5' | DF-2 (rDF-(5Sub1i(20:10)_1) (16)) | | P | | | |
| | Inf (Sub1(20:10)_1i-FIB) | | | P | | |
| | ASC (ASC-EAS2-8(17)-F) | | | | | P |

The sequences for each of the oligos in Table 15 are provided in Table 16. Upper case letters indicate DNA and lower case letters indicate RNA. The bases which can potentially contribute to a TspR1 recognition and cleavage site are written in bold.

TABLE 16

| Oligo Name | Oligo Sequence (Upper case = DNA; lower case = RNA) |
|---|---|
| EAS1-8(33)-B | AGA TCC TTG TCG CAG TGT ATA GTG AGT GCC TGG |
| EAS2-8(17)-F | CAC TGC GAC AAG GAT CT |
| DF-(5Sub1i(20:10)_1(16) | CCA GGC ACT CAC TAT A |
| rDF-(5Sub1i(20:10)_1 (16) | CCA GGC ACT CAC TAT a |
| Sub1(20:10)_1i-FIB | CCAAACCAGGCACTCACTATaGGAAG AGATG |
| ASC-EAS2-8(17)-F | CCA GGC ACT CAC TA T ACA CTG CGA CAA GGA TCT |

RE cleavage activity was monitored by observing changes in fluorescence due to separation of fluorophore and quencher moieties following cleavage of CESA complexes by TspRI. In this example, EAS1 was end-labelled with an Iowa Black FQ ("IAbFQ") moiety at its 5' end, and contained sequence corresponding to all of the bases required to form one strand of the RERS for the RE, TspRI. EAS2 was end-labelled with a 6-fluorescein ("FAM") moiety at its 3' end and contained some of the bases required to form the second strand of the RERS. EAS2 and EAST were designed to anneal to form a PESA complex (FIG. 1C). Hybridization 16.2. Reaction Components Reaction A, B, C, D, E and F were set up to contain the oligonucleotides as listed in Table 15. All Reactions contained 100 nM of EAS1 in nuclease free water (Ambion), 1×BSA (New England Biolabs), 20 mM MgCl₂ (Ambion), and 20 mM Tris HCl pH 8.5 (Sigma-Aldrich); 50 mM potassium acetate (Sigma-Aldrich); 1 mM DTT (Sigma-Aldrich) and 10 mM magnesium acetate (Sigma-Aldrich)). Reactions A to E contained 2U TspRI (New England Biolabs), whereas Reaction F did not. In addition, Reaction A contained 100 nM of each of EAS2 and DF-1; Reaction B contained 100 nM of each of EAS2 and DF-2; Reaction C contained 100 nM of each of EAS2 and InF; Reaction D contained 100 nM of EAS2; and Reaction E and F contained 100 nM of ASC. Oligonucleotides were purchased from IDT. Reactions were conducted at 47° C. in a CFX96™ Real-Time PCR Detection System (Bio-Rad) in a total volume of 25 µL. Fluorescence for each sample was programmed to be read after every 1 second in Channel 1 (FAM; scan mode SYBR/FAM only) for a total of 100 cycles (total reaction time was approximately 17 minutes).

16.3. Results: Detection of Cleavage

An increase in fluorescent signal was observed over time in Reaction E, which contained EAS1 and its full complementary strand, ASC, indicating that this structure is amenable to cleavage by TspRI. No increase in fluorescence was observed for Reaction F, which contained EAS1 and its full complementary strand, ASC, but lacked TspRI.

An increase in fluorescence was observed over time in Reaction A, indicating that the DF-1 (comprised of only DNA) could bind to the PESA, completing the RER and forming a CESA which was cleaved by the RE. This demonstrates that TspRI can cleave a duplex which contains a nick within its restriction site. An increase in fluorescence was also observed in Reaction B which contained DF-2 that has a ribonucleotide as part of the sequence that completes the RERS. This indicates that a CESA was formed and TspRI can cleave a duplex which contains a nick and a ribonucleotide within its recognition and cleavage sequence. In contrast, no increase in fluorescence was seen in Reaction C which contained a PESA and an InF indicating that these oligos had formed an EIC. Similarly, no increase in fluorescence was seen in Reaction D which only contained a PESA indicating that a full RERS is required for the RE to cleave. As such TspRI is similar to those enzymes which exhibited Pattern II as detailed in Example 6, Table 13.

It can be concluded that TspRI is an ideal candidate RE for use in EzyAmp since its activity can be manipulated by varying the structure of the duplex substrate. This enzyme is also highly thermostable and is therefore resistant to denaturation by heating. As such this enzyme could be mixed with a template, such as genomic DNA, and be heated to separate the two strands of the double helix thus providing single stranded template suitable for cleavage with a protein or nucleic acid enzyme. For example, single stranded DNA template could function as an assembly facilitator for an MNAzyme and hence could be used to initiate an EzyAmp reaction. Similarly to the TspRI, the MNAzyme would not be affected by the heat denaturation step as it has demonstrated utility in PCR reactions. Alternatively, single-stranded DNA would be accessible for binding by a Synthetic Oligo Initiator (SIO) which could then be cleaved by a thermostable protein nuclease in strategies similar to those illustrated in FIGS. 8 to 11.

Example 17

The following example demonstrates the capacity of a CESA to be cleaved by a RE following its formation in the presence of its matching DF. In this strategy, one of the fragments generated by cleavage of the CESA corresponds to a shortened version of the original DF. As such this cleavage fragment has the potential to function as a DF for another PESA as illustrated in FIG. 27A, resulting in a self-feedback signal amplification.

17.1 Oligonucleotides

In the following reaction, the CESA is composed of a PESA and a DF (DF1). In turn, the PESA is composed of EAS1 (EAS1_1) and EAS2 (EAS2_2). EAS2 of the PESA contains a region within it which is equivalent to a shortened sequence of the DF.

RE activity was monitored by changes in fluorescence corresponding to the separation of a fluorophore and a quencher. In the current example, EAS1 was end labeled with an Iowa Black FQ ("IAbFQ") at the 5' end, and a, Black Hole Quencher 1 ("BHQ_1") at the 3' end. EAS2 was labeled with a 6-fluorescein ("6-FAM") at the 5' end and anneals to EAS1. The sequences of these oligonucleotides are listed below from 5' to 3' where the bases underlined form at least part of the recognition sequence for Mnl (CCTC or GAGG). The italicized bold bases represent those that are equivalent to a shortened version of DF1 which is present in the context of EAS2.

```
EAS1_1 (EAS1)
CTCTTCCTCTCTTCCCGGATGTCGGCCTCCTAGTACAGCG
EAS2_2 (EAS2)
ATCACATCCGGAAGAGA
DF1 (DF)
GGAAGAGAT
```

17.2 Reaction Conditions

Oligonucleotides were purchased from Integrated DNA Technologies (IDT). All reactions contained a bulk mix of 100 nM each EAS1_1 and EAS2_2 in 10 mM MgCl$_2$ (Ambion), 1×BSA (New England Biolabs), 1×NEBuffer 4 (New England Biolabs), nuclease free water (Ambion) and 0.75 U Mnl I (New England Biolabs). The total reaction volume was 25 µl, The test Reaction (i) was initiated by the addition of 100 nM DF and the control Reaction (ii) was initiated by the addition of H$_2$O. The reactions were run in duplicate at at 35° C. in a CFX96™ Real-Time PCR Detection System (BioRad). Fluorescence for each sample was programmed to be read after every 30 seconds for 200 cycles (Scan Mode: FAM/SBYR only). The total run time was 125 minutes.

17.3 Results: Detection of CESA Cleavage

The average fluorescence readings for each duplicate reaction were plotted against time and are shown in FIG. 27B. In Reaction (i), the addition of DF resulted in an increase in fluorescence over time (i). In contrast, no increase in fluorescence was observed over time in the absence of DF (ii).

The result demonstrates that addition of DF is required for the formation of CESA. In turn, the cleavage of CESA by Mnl I results in dissociation of fragments including those containing the fluorophore and quencher moieties (as indicated by the increase in fluorescence). In addition, one of the cleavage fragments corresponds to a shortened version of the original DF sequence. This new DF could potentially perform the same function the initiating DF by binding to another PESA.

The invention claimed is:

1. A method for detecting a target comprising:

(a) contacting a sample putatively containing a target nucleic acid with:

(i) two or more nucleic acid partzymes having partial catalytic cores and at least one nucleic acid substrate, wherein the partzymes self-assemble by hybridizing to the target nucleic acid when present to form at least one MNAzyme with a complete catalytic core, which catalyzes production of a primary Driver Fragment oligonucleotide (DF) by cleavage or ligation of the at least one MNAzyme substrate; or (ii) an oligonucleotide that hybridizes with the target creating a duplex substrate for a first nuclease, wherein the first nuclease cleaves the substrate to produce a primary DF from the duplex substrate;

(b) contacting the primary DF with a first oligonucleotide and a second oligonucleotide wherein:

a portion of the first oligonucleotide is complementary to a portion of the second oligonucleotide, and a portion of the first oligonucleotide is complementary to a portion of the primary DF, and the primary DF hybridizes with the first oligonucleotide, and the first oligonucleotide hybridizes with the second oligonucleotide forming a recognition site and a cleavage site for a second nuclease within a primary hybridization complex formed by the first and second oligonucleotides and primary DF, wherein binding of the primary DF to the first oligonucleotide is required to complete the recognition and cleavage sites;

(c) contacting the primary hybridization complex with the second nuclease under conditions permitting interaction of the second nuclease with the recognition site and cleavage at the cleavage site of the primary hybridization complex, wherein the cleavage by the second nuclease produces a nucleic acid cleavage product indicative of the presence of the target and comprising a secondary DF distinct from the primary DF;

and wherein:

the secondary DF hybridises with a third oligonucleotide, and the third oligonucleotide hybridizes with a fourth oligonucleotide forming a recognition site and a cleavage site for a further nuclease within a secondary hybridization complex formed by the third and fourth oligonucleotides and secondary DF, wherein binding of the secondary DF to the third oligonucleotide is required to complete the recognition and cleavage sites for the further nuclease in the secondary hybridization complex, the further nuclease cleaves the secondary hybridization complex at the cleavage site of the secondary hybridization complex to produce another nucleic acid cleavage product indicative of the presence of the target and comprising an additional primary DF, the primary DF cleaved from the secondary hybridization complex hybridizes to an additional first oligonucleotide, and the additional first oligonucleotide hybridizes with an additional second oligonucleotide to thereby reproduce the primary hybridization complex; and (d) detecting any of the nucleic acid cleavage products to thereby detect the target.

2. The method of claim 1, wherein said second nuclease is capable of cleaving a double stranded oligonucleotide comprising a nick in at least one of two strands of the nuclease recognition and cleavage site within the hybridization complex.

3. The method of claim 1, wherein said MNAzyme substrate is a first strand of an oligonucleotide complex comprising first and second strands, wherein said first strand comprises an internal loop portion and bases within the internal loop portion are not hybridised to bases of the second strand, and wherein the MNAzyme is capable of cleaving the internal loop portion.

4. The method of claim 3, wherein said second strand comprises the primary DF.

5. The method of claim 3, wherein said first and second strands are linked at one end by a hairpin loop portion.

6. The method of claim 1, wherein said MNAzyme substrate is a hairpin loop portion of a hairpin oligonucleotide, said MNAzyme is capable of cleaving the hairpin loop portion, and said primary DF is located in one strand of a double-stranded stem portion in said hairpin oligonucleotide.

7. The method of claim 1, wherein the first nuclease used to produce the primary DF is selected from an endonuclease, an exonuclease, or any one of Nuclease BAL-31, Exonuclease I, Exonuclease III, T7 Exonuclease I, Exonuclease T, T7 Endonuclease I, RNase H, and Mung Bean Nuclease.

8. The method of claim 1, wherein said second nuclease and said further nuclease are the same nuclease.

9. The method of claim 1, wherein any one or more of the first oligonucleotide, the second oligonucleotide, the third oligonucleotide, and/or the fourth oligonucleotide are tethered to a support.

10. The method of claim 1, wherein said first nuclease and said second nuclease are the same nuclease.

11. The method of claim 1, wherein:
at least one of the partzymes and/or MNAzyme substrate comprises an aptamer or portion thereof, and
said aptamer or portion thereof comprises at least one of a: nucleic acid, peptide, polypeptide, protein, a derivative thereof, or a combination thereof.

12. The method of claim 1, wherein the primary hybridization complex comprises a nick in at least one of two strands located at the nuclease cleavage site for the second nuclease, and the second nuclease is a restriction enzyme.

13. The method of claim 1, wherein:
the primary DF is located 5' to the second oligonucleotide when each is hybridised to the first oligonucleotide of the primary hybridization complex, and
the final nucleotide at the primary DF 3'terminus and the first nucleotide at the second oligonucleotide 5'terminus of are each hybridised to the first oligonucleotide.

14. The method of claim 1, wherein the nucleotide sequence of the primary DF is not identical to the nucleotide sequence of the secondary DF.

15. The method of claim 1, performed as a single reaction.

* * * * *